(12) United States Patent
McCormick et al.

(10) Patent No.: US 11,358,940 B2
(45) Date of Patent: Jun. 14, 2022

(54) K-RAS MODULATORS

(71) Applicants: THE REGENTS OF THE UNIVERSITY OF CALIFORNIA, Oakland, CA (US); LEIDOS BIOMEDICAL RESEARCH, INC., Frederick, MD (US)

(72) Inventors: Frank McCormick, San Francisco, CA (US); Adam Renslo, Oakland, CA (US); David Turner, Frederick, MD (US); Anna E. Maciag, Frederick, MD (US); Marcin Dyba, Frederick, MD (US); Elizabeth D. Vo, San Francisco, CA (US); Joseph Saavedra, Thurmont, MD (US); Vandana Kumari, Frederick, MD (US)

(73) Assignees: The Regents of the University of California, Oakland, CA (US); Leidos Biomedical Research, Inc., Frederick, MD (US)

( * ) Notice: Subject to any disclaimer, the term of this patent is extended or adjusted under 35 U.S.C. 154(b) by 0 days.

(21) Appl. No.: 16/605,643

(22) PCT Filed: Apr. 20, 2018

(86) PCT No.: PCT/US2018/028593
§ 371 (c)(1),
(2) Date: Oct. 16, 2019

(87) PCT Pub. No.: WO2018/195439
PCT Pub. Date: Oct. 25, 2018

(65) Prior Publication Data
US 2020/0247762 A1    Aug. 6, 2020

Related U.S. Application Data

(60) Provisional application No. 62/487,756, filed on Apr. 20, 2017.

(51) Int. Cl.
| | | |
|---|---|---|
| C07D 251/24 | (2006.01) | |
| C07C 233/11 | (2006.01) | |
| C07C 233/31 | (2006.01) | |
| C07D 207/40 | (2006.01) | |
| C07D 213/40 | (2006.01) | |
| C07D 231/56 | (2006.01) | |
| C07D 237/08 | (2006.01) | |
| C07D 239/26 | (2006.01) | |
| C07D 241/12 | (2006.01) | |
| C07D 303/46 | (2006.01) | |
| C07D 305/06 | (2006.01) | |
| C07D 307/06 | (2006.01) | |

(Continued)

(52) U.S. Cl.
CPC .......... *C07D 251/24* (2013.01); *C07C 233/11* (2013.01); *C07C 233/31* (2013.01); *C07D 207/40* (2013.01); *C07D 213/40* (2013.01); *C07D 231/56* (2013.01); *C07D 237/08* (2013.01); *C07D 239/26* (2013.01); *C07D 241/12* (2013.01); *C07D 303/46* (2013.01); *C07D 305/06* (2013.01); *C07D 307/06* (2013.01); *C07D 307/33* (2013.01); *C07D 307/36* (2013.01); *C07D 401/06* (2013.01); *C07D 403/06* (2013.01); *C07D 403/14* (2013.01); *C07D 405/12* (2013.01); *C07D 405/14* (2013.01); *C07D 409/12* (2013.01); *C07D 471/04* (2013.01); *C07D 487/04* (2013.01)

(58) Field of Classification Search
CPC .. C07D 401/06; C07D 403/06; C07D 403/14; C07D 405/14; C07D 409/12; C07D 471/04; C07D 487/04
See application file for complete search history.

(56) References Cited

U.S. PATENT DOCUMENTS

| | | |
|---|---|---|
| 4,924,004 A | 5/1990 | Ohlendorf et al. |
| 5,436,244 A | 7/1995 | Clemence et al. |

(Continued)

FOREIGN PATENT DOCUMENTS

| | | |
|---|---|---|
| CN | 1901910 A | 1/2007 |
| EP | 2836482 B1 | 12/2019 |

(Continued)

OTHER PUBLICATIONS

STN Registry #916030-58-5, entered date Dec. 20, 2006.*

(Continued)

*Primary Examiner* — Susanna Moore
(74) *Attorney, Agent, or Firm* — Irina E. Britva; Mintz, Levin, Cohn, Ferris, Glovsky and Popeo, P.C.

(57) ABSTRACT

Provided herein are the K-Ras inhibitors of the formulae:

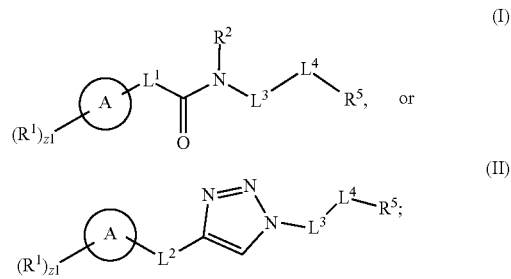

Also provided are compositions comprising thereof for treating cancer.

20 Claims, 21 Drawing Sheets
Specification includes a Sequence Listing.

(51) Int. Cl.
  C07D 307/33   (2006.01)
  C07D 307/36   (2006.01)
  C07D 401/06   (2006.01)
  C07D 403/06   (2006.01)
  C07D 403/14   (2006.01)
  C07D 405/12   (2006.01)
  C07D 405/14   (2006.01)
  C07D 409/12   (2006.01)
  C07D 471/04   (2006.01)
  C07D 487/04   (2006.01)

(56) References Cited

U.S. PATENT DOCUMENTS

| | | |
|---|---|---|
| 5,475,109 A | 12/1995 | Seinick et al. |
| 6,916,817 B1 | 7/2005 | Tucker |
| 8,324,239 B2 | 12/2012 | Barnes et al. |
| 8,383,659 B2 | 2/2013 | Nanchen et al. |
| 10,857,140 B2 | 12/2020 | McCormick et al. |
| 2007/0112000 A1 | 5/2007 | Barton et al. |
| 2014/0288045 A1 | 9/2014 | Ren et al. |
| 2015/0087628 A1 | 3/2015 | Ostrem et al. |

FOREIGN PATENT DOCUMENTS

| | | | |
|---|---|---|---|
| JP | S61227567 A | 10/1986 | |
| JP | 7242641 A | 9/1995 | |
| JP | 2006504669 A | 2/2006 | |
| JP | 2006506451 A | 2/2006 | |
| JP | 2006519827 A | 8/2006 | |
| JP | 2009526807 A | 7/2009 | |
| WO | 1996006078 | 2/1996 | |
| WO | 1996040146 | 12/1996 | |
| WO | 2001012189 | 2/2001 | |
| WO | 2003004474 | 1/2003 | |
| WO | 2004076449 A2 | 9/2004 | |
| WO | 2005032472 A1 | 4/2005 | |
| WO | 2005047286 A1 | 5/2005 | |
| WO | 2005058883 | 6/2005 | |
| WO | 2005073198 A1 | 8/2005 | |
| WO | 2007109154 | 9/2007 | |
| WO | 2009015237 A1 | 1/2009 | |
| WO | 2009018505 A1 | 2/2009 | |
| WO | 2010138758 A1 | 12/2010 | |
| WO | 2013155223 A1 | 10/2013 | |
| WO | 2014027053 A1 | 2/2014 | |
| WO | 2014093230 A1 | 6/2014 | |
| WO | 2014152588 A | 9/2014 | |
| WO | 2014152588 A1 | 9/2014 | |
| WO | 2015048570 A2 | 4/2015 | |
| WO | 2016161361 A1 | 10/2016 | |
| WO | 2016179558 A1 | 11/2016 | |
| WO | WO-2017181177 A1 * | 10/2017 | ............ C07D 413/14 |

OTHER PUBLICATIONS

STN search report (CA Registry No. 1384596-49-9, available Jul. 27, 2012, downloaded on Feb. 23, 2021, p. 1). (Year: 2012).*
CAS RN 120014-29-1, STN entry Date Apr. 7, 1989 for compound named 1-benzoyl-4-piperidinecarboxaldehyde. OPSIN: Open Parser for Systematic IUPAC nomenclature.
Registry (STN) No. 939705-56-3, Jun. 28, 2007.
Registry (STN) No. 1046208-96-1, Sep. 4, 2008.
Registry (STN) No. 1322872-96-7, Aug. 24, 2011.
Registry (STN) No. 1322930-26-6, Aug. 25, 2011.
Registry (STN) No. 1335283-57-2, Oct. 14, 2011.
Registry (STN) No. 1335636-92-4, Oct. 16, 2011.
Registry (STN) No. 1420531-71-0, Feb. 13, 2013.
Registry (STN) No. 9277551-13-1, Feb. 13, 2013.
Shaik et al., "Design and synthesis of imidazo [2,1-b] thiazole linked triazole conjugates: Microtubule-destabilizing agents", European Journal of Medicinal Chemistry, Editions Scientifique Elsevier, Paris, FR, vol. 126 Sep. 20, 2016, pp. 36-51.
Shi et al., "Amino(methyl)pyrrolidines as novel scaffolds for factor Xa inhibitors," Bioorganic & Medicinal Chemistry Letters, Nov. 1, 2007, e-published Aug. 21, 2007, 17(21): 5952-5958.
Stratmann et al., "Welwitindolinones, Unusual Alkaloids from the Blue-Green Algae Hapalosiphon welwitschii and Westiella intricata. Relationship to Fischerindoles and Hapalinodoles," J Am Chem Soc, 1994, 116(22):9935-9942.
Tome, A. C., Product class 13: 1,2,3-triazoles, Science of Synthesis, 13, 2004, 415-601.
Turner et al., "Simple plate-based, parallel synthesis of disulfide fragments using the CuAAC click reaction," ACS Comb. Sci., Dec. 8, 2014,16(12):661-664.
Turner et al., "Supporting inforamtion Simple plate-based, parallel synthesis of disulfide fragments using the CuAAC click reaction," ACS Comb Sci., 2014, 16:661-664, supplemental information, 49 total pages.
Wang et al., Targeting Mutant KRAS for anticancer Therapeutics: A Review of Novel Small Molecule Modulators, Journal of Medicinal Chemistry, Apr. 23, 2013, pp. 5219-5230, vol. 56, No. 13.
Winter et al., "Structure-Activity Rltionships of Chromone Derivatiaves toward the Mechanism of Interaction with and Inhibition of Breast Cancer Resistance Protein ABCG2", Journal of Medicinal Chemistry, vol. 56, No. 24, 2013, pp. 9849-9860.
International Search Report for PCT/US2018/028593 dated Oct. 29, 2018, 12 pages.
Written Opinion for PCT/US2018/028593 dated Oct. 29, 2018, 14 pages.
Registry (STN) No. 1420450-66-3, Feb. 13, 2013.
Burlingame, M.A. et al. (2011). "Simple one-pot synthesis of disulfide fragments for use in disulfide-exchange screening," ACS Comb. Sci. 13:205-208.
Burlingame, M.A. et al. (2011). "Simple one-pot synthesis of disulfide fragments for use in disulfide-exchange screening," ACS Comb. Sci. 13:205-208, supplemental information part 1, 3 total pages.
Burlingame, M.A. et al. (2011). "Simple one-pot synthesis of disulfide fragments for use in disulfide-exchange screening," ACS Comb. Sci. 13:205-208, supplemental information part 2, 78 total pages.
Colombano et al., "A novel potent nicotinamide phosphoribosyltransferase inhibitor synthesized via click chemistry", Journal of Medicinal Chemistry, Jan. 1, 2010, pp. 616-623, vol. 53, No. 2.
Database Registry, Chemical Abstracts Service, Columbus, Ohio, US; May 27, 2004, XP002792951, retrieved from STN Database accession No. 686272-37-7.
Database Registry, Chemical Abstracts Service, Columbus, Ohio, US; Nov. 2, 2008, XP002792950, retrieved from STN Database accession No. 1069483-13-1.
Database Registry, Chemical Abstracts Service, Columbus, Ohio, US; Nov. 3, 2008, XP002792952, retrieved from STN Database accession No. 1069948-57-7.
Database Registry, Chemical Abstracts Service, Columbus, Ohio, US; Nov. 4, 2008, XP002792949, retrieved from STN Database accession No. 1070668-79-7.
Database Registry, Chemical Abstracts Service, Columbus, Ohio, US; Aug. 10, 2010, XP002792953, retrieved from STN Database accession No. 11235624-64-2.
De Costa et al., "Synthesis and Biological Evaluation of Conformationally Restricted 2-(1-Pyrrolidinyl)-N-[2-(3, 4-dichlorophenyl)ethyl]-N-met hylethylenediamines as a c Receptor Ligands. 1. Pyrrolidine, Piperidine, Homopiperidine, and Tetrahydroisoquinoline Classes", J. Med. Chem, Jan. 1, 1992, pp. 4334-4343.
Durust, Yasar et al., "Synthesis of novel triazoles bearing 1,2,4-oxadiazole and phenylsulfonyl groups by 1,3-dipolar cycloaddition of some organic azides and their biological activities",Turkish Journal of Chemistry, 38(5) 2014, 739-755.
Gentile, D.R. et al. (Dec. 21, 2017, e-published Oct. 12, 2017). "Ras Binder Induces a Modified Switch-II Pocket in GTP and GDP States," Cell Chemical Biology 24(12):1455-1466.

(56) References Cited

OTHER PUBLICATIONS

Harkala, Karna Ji et al., "Synthesis and biological evaluation of benzimidazole-linked 1,2,3-triazole congeners as agents", Organic and Medicinal Chemistry Letters, vol. 4, No. 14, 2014, pp. 1-4.
Iddon, Brian et al., "Azoles. Part 13. Synthesis and bromine .fwdarw. lithium exchange reactions of some 1-substituted 4, 5-dibromo-1H-1,2,3-triazoles and 2-substitute 4,5-dibromo-2H1,2,3-triazoles", Journal of the Chemical Society, Perkin Transactions 1: Organic and Bio-Organic Chemistry, (12), 1996, 1341-1347.
Imase et al., "A New Route to Tricyclic 2-Pyridone Frameworks via Formation of Bicyclic N-Alkenyl Alkynylamides Followed by Gold-catalyzed Cycloisomerization", Chemistry Letter, 2009, Vo. 38, No. 12, pp. 1152-1153.
Madsen et al., "Synthesis of Rhodamine 6G-Based Compounds for the ATRP Synthesis f Flourescently Labeled biocompatible Polymers", BioMacromolecules, 2011, vol. 12, pp. 2225-2234.
Pruet, J. et al., "Optimized 5-membered Heterocycle-Linked Pterins for the Inhibition of Ricin Toxin A", ACS Medicinal Chemistry Letters, vol. 3, No. 7, 2012.
Liu, Q. et al. (Feb. 21, 2013). "Developing irreversible inhibitors of the protein kinase cysteinome," Chem. & Biol. Rev. 20:146-159.
PUBCHEM 11750091, created Oct. 26, 2006, p. 2, Fig.
PUBCHEM 110091647, created Feb. 25, 2011, located at https://pubchem.ncbi.nlm.nih.gov/substance/110091647, 6 pages.
PUBCHEM 74797094, created Jun. 11, 2009, located at https://pubchem.ncbi.nlm.nih.gov/substance/74797094, 5 pages.
PubChem-CID-56217953, (Z)-N-[[1-(Benzenesulfonyl)piperidin-4-yl]methy]-2-cyano-3-(2,5-dimethyl-1-propylpyrrol-3-yl]pro-2-enamide. Create Date: Jan. 25, 2012, p. 2, Fig.
PubChem-CID-56178526, (Z)-2-Cyano-N-[[1-[(4-methoxyphenyl)methy]piperidin-4-yl]methyl]-3-[1-(1-methoxypropan-2-yl)-2,5-dimethylpyrrol-3-yl]prop-2-enamide, Create Date: Jan. 25, 2012, p. 2, Fig.
PubChem-CID-56314596, (Z)-2-Cyano-[1-[(4-methoxyphenyl)-2,5-dimethylpyrrol-3-yl]-N-[(1-propan-2-ylpyrrolidin-3-yl) methyl]prop-2-enamide, Create Date: Jan. 25, 2012, p. 2, Fig.
PubChem-CID-77141576, 1-Methyl-4-[4-(2-methylsulfonylethenyl)piperidin-1-yl]-2-oxoquinoline-3-carbonitrile, Create Date: Sep. 10, 2014, p. 2, Fig.
PUBCHEM 223343680, created Nov. 10, 2014, located at https://pubchem.ncbi.nlm.nih.gov/substance/223343680, 5 pages.
Registry (STN) No. 9277551-13-1, Mar. 20, 2007.
Registry (STN) No. 927581-98-4, Mar. 20, 2007.
Registry (STN) No. 938827-79-3, Jun. 25, 2007.
Registry (STN) No. 838705-56-3, Jun. 28, 2007.
Registry (STN) No. 1060988-53-5, Oct. 14, 2008.
Registry (STN) No. 1099889-61-8, Feb. 3, 2009.
Registry (STN) No. 1235685-68-3, Aug. 10, 2010.
Registry (STN) No. 1276209-51-8, Apr. 7, 2011.
Registry (STN) No. 1276217-66-3, Apr. 7, 2011.
Registry (STN) No. 1276225-82-1, Apr. 7, 2011.
Registry (STN) No. 1276249-08-1, Apr. 7, 2011.
Registry (STN) No. 1302884-07-6, May 30, 2011.
Registry (STN) No. 1302915-05-4, May 30, 2011.
Registry (STN) No. 1302950-32-8, May 30, 2011.
Registry (STN) No. 1302979-50-5, May 30, 2011.
Registry (STN) No. 1303982-77-9, May 30, 2011.
Registry (STN) No. 1303073-87-1, May 31, 2011.
Registry (STN) No. 1303187-17-8, May 31, 2011.
Registry (STN) No. 1303228-57-0, May 31, 2011.
Registry (STN) No. 1303251-45-7, May 31, 2011.
Registry (STN) No. 1303294-15-6, May 31, 2011.
Registry (STN) No. 1322620-59-6, Aug. 24, 2011.
Registry (STN) No. 1322804-03-4, Aug. 24, 2011.
Registry (STN) No. 1322808-30-9, Aug. 24, 2011.
Extended European Search Report for European Patent Application No. 16790206.3 dated Dec. 5, 2018 (5 pages).
International Search Report and Written Opinion for PCT Application No. PCT/US2016/031344 dated Aug. 19, 2016 (10 pages).
Geske et al., "Evaluation of a focused library of N-aryl L-homoserine lactones reveals a new set of potent quorum sensing modulators", Bioorganic & Medicinal Chemistry Letters, 2008, 18, pp. 5978-5981.
Australian Examination Report No. 1 from corresponding application No. 2018255413 dated Sep. 8, 2021 (9 pages).
Registry (STN) No. 903676-36-8, Nov. 1, 2021.
Registry (STN) No. 1839919-81-1, Jan. 1, 2006.
Registry (STN) No. 1484135-82-1, Dec. 1, 2013.
Registry (STN) No. 1285326-06-8, Apr. 19, 2021.
Registry (STN) No. 1535205-78-7, Apr. 19, 2021.
Registry (STN) No. 1372050-86-6, May 1, 2012.
Registry (STN) No. 1783181-50-9, Jun. 18, 2015.
Registry (STN) No. 1783236-10-1, Jun. 18, 2015.
Registry (STN) No. 925605-78-3, Mar. 8, 2007.
Registry (STN) No. 1197616-23-1, Dec. 16, 2009.
Registry (STN) No. 1370924-59-6, Apr. 29, 2012.
Registry (STN) No. 791079-19-7, Dec. 1, 2004.
Registry (STN) No. 959240-11-0, Dec. 21, 2007.
Registry (STN) No. 1090732-25-4, Dec. 28, 2008.
European Examination Report from corresponding application No. 18723515.2 dated Jan. 7, 2022 (8 pages).

* cited by examiner

K-Ras SEQ ID NO: 1   FAINNTKSFEDIHHYREQIKRVKD
H-Ras SEQ ID NO: 2   FAINNTKSFEDIHQYREQIKRVKD
N-Ras SEQ ID NO: 3    FAINNTKSFADINLYREQIKRVKD

FNL-0001

FNL-0013

FNL-00014

FNL-0015

FNL-0024

FNL-0028

FNL-0016

FNL-0010

FNL-0012

| Compound | % labeling KRAS4b H95C (MALDI-TOF MS) | | |
| --- | --- | --- | --- |
| | 4h | 8h | 24h |
| FNL0042 (S) | 12 | 13 | 48 |
| FNL0044 (R) | 21 | 37 | 86 |
| FNL0043 (S) | 2 | 3 | 14 |
| FNL0045 (R) | 11 | 25 | 68 |

FNL-0088    FNL-0090    FNL-0092    FNL-0112

SEQUENCE LISTING

<160> NUMBER OF SEQ ID NOS: 5

<210> SEQ ID NO 1
<211> LENGTH: 24
<212> TYPE: PRT
<213> ORGANISM: Artificial sequence
<220> FEATURE:
<223> OTHER INFORMATION: Synthetic Polypeptide

<400> SEQUENCE: 1

Phe Ala Ile Asn Asn Thr Lys Ser Phe Glu Asp Ile His His Tyr Arg
1               5                   10                  15

Glu Gln Ile Lys Arg Val Lys Asp
            20

<210> SEQ ID NO 2
<211> LENGTH: 24
<212> TYPE: PRT
<213> ORGANISM: Artificial sequence
<220> FEATURE:
<223> OTHER INFORMATION: Synthetic Polypeptide

<400> SEQUENCE: 2

Phe Ala Ile Asn Asn Thr Lys Ser Phe Glu Asp Ile His Gln Tyr Arg
1               5                   10                  15

Glu Gln Ile Lys Arg Val Lys Asp
            20

<210> SEQ ID NO 3
<211> LENGTH: 24
<212> TYPE: PRT
<213> ORGANISM: Artificial sequence
<220> FEATURE:
<223> OTHER INFORMATION: Synthetic Polypeptide

<400> SEQUENCE: 3

Phe Ala Ile Asn Asn Thr Lys Ser Phe Ala Asp Ile Asn Leu Tyr Arg
1               5                   10                  15

Glu Gln Ile Lys Arg Val Lys Asp
            20

<210> SEQ ID NO 4
<211> LENGTH: 189
<212> TYPE: PRT
<213> ORGANISM: Homo sapiens

<400> SEQUENCE: 4

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

```
Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 5
<211> LENGTH: 188
<212> TYPE: PRT
<213> ORGANISM: Homo sapiens

<400> SEQUENCE: 5

Met Thr Glu Tyr Lys Leu Val Val Val Gly Ala Gly Gly Val Gly Lys
  1               5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

K-RAS MODULATORS

CROSS-REFERENCE TO RELATED APPLICATIONS

This application is a national stage entry of PCT Application No. PCT/US18/28593 filed Apr. 20, 2018, which claims the benefit of U.S. Provisional Application No. 62/487,756 filed Apr. 20, 2017, the disclosure of each of which is incorporated by reference herein in its entirety.

STATEMENT AS TO RIGHTS TO INVENTIONS MADE UNDER FEDERALLY SPONSORED RESEARCH AND DEVELOPMENT

The invention was made with government support under contract no. HHSN261200800001E and grant nos. R35 CA197709 and U01 CA168370 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-592001WO_ST25.TXT, created on Apr. 18, 2018, 4,781 bytes, machine format IBM-PC, MS Windows operating system, is hereby incorporated by reference.

BACKGROUND OF THE INVENTION

K-Ras is the most frequently mutated oncogene in human cancer. Past attempts to directly modulate the activity of this enzyme have been unsuccessful. Ras proteins are small guanine nucleotide-binding proteins that act as molecular switches by cycling between active GTP-bound and inactive GDP-bound conformations. The Ras proteins play a critical role in the regulation of cell proliferation, differentiation, and survival. Dysregulation of the Ras signaling pathway is almost invariably associated with disease. Hyper-activating somatic mutations in Ras are among the most common lesions found in human cancer. Although mutation of any one of the three Ras isoforms (K-Ras, N-Ras, or H-Ras) has been shown to lead to oncogenic transformation, K-Ras mutations are by far the most common in human cancer. For example, K-Ras mutations are known to be often associated with pancreatic, colorectal and non-small-cell lung carcinomas. There is a need in the art for effective Ras inhibitors and anticancer compounds. Disclosed herein are solutions to these and other problems in the art.

BRIEF SUMMARY OF THE INVENTION

Described herein, inter alia, is the use of K-Ras inhibitors (e.g., for treating cancer).

In an aspect is provided a compound having the formula:

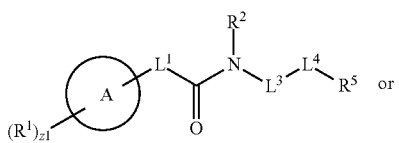

(I)

-continued

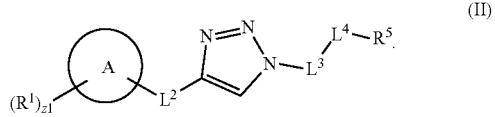

(II)

Ring A is an aryl or heteroaryl.

$R^1$ is independently halogen, $-CX^1_3$, $-CHX^1_2$, $-CH_2X^1$, $-CN$, $-SO_{m1}R^{1D}$, $-SO_{v1}NR^{1A}R^{1B}$, $-NHNR^{1A}R^{1B}$, $-ONR^{1A}R^{1B}$, $-NHC=(O)NHNR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl.

The symbol z1 is an integer from 0 to 4.

$R^2$ is independently hydrogen, $-CX^2_3$, $-CHX^2_2$, $-CH_2X^2$, $-C(O)R^{2A}$, $-C(O)OR^{2A}$, $-C(O)NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

$L^1$ is a bond, substituted or unsubstituted alkylene, substituted or unsubstituted cycloalkylene, or

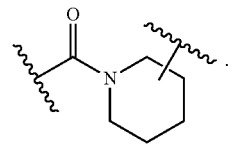

$L^2$ is a bond, $-O-$, $-C(O)-$, $-C(O)O-$, $-OC(O)-$, $-S-$, $-SO-$, $-S(O)_2-$, $-NH-$, $-NHC(O)-$, $-C(O)NH-$, $-SO_2NH-$, $-NHSO_2-$, $-OC(O)NH-$, $-NHC(O)O-$, $-NHC(O)NH-$, $-C(O)OCH_2-$, $-CH_2OC(O)-$, $-C(O)NHCH_2-$, $-CH_2NHC(O)-$, $-CH_2NHCH_2-$, substituted or unsubstituted alkylene, or substituted or unsubstituted heteroalkylene.

$L^3$ is a bond, $-S(O)_2-$, $-N(R^3)-$, $-O-$, $-S-$, $-C(O)-$, $-C(O)N(R^3)-$, $-N(R^3)C(O)-$, $-N(R^3)C(O)NH-$, $-NHC(O)N(R^3)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^3$ is independently hydrogen, $-CX^3_3$, $-CHX^3_2$, $-CH_2X^3$, $-C(O)R^{3A}$, $-C(O)OR^{3A}$, $-C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^4$ is a bond, $-S(O)_2-$, $-N(R^4)-$, $-O-$, $-S-$, $-C(O)-$, $-C(O)N(R^4)-$, $-N(R^4)C(O)-$, $-N(R^4)C(O)NH-$, $-NHC(O)N(R^4)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^4$ is independently hydrogen, $-CX^4_3$, $-CHX^4_2$, $-CH_2X^4$, $-C(O)R^{4A}$, $-C(O)OR^{4A}$, $-C(O)NR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or E.

E is a histidine binding moiety.

Each $R^{1A}$, $R^{1B}$, $R^{1C}$, $R^{1D}$, $R^{2A}$, $R^{2B}$, $R^{3A}$, $R^{3B}$, $R^{4A}$, and $R^{4B}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl.

Each X, $X^1$, $X^2$, $X^3$, and $X^4$ is independently —F, —Cl, —Br, or —I.

The symbol n1 is independently an integer from 0 to 4.

The symbols m1 and v1 are independently 1 or 2.

In embodiments, when Ring A is aryl, $L^1$ is a bond, substituted or unsubstituted alkylene, or substituted or unsubstituted cycloalkylene.

In another aspect is provided a pharmaceutical composition including a compound described herein and a pharmaceutically acceptable excipient.

In another aspect is provided a method of treating cancer in a patient in need of such treatment.

In an aspect is provided a method of reducing the level of activity of a K-Ras protein, the method including contacting the K-Ras protein with a compound described herein.

In another aspect is provided a method of modulating a K-Ras protein, the method including contacting the K-Ras protein with a compound described herein.

BRIEF DESCRIPTION OF THE DRAWINGS

(FIG. 8A) Inhibition of proliferation in KRas4B G12D MEFs after 24 h treatment with FNL-0012; (FIG. 8B) Structures of FNL-0010 and FNL-0012; (FIG. 8C) Dose-dependent growth arrest in KRas4b G12D MEFs after 45 h treatment with FNL-0012; (FIG. 8D) Decrease in KRas protein level and MAPK signaling in KRas4b G12D MEFs after 45 h with FNL-0012; (FIG. 8E) Decrease in P-MEK and P-Erk in HupT4 pancreas carcinoma cells after 24 h with FNL-0012, but not with FNL-0010; (FIG. 8F) Growth arrest in HupT4 cells treated with FNL-0012 for 24 h.

FIG. 10A. Structures of FNL-0010, FNL-0012, and FNL-0030. FIG. 10B. MALDI-TOF analysis of KRas H95C (1-169) reacted with FNL-0010, FNL-0012, and FNL-0030 for 24 h.

FIG. 11A. Compound FNL-0012 (12), FNL-0036 (36), FNL-0037 (37), FNL-0038 (38). FIG. 11B. Growth arrest in HupT4 treated with FNL-0012, but not with control compounds (structures depicted in FIG. 11A). Images were taken at 72 h time point. FIG. 11C. HupT4 were treated with DMSO (D), left untreated (–), or 40 µM compound FNL-0012 (12), FNL-0036 (36), FNL-0037 (37), FNL-0038 (38). Decrease in MAPK signaling after 24 h, and decrease in KRas protein level and MAPK signaling after 72 h of treatment with FNL-0012, but not the controls.

FIG. 12A: Growth arrest caused by treatment with FNL-0012 in KRas4b G12D MEFs only, not in BRAF V600E MEFs. FIG. 12B: Decrease in MEK phosphorylation in KRas MEFs (G12D or G12D/H95Q), not in BRAF V600E MEFs.

FIG. 14A: Structures of a single enantiomer derivatives of compound FNL-0012: FNL-0042 (S) or FNL-0044 (R), and derivatives of FNL-0030: FNL-0043 (S) and FNL-0045 (R). FIG. 14B: MALDI-TOF MS analysis indicated significantly higher level of covalent labeling of KRAS4b H95C by R enantiomer. FIG. 14C: HupT4 cells were treated with single enantiomer derivatives at 40 µM for 48 h. In both cases, the R enantiomer caused growth arrest, with S isomer being inactive.

FIG. 15A depicts a series of analogues of FNL-0045. FIG. 15B depicts graphs of cell proliferation experiments with KRAS4b G12D, KRAS4b G12V, HRas WT/P53-, and SUIT-2, for the compounds FNL-0088 (left) and FNL-0090 (right).

I. DEFINITIONS

Figure 1:
FIG. 1. H95 located in G-domain of K-Ras, and sequence comparison of K, N, and HRas at this site. Targeting H95 would affect both splice variants of KRas, 4A and 4B. The sequences depicted in the figures correspond to: FAINNTKSFEDIHHYREQIKRVKD (SEQ ID NO: 1), FAINNTKSFEDIHQYREQIKRVKD (SEQ ID NO:2), and FAINNTKSFADINLYREQIKRVKD (SEQ ID NO:3).
Figure 2:
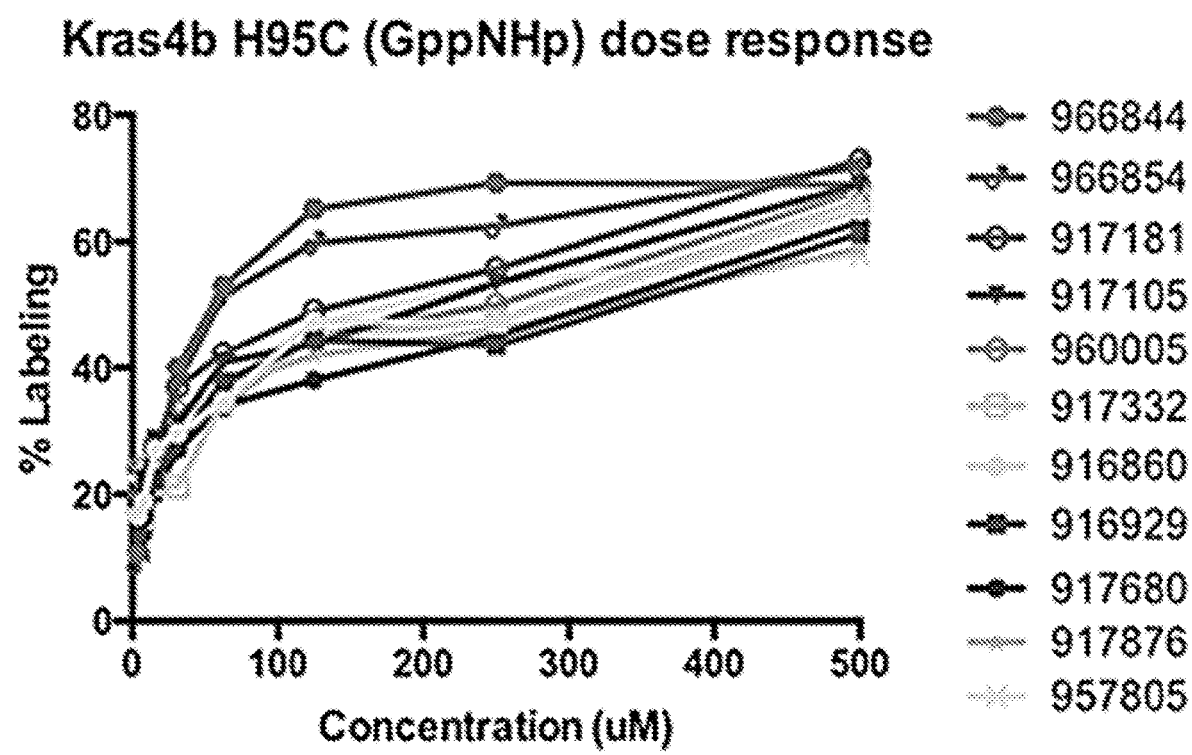
FIG. 2. Dose response experiments identified triazoles 966844 and 966854 and phenylacetamide 917105 as strong binders at H95 site of KRas.
Figure 3:
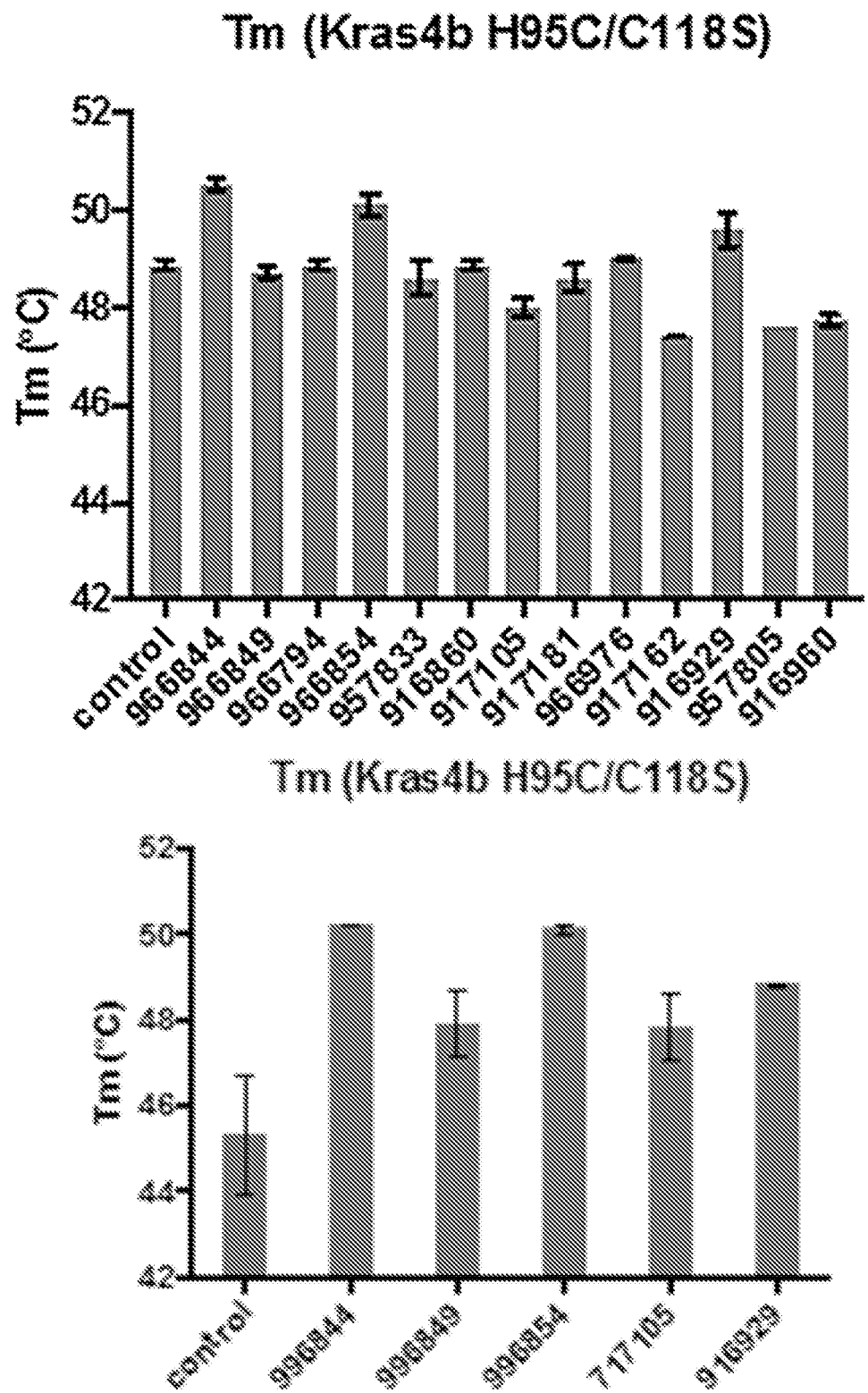
FIG. 3. Thermal melting analysis that revealed significant shifts in Tm upon fragment binding identified triazoles 966844 and 966854 and phenylacetamide 917105 as strong binders at H95 site of KRas.
Figure 4:
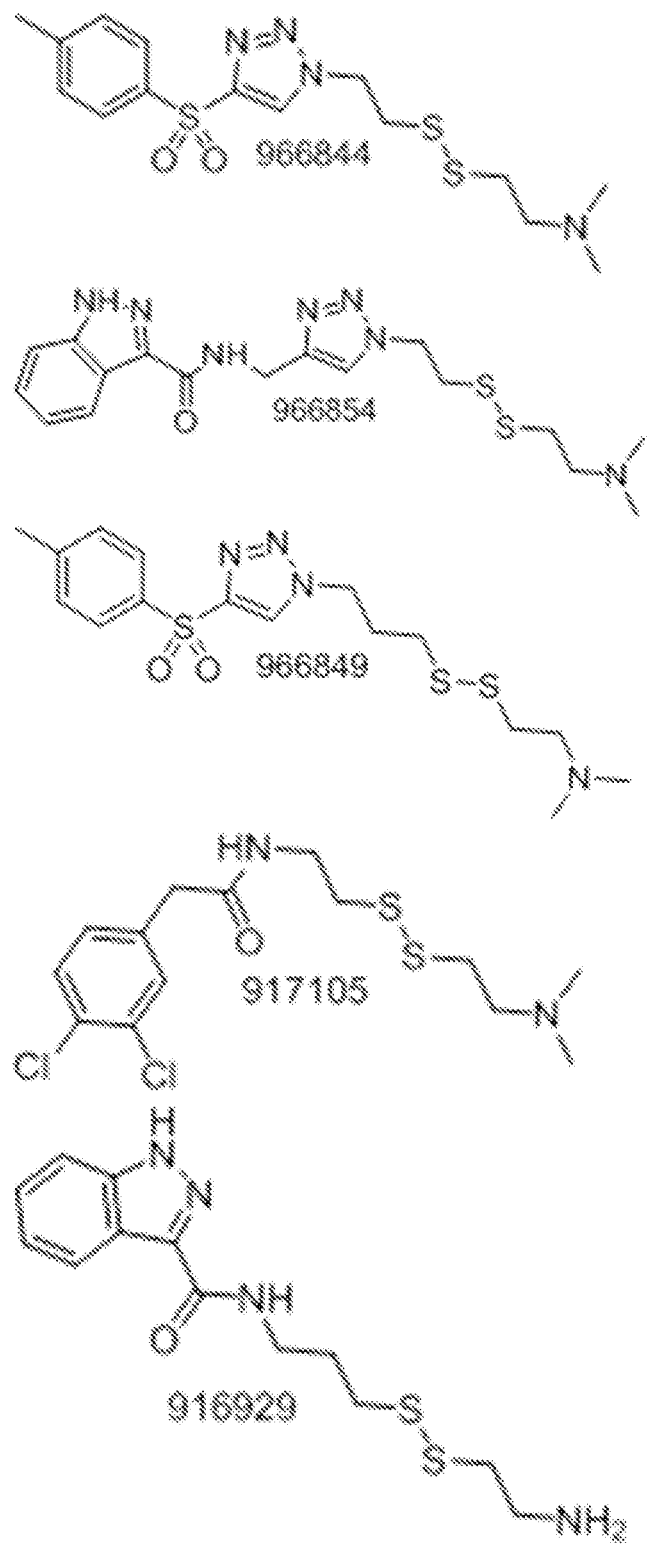
FIG. 4. Select compound structures.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., selected from the group consisting of O, N, P, Si, and S, and wherein the nitrogen and sulfur atoms may optionally be oxidized, and the nitrogen heteroatom may optionally be quaternized). The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR'R", —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. In some embodiments, fused ring aryl includes two or more rings fused together wherein at least one of the fused rings is an aromatic hydrocarbon ring, and at least one ring is a non-aromatic ring comprising a heteroatom, for example

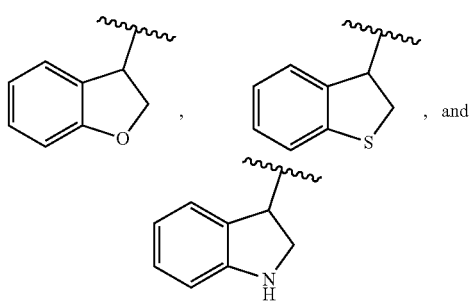

are each considered aryl as defined herein. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring), for example,

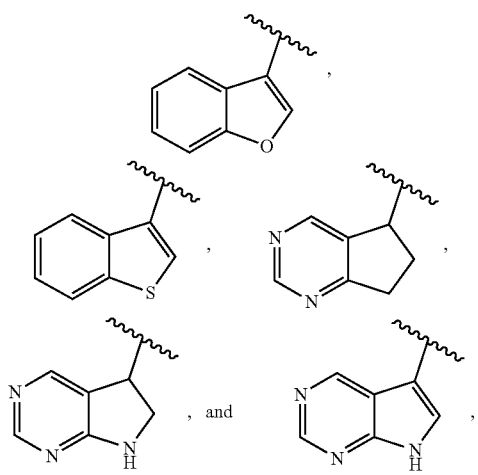

are considered heteroaryl. A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "$\sim\!\!\sim\!\!\sim$" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

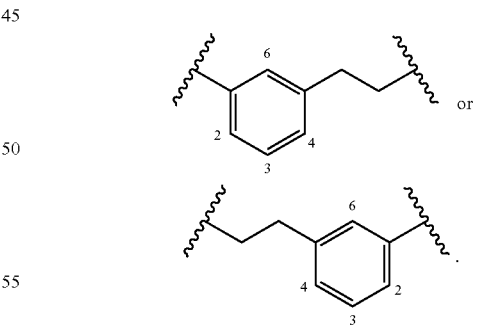

An alkylarylene moiety may be substituted (e.g. with a substituent group) on the alkylene moiety or the arylene linker (e.g. at carbons 2, 3, 4, or 6) with halogen, oxo, —N₃, —CF₃, —CCl₃, —CBr₃, —CI₃, —CN, —CHO, —OH, —NH₂, —COOH, —CONH₂, —NO₂, —SH, —SO₂CH₃ —SO₃H, —OSO₃H, —SO₂NH₂, —NHNH₂, —ONH₂, —NHC(O)NHNH₂, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —NR'NR"R'", —ONR'R", —NR'C(O)NR"NR'"R"", —CN, —NO₂, —NR'SO₂R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, halogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂CH₃, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —NR'NR"R'", —ONR'R", —NR'C(O)NR"NR'"R"", —CN, —NO₂, —R', —N₃, —CH(Ph)₂, fluoro(C₁-C₄)alkoxy, and fluoro(C₁-C₄)alkyl, —NR'SO₂R", —NR'C(O)R", —NR'C(O)—OR", —NR'OR", in a number ranging from zero to the total number of open valences on the aromatic ring system; and where R', R", R'", and R"" are preferably independently selected from hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH₂)$_r$—B—, wherein A and B are independently —CRR'—, —O—, —NR—, —S—, —S(O)—, —S(O)₂—, —S(O)₂NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)₂—, or —S(O)₂NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), Boron (B), and silicon (Si).

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$F, —OCH$_2$I, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered), and (B) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$F, —OCH$_2$I, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered), and (ii) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$F, —OCH$_2$I, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered), and (b) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$F, —OCH$_2$I, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol or additional number may be used to distinguish each appearance of that particular R group.

For example, where multiple $R^1$ substituents are present, each $R^1$ substituent may be distinguished as $R^{1.1}$, $R^{1.2}$, $R^{1.3}$, $R^{1.4}$, etc., wherein each of $R^{1.1}$, $R^{1.2}$, $R^{1.3}$, $R^{1.4}$, etc. is defined within the scope of the definition of $R^1$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dyes, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. In some embodiments of the compositions or methods described herein, treating cancer includes slowing the rate of growth or spread of cancer cells, reducing metastasis, or reducing the growth of metastatic tumors. The term "treating" and conjugations thereof, include prevention of an injury, pathology, condition, or disease. In embodiments, "treating" does not include prevention.

An "effective amount" is an amount sufficient for a compound to accomplish a stated purpose relative to the absence of the compound (e.g. achieve the effect for which it is administered, treat a disease, reduce enzyme activity, increase enzyme activity, reduce signaling pathway, reduce one or more symptoms of a disease or condition (e.g. reduce signaling pathway stimulated by GTP bound K-Ras (e.g., human K-Ras 4A and/or human K-Ras 4B), reduce the signaling pathway activity of K-Ras (e.g., human K-Ras 4A and/or human K-Ras 4B), reduce the signaling pathway activity of K-Ras4A, reduce the signaling pathway activity of K-Ras4B, reduce the signaling pathway activity of a mutant K-Ras (e.g., human K-Ras 4A and/or human K-Ras 4B), inhibit the binding of K-Ras (e.g., human K-Ras 4A and/or human K-Ras 4B) to SOS, inhibit the binding of K-Ras (e.g., human K-Ras 4A and/or human K-Ras 4B) to a GEF, reduce the localization of K-Ras (e.g., human K-Ras 4A and/or human K-Ras 4B) to a membrane, reduce the prenylation of K-Ras (e.g., human K-Ras 4A and/or human K-Ras 4B), inhibit the localization of K-Ras (e.g., human K-Ras 4A and/or human K-Ras 4B) to a membrane). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist (e.g. disrupt the protein-protein interaction between K-Ras (e.g., human K-Ras 4A and/or human K-Ras 4B) and a signaling pathway binding protein such as PI3K, disrupt the interaction of K-Ras (e.g., human K-Ras 4A and/or human K-Ras 4B) and GEF, disrupt the interaction of K-Ras (e.g., human K-Ras 4A and/or human K-Ras 4B) and SOS, disrupt the interaction of K-Ras (e.g., human K-Ras 4A and/or human K-Ras 4B) with Raf, disrupt the localization of K-Ras (e.g., human K-Ras 4A and/or human K-Ras 4B) to a membrane, disrupt the prenylation of K-Ras (e.g., human K-Ras 4A and/or human K-Ras 4B)). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g. signaling pathway) of a protein (e.g. K-Ras, mutant K-Ras, K-Ras G12C, K-Ras G12D, K-Ras G13C, K-Ras G13D, K-Ras G12V, K-Ras G12S) in the absence of a compound as described herein (including embodiments, examples, figures, or Tables).

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme (e.g. K-Ras, K-Ras4A, K-Ras4B, mutant K-Ras, K-Ras G12C, K-Ras G13C, K-Ras G12D, K-Ras G13D, K-Ras G12V, K-Ras G12S). In some embodiments, the protein may be K-Ras (e.g., human K-Ras 4A and/or human K-Ras 4B). In some embodiments, the protein may be a mutant K-Ras (e.g., human K-Ras 4A and/or human K-Ras 4B) (e.g. K-Ras G12C, K-Ras G13C, K-Ras G12D, K-Ras G13D, K-Ras G12V, K-Ras G12S). In some embodiments, the protein may be K-Ras4A. In some embodiments, the protein may be K-Ras4B. In some embodiments contacting includes allowing a compound described herein to interact with a protein or enzyme that is involved in a signaling pathway.

As defined herein, the term "inhibition", "inhibit", "inhibiting" and the like in reference to a protein-inhibitor interaction means negatively affecting (e.g. decreasing) the activity or function of the protein (e.g. decreasing the signaling pathway stimulated by GTP bound K-Ras (e.g., human K-Ras 4A and/or human K-Ras 4B) (e.g. K-Ras, K-Ras G12C, K-Ras G13C, K-Ras G12D, K-Ras G13D, K-Ras G12V, K-Ras G12S), nucleotide exchange, effector protein binding, effector protein activation, guanine exchange factor (GEF) binding, SOS binding, GEF-facilitated nucleotide exchange, phosphate release, nucleotide release, nucleotide binding, membrane localization, prenylation of the protein) relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway (e.g. reduction of a pathway involving GTP bound K-Ras (e.g., human K-Ras 4A and/or human K-Ras 4B) (e.g. K-Ras, K-Ras G12C, K-Ras G13C, K-Ras G12D, K-Ras G13D, K-Ras G12V, K-Ras G12S), reduction of a pathway involving mutant K-Ras (e.g., human K-Ras 4A and/or human K-Ras 4B) (e.g. K-Ras G12C, K-Ras G13C, K-Ras G12D, K-Ras G13D, K-Ras G12V, K-Ras G12S)). Thus, inhibition includes, at least in part, partially or totally blocking stimulation, decreasing, preventing, or delaying activation, or inactivating, desensitizing, or down-regulating the signaling pathway or enzymatic activity or the amount of a protein (e.g. K-Ras, K-Ras G12C, K-Ras G13C, K-Ras G12D, K-Ras G13D, K-Ras G12V, K-Ras G12S). In some embodiments, inhibition refers to inhibition of interactions of K-Ras (e.g., human K-Ras 4A and/or human K-Ras 4B) (K-Ras, K-Ras G12C, K-Ras G13C, K-Ras G12D, K-Ras G13D, K-Ras G12V, K-Ras G12S) with signaling pathway binding partners (e.g. PI3K, SOS, Raf). In some embodiments, inhibition refers to inhibition of interactions of K-Ras (e.g., human K-Ras 4A and/or human K-Ras 4B) with a GEF (e.g. SOS). In some embodiments, inhibition refers to inhibition of K-Ras (e.g., human K-Ras 4A and/or human K-Ras 4B) prenylation. In some embodiments, inhibition refers to inhibition of K-Ras (e.g., human K-Ras 4A and/or human K-Ras 4B) localization. In some embodiments, inhibition refers to inhibition of K-Ras (e.g., human K-Ras 4A and/or human K-Ras 4B) membrane localization.

The term "modulator" refers to a composition that increases or decreases the level of a target molecule or the function (e.g., effector protein binding, effector protein activation, guanine exchange factor (GEF) binding, SOS binding, prenylation, localization) of a target molecule or the physical state (e.g. K-Ras (e.g., human K-Ras 4A and/or human K-Ras 4B) subcellular localization, K-Ras (e.g., human K-Ras 4A and/or human K-Ras 4B) post-translational processing, K-Ras (e.g., human K-Ras 4A and/or human K-Ras 4B) post-translational modifications (prenylation)) of the target of the molecule (e.g. a target may be K-Ras (e.g., human K-Ras 4A and/or human K-Ras 4B) and the function may be to hydrolyze GTP or activate a signaling pathway that is activated by GTP bound K-Ras (e.g., human K-Ras 4A and/or human K-Ras 4B), interaction of K-Ras (e.g., human K-Ras 4A and/or human K-Ras 4B) with protein binding partners (e.g. PI3K, SOS, Raf)) relative to the absence of the composition. In some embodiments, a K-Ras (e.g., human K-Ras 4A and/or human K-Ras 4B) disease modulator is a compound that reduces the severity of one or more symptoms of a disease associated with K-Ras (e.g., human K-Ras 4A and/or human K-Ras 4B) (e.g. cancer, metastatic cancer) relative to the absence of the compound. A K-Ras (e.g., human K-Ras 4A and/or human K-Ras 4B) modulator is a compound that increases or decreases the activity or function or level of activity or level of function of K-Ras (e.g., human K-Ras 4A and/or human K-Ras 4B) or level of K-Ras (e.g., human K-Ras 4A and/or human K-Ras 4B) or level of K-Ras (e.g., human K-Ras 4A and/or human K-Ras 4B) in a particular physical state relative to the absence of the compound. A mutant K-Ras (e.g., human K-Ras 4A and/or human K-Ras 4B) modulator is a compound that that increases or decreases the activity or function or level of activity or level of function of mutant K-Ras (e.g., human K-Ras 4A and/or human K-Ras 4B) or level of mutant K-Ras (e.g., human K-Ras 4A and/or human K-Ras 4B) or level of mutant K-Ras (e.g., human K-Ras 4A and/or human K-Ras 4B) in a particular physical state relative to the absence of the modulator (e.g., a compound described herein). A K-Ras G12C modulator, K-Ras G12D modulator, K-Ras G13C modulator, K-Ras G12V modulator, K-Ras G12S modulator, or K-Ras G13D modulator is a compound that increases or decreases the activity or function or level of activity or level of function of that particular mutant K-Ras (e.g., human K-Ras 4A and/or human K-Ras 4B) or level of that particular mutant K-Ras (e.g., human K-Ras 4A and/or human K-Ras 4B) or level of that particular mutant K-Ras (e.g., human K-Ras 4A and/or human K-Ras 4B) in a particular physical state relative to the absence of the compound. A K-Ras (e.g., human K-Ras 4A and/or human K-Ras 4B) inhibitor is a compound that decreases the activity or function or level of activity or level of function of K-Ras (e.g., human K-Ras 4A and/or human K-Ras 4B) or level of K-Ras (e.g., human K-Ras 4A and/or human K-Ras 4B) or level of K-Ras (e.g., human K-Ras 4A and/or human K-Ras 4B) in a particular physical state relative to the absence of the compound. A mutant K-Ras (e.g., human K-Ras 4A and/or human K-Ras 4B) inhibitor is a compound that that decreases the activity or function or level of activity or level of function of mutant K-Ras (e.g., human K-Ras 4A and/or human K-Ras 4B) or level of mutant K-Ras (e.g., human K-Ras 4A and/or human K-Ras 4B) or level of mutant K-Ras (e.g., human K-Ras 4A and/or human K-Ras 4B) in a particular physical state relative to the absence of the compound. A K-Ras G12C inhibitor, K-Ras G12D inhibitor, K-Ras G13C inhibitor, K-Ras G12V inhibitor, K-Ras G12S inhibitor, or K-Ras G13D inhibitor is a compound that decreases the activity or function or level of activity or level of function of that particular mutant K-Ras (e.g., human K-Ras 4A and/or human K-Ras 4B) or level of that particular mutant K-Ras (e.g., human K-Ras 4A and/or human K-Ras 4B) or level of that particular mutant K-Ras (e.g., human K-Ras 4A and/or human K-Ras 4B) in a particular physical state relative to the absence of the compound.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g. caused by) a K-Ras (e.g., human K-Ras 4A and/or human K-Ras 4B). In some embodiments, the disease is a disease related to (e.g. caused by) a K-Ras (e.g., human K-Ras 4A and/or human K-Ras 4B) (e.g. K-Ras G12C, G13C, G12D, G12V, G12S, or G13D) or aberrant K-Ras (e.g., human K-Ras 4A and/or human K-Ras 4B) signaling pathway activity (e.g. lung cancer, breast cancer, colon cancer, colorectal cancer, pancreatic cancer, leukemia). Examples of diseases, disorders, or conditions include, but are not limited to cancer. Examples of diseases, disorders, or conditions include, but are not limited to MYH-associated polyposis. In some instances, "disease" or "condition" refers to cancer. In some instances, "disease" or "condition" refers to MYH-associated polyposis. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals (e.g. humans), including leukemia, lymphoma, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

"Ras associated cancer" (also referred to herein as "Ras related cancer") refers to a cancer caused by aberrant Ras activity, level, or signaling. A "cancer associated with aberrant K-Ras activity" (also referred to herein as "K-Ras related cancer") is a cancer caused by aberrant K-Ras activity or signaling (e.g. a mutant K-Ras). K-Ras related cancers may include lung cancer, non-small cell lung cancer, breast cancer, leukemia, pancreatic cancer, colon cancer, colorectal cancer. Other cancers that are associated with aberrant activity of one or more of K-Ras (e.g., human K-Ras 4A and/or human K-Ras 4B) and mutant K-Ras (e.g., human K-Ras 4A and/or human K-Ras 4B) (including K-Ras G12C, K-Ras G13C, K-Ras G12D, K-Ras G12V, K-Ras G12S, K-Ras G13D mutants) are well known in the art and determining such cancers are within the skill of a person of skill in the art.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "administer (or administering) a Ras inhibitor" or "administer (or administering) a K-Ras inhibitor" means administering a compound that inhibits the activity or level (e.g. amount) or level of a signaling pathway of one or more K-Ras (e.g., human K-Ras 4A and/or human K-Ras 4B) proteins (K-Ras, mutant K-Ras, K-Ras G12C, K-Ras G12V, K-Ras G12S, K-Ras G12D, K-Ras G13C, K-Ras G13D). Administration may include, without being limited by mechanism, allowing sufficient time for the K-Ras (e.g., human K-Ras 4A and/or human K-Ras 4B) inhibitor to reduce the activity of one or more K-Ras (e.g., human K-Ras 4A and/or human K-Ras 4B) proteins or for the K-Ras (e.g., human K-Ras 4A and/or human K-Ras 4B) inhibitor to reduce one or more symptoms of a disease (e.g. cancer, wherein the K-Ras (e.g., human K-Ras 4A and/or human K-Ras 4B) inhibitor may arrest the cell cycle, slow the cell cycle, reduce DNA replication, reduce cell replication, reduce cell growth, reduce metastasis, or cause cell death).

The compounds described herein can be used in combination with one another, with other active agents known to be useful in treating a disease associated with cells expressing a particular K-Ras (e.g., human K-Ras 4A and/or human K-Ras 4B) or mutant K-Ras (e.g., human K-Ras 4A and/or human K-Ras 4B) (e.g. cancer), or with adjunctive agents that may not be effective alone, but may contribute to the efficacy of the active agent. In embodiments, the administering does not include administration of any active agent other than the recited active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), and the like.

The compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In therapeutic use for the treatment of cancer, compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer or with adjunctive agents that may not be effective alone, but may contribute to the efficacy of the active agent.

The term "associated" or "associated with" in the context of a substance or substance activity or function associated with a disease (e.g. a protein associated disease, a cancer associated with aberrant K-Ras (e.g., human K-Ras 4A and/or human K-Ras 4B) activity, K-Ras (e.g., human K-Ras 4A and/or human K-Ras 4B) associated cancer, mutant K-Ras (e.g., human K-Ras 4A and/or human K-Ras 4B) associated cancer, activated K-Ras (e.g., human K-Ras 4A and/or human K-Ras 4B) associated cancer, K-Ras G12C associated cancer, K-Ras G12V associated cancer, K-Ras G12S associated cancer, K-Ras G13C associated cancer, K-Ras G12D associated cancer, K-Ras G13D associated cancer) means that the disease (e.g. cancer) is caused by (in whole or in part), or a symptom of the disease is caused by (in whole or in part) the substance or substance activity or function. For example, a cancer associated with aberrant K-Ras (e.g., human K-Ras 4A and/or human K-Ras 4B) activity or function may be a cancer that results (entirely or partially) from aberrant K-Ras (e.g., human K-Ras 4A and/or human K-Ras 4B) activity or function (e.g. enzyme activity, protein-protein interaction, signaling pathway) or a cancer wherein a particular symptom of the disease is caused (entirely or partially) by aberrant K-Ras (e.g., human K-Ras 4A and/or human K-Ras 4B) activity or function. As used herein, what is described as being associated with a disease, if a causative agent, could be a target for treatment of the disease. For example, a cancer associated with aberrant K-Ras (e.g., human K-Ras 4A and/or human K-Ras 4B) activity or function or a K-Ras (e.g., human K-Ras 4A and/or human K-Ras 4B) associated cancer, may be treated with a K-Ras (e.g., human K-Ras 4A and/or human K-Ras 4B) modulator or K-Ras (e.g., human K-Ras 4A and/or human K-Ras 4B) inhibitor, in the instance where increased K-Ras (e.g., human K-Ras 4A and/or human K-Ras 4B) activity or function (e.g. signaling pathway activity) causes the cancer. For example, a cancer associated with K-Ras G12V may be a cancer that a subject with K-Ras G12V is at higher risk of developing as compared to a subject without K-Ras G12V.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP 16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox L-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat;

imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin 1I (including recombinant interleukin II, or rIL.sub.2), interferon alfa-2a; interferon alfa-2b; interferon alfa-n1; interferon alfa-n3; interferon beta-la; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, Ras inhibitors, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "electrophilic" as used herein refers to a chemical group that is capable of accepting electron density. An "electrophilic substituent", "electrophilic chemical moiety", or "electrophilic moiety" refers to an electron-poor chemical group, substitutent, or moiety (monovalent chemical group), which may react with an electron-donating group, such as a nucleophile, by accepting an electron pair or electron density to form a bond. In some embodiments, the electrophilic substituent of the compound is capable of reacting with a histidine residue. In some embodiments, the electrophilic substituent is capable of forming a covalent bond with a histidine residue (e.g., K-Ras (e.g., human K-Ras 4A and/or human K-Ras 4B) histidine residue, residue corresponding to H95 of human K-Ras 4A and/or 4B) and may be referred to as a "covalent histidine binding moiety" or "covalent histidine binding substituent". The covalent bond formed between the electrophilic substituent and a nitrogen of the histidine sidechain may be a reversible or irreversible bond.

The term "histidine binding moiety" as used herein refers to a monovalent chemical group that is capable of contacting a histidine amino acid (e.g., in a protein, in a K-Ras (e.g., human K-Ras 4A and/or human K-Ras 4B) protein) and may interact with the histidine amino acid. In some embodiments, the histidine binding moiety is an electrophilic substituent. In embodiments, the histidine binding moiety is capable of reacting with a histidine residue. In some embodiments, the histidine binding moiety is capable of forming a covalent bond with a histidine residue (e.g., K-Ras (e.g., human K-Ras 4A and/or human K-Ras 4B) histidine residue, residue corresponding to H95 of human K-Ras 4A or 4B) and may be referred to as a "covalent histidine binding moiety" or "covalent histidine binding substituent". The covalent bond formed between the histidine binding moiety and a nitrogen of the histidine may be a reversible or irreversible bond.

The term "irreversible covalent bond" and "irreversible bond" is used in accordance with its plain ordinary meaning in the art and refers to the resulting association between atoms or molecules of (e.g., electrophilic chemical moiety and nucleophilic moiety) wherein the probability of dissociation is low. In embodiments, the irreversible covalent bond does not easily dissociate under normal biological conditions. In embodiments, the irreversible covalent bond is formed through a chemical reaction between two species (e.g., electrophilic chemical moiety and nucleophilic moiety).

"Nucleophilic" as used herein refers to a chemical group that is capable of donating electron density.

The term "K-Ras" or "KRAS" or "KRas" refers to the nucleotide sequences or proteins of human K-Ras (e.g. UniProt P01116, human K-Ras4A (e.g., NP_203524.1, NM_033360.3)), human K-Ras4B (e.g., NP_004976.2, NM_4985.4)), or both K-Ras4A and K-Ras4B). K-Ras is understood to play an important role in the regulation of cell proliferation. The term "K-Ras" includes both the wild-type form of the nucleotide sequences or proteins as well as any mutants thereof. In some embodiments, "K-Ras" is wild-type K-Ras. In some embodiments, "K-Ras" is one or more mutant forms. The term "K-Ras" XYZ refers to a nucleotide sequence or protein of a mutant K-Ras wherein the Y numbered amino acid of K-Ras that has an X amino acid in the wildtype instead has a Z amino acid in the mutant (e.g. K-Ras G12C has a G in wildtype protein but a C in the K-Ras G12C mutant protein). In some embodiments K-Ras refers to K-Ras4A and K-Ras4B. In some embodiments, K-Ras refers to K-Ras4A. In some embodiments, K-Ras refers to K-Ras4B. In embodiments K-Ras refers to a protein having an amino acid sequence described herein.

```
K-Ras 4A WT Human
                                         (SEQ ID NO: 4)
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHHYREQI KRVKDSEDVP MVLVGNKCDL
```

```
PSRTVDTKQA QDLARSYGIP FIETSAKTRQ RVEDAFYTLV

REIRQYRLKK ISKEEKTPGC VKIKKCIIM

K-Ras 4B WT Human
                                         (SEQ ID NO: 5)
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHHYREQI KRVKDSEDVP MVLVGNKCDL

PSRTVDTKQA QDLARSYGIP FIETSAKTRQ GVDDAFYTLV

REIRKHKEKM SKDGKKKKKK SKTKCVIM
```

The term "K-Ras inhibitor test compound" as used herein refers to a compound that is being characterized in an assay for the ability to inhibit an activity, function, or level (e.g. amount) of K-Ras (e.g., human K-Ras 4A and/or human K-Ras 4B) protein.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of a K-Ras (e.g., human K-Ras 4A and/or human K-Ras 4B) with a compound as described herein may result in a change in one or more protein-protein interactions of the K-Ras (e.g., human K-Ras 4A and/or human K-Ras 4B) or interactions between the K-Ras (e.g., human K-Ras 4A and/or human K-Ras 4B) and a membrane, resulting in changes in cell growth, proliferation, or survival.

An amino acid residue in a protein "corresponds" to a given residue when it occupies the same essential structural position within the protein as the given residue. For example, a selected residue in a selected protein corresponds to Gly 12 of Human K-Ras4A (e.g., SEQ ID NO:4) or Human K-Ras 4B (e.g., SEQ ID NO:5) or both when the selected residue occupies the same essential spatial or other structural relationship as Gly 12 in Human K-Ras4A or Human K-Ras 4B or both. In some embodiments, where a selected protein is aligned for maximum homology with the Human K-Ras4A or Human K-Ras 4B protein, the position in the aligned selected protein aligning with Gly 12 is said to correspond to Gly 12 (e.g., Gly 12 of SEQ ID NO:4 or Gly 12 of SEQ ID NO:5). Instead of a primary sequence alignment, a three dimensional structural alignment can also be used, e.g., where the structure of the selected protein is aligned for maximum correspondence with the Human K-Ras4A or Human K-Ras 4B protein and the overall structures compared. In this case, an amino acid that occupies the same essential position as Gly 12 in the structural model is said to correspond to the Gly 12 residue (e.g., Gly 12 of SEQ ID NO:4 or Gly 12 of SEQ ID NO:5). Another example is wherein a selected residue in a selected protein corresponds to H95 of Human K-Ras 4A or 4B when the selected residue (e.g., histidine residue) occupies essential the same sequence, spatial, or other structural position within the protein as H95 in Human K-Ras 4A or 4B (e.g., H95 of SEQ ID NO:4 or H95 of SEQ ID NO:5).

The terms "unsubstituted vinyl sulfone moiety", "unsubstituted vinyl sulfonamide moiety", "unsubstituted fluoro (C$_1$-C$_4$)alkylketone moiety", "unsubstituted chloro(C$_1$-C$_4$) alkylketone moiety", "unsubstituted acrylamide moiety", "unsubstituted disulfide moiety", "unsubstituted thiol moiety", "unsubstituted phosphonate moiety", "unsubstituted aldehyde moiety", "unsubstituted enone moiety", "unsubstituted diazomethylketone moiety", "unsubstituted diazomethylamide moiety", "unsubstituted cyanocyclopropyl carboxamide moiety", "unsubstituted epoxide moiety", "unsubstituted epoxyketone moiety", "unsubstituted epoxyamide moiety", "unsubstituted aryl aldehyde moiety", "unsubstituted aryl dialdehyde moiety", "unsubstituted dialdehyde moiety", "unsubstituted nitrogen mustard moiety", "unsubstituted propargyl moiety", or "unsubstituted propargylamide moiety" are used according to their plain ordinary chemical meaning and refer to those monovalent chemical groups named having the lowest molecular weight for each such group while obeying the rules of chemical valency. A substituted form of one of the named groups (e.g., vinyl sulfone moiety) may be substituted with one or more of any of the substituent groups described herein (e.g., substituted with a substituent group, a size-limited substituent group, or lower substituent group) while obeying the rules of chemical valency.

II. COMPOUNDS

In an aspect is provided a compound having the formula:

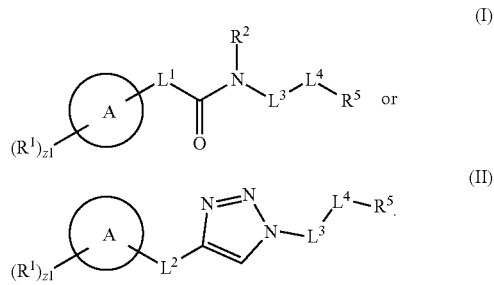

Ring A is an aryl or heteroaryl.

R$^1$ is independently halogen, —CX$^1_3$, —CHX$^1_2$, —CH$_2$X$^1$, —CN, —SO$_{n1}$R$^{1D}$, —SO$_{v1}$NR$^{1A}$R$^{1B}$, —NHNR$^{1A}$R$^{1B}$, —ONR$^{1A}$R$^{1B}$, —NHC=(O)NHNR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, —OCX$^1_3$, —OCHX$^1_2$, —OCH$_2$X$^1$, —N$_3$, substituted (e.g., substituted with a substituent group, a size-limited substituent group, or lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{12}$, C$_6$-C$_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered); two adjacent $R^1$ substituents may optionally be joined to form a substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

The symbol z1 is an integer from 0 to 4.

$R^2$ is independently hydrogen, —$CX^2_3$, —$CHX^2_2$, —$CH_2X^2$, —$C(O)R^{2A}$, —$C(O)OR^{2A}$, —$C(O)NR^{2A}R^{2B}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

$L^1$ is a bond, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), or

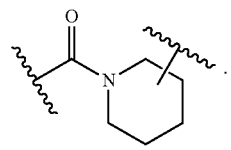

$L^2$ is a bond, —O—, —C(O)—, —C(O)O—, —OC(O)—, —S—, —SO—, —S(O)$_2$—, —NH—, —NHC(O)—, —C(O)NH—, —SO$_2$NH—, —NHSO$_2$—, —OC(O)NH—, —NHC(O)O—, —NHC(O)NH—, —C(O)OCH$_2$—, —CH$_2$OC(O)—, —C(O)NHCH$_2$—, —CH$_2$NHC(O)—, —CH$_2$NHCH$_2$—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), or substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered).

$L^3$ is a bond, —S(O)$_2$—, —N($R^3$)—, —O—, —S—, —C(O)—, —C(O)N($R^3$)—, —N($R^3$)C(O)—, —N($R^3$)C(O)NH—, —NHC(O)N($R^3$)—, —C(O)O—, —OC(O)—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenylene), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered).

$R^3$ is independently hydrogen, —$CX^3_3$, —$CHX^3_2$, —$CH_2X^3$, —$C(O)R^{3A}$, —$C(O)OR^{3A}$, —$C(O)NR^{3A}R^{3B}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

$L^4$ is a bond, —S(O)$_2$—, —N($R^4$)—, —O—, —S—, —C(O)—, —C(O)N($R^4$)—, —N($R^4$)C(O)—, —N($R^4$)C(O)NH—, —NHC(O)N($R^4$)—, —C(O)O—, —OC(O)—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenylene), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered).

$R^4$ is independently hydrogen, —$CX^4_3$, —$CHX^4_2$, —$CH_2X^4$, —$C(O)R^{4A}$, —$C(O)OR^{4A}$, —$C(O)NR^{4A}R^{4B}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

$R^5$ is independently hydrogen, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered), or E.

E is a histidine binding moiety.

Each $R^{1A}$, $R^{1B}$, $R^{1C}$, $R^{1D}$, $R^{2A}$, $R^{2B}$, $R^{3A}$, $R^{3B}$, $R^{4A}$, and $R^{4B}$ is independently hydrogen, —$CX_3$, —CN, —COOH, —$CONH_2$, —$CHX_2$, —$CH_2X$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered); $R^{1A}$ and $R^{1B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered); $R^{2A}$ and $R^{2B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered); $R^{3A}$ and $R^{3B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered); $R^{4A}$ and $R^{4B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

Each X, $X^1$, $X^2$, $X^3$, and $X^4$ is independently —F, —Cl, —Br, or —I.

The symbol n1 is independently an integer from 0 to 4.

The symbols m1 and v1 are independently 1 or 2.

In embodiments, the compound has the formula:

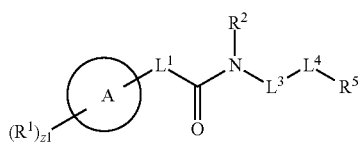
(I)

and $R^1$, $R^2$, $R^5$, Ring A, $L^1$, $L^3$, $L^4$, and z1 are as described herein.

In embodiments, the compound has the formula:

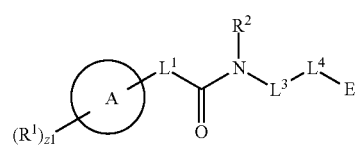
(I)

and $R^1$, $R^2$, E, Ring A, $L^1$, $L^3$, $L^4$, and z1 are as described herein.

In embodiments, the compound has the formula:

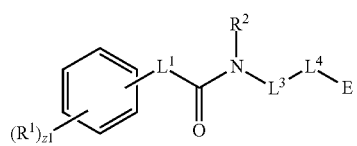

and $R^1$, $R^2$, E, Ring A, $L^1$, $L^3$, $L^4$, and z1 are as described herein.

In embodiments, the compound has the formula:

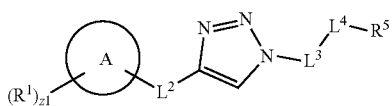
(II)

and $R^1$, $R^5$, Ring A, $L^2$, $L^3$, $L^4$, and z1 are as described herein.

In embodiments, the compound has the formula:

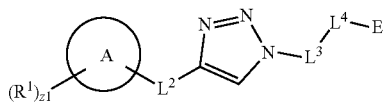

and $R^1$, E, Ring A, $L^2$, $L^3$, $L^4$, and z1 are as described herein.

In embodiments, Ring A is aryl (e.g. $C_6$-$C_{12}$ aryl, $C_6$-$C_{10}$ aryl, or $C_6$ aryl). In embodiments, Ring A is $C_6$-$C_{12}$ aryl. In embodiments, Ring A is $C_6$-$C_{10}$ aryl. In embodiments, Ring A is $C_6$ aryl. It will be understood when z1 is 0, Ring A is unsubstituted (e.g., unsubstituted aryl or unsubstituted heteroaryl) in addition to the bond to $L^2$. It will be understood when z1 is greater than 0 (e.g., 1, 2, 3, or 4), Ring A is substituted with one or more $R^1$ substituents (e.g., $R^1$-substituted aryl or $R^1$-substituted heteroaryl) in addition to the bond to $L^2$.

In embodiments, Ring A is heteroaryl (e.g. 5 to 12 membered heteroaryl, 5 to 10 membered heteroaryl, 5 to 9 membered heteroaryl, or 5 to 6 membered heteroaryl). In embodiments, Ring A is 5 to 12 membered heteroaryl. In embodiments, Ring A is 5 to 10 membered heteroaryl. In embodiments, Ring A is 5 to 9 membered heteroaryl. In embodiments, Ring A is 5 to 6 membered heteroaryl.

In embodiments, Ring A is naphthyl. In embodiments, Ring A is biphenyl. In embodiments, Ring A is phenyl. In embodiments, Ring A is pyridyl. In embodiments, Ring A is pyrazolyl. In embodiments, Ring A is imidazolyl. In embodiments, Ring A is oxazolyl. In embodiments, Ring A is isoxazolyl. In embodiments, Ring A is thiazolyl. In embodiments, Ring A is furanyl. In embodiments, Ring A is pyrrolyl. In embodiments, Ring A is thienyl.

In embodiments, Ring A is indolinyl. In embodiments, Ring A is indazolyl. In embodiments, Ring A is benzimidazolyl. In embodiments, Ring A is benzoxazolyl. In embodiments, Ring A is azaindolyl. In embodiments, Ring A is purinyl. In embodiments, Ring A is indolyl. In embodiments, Ring A is pyrazinyl. In embodiments, Ring A is pyrrolyl. In embodiments, Ring A is imidazolyl. In embodiments, Ring A is pyrazolyl. In embodiments, Ring A is triazolyl. In embodiments, Ring A is tetrazolyl. In embodiments, Ring A is benzofuranyl. In embodiments, Ring A is indolyl. In embodiments, Ring A is benzothienyl.

In embodiments, -(Ring A)-$(R^1)_{z1}$ has the formula:

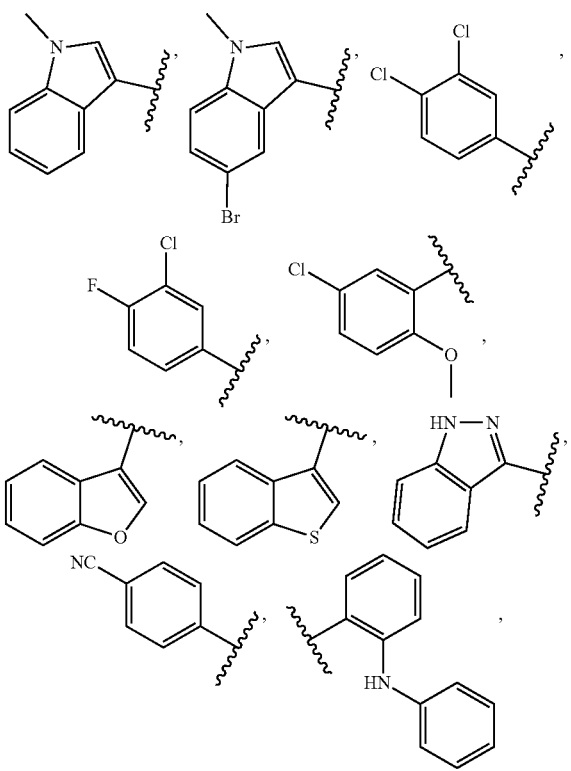

-continued
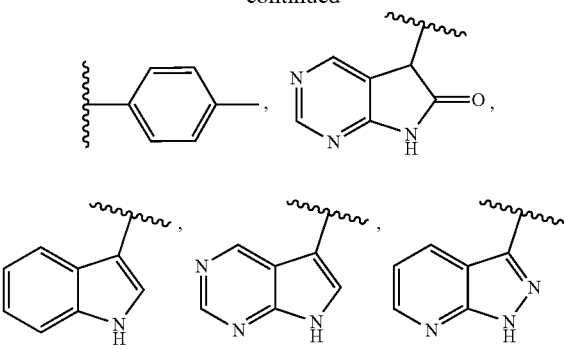
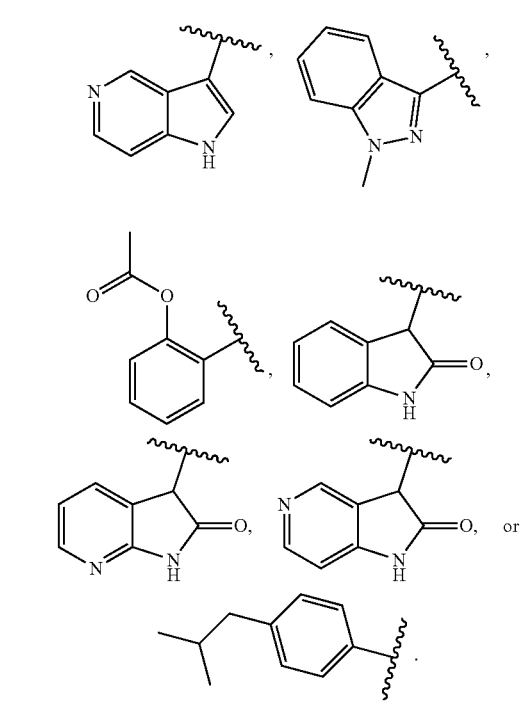
In embodiments, -(Ring A)-(R$^1$)$_{z1}$ has the formula:
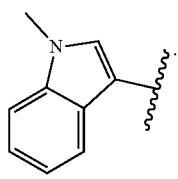 [SMILES: *c1cn(C)c2ccccc12]
In embodiments, -(Ring A)-(R$^1$)$_{z1}$ has the formula:
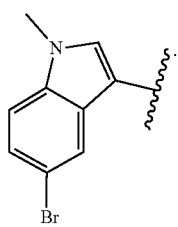 [SMILES: *c1cn(C)c2ccc(Br)cc12]
In embodiments, -(Ring A)-(R$^1$)$_{z1}$ has the formula:
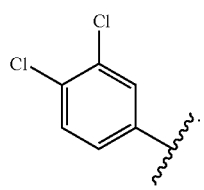 [SMILES: *c1ccc(Cl)c(Cl)c1]
In embodiments, -(Ring A)-(R$^1$)$_{z1}$ has the formula:
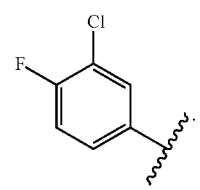
In embodiments, -(Ring A)-(R$^1$)$_{z1}$ has the formula:
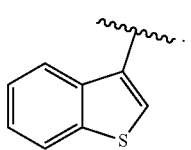 [SMILES: *c1csc2ccccc12]
In embodiments, -(Ring A)-(R$^1$)$_{z1}$ has the formula:
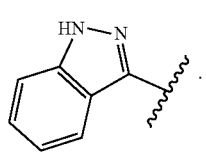 [SMILES: *c1n[nH]c2ccccc12]
In embodiments, -(Ring A)-(R$^1$)$_{z1}$ has the formula:

In embodiments, -(Ring A)-(R$^1$)$_{z1}$ has the formula:

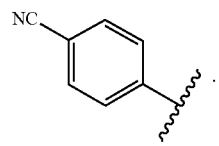 [SMILES: *c1ccc(C#N)cc1]

In embodiments, -(Ring A)-(R$^1$)$_{z1}$ has the formula:

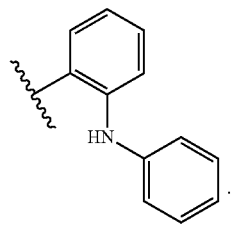 [SMILES: *c1ccccc1Nc1ccccc1]

In embodiments, -(Ring A)-(R$^1$)$_{z1}$ has the formula:

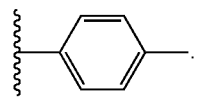

In embodiments, -(Ring A)-(R$^1$)$_{z1}$ has the formula:

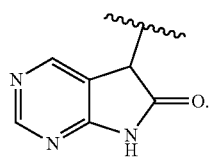

In embodiments, -(Ring A)-(R$^1$)$_{z1}$ has the formula:

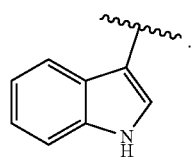 [SMILES: *c1c[nH]c2ccccc12]

In embodiments, -(Ring A)-(R$^1$)$_{z1}$ has the formula:

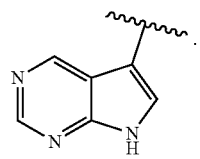 [SMILES: *c1c[nH]c2ncncc12]

In embodiments, -(Ring A)-(R$^1$)$_{z1}$ has the formula:

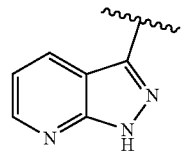

In embodiments, -(Ring A)-(R$^1$)$_{z1}$ has the formula:

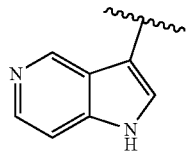

In embodiments, -(Ring A)-(R$^1$)$_{z1}$ has the formula:

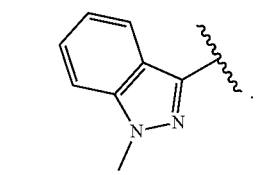 [SMILES: *c1nn(C)c2ccccc12]

In embodiments, -(Ring A)-(R$^1$)$_{z1}$ has the formula:

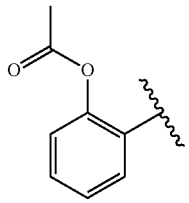

In embodiments, -(Ring A)-(R$^1$)$_{z1}$ has the formula:

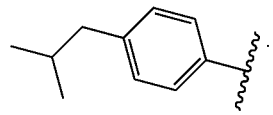 [SMILES: *c1ccc(CC(C)C)cc1]

In embodiments, -(Ring A)-(R$^1$)$_{z1}$ has the formula:

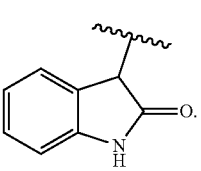 [SMILES: *C1C(=O)Nc2ccccc21]

In embodiments, -(Ring A)-$(R^1)_{z1}$ has the formula:

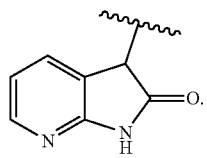 [SMILES: *C1C(=O)Nc2ncccc21]

In embodiments, -(Ring A)-$(R^1)_{z1}$ has the formula:

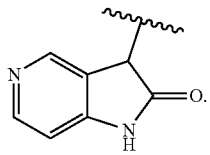 [SMILES: *C1C(=O)Nc2ccncc21]

In embodiments, $R^1$ is independently halogen, $-CX^1_3$, $-CHX^1_2$, $-CH_2X^1$, $-CN$, $-SO_{n1}R^{1D}$, $-SO_{v1}NR^{1A}R^{1B}$, $-NHNR^{1A}R^{1B}$, $-ONR^{1A}R^{1B}$, $-NHC=(O)NHNR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-OCX^1_3$, $-OCHX^1_2$, $-OCH_2X^1$ substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered); two adjacent $R^1$ substituents may optionally be joined to form a substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, $R^1$ is independently halogen, $-CX^1_3$, $-CHX^1_2$, $-CH_2X^1$, $-CN$, $-SR^{1D}$, $-SO_2R^{1D}$, $-NHC(O)NR^{1A}R^{1B}$, $-N(O)_2$, $-NR^{1A}R^{1B}$, $-C(O)R^{1C}$, $-C(O)OR^{1C}$, $-C(O)NR^{1A}R^{1B}$, $-OR^{1D}$, $-OCX^1_3$, $-OCHX^1_2$, $-OCH_2X^1$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, $R^1$ is independently halogen, $-CX^1_3$, $-CHX^1_2$, $-CH_2X^1$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^1_3$, $-OCHX^1_2$, $OCH_2X^1$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, $R^1$ is independently halogen, $-CX^1_3$, $-CHX^1_2$, $-CH_2X^1$, $-OH$, $-CN$, $-SO_2CH_3$, $-NO_2$, $-N(CH_3)_2$, $-NH_2$, $-SH$, $-COOH$, $-OCX^1_3$, $-OCHX^1_2$, $-CH_3$, $-CH_2CH_3$, $-OCH_3$, $-OCH_2CH_3$, $-SCH_3$, or $-SCH_2CH_3$.

In embodiments, $R^1$ is $-SO_{n1}R^{1D}$. In embodiments, $R^1$ is $-SO_{v1}NR^{1A}R^{1B}$. In embodiments, $R^1$ is $-NHNR^{1A}R^{1B}$. In embodiments, $R^1$ is $-ONR^{1A}R^{1B}$. In embodiments, $R^1$ is $-NHC=(O)NHNR^{1A}R^{1B}$. In embodiments, $R^1$ is $-NHC(O)NR^{1A}R^{1B}$. In embodiments, $R^1$ is $-N(O)_{m1}$. In embodiments, $R^1$ is $-NR^{1A}R^{1B}$. In embodiments, $R^1$ is $-C(O)R^{1C}$.

In embodiments, $R^1$ is —C(O)—$OR^{1C}$. In embodiments, $R^1$ is —C(O)$NR^{1A}R^{1B}$. In embodiments, $R^1$ is —$OR^{1D}$. In embodiments, $R^1$ is —$NR^{1A}SO_2R^{1D}$. In embodiments, $R^1$ is —$NR^{1A}C(O)R^{1C}$. In embodiments, $R^1$ is —$NR^{1A}C(O)OR^{1C}$. In embodiments, $R^1$ is —$NR^{1A}OR^{1C}$. In embodiments, $R^1$ is substituted or unsubstituted $C_1$-$C_6$ alkyl. In embodiments, $R^1$ is substituted or unsubstituted 2 to 6 membered heteroalkyl. In embodiments, $R^1$ is substituted or unsubstituted $C_3$-$C_8$ cycloalkyl. In embodiments, $R^1$ is substituted or unsubstituted 3 to 6 membered heterocycloalkyl. In embodiments, $R^1$ is substituted or unsubstituted phenyl. In embodiments, $R^1$ is substituted or unsubstituted 5 to 6 membered heteroaryl. In embodiments, $R^1$ is independently halogen. In embodiments, $R^1$ is independently —$CX^{13}$. In embodiments, $R^1$ is independently —$CHX^{12}$. In embodiments, $R^1$ is independently —$CH_2X$. In embodiments, $R^1$ is independently —OH. In embodiments, $R^1$ is independently —SH. In embodiments, $R^1$ is independently —COOH. In embodiments, $R^1$ is independently —$OCX^1_3$. In embodiments, $R^1$ is independently —$OCHX^{12}$. In embodiments, $R^1$ is independently —$OCH_2X^1$. In embodiments, $R^1$ is independently —$CH_3$. In embodiments, $R^1$ is independently —$CH_2CH_3$. In embodiments, $R^1$ is independently —$OCH_3$. In embodiments, $R^1$ is independently —$OCH_2CH_3$. In embodiments, $R^1$ is independently —$SCH_3$. In embodiments, $R^1$ is independently —$SCH_2CH_3$. In embodiments, $R^1$ is independently —CN. In embodiments, $R^1$ is independently —$SO_2CH_3$. In embodiments, $R^1$ is independently —$NO_2$. In embodiments, $R^1$ is independently —$N(CH_3)_2$. In embodiments, $R^1$ is independently —$NH(CH_3)$. In embodiments, $R^1$ is independently —NH(unsubstituted phenyl). In embodiments, $R^1$ is independently —NH(unsubstituted 5 to 6 membered heteroaryl). In embodiments, $R^1$ is independently —$NH_2$. In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted n-propyl. In embodiments, $R^1$ is independently unsubstituted isopropyl. In embodiments, $R^1$ is independently unsubstituted butyl. In embodiments, $R^1$ is independently unsubstituted n-butyl. In embodiments, $R^1$ is independently unsubstituted isobutyl. In embodiments, $R^1$ is independently unsubstituted tert-butyl. In embodiments, $R^1$ is independently unsubstituted pentyl. In embodiments, $R^1$ is independently unsubstituted hexyl. In embodiments, $R^1$ is independently unsubstituted heptyl. In embodiments, $R^1$ is independently unsubstituted octyl. In embodiments, $R^1$ is independently —F. In embodiments, $R^1$ is independently —Cl. In embodiments, $R^1$ is independently —Br. In embodiments, $R^1$ is independently —I. In embodiments, $R^1$ is independently unsubstituted methoxy. In embodiments, $R^1$ is independently unsubstituted ethoxy. In embodiments, $R^1$ is independently —$CF_3$. In embodiments, $R^1$ is independently —$CCl_3$. In embodiments, $R^1$ is an unsubstituted phenyl. In embodiments, $R^1$ is an unsubstituted pyridyl. In embodiments, $R^1$ is independently halogen. In embodiments, $R^1$ is independently —$CONH_2$. In embodiments, $R^1$ is independently —$SO_3H$. In embodiments, $R^1$ is independently —$SO_4H$. In embodiments, $R^1$ is independently —$SO_2NH_2$. In embodiments, $R^1$ is independently —$NHNH_2$. In embodiments, $R^1$ is independently —$ONH_2$. In embodiments, $R^1$ is independently —NHC(O)$NHNH_2$. In embodiments, $R^1$ is independently —NHC(O)$NH_2$. In embodiments, $R^1$ is independently —$NHSO_2H$. In embodiments, $R^1$ is independently —NHC(O)H. In embodiments, $R^1$ is independently —NHC(O)OH. In embodiments, $R^1$ is independently —NHOH. In embodiments, $R^1$ is independently —$OCOCH_3$. In embodiments, $R^1$ is independently —$NR^{1A}R^{1B}$. In embodiments, $R^1$ is independently —$NHR^{1B}$, wherein $R^{1B}$ is a substituted or unsubstituted aryl or substituted or unsubstituted heteroaryl. In embodiments, $R^1$ is independently —$NHR^{1B}$, wherein $R^{1B}$ is an unsubstituted aryl or unsubstituted heteroaryl. In embodiments, $R^1$ is independently

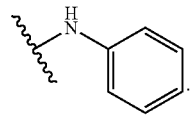 [SMILES: *Nc1ccccc1]

In embodiments, $R^1$ is independently substituted (e.g., substituted with a substituent group, a size-limited substituent group, or lower substituent group) or unsubstituted alkyl. In embodiments, $R^1$ is independently substituted (e.g., substituted with a substituent group, a size-limited substituent group, or lower substituent group) alkyl. In embodiments, $R^1$ is independently unsubstituted alkyl. In embodiments, $R^1$ is independently substituted or unsubstituted alkyl (e.g., $C_1$-$C_8$, $C_1$-$C_6$, $C_1$-$C_4$, or $C_1$-$C_2$). In embodiments, $R^1$ is independently substituted alkyl (e.g., $C_1$-$C_8$, $C_1$-$C_6$, $C_1$-$C_4$, or $C_1$-$C_2$). In embodiments, $R^1$ is independently unsubstituted alkyl (e.g., $C_1$-$C_8$, $C_1$-$C_6$, $C_1$-$C_4$, or $C_1$-$C_2$).

In embodiments, $R^1$ is independently substituted (e.g., substituted with a substituent group, a size-limited substituent group, or lower substituent group) or unsubstituted heteroalkyl. In embodiments, $R^1$ is independently substituted (e.g., substituted with a substituent group, a size-limited substituent group, or lower substituent group) heteroalkyl. In embodiments, $R^1$ is independently unsubstituted heteroalkyl. In embodiments, $R^1$ is independently substituted or unsubstituted heteroalkyl (e.g., 2 to 8 membered, 2 to 6 membered, 4 to 6 membered, 2 to 3 membered, or 4 to 5 membered). In embodiments, $R^1$ is independently substituted heteroalkyl (e.g., 2 to 8 membered, 2 to 6 membered, 4 to 6 membered, 2 to 3 membered, or 4 to 5 membered). In embodiments, $R^1$ is independently an unsubstituted heteroalkyl (e.g., 2 to 8 membered, 2 to 6 membered, 4 to 6 membered, 2 to 3 membered, or 4 to 5 membered).

In embodiments, $R^1$ is independently substituted (e.g., substituted with a substituent group, a size-limited substituent group, or lower substituent group) or unsubstituted cycloalkyl. In embodiments, $R^1$ is independently substituted (e.g., substituted with a substituent group, a size-limited substituent group, or lower substituent group) cycloalkyl. In embodiments, $R^1$ is independently an unsubstituted cycloalkyl. In embodiments, $R^1$ is independently substituted or unsubstituted cycloalkyl (e.g., $C_3$-$C_8$, $C_3$-$C_6$, $C_4$-$C_6$, or $C_5$-$C_6$). In embodiments, $R^1$ is independently substituted cycloalkyl (e.g., $C_3$-$C_8$, $C_3$-$C_6$, $C_4$-$C_6$, or $C_5$-$C_6$). In embodiments, $R^1$ is independently unsubstituted cycloalkyl (e.g., $C_3$-$C_8$, $C_3$-$C_6$, $C_4$-$C_6$, or $C_5$-$C_6$).

In embodiments, $R^1$ is independently substituted (e.g., substituted with a substituent group, a size-limited substituent group, or lower substituent group) or unsubstituted heterocycloalkyl. In embodiments, $R^1$ is independently substituted (e.g., substituted with a substituent group, a size-limited substituent group, or lower substituent group) heterocycloalkyl. In embodiments, $R^1$ is independently an unsubstituted heterocycloalkyl. In embodiments, $R^1$ is independently substituted or unsubstituted heterocycloalkyl (e.g., 3 to 8 membered, 3 to 6 membered, 4 to 6 membered, 4 to 5 membered, or 5 to 6 membered). In embodiments, $R^1$ is independently substituted heterocycloalkyl (e.g., 3 to 8 membered, 3 to 6 membered, 4 to 6 membered, 4 to 5 membered, or 5 to 6 membered). In embodiments, $R^1$ an unsubstituted heterocycloalkyl (e.g., 3 to 8 membered, 3 to 6 membered, 4 to 6 membered, 4 to 5 membered, or 5 to 6 membered).

In embodiments, $R^1$ is independently substituted (e.g., substituted with a substituent group, a size-limited substituent group, or lower substituent group) or unsubstituted aryl. In embodiments, $R^1$ is independently substituted (e.g., substituted with a substituent group, a size-limited substituent group, or lower substituent group) aryl. In embodiments, $R^1$ is independently an unsubstituted aryl. In embodiments, $R^1$ is independently substituted or unsubstituted aryl (e.g., $C_6$-$C_{10}$ or phenyl). In embodiments, $R^1$ is independently substituted aryl (e.g., $C_6$-$C_{10}$ or phenyl). In embodiments, $R^1$ is independently an unsubstituted aryl (e.g., $C_6$-$C_{10}$ or phenyl).

In embodiments, $R^1$ is independently substituted (e.g., substituted with a substituent group, a size-limited substituent group, or lower substituent group) or unsubstituted heteroaryl. In embodiments, $R^1$ is independently substituted (e.g., substituted with a substituent group, a size-limited substituent group, or lower substituent group) heteroaryl. In embodiments, $R^1$ is independently an unsubstituted heteroaryl. In embodiments, $R^1$ is independently substituted or unsubstituted heteroaryl (e.g., 5 to 10 membered, 5 to 9 membered, or 5 to 6 membered). In embodiments, $R^1$ is independently substituted heteroaryl (e.g., 5 to 10 membered, 5 to 9 membered, or 5 to 6 membered). In embodiments, $R^1$ is independently an unsubstituted heteroaryl (e.g., 5 to 10 membered, 5 to 9 membered, or 5 to 6 membered).

In embodiments, $R^1$ is independently halogen, —$CX^1_3$, —$CHX^1_2$, —$CH_2X^1$, —CN, —$SR^{1D}$, —$SO_2RD$, —$NR^{1A}R^{1B}$, —$OR^{1D}$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^1$ is independently halogen, —$CX^1_3$, —$CHX^1_2$, —$CH_2X^1$, —CN, —$SO_2CH_3$, —NHPh (Ph=phenyl), —$CH_3$, or —$CH_2CH_3$. In embodiments, $R^1$ is independently halogen, —$CX^1_3$, —$CHX^1_2$, —$CH_2X^1$, —CN, —$SR^{1D}$, —$N(O)_2$, —$SO_2RD$, —$NR^{1A}R^{1B}$, —$OR^{1D}$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^1$ is independently halogen, —$CX^1_3$, —$CHX^1_2$, —$CH_2X^1$, —$OCX^1_3$, —$OCHX^1_2$, —$OCH_2X^1$, —CN, —$N(O)_2$, —$SO_2CH_3$, —$N(CH_3)_2$, —$OCH_3$, —$OCH_2CH_3$, —$CH_3$, or —$CH_2CH_3$.

In embodiments, two adjacent $R^1$ substituents may optionally be joined to form a substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, two adjacent $R^1$ substituents may optionally be joined to form a substituted (e.g., substituted with a substituent group, a size-limited substituent group, or lower substituent group) or unsubstituted cycloalkyl. In embodiments, two adjacent $R^1$ substituents may optionally be joined to form a substituted (e.g., substituted with a substituent group, a size-limited substituent group, or lower substituent group) cycloalkyl. In embodiments, two adjacent $R^1$ substituents may optionally be joined to form an unsubstituted cycloalkyl. In embodiments, two adjacent $R^1$ substituents may optionally be joined to form a substituted or unsubstituted cycloalkyl (e.g., $C_3$-$C_8$, $C_3$-$C_6$, $C_4$-$C_6$, or $C_5$-$C_6$). In embodiments, two adjacent $R^1$ substituents may optionally be joined to form a substituted cycloalkyl (e.g., $C_3$-$C_8$, $C_3$-$C_6$, $C_4$-$C_6$, or $C_5$-$C_6$). In embodiments, two adjacent $R^1$ substituents may optionally be joined to form an unsubstituted cycloalkyl (e.g., $C_3$-$C_8$, $C_3$-$C_6$, $C_4$-$C_6$, or $C_5$-$C_6$).

In embodiments, two adjacent $R^1$ substituents may optionally be joined to form a substituted (e.g., substituted with a substituent group, a size-limited substituent group, or lower substituent group) or unsubstituted heterocycloalkyl. In embodiments, two adjacent $R^1$ substituents may optionally be joined to form a substituted (e.g., substituted with a substituent group, a size-limited substituent group, or lower substituent group) heterocycloalkyl. In embodiments, two adjacent $R^1$ substituents may optionally be joined to form an unsubstituted heterocycloalkyl. In embodiments, two adjacent $R^1$ substituents may optionally be joined to form a substituted or unsubstituted heterocycloalkyl (e.g., 3 to 8 membered, 3 to 6 membered, 4 to 6 membered, 4 to 5 membered, or 5 to 6 membered). In embodiments, two adjacent $R^1$ substituents may optionally be joined to form a substituted heterocycloalkyl (e.g., 3 to 8 membered, 3 to 6 membered, 4 to 6 membered, 4 to 5 membered, or 5 to 6 membered). In embodiments, two adjacent $R^1$ substituents may optionally be joined to form an unsubstituted heterocycloalkyl (e.g., 3 to 8 membered, 3 to 6 membered, 4 to 6 membered, 4 to 5 membered, or 5 to 6 membered).

In embodiments, two adjacent $R^1$ substituents may optionally be joined to form a substituted (e.g., substituted with a substituent group, a size-limited substituent group, or lower substituent group) or unsubstituted aryl. In embodiments, two adjacent $R^1$ substituents may optionally be joined to form a substituted (e.g., substituted with a substituent group, a size-limited substituent group, or lower substituent group) aryl. In embodiments, two adjacent $R^1$ substituents may optionally be joined to form an unsubstituted aryl. In embodiments, two adjacent $R^1$ substituents may optionally be joined to form a substituted or unsubstituted aryl (e.g., $C_6$-$C_{10}$ or phenyl). In embodiments, two adjacent $R^1$ substituents may optionally be joined to form a substituted aryl (e.g., $C_6$-$C_{10}$ or phenyl). In embodiments, two adjacent $R^1$ substituents may optionally be joined to form an unsubstituted aryl (e.g., $C_6$-$C_{10}$ or phenyl).

In embodiments, two adjacent $R^1$ substituents may optionally be joined to form a substituted (e.g., substituted with a substituent group, a size-limited substituent group, or lower substituent group) or unsubstituted heteroaryl. In embodiments, two adjacent $R^1$ substituents may optionally be joined to form a substituted (e.g., substituted with a substituent group, a size-limited substituent group, or lower substituent group) heteroaryl. In embodiments, two adjacent $R^1$ substituents may optionally be joined to form an unsubstituted heteroaryl. In embodiments, two adjacent $R^1$ substituents may optionally be joined to form a substituted or unsubstituted heteroaryl (e.g., 5 to 10 membered, 5 to 9 membered, or 5 to 6 membered). In embodiments, two adjacent $R^1$ substituents may optionally be joined to form a substituted heteroaryl (e.g., 5 to 10 membered, 5 to 9 membered, or 5 to 6 membered). In embodiments, two adjacent $R^1$ substituents may optionally be joined to form an unsubstituted heteroaryl (e.g., 5 to 10 membered, 5 to 9 membered, or 5 to 6 membered).

In embodiments, each $R^{1A}$, $R^{1B}$, $R^{1C}$, and $R^{1D}$ is independently hydrogen, $-CX_3$, $-CN$, $-COOH$, $-CONH_2$, $-CHX_2$, $-CH_2X$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, each $R^{1A}$, $R^{1B}$, $R^{1C}$, and $R^{1D}$ is independently hydrogen. In embodiments, each $R^{1A}$, $R^{1B}$, $R^{1C}$, and $R^{1D}$ is independently $-CX_3$. In embodiments, each $R^{1A}$, $R^{1B}$, $R^{1C}$, and $R^{1D}$ is independently $-CN$. In embodiments, each $R^{1A}$, $R^{1B}$, $R^{1C}$, and $R^{1D}$ is independently $-COOH$. In embodiments, each $R^{1A}$, $R^{1B}$, $R^{1C}$, and $R^{1D}$ is independently $-CONH_2$. In embodiments, each $R^{1A}$, $R^{1B}$, $R^{1C}$, and $R^{1D}$ is independently $-CHX_2$. In embodiments, each $R^{1A}$, $R^{1B}$, $R^{1C}$, and $R^{1D}$ is independently $-CH_2X$. In embodiments, each $R^{1A}$, $R^{1B}$, $R^{1C}$, and $R^{1D}$ is independently $-CH_3$. In embodiments, each $R^{1A}$, $R^{1B}$, $R^{1C}$, and $R^{1D}$ is independently $-CH_2CH_3$.

In embodiments, each $R^{1A}$, $R^{1B}$, $R^{1C}$, and $R^{1D}$ is independently hydrogen, $-CX_3$, $-CN$, $-COOH$, $-CONH_2$, $-CHX_2$, $-CH_2X$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^{1A}$ and $R^{1B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{1A}$ and $R^{1B}$ substituents bonded to the same nitrogen atom may optionally be joined to independently form an unsubstituted heterocycloalkyl (e.g., 3 to 10 membered, 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered). In embodiments, X is independently $-F$. In embodiments, X is independently $-Cl$. In embodiments, X is independently $-Br$. In embodiments, X is independently $-I$.

In embodiments, z1 is 0. In embodiments, z1 is 1. In embodiments, z1 is 2. In embodiments, z1 is 3. In embodiments, z1 is 4. In embodiments, $X^1$ is independently $-F$. In embodiments, $X^1$ is independently $-Cl$. In embodiments, $X^1$ is independently $-Br$. In embodiments, $X^1$ is independently $-I$. In embodiments, n1 is independently 0. In embodiments, n1 is independently 1. In embodiments, n1 is independently 2. In embodiments, n1 is independently 3. In embodiments, n1 is independently 4. In embodiments, m1 is independently 1. In embodiments, m1 is independently 2. In embodiments, v1 is independently 1. In embodiments, v1 is independently 2.

In embodiments, the compound has the formula:

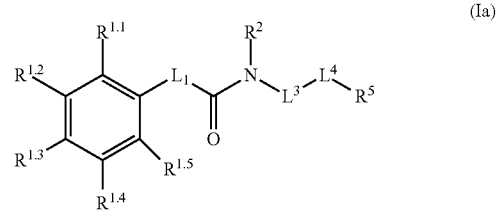

and $R^2$, $R^5$, $L^1$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

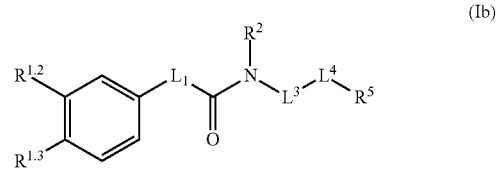

and $R^{1.2}$, $R^{1.3}$, $R^2$, $R^5$, $L^1$, $L^3$, and $L^4$ are as described herein.

In embodiments, the compound has the formula:

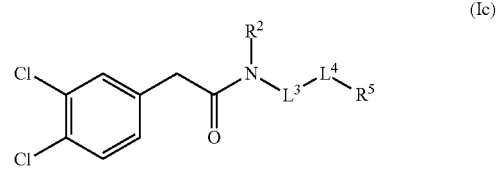

and $R^2$, $R^5$, $L^3$, and $L^4$ are as described herein.

In embodiments, the compound has the formula:

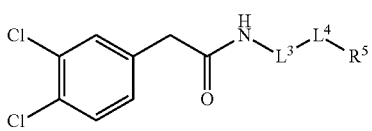

(Id)

and $R^5$, $L^3$, and $L^4$ are as described herein.

In embodiments, the compound has the formula:

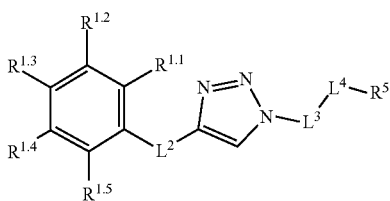

(IIa)

and $R^5$, $L^2$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

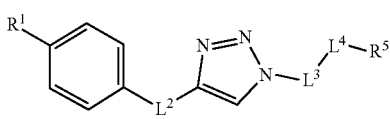

(IIb)

and $R^1$, $R^5$, $L^2$, $L^3$, and $L^4$ are as described herein.

In embodiments, the compound has the formula:

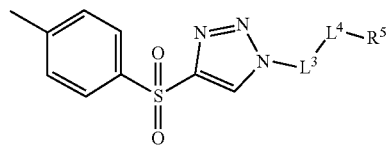

(IIc)

and $R^5$, $L^3$, and $L^4$ are as described herein.

In embodiments, the compound has the formula:

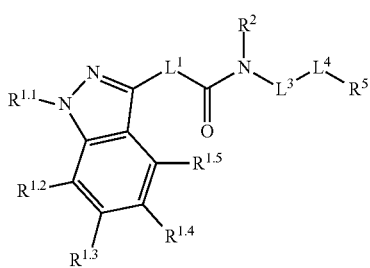

(Ib)

and $R^2$, $R^5$, $L^1$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

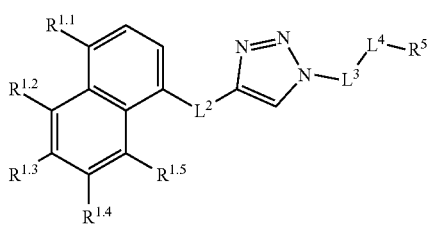

(IIb)

and $R^5$, $L^2$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

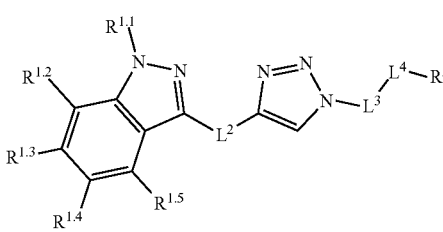

(IIc)

and $R^5$, Ring A, $L^2$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

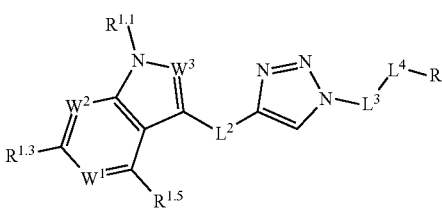

(IId)

and $R^5$, Ring A, $L^2$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent. $W^1$ is —N═ or —C($R^{1.4}$)═. In embodiments, $W^1$ is —N═. In embodiments, $W^1$ is —C($R^{1.4}$)═. In embodiments, $W^1$ is —CH═. $W^2$ is —N═ or —C($R^{1.2}$)═. In embodiments, $W^2$ is —N═. In embodiments, $W^2$ is —C($R^{1.2}$)═. In embodiments, $W^2$ is —CH═. $W^3$ is —N═ or —CH═. In embodiments, $W^3$ is —N═. In embodiments, $W^3$ is —CH═.

In embodiments, the compound has the formula:

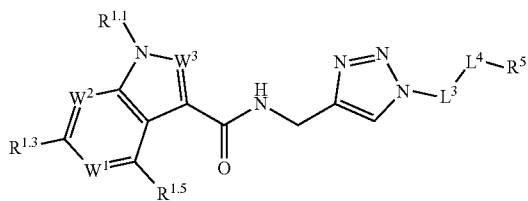

(IIda)

and $W^1$, $W^2$, $W^3$, $R^5$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

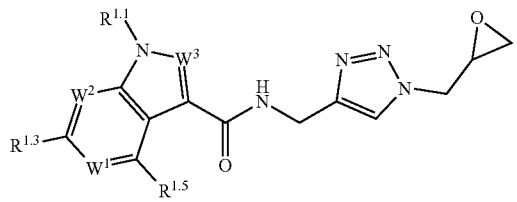

(IIda)

and $W^1$, $W^2$, and $W^3$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

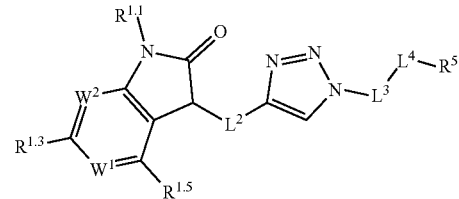

(IIe)

and $R^5$, Ring A, $L^2$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

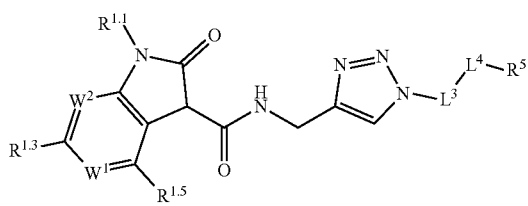

(IIda)

and $W^1$, $W^2$, $R^5$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

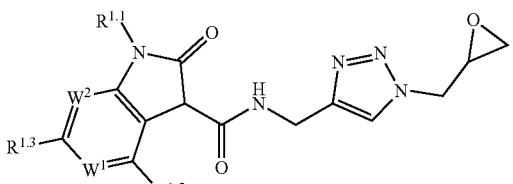

(IIda)

and $W^1$ and $W^2$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

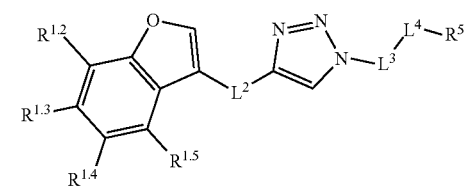

(IIf)

and $R^5$, Ring A, $L^2$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

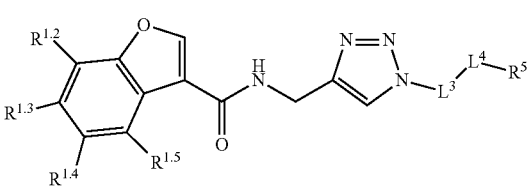

(IIda)

and $R^5$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

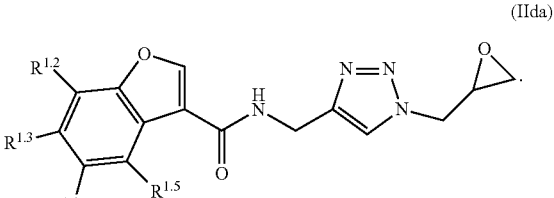

(IIda)

$R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

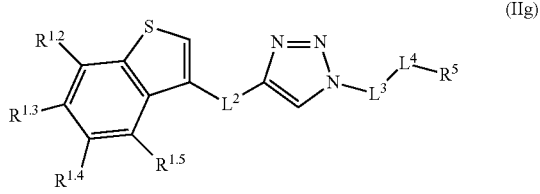
(IIg)

and $R^5$, Ring A, $L^2$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

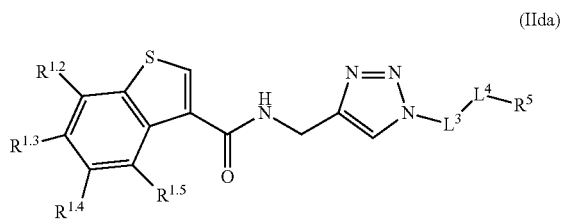
(IIda)

and $R^5$, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

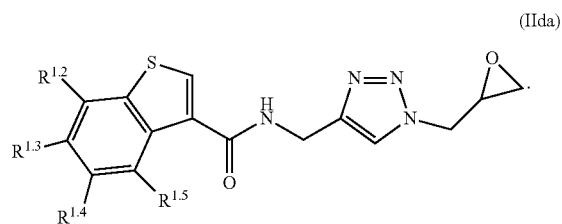
(IIda)

$R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

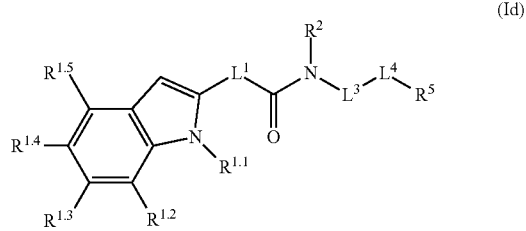
(Id)

and $R^2$, $R^5$, L, $L^3$, and $L^4$ are as described herein. $R^{1.1}$, $R^{1.2}$, $R^{1.3}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

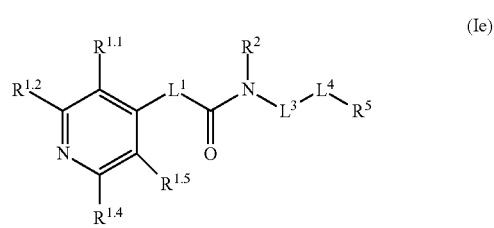
(Ie)

and $R^2$, $R^5$, $L^1$, $L^3$, and $L^4$ are as described herein. $R^{1.1}$, $R^{1.2}$, $R^{1.4}$, and $R^{1.5}$ are each independently $R^1$ at a fixed position (e.g., non-floating as shown in the formula described herein) and may independently be any $R^1$ substituent.

In embodiments, the compound has the formula:

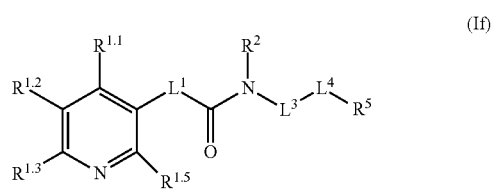
(If)

and $R^2$, $R^5$, $L^1$, $L^3$, and $L^4$ are as described herein. $R^{1.1}$, $R^{1.2}$, $R^{1.3}$, and $R^{1.5}$ are each independently $R^1$ at a fixed position (e.g., non-floating as shown in the formula described herein) and may independently be any $R^1$ substituent.

In embodiments, the compound has the formula:

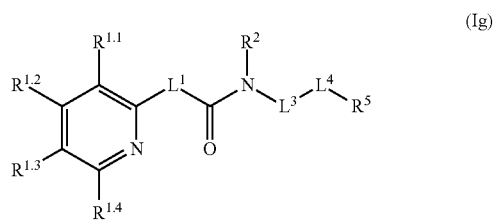
(Ig)

and $R^2$, $R^5$, $L^1$, $L^3$, and $L^4$ are as described herein. $R^{1.1}$, $R^{1.2}$, $R^{1.3}$, and $R^{1.4}$ are each independently $R^1$ at a fixed position (e.g., non-floating as shown in the formula described herein) and may independently be any $R^1$ substituent.

$R^{1.1}$ is independently hydrogen, halogen, $-CX^{1.1}{}_3$, $-CHX^{1.1}{}_2$, $-CH_2X^{1.1}$, $-CN$, $-SO_{m1}R^{1D}$, $-SO_{v1}NR^{1A}R^{1B}$, $-NHNR^{1A}R^{1B}$, $-ONR^{1A}R^{1B}$, $-NHC=(O)NHNR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-OCX^{1.1}{}_3$, $-OCHX^{1.1}{}_2$, $-OCH_2X^{1.1}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{1.1}$ is independently hydrogen.

In embodiments, $R^{1.1}$ is independently halogen, —$CX^{1.1}_3$, —$CHX^{1.1}_2$, —$CH_2X^{1.1}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{1.1}_3$, —$OCHX^{1.1}_2$, $OCH_2X^{1.1}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, $R^1$ is independently halogen, —$CX^{1.1}_3$, —$CHX^{1.1}_2$, —$CH_2X^{1.1}$, —OH, —CN, —$SO_2CH_3$, —$NO_2$, —$N(CH_3)_2$, —$NH_2$, —SH, —CO OH, —$OCX^{1.1}_3$, —$OCHX^{1.1}_2$, —$CH_3$, —$CH_2CH_3$, —$OCH_3$, —$OCH_2CH_3$, —$SCH_3$, or —$SCH_2CH_3$.

In embodiments, $R^1$ is substituted or unsubstituted $C_1$-$C_6$ alkyl. In embodiments, $R^1$ is substituted or unsubstituted 2 to 6 membered heteroalkyl. In embodiments, $R^1$ is substituted or unsubstituted $C_3$-$C_8$ cycloalkyl. In embodiments, $R^{1.1}$ is substituted or unsubstituted 3 to 6 membered heterocycloalkyl. In embodiments, $R^{1.1}$ is substituted or unsubstituted phenyl. In embodiments, $R^{1.1}$ is substituted or unsubstituted 5 to 6 membered heteroaryl. In embodiments, $R^{1.1}$ is independently halogen. In embodiments, $R^{1.1}$ is independently —$CX^{1.1}_3$. In embodiments, $R^{1.1}$ is independently —$CHX^{1.1}_2$. In embodiments, $R^{1.1}$ is independently —$CH_2X^{1.1}$. In embodiments, $R^{1.1}$ is independently —OH. In embodiments, $R^{1.1}$ is independently —SH. In embodiments, $R^{1.1}$ is independently —COOH. In embodiments, $R^{1.1}$ is independently —$OCX^{1.1}_3$. In embodiments, $R^{1.1}$ is independently —$OCHX^{1.1}_2$. In embodiments, $R^{1.1}$ is independently —$OCH_2X^{1.1}$. In embodiments, $R^{1.1}$ is independently —$CH_3$. In embodiments, $R^{1.1}$ is independently —$CH_2CH_3$. In embodiments, $R^{1.1}$ is independently —$OCH_3$. In embodiments, $R^{1.1}$ is independently —$OCH_2CH_3$. In embodiments, $R^{1.1}$ is independently —$SCH_3$. In embodiments, $R^{1.1}$ is independently —$SCH_2CH_3$. In embodiments, $R^{1.1}$ is independently —CN. In embodiments, $R^{1.1}$ is independently —$SO_2CH_3$. In embodiments, $R^{1.1}$ is independently —$NO_2$. In embodiments, $R^{1.1}$ is independently —$N(CH_3)_2$. In embodiments, $R^{1.1}$ is independently —$NH(CH_3)$. In embodiments, $R^{1.1}$ is independently —NH(unsubstituted phenyl). In embodiments, $R^{1.1}$ is independently —NH(unsubstituted 5 to 6 membered heteroaryl). In embodiments, $R^{1.1}$ is independently —$NH_2$. In embodiments, $R^{1.1}$ is independently unsubstituted methyl. In embodiments, $R^{1.1}$ is independently unsubstituted ethyl. In embodiments, $R^{1.1}$ is independently unsubstituted propyl. In embodiments, $R^{1.1}$ is independently unsubstituted n-propyl. In embodiments, $R^{1.1}$ is independently unsubstituted isopropyl. In embodiments, $R^{1.1}$ is independently unsubstituted butyl. In embodiments, $R^{1.1}$ is independently unsubstituted n-butyl. In embodiments, $R^{1.1}$ is independently unsubstituted isobutyl. In embodiments, $R^{1.1}$ is independently unsubstituted tert-butyl. In embodiments, $R^{1.1}$ is independently unsubstituted pentyl. In embodiments, $R^{1.1}$ is independently unsubstituted hexyl. In embodiments, $R^{1.1}$ is independently unsubstituted heptyl. In embodiments, $R^{1.1}$ is independently unsubstituted octyl. In embodiments, $R^{1.1}$ is independently —F. In embodiments, $R^{1.1}$ is independently —Cl. In embodiments, $R^{1.1}$ is independently —Br. In embodiments, $R^{1.1}$ is independently —I. In embodiments, $R^{1.1}$ is independently unsubstituted methoxy. In embodiments, $R^{1.1}$ is independently unsubstituted ethoxy. In embodiments, $R^{1.1}$ is independently —$CF_3$. In embodiments, $R^{1.1}$ is independently —$CCl_3$. In embodiments, $R^{1.1}$ is an unsubstituted phenyl. In embodiments, $R^{1.1}$ is an unsubstituted pyridyl. In embodiments, $R^{1.1}$ is independently halogen. In embodiments, $R^{1.1}$ is independently —$CONH_2$. In embodiments, $R^{1.1}$ is independently —$SO_3H$. In embodiments, $R^{1.1}$ is independently —$SO_4H$. In embodiments, $R^{1.1}$ is independently —$SO_2NH_2$. In embodiments, $R^{1.1}$ is independently —$NHNH_2$. In embodiments, $R^{1.1}$ is independently —$ONH_2$. In embodiments, $R^{1.1}$ is independently —$NHC(O)NHNH_2$. In embodiments, $R^{1.1}$ is independently —$NHC(O)NH_2$. In embodiments, $R^{1.1}$ is independently —$NHSO_2H$. In embodiments, $R^{1.1}$ is independently —$NHC(O)H$. In embodiments, $R^{1.1}$ is independently —$NHC(O)OH$. In embodiments, $R^{1.1}$ is independently —NHOH. In embodiments, $X^1$ is independently —F. In embodiments, $X^1$ is independently —Cl. In embodiments, $X^1$ is independently —Br. In embodiments, $X^{11}$ is independently —I.

$R^{1.2}$ is independently hydrogen, halogen, —$CX^{1.2}_3$, —$CHX^{1.2}_2$, —$CH_2X^{1.2}$, —CN, —$SO_{n1}R^{1D}$, —$SO_{v1}NR^{1A}R^{1B}$, —$NHNR^{1A}R^{1B}$, —$ONR^{1A}R^{1B}$, —NHC=(O)$NHNR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$OCX^{1.2}_3$, —$OCHX^{1.2}_2$, —$OCH_2X^{1.2}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{1.2}$ is independently hydrogen.

In embodiments, $R^{1.2}$ is independently halogen, $-CX^{1.2}_3$, $-CHX^{1.2}_2$, $-CH_2X^{1.2}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{1.2}_3$, $-OCHX^{1.2}_2$, $OCH_2X^{1.2}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, $R^{1.2}$ is independently halogen, $-CX^{1.2}_3$, $-CHX^{1.2}_2$, $-CH_2X^{1.2}$, $-OH$, $-CN$, $-SO_2CH_3$, $-NO_2$, $-N(CH_3)_2$, $-NH_2$, $-SH$, $-CO OH$, $-OCX^{1.2}_3$, $-OCHX^{1.2}_2$, $-CH_3$, $-CH_2CH_3$, $-OCH_3$, $-OCH_2CH_3$, $-SCH_3$, or $-SCH_2CH_3$.

In embodiments, $R^{1.2}$ is substituted or unsubstituted $C_1$-$C_6$ alkyl. In embodiments, $R^{1.2}$ is substituted or unsubstituted 2 to 6 membered heteroalkyl. In embodiments, $R^{1.2}$ is substituted or unsubstituted $C_3$-$C_8$ cycloalkyl. In embodiments, $R^{1.2}$ is substituted or unsubstituted 3 to 6 membered heterocycloalkyl. In embodiments, $R^{1.2}$ is substituted or unsubstituted phenyl. In embodiments, $R^{1.2}$ is substituted or unsubstituted 5 to 6 membered heteroaryl. In embodiments, $R^{1.2}$ is independently halogen. In embodiments, $R^{1.2}$ is independently $-CX^{1.2}_3$. In embodiments, $R^{1.2}$ is independently $-CHX^{1.2}_2$. In embodiments, $R^{1.2}$ is independently $-CH_2X^{1.2}$. In embodiments, $R^{1.2}$ is independently $-OH$. In embodiments, $R^{1.2}$ is independently $-SH$. In embodiments, $R^{1.2}$ is independently $-COOH$. In embodiments, $R^{1.2}$ is independently $-OCX^{1.2}_3$. In embodiments, $R^{1.2}$ is independently $-OCHX^{1.2}_2$. In embodiments, $R^{1.2}$ is independently $-OCH_2X^{1.2}$. In embodiments, $R^{1.2}$ is independently $-CH_3$. In embodiments, $R^{1.2}$ is independently $-CH_2CH_3$. In embodiments, $R^{1.2}$ is independently $-OCH_3$. In embodiments, $R^{1.2}$ is independently $-OCH_2CH_3$. In embodiments, $R^{1.2}$ is independently $-SCH_3$. In embodiments, $R^{1.2}$ is independently $-SCH_2CH_3$. In embodiments, $R^{1.2}$ is independently $-CN$. In embodiments, $R^{1.2}$ is independently $-SO_2CH_3$. In embodiments, $R^{1.2}$ is independently $-NO_2$. In embodiments, $R^{1.2}$ is independently $-N(CH_3)_2$. In embodiments, $R^{1.2}$ is independently $-NH(CH_3)$. In embodiments, $R^{1.2}$ is independently $-NH$(unsubstituted phenyl). In embodiments, $R^{1.2}$ is independently $-NH$(unsubstituted 5 to 6 membered heteroaryl). In embodiments, $R^{1.2}$ is independently $-NH_2$. In embodiments, $R^{1.2}$ is independently unsubstituted methyl. In embodiments, $R^{1.2}$ is independently unsubstituted ethyl. In embodiments, $R^{1.2}$ is independently unsubstituted propyl. In embodiments, $R^{1.2}$ is independently unsubstituted n-propyl. In embodiments, $R^{1.2}$ is independently unsubstituted isopropyl. In embodiments, $R^{1.2}$ is independently unsubstituted butyl. In embodiments, $R^{1.2}$ is independently unsubstituted n-butyl. In embodiments, $R^{1.2}$ is independently unsubstituted isobutyl. In embodiments, $R^{1.2}$ is independently unsubstituted tert-butyl. In embodiments, $R^{1.2}$ is independently unsubstituted pentyl. In embodiments, $R^{1.2}$ is independently unsubstituted hexyl. In embodiments, $R^{1.2}$ is independently unsubstituted heptyl. In embodiments, $R^{1.2}$ is independently unsubstituted octyl. In embodiments, $R^{1.2}$ is independently $-F$. In embodiments, $R^{1.2}$ is independently $-Cl$. In embodiments, $R^{1.2}$ is independently $-Br$. In embodiments, $R^{1.2}$ is independently $-I$. In embodiments, $R^{1.2}$ is independently unsubstituted methoxy. In embodiments, $R^{1.2}$ is independently unsubstituted ethoxy. In embodiments, $R^{1.2}$ is independently $-CF_3$. In embodiments, $R^{1.2}$ is independently $-CCl_3$. In embodiments, $R^{1.2}$ is an unsubstituted phenyl. In embodiments, $R^{1.2}$ is an unsubstituted pyridyl. In embodiments, $R^{1.2}$ is independently halogen. In embodiments, $R^{1.2}$ is independently $-CONH_2$. In embodiments, $R^{1.2}$ is independently $-SO_3H$. In embodiments, $R^{1.2}$ is independently $-SO_4H$. In embodiments, $R^{1.2}$ is independently $-SO_2NH_2$. In embodiments, $R^{1.2}$ is independently $-NHNH_2$. In embodiments, $R^{1.2}$ is independently $-ONH_2$. In embodiments, $R^{1.2}$ is independently $-NHC(O)NHNH_2$. In embodiments, $R^{1.2}$ is independently $-NHC(O)NH_2$. In embodiments, $R^{1.2}$ is independently $-NHSO_2H$. In embodiments, $R^{1.2}$ is independently $-NHC(O)H$. In embodiments, $R^{1.2}$ is independently $-NHC(O)OH$. In embodiments, $R^{1.2}$ is independently $-NHOH$. In embodiments, $X^{1.2}$ is independently $-F$. In embodiments, $X^{1.2}$ is independently $-Cl$. In embodiments, $X^{1.2}$ is independently $-Br$. In embodiments, $X^{1.2}$ is independently $-I$.

$R^{1.3}$ is independently hydrogen, halogen, $-CX^{1.3}_3$, $-CHX^{1.3}_2$, $-CH_2X^{1.3}$, $-CN$, $-SO_{n1}R^{1D}$, $-SO_{v1}NR^{1A}R^{1B}$, $-NHNR^{1A}R^{1B}$, $-ONR^{1A}R^{1B}$, $-NHC(O)NHNR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-OCX^{1.3}_3$, $-OCHX^{1.3}_2$, $-OCH_2X^{1.3}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{1.3}$ is independently hydrogen.

In embodiments, $R^{1.3}$ is independently halogen, —$CX^{1.3}_3$, —$CHX^{1.3}_2$, —$CH_2X^{1.3}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^{1.3}_3$, —$OCHX^{1.3}_2$, $OCH_2X^{1.3}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, $R^{1.3}$ is independently halogen, —$CX^{1.3}_3$, —$CHX^{1.3}_2$, —$CH_2X^{1.3}$, —OH, —CN, —$SO_2CH_3$, —$NO_2$, —$N(CH_3)_2$, —$NH_2$, —SH, —CO OH, —$OCX^{1.3}_3$, —$OCHX^{1.3}_2$, —$CH_3$, —$CH_2CH_3$, —$OCH_3$, —$OCH_2CH_3$, —$SCH_3$, or —$SCH_2CH_3$.

In embodiments, $R^{1.3}$ is substituted or unsubstituted $C_1$-$C_6$ alkyl. In embodiments, $R^{1.3}$ is substituted or unsubstituted 2 to 6 membered heteroalkyl. In embodiments, $R^{13}$ is substituted or unsubstituted $C_3$-$C_8$ cycloalkyl. In embodiments, $R^{1.3}$ is substituted or unsubstituted 3 to 6 membered heterocycloalkyl. In embodiments, $R^{1.3}$ is substituted or unsubstituted phenyl. In embodiments, $R^{1.3}$ is substituted or unsubstituted 5 to 6 membered heteroaryl. In embodiments, $R^{1.3}$ is independently halogen. In embodiments, $R^{1.3}$ is independently —$CX^{1.3}_3$. In embodiments, $R^{1.3}$ is independently —$CHX^{1.3}_2$. In embodiments, $R^{1.3}$ is independently —$CH_2X^{1.3}$. In embodiments, $R^{1.3}$ is independently —OH. In embodiments, $R^{1.3}$ is independently —SH. In embodiments, $R^{1.3}$ is independently —COOH. In embodiments, $R^{1.3}$ is independently —$OCX^{1.3}_3$. In embodiments, $R^{1.3}$ is independently —$OCHX^{1.3}_2$. In embodiments, $R^{1.3}$ is independently —$OCH_2X^{1.3}$. In embodiments, $R^{1.3}$ is independently —$CH_3$. In embodiments, $R^{1.3}$ is independently —$CH_2CH_3$. In embodiments, $R^{1.3}$ is independently —$OCH_3$. In embodiments, $R^{1.3}$ is independently —$OCH_2CH_3$. In embodiments, $R^{1.3}$ is independently —$SCH_3$. In embodiments, $R^{1.3}$ is independently —$SCH_2CH_3$. In embodiments, $R^{1.3}$ is independently —CN. In embodiments, $R^{1.3}$ is independently —$SO_2CH_3$. In embodiments, $R^{1.3}$ is independently —$NO_2$. In embodiments, $R^{1.3}$ is independently —$N(CH_3)_2$. In embodiments, $R^{1.3}$ is independently —$NH(CH_3)$. In embodiments, $R^{1.3}$ is independently —NH(unsubstituted phenyl). In embodiments, $R^{1.3}$ is independently —NH(unsubstituted 5 to 6 membered heteroaryl). In embodiments, $R^{1.3}$ is independently —$NH_2$. In embodiments, $R^{1.3}$ is independently unsubstituted methyl. In embodiments, $R^{1.3}$ is independently unsubstituted ethyl. In embodiments, $R^{1.3}$ is independently unsubstituted propyl. In embodiments, $R^{1.3}$ is independently unsubstituted n-propyl. In embodiments, $R^{1.3}$ is independently unsubstituted isopropyl. In embodiments, $R^{1.3}$ is independently unsubstituted butyl. In embodiments, $R^{1.3}$ is independently unsubstituted n-butyl. In embodiments, $R^{1.3}$ is independently unsubstituted isobutyl. In embodiments, $R^{1.3}$ is independently unsubstituted tert-butyl. In embodiments, $R^{1.3}$ is independently unsubstituted pentyl. In embodiments, $R^{1.3}$ is independently unsubstituted hexyl. In embodiments, $R^{1.3}$ is independently unsubstituted heptyl. In embodiments, $R^{1.3}$ is independently unsubstituted octyl. In embodiments, $R^{1.3}$ is independently —F. In embodiments, $R^{1.3}$ is independently —Cl. In embodiments, $R^{1.3}$ is independently —Br. In embodiments, $R^{1.3}$ is independently —I. In embodiments, $R^{1.3}$ is independently unsubstituted methoxy. In embodiments, $R^{1.3}$ is independently unsubstituted ethoxy. In embodiments, $R^{1.3}$ is independently —$CF_3$. In embodiments, $R^{1.3}$ is independently —$CCl_3$. In embodiments, $R^{1.3}$ is an unsubstituted phenyl. In embodiments, $R^{1.3}$ is an unsubstituted pyridyl. In embodiments, $R^{1.3}$ is independently halogen. In embodiments, $R^{1.3}$ is independently —$CONH_2$. In embodiments, $R^{1.3}$ is independently —$SO_3H$. In embodiments, $R^{1.3}$ is independently —$SO_4H$. In embodiments, $R^{1.3}$ is independently —$SO_2NH_2$. In embodiments, $R^{1.3}$ is independently —$NHNH_2$. In embodiments, $R^{1.3}$ is independently —$ONH_2$. In embodiments, $R^{1.3}$ is independently —$NHC(O)NHNH_2$. In embodiments, $R^{1.3}$ is independently —$NHC(O)NH_2$. In embodiments, $R^{1.3}$ is independently —$NHSO_2H$. In embodiments, $R^{1.3}$ is independently —$NHC(O)H$. In embodiments, $R^{1.3}$ is independently —$NHC(O)OH$. In embodiments, $R^{1.3}$ is independently —NHOH. In embodiments, $X^{1.3}$ is independently —F. In embodiments, $X^{1.3}$ is independently —Cl. In embodiments, $X^{1.3}$ is independently —Br. In embodiments, $X^{1.3}$ is independently —I.

$R^{1.4}$ is independently hydrogen, halogen, —$CX^{1.4}_3$, —$CHX^{1.4}_2$, —$CH_2X^{1.4}$, —CN, —$SO_{n1}R^{1D}$, —$SO_{v1}NR^{1A}R^{1B}$, —$NHNR^{1A}R^{1B}$, —$ONR^{1A}R^{1B}$, —NHC=(O)$NHNR^{1A}R^{1B}$, —NHC(O)$NR^{1A}R^{1B}$, —N(O)$_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$OCX^{1.4}_3$, —$OCHX^{1.4}_2$, —$OCH_2X^{1.4}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{1.4}$ is independently hydrogen.

In embodiments, $R^{1.4}$ is independently halogen, —$CX^{1.4}_3$, —$CHX^{1.4}_2$, —$CH_2X^{1.4}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{1.4}_3$, —$OCHX^{1.4}_2$, $OCH_2X^{1.4}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, $R^{1.4}$ is independently halogen, —$CX^{1.4}_3$, —$CHX^{1.4}_2$, —$CH_2X^{1.4}$, —OH, —CN, —$SO_2CH_3$, —$NO_2$, —$N(CH_3)_2$, —$NH_2$, —SH, —CO OH, —$OCX^{1.4}_3$, —$OCHX^{1.4}_2$, —$CH_3$, —$CH_2CH_3$, —$OCH_3$, —$OCH_2CH_3$, —$SCH_3$, or —$SCH_2CH_3$.

In embodiments, $R^{1.4}$ is substituted or unsubstituted $C_1$-$C_6$ alkyl. In embodiments, $R^{1.4}$ is substituted or unsubstituted 2 to 6 membered heteroalkyl. In embodiments, $R^{1.4}$ is substituted or unsubstituted $C_3$-$C_8$ cycloalkyl. In embodiments, $R^{1.4}$ is substituted or unsubstituted 3 to 6 membered heterocycloalkyl. In embodiments, $R^{1.4}$ is substituted or unsubstituted phenyl. In embodiments, $R^{1.4}$ is substituted or unsubstituted 5 to 6 membered heteroaryl. In embodiments, $R^{1.4}$ is independently halogen. In embodiments, $R^{1.4}$ is independently —$CX^{1.4}_3$. In embodiments, $R^{1.4}$ is independently —$CHX^{1.4}_2$. In embodiments, $R^{1.4}$ is independently —$CH_2X^{1.4}$. In embodiments, $R^{1.4}$ is independently —OH. In embodiments, $R^{1.4}$ is independently —SH. In embodiments, $R^{1.4}$ is independently —COOH. In embodiments, $R^{1.4}$ is independently —$OCX^{1.4}_3$. In embodiments, $R^{1.4}$ is independently —$OCHX^{1.4}_2$. In embodiments, $R^{1.4}$ is independently —$OCH_2X^{1.4}$. In embodiments, $R^{1.4}$ is independently —$CH_3$. In embodiments, $R^{1.4}$ is independently —$CH_2CH_3$. In embodiments, $R^{1.4}$ is independently —$OCH_3$. In embodiments, $R^{1.4}$ is independently —$OCH_2CH_3$. In embodiments, $R^{1.4}$ is independently —$SCH_3$. In embodiments, $R^{1.4}$ is independently —$SCH_2CH_3$. In embodiments, $R^{1.4}$ is independently —CN. In embodiments, $R^{1.4}$ is independently —$SO_2CH_3$. In embodiments, $R^{1.4}$ is independently —$NO_2$. In embodiments, $R^{1.4}$ is independently —$N(CH_3)_2$. In embodiments, $R^{1.4}$ is independently —$NH(CH_3)$. In embodiments, $R^{1.4}$ is independently —NH(unsubstituted phenyl). In embodiments, $R^{1.4}$ is independently —NH(unsubstituted 5 to 6 membered heteroaryl). In embodiments, $R^{1.4}$ is independently —$NH_2$. In embodiments, $R^{1.4}$ is independently unsubstituted methyl. In embodiments, $R^{1.4}$ is independently unsubstituted ethyl. In embodiments, $R^{1.4}$ is independently unsubstituted propyl. In embodiments, $R^{1.4}$ is independently unsubstituted n-propyl. In embodiments, $R^{1.4}$ is independently unsubstituted isopropyl. In embodiments, $R^{1.4}$ is independently unsubstituted butyl. In embodiments, $R^{1.4}$ is independently unsubstituted n-butyl. In embodiments, $R^{1.4}$ is independently unsubstituted isobutyl. In embodiments, $R^{1.4}$ is independently unsubstituted tert-butyl. In embodiments, $R^{1.4}$ is independently unsubstituted pentyl. In embodiments, $R^{1.4}$ is independently unsubstituted hexyl. In embodiments, $R^{1.4}$ is independently unsubstituted heptyl. In embodiments, $R^{1.4}$ is independently unsubstituted octyl. In embodiments, $R^{1.4}$ is independently —F. In embodiments, $R^{1.4}$ is independently —Cl. In embodiments, $R^{1.4}$ is independently —Br. In embodiments, $R^{1.4}$ is independently —I. In embodiments, $R^{1.4}$ is independently unsubstituted methoxy. In embodiments, $R^{1.4}$ is independently unsubstituted ethoxy. In embodiments, $R^{1.4}$ is independently —$CF_3$. In embodiments, $R^{1.4}$ is independently —$CCl_3$. In embodiments, $R^{1.4}$ is an unsubstituted phenyl. In embodiments, $R^{1.4}$ is an unsubstituted pyridyl. In embodiments, $R^{1.4}$ is independently halogen. In embodiments, $R^{1.4}$ is independently —$CONH_2$. In embodiments, $R^{1.4}$ is independently —$SO_3H$. In embodiments, $R^{1.4}$ is independently —$SO_4H$. In embodiments, $R^{1.4}$ is independently —$SO_2NH_2$. In embodiments, $R^{1.4}$ is independently —$NHNH_2$. In embodiments, $R^{1.4}$ is independently —$ONH_2$. In embodiments, $R^{1.4}$ is independently —$NHC(O)NHNH_2$. In embodiments, $R^{1.4}$ is independently —$NHC(O)NH_2$. In embodiments, $R^{1.4}$ is independently —$NHSO_2H$. In embodiments, $R^{1.4}$ is independently —NHC(O)H. In embodiments, $R^{1.4}$ is independently —NHC(O)OH. In embodiments, $R^{1.4}$ is independently —NHOH. In embodiments, $X^{14}$ is independently —F. In embodiments, $X^{14}$ is independently —Cl. In embodiments, $X^{14}$ is independently —Br. In embodiments, $X^{14}$ is independently —I.

$R^{1.5}$ is independently hydrogen, halogen, —$CX^{1.5}_3$, —$CHX^{1.5}_2$, —$CH_2X^{1.5}$, —CN, —$SO_{n1}R^{1D}$, —$SO_{v1}NR^{1A}R^{1B}$, —$NHNR^{1A}R^{1B}$, —$ONR^{1A}R^{1B}$, —NHC=(O)$NHNR^{1A}R^{1B}$, —NHC(O)$NR^{1A}R^{1B}$, —$N(O)_{m1}$, —$NR^{1A}R^{1B}$, —$C(O)R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$OCX^{1.5}_3$, —$OCHX^{1.5}_2$, —$OCH_2X^{1.5}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{1.5}$ is independently hydrogen.

In embodiments, $R^{1.5}$ is independently halogen, $-CX^{1.5}_3$, $-CHX^{1.5}_2$, $-CH_2X^{1.5}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{1.5}_3$, $-OCHX^{1.5}_2$, $OCH_2X^{1.5}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, $R^{1.5}$ is independently halogen, $-CX^{1.5}_3$, $-CHX^{1.5}_2$, $-CH_2X^{1.5}$, $-OH$, $-CN$, $-SO_2CH_3$, $-NO_2$, $-N(CH_3)_2$, $-NH_2$, $-SH$, $-CO OH$, $-OCX^{1.5}_3$, $-OCHX^{1.5}_2$, $-CH_3$, $-CH_2CH_3$, $-OCH_3$, $-OCH_2CH_3$, $-SCH_3$, or $-SCH_2CH_3$.

In embodiments, $R^{1.5}$ is substituted or unsubstituted $C_1$-$C_6$ alkyl. In embodiments, $R^{1.5}$ is substituted or unsubstituted 2 to 6 membered heteroalkyl. In embodiments, $R^{1.5}$ is substituted or unsubstituted $C_3$-$C_8$ cycloalkyl. In embodiments, $R^{1.5}$ is substituted or unsubstituted 3 to 6 membered heterocycloalkyl. In embodiments, $R^{1.5}$ is substituted or unsubstituted phenyl. In embodiments, $R^{1.5}$ is substituted or unsubstituted 5 to 6 membered heteroaryl. In embodiments, $R^{1.5}$ is independently halogen. In embodiments, $R^{1.5}$ is independently $-CX^{1.5}_3$. In embodiments, $R^{1.5}$ is independently $-CHX^{1.5}_2$. In embodiments, $R^{1.5}$ is independently $-CH_2X^{1.5}$. In embodiments, $R^{1.5}$ is independently $-OH$. In embodiments, $R^{1.5}$ is independently $-SH$. In embodiments, $R^{1.5}$ is independently $-COOH$. In embodiments, $R^{1.5}$ is independently $-OCX^{1.5}_3$. In embodiments, $R^{1.5}$ is independently $-OCHX^{1.5}_2$. In embodiments, $R^{1.5}$ is independently $-OCH_2X^{1.5}$. In embodiments, $R^{1.5}$ is independently $-CH_3$. In embodiments, $R^{1.5}$ is independently $-CH_2CH_3$. In embodiments, $R^{1.5}$ is independently $-OCH_3$. In embodiments, $R^{1.5}$ is independently $-OCH_2CH_3$. In embodiments, $R^{1.5}$ is independently $-SCH_3$. In embodiments, $R^{1.5}$ is independently $-SCH_2CH_3$. In embodiments, $R^{1.5}$ is independently $-CN$. In embodiments, $R^{1.5}$ is independently $-SO_2CH_3$. In embodiments, $R^{1.5}$ is independently $-NO_2$. In embodiments, $R^{1.5}$ is independently $-N(CH_3)_2$. In embodiments, $R^{1.5}$ is independently $-NH(CH_3)$. In embodiments, $R^{1.5}$ is independently $-NH$(unsubstituted phenyl). In embodiments, $R^{1.5}$ is independently $-NH$(unsubstituted 5 to 6 membered heteroaryl). In embodiments, $R^{1.5}$ is independently $-NH_2$. In embodiments, $R^{1.5}$ is independently unsubstituted methyl. In embodiments, $R^{1.5}$ is independently unsubstituted ethyl. In embodiments, $R^{1.5}$ is independently unsubstituted propyl. In embodiments, $R^{1.5}$ is independently unsubstituted n-propyl. In embodiments, $R^{1.5}$ is independently unsubstituted isopropyl. In embodiments, $R^{1.5}$ is independently unsubstituted butyl. In embodiments, $R^{1.5}$ is independently unsubstituted n-butyl. In embodiments, $R^{1.5}$ is independently unsubstituted isobutyl. In embodiments, $R^{1.5}$ is independently unsubstituted tert-butyl. In embodiments, $R^{1.5}$ is independently unsubstituted pentyl. In embodiments, $R^{1.5}$ is independently unsubstituted hexyl. In embodiments, $R^{1.5}$ is independently unsubstituted heptyl. In embodiments, $R^{1.5}$ is independently unsubstituted octyl. In embodiments, $R^{1.5}$ is independently $-F$. In embodiments, $R^{1.5}$ is independently $-Cl$. In embodiments, $R^{1.5}$ is independently $-Br$. In embodiments, $R^{1.5}$ is independently $-I$. In embodiments, $R^{1.5}$ is independently unsubstituted methoxy. In embodiments, $R^{1.5}$ is independently unsubstituted ethoxy. In embodiments, $R^{1.5}$ is independently $-CF_3$. In embodiments, $R^{1.5}$ is independently $-CCl_3$. In embodiments, $R^{1.5}$ is an unsubstituted phenyl. In embodiments, $R^{1.5}$ is an unsubstituted pyridyl. In embodiments, $R^{1.5}$ is independently halogen. In embodiments, $R^{1.5}$ is independently $-CONH_2$. In embodiments, $R^{1.5}$ is independently $-SO_3H$. In embodiments, $R^{1.5}$ is independently $-SO_4H$. In embodiments, $R^{1.5}$ is independently $-SO_2NH_2$. In embodiments, $R^{1.5}$ is independently $-NHNH_2$. In embodiments, $R^{1.5}$ is independently $-ONH_2$. In embodiments, $R^{1.5}$ is independently $-NHC(O)NHNH_2$. In embodiments, $R^{1.5}$ is independently $-NHC(O)NH_2$. In embodiments, $R^{1.5}$ is independently $-NHSO_2H$. In embodiments, $R^{1.5}$ is independently $-NHC(O)H$. In embodiments, $R^{1.5}$ is independently $-NHC(O)OH$. In embodiments, $R^{1.5}$ is independently $-NHOH$. In embodiments, $X^{1.5}$ is independently $-F$. In embodiments, $X^{1.5}$ is independently $-Cl$. In embodiments, $X^{1.5}$ is independently $-Br$. In embodiments, $X^{1.5}$ is independently $-I$.

In embodiments, $R^2$ is independently hydrogen. In embodiments, $R^2$ is $-C(O)R^{2A}$. In embodiments, $R^2$ is independently $-C(O)OR^{2A}$. In embodiments, $R^2$ is independently $-C(O)NR^{2A}R^{2B}$. In embodiments, $R^2$ is independently $-CX^{23}$. In embodiments, $R^2$ is independently $-CHX^2_2$. In embodiments, $R^2$ is independently $-CH_2X^2$. In embodiments, $R^2$ is independently $-OH$. In embodiments, $R^2$ is independently $-COOH$. In embodiments, $R^2$ is independently $-OCX^2_3$. In embodiments, $R^2$ is independently $-OCHX^2_2$. In embodiments, $R^2$ is independently $-CH_3$. In embodiments, $R^2$ is independently $-CH_2CH_3$. In embodiments, $R^2$ is independently $-OCH_3$. In embodiments, $R^2$ is independently $-OCH_2CH_3$. In embodiments, $R^2$ is independently unsubstituted methyl. In embodiments, $R^2$ is independently unsubstituted ethyl. In embodiments, $R^2$ is independently unsubstituted propyl. In embodiments, $R^2$ is independently unsubstituted n-propyl. In embodiments, $R^2$ is independently unsubstituted isopropyl. In embodiments, $R^2$ is independently unsubstituted butyl. In embodiments, $R^2$ is independently unsubstituted n-butyl. In embodiments, $R^2$ is independently unsubstituted isobutyl. In embodiments, $R^2$ is independently unsubstituted tert-butyl. In embodiments, $R^2$ is independently unsubstituted pentyl. In embodiments, $R^2$ is independently unsubstituted hexyl. In embodiments, $R^2$ is independently unsubstituted heptyl. In embodiments, $R^2$ is independently unsubstituted octyl. In embodiments, $R^2$ is independently —$CF_3$. In embodiments, $R^2$ is independently —$CCl_3$. In embodiments, $X^2$ is independently —F. In embodiments, $X^2$ is independently —Cl. In embodiments, $X^2$ is independently —Br. In embodiments, $X^2$ is independently —I.

In embodiments, $R^2$ is substituted (e.g., substituted with a substituent group, a size-limited substituent group, or lower substituent group) or unsubstituted alkyl. In embodiments, $R^2$ is substituted (e.g., substituted with a substituent group, a size-limited substituent group, or lower substituent group) alkyl. In embodiments, $R^2$ is unsubstituted alkyl. In embodiments, $R^2$ is substituted or unsubstituted alkyl (e.g., $C_1$-$C_8$, $C_1$-$C_6$, $C_1$-$C_4$, or $C_1$-$C_2$). In embodiments, $R^2$ is substituted alkyl (e.g., $C_1$-$C_8$, $C_1$-$C_6$, $C_1$-$C_4$, or $C_1$-$C_2$). In embodiments, $R^2$ is unsubstituted alkyl (e.g., $C_1$-$C_8$, $C_1$-$C_6$, $C_1$-$C_4$, or $C_1$-$C_2$).

In embodiments, $R^2$ is substituted (e.g., substituted with a substituent group, a size-limited substituent group, or lower substituent group) or unsubstituted heteroalkyl. In embodiments, $R^2$ is substituted (e.g., substituted with a substituent group, a size-limited substituent group, or lower substituent group) heteroalkyl. In embodiments, $R^2$ is unsubstituted heteroalkyl. In embodiments, $R^2$ is substituted or unsubstituted heteroalkyl (e.g., 2 to 8 membered, 2 to 6 membered, 4 to 6 membered, 2 to 3 membered, or 4 to 5 membered). In embodiments, $R^2$ is substituted heteroalkyl (e.g., 2 to 8 membered, 2 to 6 membered, 4 to 6 membered, 2 to 3 membered, or 4 to 5 membered). In embodiments, $R^2$ is an unsubstituted heteroalkyl (e.g., 2 to 8 membered, 2 to 6 membered, 4 to 6 membered, 2 to 3 membered, or 4 to 5 membered).

In embodiments, $R^2$ is substituted (e.g., substituted with a substituent group, a size-limited substituent group, or lower substituent group) or unsubstituted cycloalkyl. In embodiments, $R^2$ is substituted (e.g., substituted with a substituent group, a size-limited substituent group, or lower substituent group) cycloalkyl. In embodiments, $R^2$ is an unsubstituted cycloalkyl. In embodiments, $R^2$ is substituted or unsubstituted cycloalkyl (e.g., $C_3$-$C_8$, $C_3$-$C_6$, $C_4$-$C_6$, or $C_5$-$C_6$). In embodiments, $R^2$ is substituted cycloalkyl (e.g., $C_3$-$C_8$, $C_3$-$C_6$, $C_4$-$C_6$, or $C_5$-$C_6$). In embodiments, $R^2$ is unsubstituted cycloalkyl (e.g., $C_3$-$C_8$, $C_3$-$C_6$, $C_4$-$C_6$, or $C_5$-$C_6$).

In embodiments, $R^2$ is substituted (e.g., substituted with a substituent group, a size-limited substituent group, or lower substituent group) or unsubstituted heterocycloalkyl. In embodiments, $R^2$ is substituted (e.g., substituted with a substituent group, a size-limited substituent group, or lower substituent group) heterocycloalkyl. In embodiments, $R^2$ is an unsubstituted heterocycloalkyl. In embodiments, $R^2$ is substituted or unsubstituted heterocycloalkyl (e.g., 3 to 8 membered, 3 to 6 membered, 4 to 6 membered, 4 to 5 membered, or 5 to 6 membered). In embodiments, $R^2$ is substituted heterocycloalkyl (e.g., 3 to 8 membered, 3 to 6 membered, 4 to 6 membered, 4 to 5 membered, or 5 to 6 membered). In embodiments, $R^2$ an unsubstituted heterocycloalkyl (e.g., 3 to 8 membered, 3 to 6 membered, 4 to 6 membered, 4 to 5 membered, or 5 to 6 membered).

In embodiments, $R^2$ is substituted (e.g., substituted with a substituent group, a size-limited substituent group, or lower substituent group) or unsubstituted aryl. In embodiments, $R^2$ is substituted (e.g., substituted with a substituent group, a size-limited substituent group, or lower substituent group) aryl. In embodiments, $R^2$ is an unsubstituted aryl. In embodiments, $R^2$ is substituted or unsubstituted aryl (e.g., $C_6$-$C_{10}$ or phenyl). In embodiments, $R^2$ is substituted aryl (e.g., $C_6$-$C_{10}$ or phenyl). In embodiments, $R^2$ is an unsubstituted aryl (e.g., $C_6$-$C_{10}$ or phenyl).

In embodiments, $R^2$ is substituted (e.g., substituted with a substituent group, a size-limited substituent group, or lower substituent group) or unsubstituted heteroaryl. In embodiments, $R^2$ is substituted (e.g., substituted with a substituent group, a size-limited substituent group, or lower substituent group) heteroaryl. In embodiments, $R^2$ is an unsubstituted heteroaryl. In embodiments, $R^2$ is substituted or unsubstituted heteroaryl (e.g., 5 to 10 membered, 5 to 9 membered, or 5 to 6 membered). In embodiments, $R^2$ is substituted heteroaryl (e.g., 5 to 10 membered, 5 to 9 membered, or 5 to 6 membered). In embodiments, $R^2$ is an unsubstituted heteroaryl (e.g., 5 to 10 membered, 5 to 9 membered, or 5 to 6 membered).

In embodiments, each $R^{2A}$ and $R^{2B}$ is independently hydrogen, —$CX_3$, —CN, —COOH, —$CONH_2$, —$CHX_2$, —$CH_2X$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, each $R^{2A}$ and $R^{2B}$ is independently hydrogen. In embodiments, each $R^{2A}$ and $R^{2B}$ is independently —$CX_3$. In embodiments, each $R^{2A}$ and $R^{2B}$ is independently —CN. In embodiments, each $R^{2A}$ and $R^{2B}$ is independently —COOH. In embodiments, each $R^{2A}$ and $R^{2B}$ is independently —$CONH_2$. In embodiments, each $R^{2A}$ and $R^{2B}$ is independently —$CHX_2$. In embodiments, each $R^{2A}$ and $R^{2B}$ is independently —$CH_2X$. In embodiments, each $R^{2A}$ and $R^{2B}$ is independently —$CH_3$. In embodiments, each $R^{2A}$ and $R^{2B}$ is independently —$CH_2CH_3$.

In embodiments, each $R^{2A}$ and $R^{2B}$ is independently hydrogen, —$CX_3$, —CN, —COOH, —$CONH_2$, —$CHX_2$, —$CH_2X$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^{2A}$ and $R^{2B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{2A}$ and $R^{2B}$ substituents bonded to the same nitrogen atom may optionally be joined to independently form an unsubstituted heterocycloalkyl (e.g., 3 to 10 membered, 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered).

In embodiments, $L^1$ is a bond, substituted (e.g., substituted with a substituent group, a size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted cycloalkylene (e.g., $C_3$-$C_8$, $C_3$-$C_6$, $C_4$-$C_6$, or $C_5$-$C_6$), or

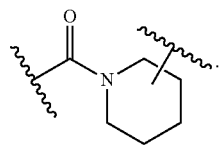

In embodiments, $L^1$ is a bond, unsubstituted alkylene (e.g., $C_1$-$C_8$, $C_1$-$C_6$, $C_1$-$C_4$, or $C_1$-$C_2$), or unsubstituted cycloalkylene (e.g., $C_3$-$C_8$, $C_3$-$C_6$, $C_4$-$C_6$, or $C_5$-$C_6$). In embodiments, $L^1$ is a bond. In embodiments, $L^1$ is —$CH_2$—. In embodiments, $L^1$ is —$C(CH_3)_2$—. In embodiments, $L^1$ is unsubstituted cyclopropylene. In embodiments, $L^1$ is a bond. In embodiments, $L^1$ is

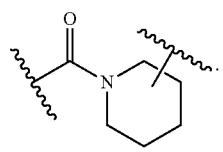

In embodiments, $L^1$ is

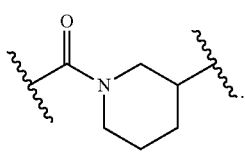 [SMILES: *C(=O)N1CCCC(*)C1]

In embodiments, $L^1$ is

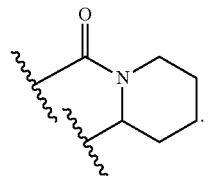 [SMILES: *C(=O)N1CCCCC1*]

In embodiments, $L^1$ is

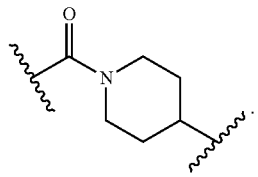 [SMILES: *C(=O)N1CCC(*)CC1]

In embodiments, $L^1$ is

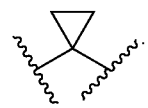

In some embodiments, when Ring A is aryl, $L^1$ is a bond, substituted or unsubstituted alkylene, or substituted or unsubstituted cycloalkylene.

In embodiments, $L^1$ is a bond, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), or

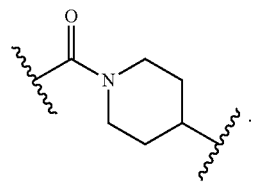 [SMILES: *C(=O)N1CCC(*)CC1]

In embodiments, $L^1$ is an unsubstituted methylene. In embodiments, $L^1$ is a bond. In embodiments, $L^1$ is

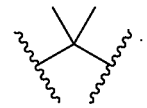 [SMILES: *C(*)(C)C]

In embodiments, $L^1$ is substituted (e.g., substituted with a substituent group, a size-limited substituent group, or lower substituent group) or unsubstituted alkylene. In embodiments, $L^1$ is substituted (e.g., substituted with a substituent group, a size-limited substituent group, or lower substituent group) alkylene. In embodiments, $L^1$ is unsubstituted alkylene. In embodiments, $L^1$ is substituted or unsubstituted alkylene (e.g., $C_1$-$C_8$, $C_1$-$C_6$, $C_1$-$C_4$, or $C_1$-$C_2$). In embodiments, $L^1$ is substituted alkylene (e.g., $C_1$-$C_8$, $C_1$-$C_6$, $C_1$-$C_4$, or $C_1$-$C_2$). In embodiments, $L^1$ is unsubstituted alkylene (e.g., $C_1$-$C_8$, $C_1$-$C_6$, $C_1$-$C_4$, or $C_1$-$C_2$).

In embodiments, $L^1$ is substituted (e.g., substituted with a substituent group, a size-limited substituent group, or lower substituent group) or unsubstituted cycloalkylene. In embodiments, $L^1$ is substituted (e.g., substituted with a substituent group, a size-limited substituent group, or lower substituent group) cycloalkylene. In embodiments, $L^1$ is an unsubstituted cycloalkylene. In embodiments, $L^1$ is substituted or unsubstituted cycloalkylene (e.g., $C_3$-$C_8$, $C_3$-$C_6$, $C_4$-$C_6$, or $C_5$-$C_6$). In embodiments, $L^1$ is substituted cycloalkylene (e.g., $C_3$-$C_8$, $C_3$-$C_6$, $C_4$-$C_6$, or $C_5$-$C_6$). In embodiments, $L^1$ is unsubstituted cycloalkylene (e.g., $C_3$-$C_8$, $C_3$-$C_6$, $C_4$-$C_6$, or $C_5$-$C_6$).

In embodiments, $L^2$ is a bond, —O—, —C(O)—, —C(O)O—, —OC(O)—, —S—, —SO—, —S(O)$_2$—, —NH—, —NHC(O)—, —C(O)NH—, —SO$_2$NH—, —NHSO$_2$—, —OC(O)NH—, —NHC(O)O—, —NHC(O)NH—, —C(O)OCH$_2$—, —CH$_2$OC(O)—, —C(O)NHCH$_2$—, —CH$_2$NHC(O)—, —CH$_2$NHCH$_2$—, substituted (e.g., substituted with a substituent group, a size-limited substituent group, or lower substituent group) or unsubstituted alkylene (e.g., $C_1$-$C_8$, $C_1$-$C_6$, $C_1$-$C_4$, or $C_1$-$C_2$), or substituted (e.g., substituted with a substituent group, a size-limited substituent group, or lower substituent group) or unsubstituted heteroalkylene (e.g., 2 to 8 membered, 2 to 6 membered, 4 to 6 membered, 2 to 3 membered, or 4 to 5 membered). In embodiments, $L^2$ is a bond, —S(O)$_2$—, —C(O)OCH$_2$—, —CH$_2$OC(O)—, —C(O)NHCH$_2$—, —CH$_2$NHC(O)—, —CH$_2$NHCH$_2$—, or —CH$_2$—. In embodiments, $L^2$ is a bond. In embodiments, $L^2$ is —S(O)$_2$—. In embodiments, $L^2$ is —C(O)OCH$_2$—. In embodiments, $L^2$ is —C(O)NHCH$_2$—. In embodiments, $L^2$ is —CH$_2$NHCH$_2$—. In embodiments, $L^2$ is —CH$_2$—. In embodiments, $L^2$ is —CH$_2$CH$_2$—. In embodiments, $L^2$ is —C(CH$_3$)$_2$—. In embodiments, $L^2$ is —O—. In embodiments, $L^2$ is —C(O)—. In embodiments, $L^2$ is —C(O)O—. In embodiments, $L^2$ is —OC(O)—. In embodiments, $L^2$ is —S—. In embodiments, $L^2$ is —SO—. In embodiments, $L^2$ is —NH—. In embodiments, $L^2$ is —NHC(O)—. In embodiments, $L^2$ is —C(O)NH—. In embodiments, $L^2$ is —SO$_2$NH—. In embodiments, $L^2$ is —NHSO$_2$—. In embodiments, $L^2$ is —OC(O)NH—. In embodiments, $L^2$ is —NHC(O)O—. In embodiments, $L^2$ is —NHC(O)NH—. In embodiments, $L^2$ is —CH$_2$OC(O)—. In embodiments, $L^2$ is —CH$_2$NHC(O)—. In embodiments, $L^2$ is —CH$_2$CONH—. In embodiments, $L^2$ is

In embodiments, $L^2$ is substituted (e.g., substituted with a substituent group, a size-limited substituent group, or lower substituent group) or unsubstituted alkylene. In embodiments, $L^2$ is substituted (e.g., substituted with a substituent group, a size-limited substituent group, or lower substituent group) alkylene. In embodiments, $L^2$ is unsubstituted alkylene. In embodiments, $L^2$ is substituted or unsubstituted alkylene (e.g., $C_1$-$C_8$, $C_1$-$C_6$, $C_1$-$C_4$, or $C_1$-$C_2$). In embodiments, $L^2$ is substituted alkylene (e.g., $C_1$-$C_8$, $C_1$-$C_6$, $C_1$-$C_4$, or $C_1$-$C_2$). In embodiments, $L^2$ is unsubstituted alkylene (e.g., $C_1$-$C_8$, $C_1$-$C_6$, $C_1$-$C_4$, or $C_1$-$C_2$).

In embodiments, $L^2$ is substituted (e.g., substituted with a substituent group, a size-limited substituent group, or lower substituent group) or unsubstituted heteroalkylene. In embodiments, $L^2$ is substituted (e.g., substituted with a substituent group, a size-limited substituent group, or lower substituent group) heteroalkylene. In embodiments, $L^2$ is unsubstituted heteroalkylene. In embodiments, $L^2$ is substituted or unsubstituted heteroalkylene (e.g., 2 to 8 membered, 2 to 6 membered, 4 to 6 membered, 2 to 3 membered, or 4 to 5 membered). In embodiments, $L^2$ is substituted heteroalkylene (e.g., 2 to 8 membered, 2 to 6 membered, 4 to 6 membered, 2 to 3 membered, or 4 to 5 membered). In embodiments, $L^2$ is an unsubstituted heteroalkylene (e.g., 2 to 8 membered, 2 to 6 membered, 4 to 6 membered, 2 to 3 membered, or 4 to 5 membered).

In embodiments, $L^3$ is a bond, —S(O)$_2$—, —N(R$^3$)—, —O—, —S—, —C(O)—, —C(O)N(R$^3$)—, —N(R$^3$)C(O)—, —N(R$^3$)C(O)NH—, —NHC(O)N(R$^3$)—, —C(O)O—, —OC(O)—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenylene), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered).

In embodiments, $L^3$ is a bond, —S(O)$_2$—, —NH—, —C(O)NH—, —NHC(O)—, substituted (e.g., substituted with a substituent group, a size-limited substituent group, or lower substituent group) or unsubstituted $C_1$-$C_6$ alkylene, substituted (e.g., substituted with a substituent group, a size-limited substituent group, or lower substituent group) or unsubstituted 2 to 6 membered heteroalkylene, substituted (e.g., substituted with a substituent group, a size-limited substituent group, or lower substituent group) or unsubstituted $C_3$-$C_6$ cycloalkylene, substituted (e.g., substituted with a substituent group, a size-limited substituent group, or lower substituent group) or unsubstituted 3 to 6 membered heterocycloalkylene, substituted (e.g., substituted with a substituent group, a size-limited substituent group, or lower substituent group) or unsubstituted phenylene, or substituted (e.g., substituted with a substituent group, a size-limited substituent group, or lower substituent group) or unsubstituted 5 to 6 membered heteroarylene.

In embodiments, $L^3$ is a bond. In embodiments, $L^3$ is —S(O)$_2$—. In embodiments, $L^3$ is —N(R$^3$)—. In embodiments, $L^3$ is —O—. In embodiments, $L^3$ is —S—. In embodiments, $L^3$ is —C(O)—. In embodiments, $L^3$ is —C(O)N(R$^3$)—. In embodiments, $L^3$ is —N(R$^3$)C(O)—. In embodiments, $L^3$ is —N(R$^3$)C(O)NH—. In embodiments, $L^3$ is —NHC(O)N(R$^3$)—. In embodiments, $L^3$ is —C(O)

O—. In embodiments, L³ is —OC(O)—. In embodiments, L³ is —NH—. In embodiments, L³ is —C(O)NH—. In embodiments, L³ is —NHC(O)—. In embodiments, L³ is —NHC(O)NH—. In embodiments, L³ is substituted (e.g., substituted with a substituent group, a size-limited substituent group, or lower substituent group) or unsubstituted methylene. In embodiments, L³ is unsubstituted methylene. In embodiments, L³ is

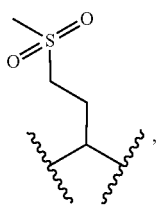

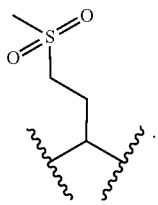 [SMILES: *C(*)CCS(C)(=O)=O]

In embodiments, L³ is

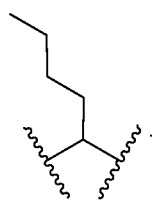 [SMILES: *C(*)CCCC]

In embodiments, L³ is

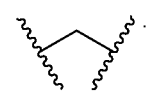

In embodiments, L³ is

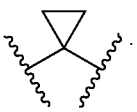

In embodiments, L³ is

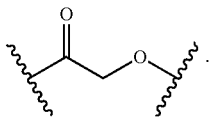

In embodiments, L³ is a bond, substituted or unsubstituted methylene, substituted or unsubstituted ethylene, substituted or unsubstituted propylene, substituted or unsubstituted butylene, substituted or unsubstituted C₅ alkylene, substituted or unsubstituted C₆ alkylene, substituted or unsubstituted ethenylene, substituted or unsubstituted propenylene, substituted or unsubstituted butenylene, substituted or unsubstituted C₅ alkenylene, or substituted or unsubstituted C₆ alkenylene. In embodiments, L³ is a bond, unsubstituted methylene, unsubstituted ethylene, unsubstituted propylene, unsubstituted butylene, unsubstituted C5 alkylene, unsubstituted C₆ alkylene, unsubstituted ethenylene, unsubstituted propenylene, unsubstituted butenylene, unsubstituted C5 alkenylene, or unsubstituted C₆ alkenylene. In embodiments, L³ is a bond. In embodiments, L³ is a substituted or unsubstituted 2 membered heteroalkyl, substituted or unsubstituted 3 membered heteroalkyl, substituted or unsubstituted 4 membered heteroalkyl, substituted or unsubstituted 5 membered heteroalkyl, substituted or unsubstituted 6 membered heteroalkyl. In embodiments, L³ is an unsubstituted 2 membered heteroalkyl, unsubstituted 3 membered heteroalkyl, unsubstituted 4 membered heteroalkyl, unsubstituted 5 membered heteroalkyl, or unsubstituted 6 membered heteroalkyl. In embodiments, L³ is

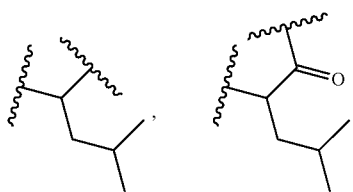

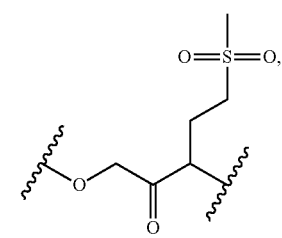

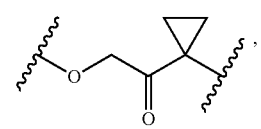

-continued

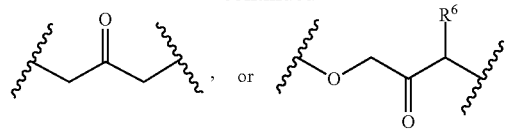

In embodiments, $L^3$ is

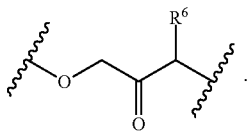

In embodiments, $L^3$ is

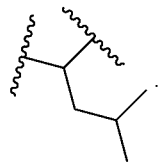 [SMILES: *C(*)CC(C)C]

In embodiments, $L^3$ is

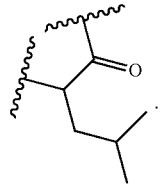 [SMILES: *C(=O)C(*)CC(C)C]

In embodiments, $L^3$ is

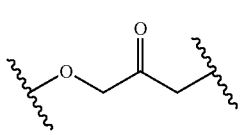

In embodiments, $L^3$ is

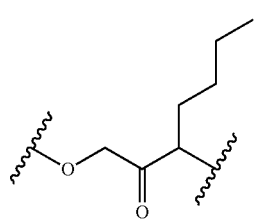

In embodiments, $L^3$ is

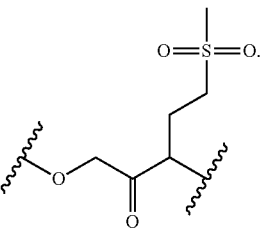 [SMILES: *OCC(=O)C(*)CCS(C)(=O)=O]

In embodiments, $L^3$ is

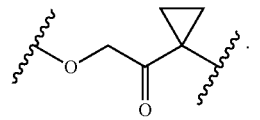 [SMILES: *OCC(=O)C1(*)CC1]

In embodiments, $L^3$ is

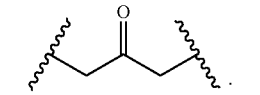 [SMILES: *CC(=O)C*]

In embodiments, $L^3$ is

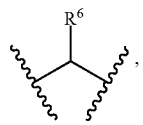

wherein $R^6$ is as described herein.

In embodiments, $L^3$ is substituted (e.g., substituted with a substituent group, a size-limited substituent group, or lower substituent group) or unsubstituted alkylene. In embodiments, $L^3$ is substituted (e.g., substituted with a substituent group, a size-limited substituent group, or lower substituent group) alkylene. In embodiments, $L^3$ is unsubstituted alkylene. In embodiments, $L^3$ is substituted or unsubstituted alkylene (e.g., $C_1$-$C_8$, $C_1$-$C_6$, $C_1$-$C_4$, or $C_1$-$C_2$). In embodiments, $L^3$ is substituted alkylene (e.g., $C_1$-$C_8$, $C_1$-$C_6$, $C_1$-$C_4$, or $C_1$-$C_2$). In embodiments, $L^3$ is unsubstituted alkylene (e.g., $C_1$-$C_8$, $C_1$-$C_6$, $C_1$-$C_4$, or $C_1$-$C_2$).

In embodiments, $L^3$ is substituted (e.g., substituted with a substituent group, a size-limited substituent group, or lower substituent group) or unsubstituted heteroalkylene. In embodiments, $L^3$ is substituted (e.g., substituted with a substituent group, a size-limited substituent group, or lower substituent group) heteroalkylene. In embodiments, $L^3$ is unsubstituted heteroalkylene. In embodiments, $L^3$ is substituted or unsubstituted heteroalkylene (e.g., 2 to 8 membered, 2 to 6 membered, 4 to 6 membered, 2 to 3 membered, or 4 to 5 membered). In embodiments, $L^3$ is substituted heteroalkylene (e.g., 2 to 8 membered, 2 to 6 membered, 4 to 6 membered, 2 to 3 membered, or 4 to 5 membered). In embodiments, $L^3$ is an unsubstituted heteroalkylene (e.g., 2 to 8 membered, 2 to 6 membered, 4 to 6 membered, 2 to 3 membered, or 4 to 5 membered).

In embodiments, $L^3$ is substituted (e.g., substituted with a substituent group, a size-limited substituent group, or lower substituent group) or unsubstituted cycloalkylene. In embodiments, $L^3$ is substituted (e.g., substituted with a substituent group, a size-limited substituent group, or lower substituent group) cycloalkylene. In embodiments, $L^3$ is an unsubstituted cycloalkylene. In embodiments, $L^3$ is substituted or unsubstituted cycloalkylene (e.g., $C_3$-$C_8$, $C_3$-$C_6$, $C_4$-$C_6$, or $C_5$-$C_6$). In embodiments, $L^3$ is substituted cycloalkylene (e.g., $C_3$-$C_8$, $C_3$-$C_6$, $C_4$-$C_6$, or $C_5$-$C_6$). In embodiments, $L^3$ is unsubstituted cycloalkylene (e.g., $C_3$-$C_8$, $C_3$-$C_6$, $C_4$-$C_6$, or $C_5$-$C_6$).

In embodiments, $L^3$ is substituted (e.g., substituted with a substituent group, a size-limited substituent group, or lower substituent group) or unsubstituted heterocycloalkylene. In embodiments, $L^3$ is substituted (e.g., substituted with a substituent group, a size-limited substituent group, or lower substituent group) heterocycloalkylene. In embodiments, $L^3$ is an unsubstituted heterocycloalkylene. In embodiments, $L^3$ is substituted or unsubstituted heterocycloalkylene (e.g., 3 to 8 membered, 3 to 6 membered, 4 to 6 membered, 4 to 5 membered, or 5 to 6 membered). In embodiments, $L^3$ is substituted heterocycloalkylene (e.g., 3 to 8 membered, 3 to 6 membered, 4 to 6 membered, 4 to 5 membered, or 5 to 6 membered). In embodiments, $L^3$ an unsubstituted heterocycloalkylene (e.g., 3 to 8 membered, 3 to 6 membered, 4 to 6 membered, 4 to 5 membered, or 5 to 6 membered).

In embodiments, $L^3$ is substituted (e.g., substituted with a substituent group, a size-limited substituent group, or lower substituent group) or unsubstituted arylene. In embodiments, $L^3$ is substituted (e.g., substituted with a substituent group, a size-limited substituent group, or lower substituent group) arylene. In embodiments, $L^3$ is an unsubstituted arylene. In embodiments, $L^3$ is substituted or unsubstituted arylene (e.g., $C_6$-$C_{10}$ or phenylene). In embodiments, $L^3$ is substituted arylene (e.g., $C_6$-$C_{10}$ or phenylene). In embodiments, $L^3$ is an unsubstituted arylene (e.g., $C_6$-$C_{10}$ or phenylene).

In embodiments, $L^3$ is substituted (e.g., substituted with a substituent group, a size-limited substituent group, or lower substituent group) or unsubstituted heteroarylene. In embodiments, $L^3$ is substituted (e.g., substituted with a substituent group, a size-limited substituent group, or lower substituent group) heteroarylene. In embodiments, $L^3$ is an unsubstituted heteroarylene. In embodiments, $L^3$ is substituted or unsubstituted heteroarylene (e.g., 5 to 10 membered, 5 to 9 membered, or 5 to 6 membered). In embodiments, $L^3$ is substituted heteroarylene (e.g., 5 to 10 membered, 5 to 9 membered, or 5 to 6 membered). In embodiments, $L^3$ is an unsubstituted heteroarylene (e.g., 5 to 10 membered, 5 to 9 membered, or 5 to 6 membered).

In embodiments, $L^3$ is a bond, —S(O)$_2$—, —N(R$^3$)—, —O—, —S—, —C(O)—, —C(O)N(R$^3$)—, —N(R$^3$)C(O)—, —N(R$^3$)C(O)NH—, —NHC(O)N(R$^3$)—, —C(O)O—, —OC(O)—, R$^6$-substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), R$^6$-substituted or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), R$^6$-substituted or unsubstituted cycloalkylene (e.g., $C_3$-$C_{10}$, $C_3$-$C_8$, $C_3$-$C_6$, $C_4$-$C_6$, or $C_5$-$C_6$), R$^6$-substituted or unsubstituted heterocycloalkylene (e.g., 3 to 10 membered, 3 to 8 membered, 3 to 6 membered, 4 to 6 membered, 4 to 5 membered, or 5 to 6 membered), R$^6$-substituted or unsubstituted arylene (e.g., $C_6$-$C_{12}$, $C_6$-$C_{10}$, or phenylene), or R$^6$-substituted or unsubstituted heteroarylene (e.g., 5 to 12 membered, 5 to 10 membered, 5 to 9 membered, or 5 to 6 membered).

$R^6$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^6$ is independently —OH, substituted or unsubstituted methyl, substituted or unsubstituted ethyl, substituted or unsubstituted propyl, substituted or unsubstituted butyl, substituted or unsubstituted $C_5$ alkyl, substituted or unsubstituted $C_6$ alkyl, —SO$_2$CH$_3$, substituted or unsubstituted 2 membered heteroalkyl, substituted or unsubstituted 3 membered heteroalkyl, substituted or unsubstituted 4 membered heteroalkyl, substituted or unsubstituted 5 membered heteroalkyl, or substituted or unsubstituted 6 membered heteroalkyl.

In embodiments, $R^6$ is independently —OH, unsubstituted methyl, unsubstituted ethyl, unsubstituted propyl, unsubstituted butyl, unsubstituted $C_5$ alkyl, unsubstituted $C_6$ alkyl, —SO$_2$CH$_3$, unsubstituted 2 membered heteroalkyl, unsubstituted 3 membered heteroalkyl, unsubstituted 4 membered heteroalkyl, unsubstituted 5 membered heteroalkyl, or unsubstituted 6 membered heteroalkyl.

In embodiments, $R^6$ is independently oxo. In embodiments, $R^6$ is independently halogen. In embodiments, $R^6$ is independently —CCl$_3$. In embodiments, $R^6$ is independently —CBr$_3$. In embodiments, $R^6$ is independently —CF$_3$. In embodiments, $R^6$ is independently —CI$_3$. In embodiments, $R^6$ is independently —CH$_2$Cl. In embodiments, $R^6$ is independently —CH$_2$Br. In embodiments, $R^6$ is independently —CH$_2$F. In embodiments, $R^6$ is independently —CH$_2$I. In embodiments, $R^6$ is independently —CHCl$_2$. In embodiments, $R^6$ is independently —CHBr$_2$. In embodiments, $R^6$ is independently —CHF$_2$. In embodiments, $R^6$ is independently —CHI$_2$. In embodiments, $R^6$ is independently —CN. In embodiments, $R^6$ is independently —OH. In embodiments, $R^6$ is independently —NH$_2$. In embodiments, $R^6$ is independently —COOH. In embodiments, $R^6$ is independently —CONH$_2$. In embodiments, $R^6$ is independently —NO$_2$. In embodiments, $R^6$ is independently —SH. In embodiments, $R^6$ is independently —SO$_3$H. In embodiments, $R^6$ is independently —SO$_4$H. In embodiments, $R^6$ is independently —SO$_2$NH$_2$. In embodiments, $R^6$ is independently —NHNH$_2$. In embodiments, $R^6$ is independently —ONH$_2$. In embodiments, $R^6$ is independently —NHC(O)NHNH$_2$. In embodiments, $R^6$ is independently —NHC(O)NH$_2$. In embodiments, $R^6$ is independently —NHSO$_2$H. In embodiments, $R^6$ is independently —NHC(O)H. In embodiments, $R^6$ is independently —NHC(O)OH. In embodiments, $R^6$ is independently —NHOH. In embodiments, $R^6$ is independently —OCCl$_3$. In embodiments, $R^6$ is independently —OCBr$_3$. In embodiments, $R^6$ is independently —OCF$_3$. In embodiments, $R^6$ is independently —OCI$_3$. In embodiments, $R^6$ is independently —OCH$_2$Cl. In embodiments, $R^6$ is independently —OCH$_2$Br. In embodiments, $R^6$ is independently —OCH$_2$F. In embodiments, $R^6$ is independently —OCH$_2$I. In embodiments, R$^6$ is independently —OCHCl$_2$. In embodiments, R$^6$ is independently —OCHBr$_2$. In embodiments, R$^6$ is independently —OCHF$_2$. In embodiments, R$^6$ is independently —OCHI$_2$.

In embodiments, R$^6$ is independently —OH. In embodiments, R$^6$ is independently unsubstituted methyl. In embodiments, R$^6$ is independently unsubstituted ethyl. In embodiments, R$^6$ is independently unsubstituted propyl. In embodiments, R$^6$ is independently unsubstituted butyl. In embodiments, R$^6$ is independently unsubstituted C$_5$ alkyl. In embodiments, R$^6$ is independently unsubstituted C$_6$ alkyl. In embodiments, R$^6$ is independently —SO$_2$CH$_3$. In embodiments, R$^6$ is independently unsubstituted 2 membered heteroalkyl. In embodiments, R$^6$ is independently unsubstituted 3 membered heteroalkyl. In embodiments, R$^6$ is independently unsubstituted 4 membered heteroalkyl. In embodiments, R$^6$ is independently unsubstituted 5 membered heteroalkyl. In embodiments, R$^6$ is independently unsubstituted 6 membered heteroalkyl.

In embodiments, R$^3$ is independently hydrogen, —CX$^3{}_3$, —CHX$^3{}_2$, —CH$_2$X$^3$, —C(O)R$^{3A}$, —C(O)OR$^{3A}$, —C(O)NR$^{3A}$R$^{3B}$, substituted (e.g., substituted with a substituent group, a size-limited substituent group, or lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{12}$, C$_6$-C$_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, R$^3$ is independently hydrogen. In embodiments, R$^3$ is independently —CX$^{33}$. In embodiments, R$^3$ is independently —CHX$^{32}$. In embodiments, R$^3$ is independently —CH$_2$X$^3$. In embodiments, R$^3$ is independently —C(O)R$^{3A}$ In embodiments, R$^3$ is independently —C(O)OR$^{3A}$. In embodiments, R$^3$ is independently —C(O)NR$^{3A}$R$^{3B}$. In embodiments, R$^3$ is independently —CH$_3$. In embodiments, R$^3$ is independently —CH$_2$CH$_3$. In embodiments, R$^3$ is independently —C(O)H. In embodiments, R$^3$ is independently —C(O)OH. In embodiments, R$^3$ is independently —C(O)NH$_2$. In embodiments, X$^3$ is independently —F. In embodiments, X$^3$ is independently —Cl. In embodiments, X$^3$ is independently —Br. In embodiments, X$^3$ is independently —I.

In embodiments, R$^3$ is independently hydrogen, —CX$^3{}_3$, —CHX$^3{}_2$, —CH$_2$X$^3$, substituted (e.g., substituted with a substituent group, a size-limited substituent group, or lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{12}$, C$_6$-C$_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, R$^3$ is substituted (e.g., substituted with a substituent group, a size-limited substituent group, or lower substituent group) or unsubstituted alkyl. In embodiments, R$^3$ is substituted (e.g., substituted with a substituent group, a size-limited substituent group, or lower substituent group) alkyl. In embodiments, R$^3$ is unsubstituted alkyl. In embodiments, R$^3$ is substituted or unsubstituted alkyl (e.g., C$_1$-C$_8$, C$_1$-C$_6$, C$_1$-C$_4$, or C$_1$-C$_2$). In embodiments, R$^3$ is substituted alkyl (e.g., C$_1$-C$_8$, C$_1$-C$_6$, C$_1$-C$_4$, or C$_1$-C$_2$). In embodiments, R$^3$ is unsubstituted alkyl (e.g., C$_1$-C$_8$, C$_1$-C$_6$, C$_1$-C$_4$, or C$_1$-C$_2$).

In embodiments, R$^3$ is substituted (e.g., substituted with a substituent group, a size-limited substituent group, or lower substituent group) or unsubstituted heteroalkyl. In embodiments, R$^3$ is substituted (e.g., substituted with a substituent group, a size-limited substituent group, or lower substituent group) heteroalkyl. In embodiments, R$^3$ is unsubstituted heteroalkyl. In embodiments, R$^3$ is substituted or unsubstituted heteroalkyl (e.g., 2 to 8 membered, 2 to 6 membered, 4 to 6 membered, 2 to 3 membered, or 4 to 5 membered). In embodiments, R$^3$ is substituted heteroalkyl (e.g., 2 to 8 membered, 2 to 6 membered, 4 to 6 membered, 2 to 3 membered, or 4 to 5 membered). In embodiments, R$^3$ is an unsubstituted heteroalkyl (e.g., 2 to 8 membered, 2 to 6 membered, 4 to 6 membered, 2 to 3 membered, or 4 to 5 membered).

In embodiments, R$^3$ is substituted (e.g., substituted with a substituent group, a size-limited substituent group, or lower substituent group) or unsubstituted cycloalkyl. In embodiments, R$^3$ is substituted (e.g., substituted with a substituent group, a size-limited substituent group, or lower substituent group) cycloalkyl. In embodiments, R$^3$ is an unsubstituted cycloalkyl. In embodiments, R$^3$ is substituted or unsubstituted cycloalkyl (e.g., C$_3$-C$_8$, C$_3$-C$_6$, C$_4$-C$_6$, or C$_5$-C$_6$). In embodiments, R$^3$ is substituted cycloalkyl (e.g., C$_3$-C$_8$, C$_3$-C$_6$, C$_4$-C$_6$, or C$_5$-C$_6$). In embodiments, R$^3$ is unsubstituted cycloalkyl (e.g., C$_3$-C$_8$, C$_3$-C$_6$, C$_4$-C$_6$, or C$_5$-C$_6$).

In embodiments, R$^3$ is substituted (e.g., substituted with a substituent group, a size-limited substituent group, or lower substituent group) or unsubstituted heterocycloalkyl. In embodiments, R$^3$ is substituted (e.g., substituted with a substituent group, a size-limited substituent group, or lower substituent group) heterocycloalkyl. In embodiments, R$^3$ is an unsubstituted heterocycloalkyl. In embodiments, R$^3$ is substituted or unsubstituted heterocycloalkyl (e.g., 3 to 8 membered, 3 to 6 membered, 4 to 6 membered, 4 to 5 membered, or 5 to 6 membered). In embodiments, R$^3$ is substituted heterocycloalkyl (e.g., 3 to 8 membered, 3 to 6 membered, 4 to 6 membered, 4 to 5 membered, or 5 to 6 membered). In embodiments, R$^3$ an unsubstituted heterocycloalkyl (e.g., 3 to 8 membered, 3 to 6 membered, 4 to 6 membered, 4 to 5 membered, or 5 to 6 membered).

In embodiments, $R^3$ is substituted (e.g., substituted with a substituent group, a size-limited substituent group, or lower substituent group) or unsubstituted aryl. In embodiments, $R^3$ is substituted (e.g., substituted with a substituent group, a size-limited substituent group, or lower substituent group) aryl. In embodiments, $R^3$ is an unsubstituted aryl. In embodiments, $R^3$ is substituted or unsubstituted aryl (e.g., $C_6$-$C_{10}$ or phenyl). In embodiments, $R^3$ is substituted aryl (e.g., $C_6$-$C_{10}$ or phenyl). In embodiments, $R^3$ is an unsubstituted aryl (e.g., $C_6$-$C_{10}$ or phenyl).

In embodiments, $R^3$ is substituted (e.g., substituted with a substituent group, a size-limited substituent group, or lower substituent group) or unsubstituted heteroaryl. In embodiments, $R^3$ is substituted (e.g., substituted with a substituent group, a size-limited substituent group, or lower substituent group) heteroaryl. In embodiments, $R^3$ is an unsubstituted heteroaryl. In embodiments, $R^3$ is substituted or unsubstituted heteroaryl (e.g., 5 to 10 membered, 5 to 9 membered, or 5 to 6 membered). In embodiments, $R^3$ is substituted heteroaryl (e.g., 5 to 10 membered, 5 to 9 membered, or 5 to 6 membered). In embodiments, $R^3$ is an unsubstituted heteroaryl (e.g., 5 to 10 membered, 5 to 9 membered, or 5 to 6 membered).

In embodiments, each $R^{3A}$ and $R^{3B}$ is independently hydrogen, —$CX_3$, —CN, —COOH, —$CONH_2$, —$CHX_2$, —$CH_2X$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, each $R^{3A}$ and $R^{3B}$ is independently hydrogen. In embodiments, each $R^{3A}$ and $R^{3B}$ is independently —$CX_3$. In embodiments, each each $R^{3A}$ and $R^{3B}$ is independently —CN. In embodiments, each $R^{3A}$ and $R^{3B}$ is independently —COOH. In embodiments, each $R^{3A}$ and $R^{3B}$ is independently —$CONH_2$. In embodiments, each $R^{3A}$ and $R^{3B}$ is independently —$CHX_2$. In embodiments, each $R^{3A}$ and $R^{3B}$ is independently —$CH_2X$. In embodiments, each $R^{3A}$ and $R^{3B}$ is independently —$CH_3$. In embodiments, each $R^{3A}$ and $R^{3B}$ is independently —$CH_2CH_3$.

In embodiments, each $R^{3A}$ and $R^{3B}$ is independently hydrogen, —$CX_3$, —CN, —COOH, —$CONH_2$, —$CHX_2$, —$CH_2X$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^{3A}$ and $R^{3B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{3A}$ and $R^{3B}$ substituents bonded to the same nitrogen atom may optionally be joined to independently form an unsubstituted heterocycloalkyl (e.g., 3 to 10 membered, 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered).

In embodiments, $L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —$NHC(O)N(R^4)$—, —C(O)O—, —OC(O)—, substituted (e.g., substituted with a substituent group, a size-limited substituent group, or lower substituent group) or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenylene), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered).

In embodiments, $L^4$ is a bond, —$S(O)_2$—, —NH—, —C(O)NH—, —NHC(O)—, substituted (e.g., substituted with a substituent group, a size-limited substituent group, or lower substituent group) or unsubstituted $C_1$-$C_6$ alkylene, substituted (e.g., substituted with a substituent group, a size-limited substituent group, or lower substituent group) or unsubstituted 2 to 6 membered heteroalkylene, substituted (e.g., substituted with a substituent group, a size-limited substituent group, or lower substituent group) or unsubstituted $C_3$-$C_6$ cycloalkylene, substituted (e.g., substituted with a substituent group, a size-limited substituent group, or lower substituent group) or unsubstituted 3 to 6 membered heterocycloalkylene, substituted (e.g., substituted with a substituent group, a size-limited substituent group, or lower substituent group) or unsubstituted phenylene, or substituted (e.g., substituted with a substituent group, a size-limited substituent group, or lower substituent group) or unsubstituted 5 to 6 membered heteroarylene.

In embodiments, $L^4$ is a bond. In embodiments, $L^4$ is —S(O)$_2$—. In embodiments, $L^4$ is —N(R$^4$)—. In embodiments, $L^4$ is —O—. In embodiments, $L^4$ is —S—. In embodiments, $L^4$ is —C(O)—. In embodiments, $L^4$ is —C(O)N(R$^4$)—. In embodiments, $L^4$ is —N(R$^4$)C(O)—. In embodiments, $L^4$ is —N(R$^4$)C(O)NH—. In embodiments, $L^4$ is —NHC(O)N(R$^4$)—. In embodiments, $L^4$ is —C(O)O—. In embodiments, $L^4$ is —OC(O)—. In embodiments, $L^4$ is —NH—. In embodiments, $L^4$ is —C(O)NH—. In embodiments, $L^4$ is —NHC(O)—. In embodiments, $L^4$ is —NHC(O)NH—. In embodiments, $L^4$ is substituted (e.g., substituted with a substituent group, a size-limited substituent group, or lower substituent group) or unsubstituted methylene. In embodiments, $L^4$ is unsubstituted methylene. In embodiments, $L^4$ is

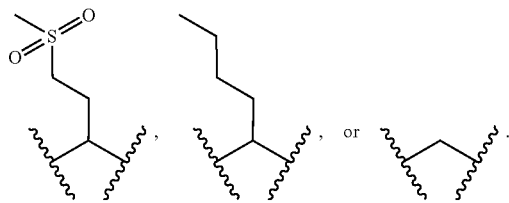

In embodiments, $L^4$ is

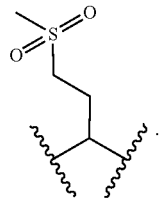 [SMILES: *C(*)CCS(C)(=O)=O]

In embodiments, $L^4$ is

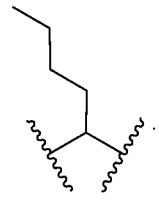 [SMILES: *C(*)CCCC]

In embodiments, $L^4$ is

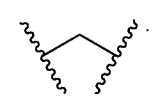

In embodiments, $L^4$ is

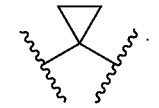 [SMILES: *C1(*)CC1]

In embodiments, $L^4$ is

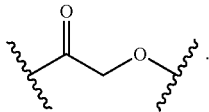 [SMILES: *OCC(*)=O]

In embodiments, $L^4$ is a bond, substituted or unsubstituted methylene, substituted or unsubstituted ethylene, substituted or unsubstituted propylene, substituted or unsubstituted butylene, substituted or unsubstituted C$_5$ alkylene, substituted or unsubstituted C$_6$ alkylene, substituted or unsubstituted ethenylene, substituted or unsubstituted propenylene, substituted or unsubstituted butenylene, substituted or unsubstituted C$_5$ alkenylene, or substituted or unsubstituted C$_6$ alkenylene. In embodiments, $L^4$ is a bond, unsubstituted methylene, unsubstituted ethylene, unsubstituted propylene, unsubstituted butylene, unsubstituted C5 alkylene, unsubstituted C$_6$ alkylene, unsubstituted ethenylene, unsubstituted propenylene, unsubstituted butenylene, unsubstituted C5 alkenylene, or unsubstituted C$_6$ alkenylene. In embodiments, $L^4$ is a bond. In embodiments, $L^4$ is a substituted or unsubstituted 2 membered heteroalkyl, substituted or unsubstituted 3 membered heteroalkyl, substituted or unsubstituted 4 membered heteroalkyl, substituted or unsubstituted 5 membered heteroalkyl, substituted or unsubstituted 6 membered heteroalkyl. In embodiments, $L^4$ is an unsubstituted 2 membered heteroalkyl, unsubstituted 3 membered heteroalkyl, unsubstituted 4 membered heteroalkyl, unsubstituted 5 membered heteroalkyl, or unsubstituted 6 membered heteroalkyl. In embodiments, $L^4$ is

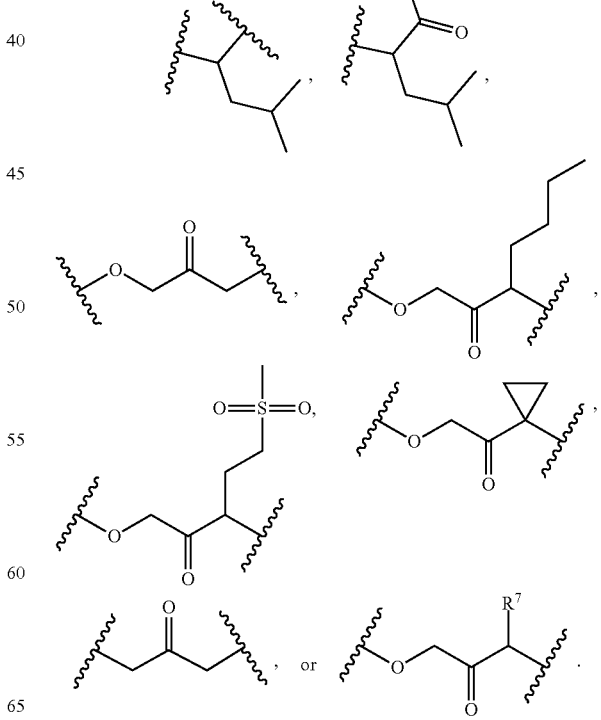

In embodiments, $L^4$ is

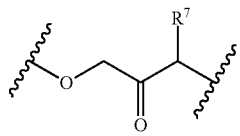

In embodiments, $L^4$ is

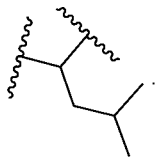 [SMILES: *C(*)CC(C)C]

In embodiments, $L^4$ is

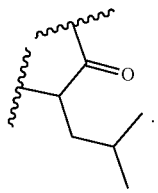 [SMILES: *C(=O)C(*)CC(C)C]

In embodiments, $L^4$ is

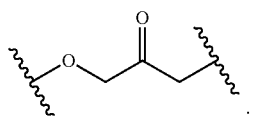 [SMILES: *CC(=O)CO*]

In embodiments, $L^4$ is

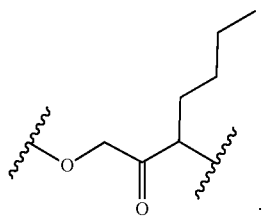 [SMILES: *OCC(=O)C(*)CCCC]

In embodiments, $L^4$ is

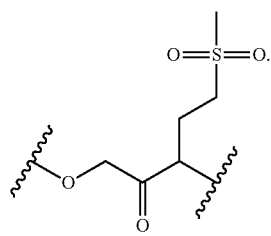 [SMILES: *OCC(=O)C(*)CCS(C)(=O)=O]

In embodiments, $L^4$ is

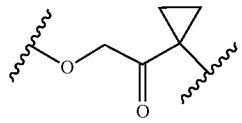

In embodiments, $L^4$ is

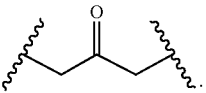 [SMILES: *CC(=O)C*]

In embodiments, $L^3$ is

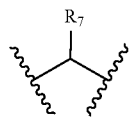

, wherein $R^7$ is as described herein.

In embodiments, $L^4$ is substituted (e.g., substituted with a substituent group, a size-limited substituent group, or lower substituent group) or unsubstituted alkylene. In embodiments, $L^4$ is substituted (e.g., substituted with a substituent group, a size-limited substituent group, or lower substituent group) alkylene. In embodiments, $L^4$ is unsubstituted alkylene. In embodiments, $L^4$ is substituted or unsubstituted alkylene (e.g., $C_1$-$C_8$, $C_1$-$C_6$, $C_1$-$C_4$, or $C_1$-$C_2$). In embodiments, $L^4$ is substituted alkylene (e.g., $C_1$-$C_8$, $C_1$-$C_6$, $C_1$-$C_4$, or $C_1$-$C_2$). In embodiments, $L^4$ is unsubstituted alkylene (e.g., $C_1$-$C_8$, $C_1$-$C_6$, $C_1$-$C_4$, or $C_1$-$C_2$).

In embodiments, $L^4$ is substituted (e.g., substituted with a substituent group, a size-limited substituent group, or lower substituent group) or unsubstituted heteroalkylene. In embodiments, $L^4$ is substituted (e.g., substituted with a substituent group, a size-limited substituent group, or lower substituent group) heteroalkylene. In embodiments, $L^4$ is unsubstituted heteroalkylene. In embodiments, $L^4$ is substituted or unsubstituted heteroalkylene (e.g., 2 to 8 membered, 2 to 6 membered, 4 to 6 membered, 2 to 3 membered, or 4 to 5 membered). In embodiments, $L^4$ is substituted heteroalkylene (e.g., 2 to 8 membered, 2 to 6 membered, 4 to 6 membered, 2 to 3 membered, or 4 to 5 membered). In embodiments, $L^4$ is an unsubstituted heteroalkylene (e.g., 2 to 8 membered, 2 to 6 membered, 4 to 6 membered, 2 to 3 membered, or 4 to 5 membered).

In embodiments, $L^4$ is substituted (e.g., substituted with a substituent group, a size-limited substituent group, or lower substituent group) or unsubstituted cycloalkylene. In embodiments, $L^4$ is substituted (e.g., substituted with a substituent group, a size-limited substituent group, or lower substituent group) cycloalkylene. In embodiments, $L^4$ is an unsubstituted cycloalkylene. In embodiments, $L^4$ is substituted or unsubstituted cycloalkylene (e.g., $C_3$-$C_8$, $C_3$-$C_6$, $C_4$-$C_6$, or $C_5$-$C_6$). In embodiments, $L^4$ is substituted cycloalkylene (e.g., $C_3$-$C_8$, $C_3$-$C_6$, $C_4$-$C_6$, or $C_5$-$C_6$). In embodiments, $L^4$ is unsubstituted cycloalkylene (e.g., $C_3$-$C_8$, $C_3$-$C_6$, $C_4$-$C_6$, or $C_5$-$C_6$).

In embodiments, $L^4$ is substituted (e.g., substituted with a substituent group, a size-limited substituent group, or lower substituent group) or unsubstituted heterocycloalkylene. In embodiments, $L^4$ is substituted (e.g., substituted with a substituent group, a size-limited substituent group, or lower substituent group) heterocycloalkylene. In embodiments, $L^4$ is an unsubstituted heterocycloalkylene. In embodiments, $L^4$ is substituted or unsubstituted heterocycloalkylene (e.g., 3 to 8 membered, 3 to 6 membered, 4 to 6 membered, 4 to 5 membered, or 5 to 6 membered). In embodiments, $L^4$ is substituted heterocycloalkylene (e.g., 3 to 8 membered, 3 to 6 membered, 4 to 6 membered, 4 to 5 membered, or 5 to 6 membered). In embodiments, $L^4$ an unsubstituted heterocycloalkylene (e.g., 3 to 8 membered, 3 to 6 membered, 4 to 6 membered, 4 to 5 membered, or 5 to 6 membered).

In embodiments, $L^4$ is substituted (e.g., substituted with a substituent group, a size-limited substituent group, or lower substituent group) or unsubstituted arylene. In embodiments, $L^4$ is substituted (e.g., substituted with a substituent group, a size-limited substituent group, or lower substituent group) arylene. In embodiments, $L^4$ is an unsubstituted arylene. In embodiments, $L^4$ is substituted or unsubstituted arylene (e.g., $C_6$-$C_{10}$ or phenylene). In embodiments, $L^4$ is substituted arylene (e.g., $C_6$-$C_{10}$ or phenylene). In embodiments, $L^4$ is an unsubstituted arylene (e.g., $C_6$-$C_{10}$ or phenylene).

In embodiments, $L^4$ is substituted (e.g., substituted with a substituent group, a size-limited substituent group, or lower substituent group) or unsubstituted heteroarylene. In embodiments, $L^4$ is substituted (e.g., substituted with a substituent group, a size-limited substituent group, or lower substituent group) heteroarylene. In embodiments, $L^4$ is an unsubstituted heteroarylene. In embodiments, $L^4$ is substituted or unsubstituted heteroarylene (e.g., 5 to 10 membered, 5 to 9 membered, or 5 to 6 membered). In embodiments, $L^4$ is substituted heteroarylene (e.g., 5 to 10 membered, 5 to 9 membered, or 5 to 6 membered). In embodiments, $L^4$ is an unsubstituted heteroarylene (e.g., 5 to 10 membered, 5 to 9 membered, or 5 to 6 membered).

In embodiments, $L^4$ is a bond, —S(O)$_2$—, —N(R$^4$)—, —O—, —S—, —C(O)—, —C(O)N(R$^4$)—, —N(R$^4$)C(O)—, —N(R$^4$)C(O)NH—, —NHC(O)N(R$^4$)—, —C(O)O—, —OC(O)—, R$^7$-substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), R$^7$-substituted or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), R$^7$-substituted or unsubstituted cycloalkylene (e.g., $C_3$-$C_{10}$, $C_3$-$C_8$, $C_3$-$C_6$, $C_4$-$C_6$, or $C_5$-$C_6$), R$^7$-substituted or unsubstituted heterocycloalkylene (e.g., 3 to 10 membered, 3 to 8 membered, 3 to 6 membered, 4 to 6 membered, 4 to 5 membered, or 5 to 6 membered), R$^7$-substituted or unsubstituted arylene (e.g., $C_6$-$C_{12}$, $C_6$-$C_{10}$, or phenylene), or R-substituted or unsubstituted heteroarylene (e.g., 5 to 12 membered, 5 to 10 membered, 5 to 9 membered, or 5 to 6 membered).

$R^7$ is independently oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^7$ is independently —OH, substituted or unsubstituted methyl, substituted or unsubstituted ethyl, substituted or unsubstituted propyl, substituted or unsubstituted butyl, substituted or unsubstituted $C_5$ alkyl, substituted or unsubstituted $C_6$ alkyl, —SO$_2$CH$_3$, substituted or unsubstituted 2 membered heteroalkyl, substituted or unsubstituted 3 membered heteroalkyl, substituted or unsubstituted 4 membered heteroalkyl, substituted or unsubstituted 5 membered heteroalkyl, or substituted or unsubstituted 6 membered heteroalkyl.

In embodiments, $R^7$ is independently —OH, unsubstituted methyl, unsubstituted ethyl, unsubstituted propyl, unsubstituted butyl, unsubstituted $C_5$ alkyl, unsubstituted $C_6$ alkyl, —SO$_2$CH$_3$, unsubstituted 2 membered heteroalkyl, unsubstituted 3 membered heteroalkyl, unsubstituted 4 membered heteroalkyl, unsubstituted 5 membered heteroalkyl, or unsubstituted 6 membered heteroalkyl.

In embodiments, $R^7$ is independently oxo. In embodiments, $R^7$ is independently halogen. In embodiments, $R^7$ is independently —CCl$_3$. In embodiments, $R^7$ is independently —CBr$_3$. In embodiments, $R^7$ is independently —CF$_3$. In embodiments, $R^7$ is independently —CI$_3$. In embodiments, $R^7$ is independently —CH$_2$Cl. In embodiments, $R^7$ is independently —CH$_2$Br. In embodiments, $R^7$ is independently —CH$_2$F. In embodiments, $R^7$ is independently —CH$_2$I. In embodiments, $R^7$ is independently —CHCl$_2$. In embodiments, $R^7$ is independently —CHBr$_2$. In embodiments, $R^7$ is independently —CHF$_2$. In embodiments, $R^7$ is independently —CHI$_2$. In embodiments, $R^7$ is independently —CN. In embodiments, $R^7$ is independently —OH. In embodiments, $R^7$ is independently —NH$_2$. In embodiments, $R^7$ is independently —COOH. In embodiments, $R^7$ is independently —CONH$_2$. In embodiments, $R^7$ is independently —NO$_2$. In embodiments, $R^7$ is independently —SH. In embodiments, $R^7$ is independently —SO$_3$H. In embodiments, $R^7$ is independently —SO$_4$H. In embodiments, $R^7$ is independently —SO$_2$NH$_2$. In embodiments, $R^7$ is independently —NHNH$_2$. In embodiments, $R^7$ is independently —ONH$_2$. In embodiments, $R^7$ is independently —NHC(O)NHNH$_2$. In embodiments, $R^7$ is independently —NHC(O)NH$_2$. In embodiments, $R^7$ is independently —NHSO$_2$H. In embodiments, $R^7$ is independently —NHC(O)H. In embodiments, $R^7$ is independently —NHC(O)OH. In embodiments, $R^7$ is independently —NHOH. In embodiments, $R^7$ is independently —OCCl$_3$. In embodiments, $R^7$ is independently —OCBr$_3$. In embodiments, $R^7$ is independently —OCF$_3$. In embodiments, $R^7$ is independently —OCI$_3$. In embodiments, $R^7$ is independently —OCH$_2$Cl. In embodiments, $R^7$ is independently —OCH$_2$Br. In embodiments, $R^7$ is independently —OCH$_2$F. In embodiments, $R^7$ is independently —OCH$_2$I. In embodiments, $R^7$ is independently —OCHCl$_2$. In embodiments, $R^7$ is independently —OCHBr$_2$. In embodiments, $R^7$ is independently —OCHF$_2$. In embodiments, $R^7$ is independently —OCHI$_2$.

In embodiments, $R^7$ is independently —OH. In embodiments, $R^7$ is independently unsubstituted methyl. In embodiments, $R^7$ is independently unsubstituted ethyl. In embodiments, $R^7$ is independently unsubstituted propyl. In embodiments, $R^7$ is independently unsubstituted butyl. In embodiments, $R^7$ is independently unsubstituted $C_5$ alkyl. In embodiments, $R^7$ is independently unsubstituted $C_6$ alkyl. In embodiments, $R^7$ is independently —SO$_2$CH$_3$. In embodiments, $R^7$ is independently unsubstituted 2 membered heteroalkyl. In embodiments, $R^7$ is independently unsubstituted 3 membered heteroalkyl. In embodiments, $R^7$ is independently unsubstituted 4 membered heteroalkyl. In embodiments, $R^7$ is independently unsubstituted 5 membered heteroalkyl. In embodiments, $R^7$ is independently unsubstituted 6 membered heteroalkyl.

In embodiments, $R^4$ is independently hydrogen, $-CX^4_3$, $-CHX^4_2$, $-CH_2X^4$, $-C(O)R^{4A}$, $-C(O)OR^{4A}$, $-C(O)NR^{4A}R^{4B}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^4$ is independently hydrogen. In embodiments, $R^4$ is independently $-CX^{43}$. In embodiments, $R^4$ is independently $-CHX^{42}$. In embodiments, $R^4$ is independently $-CH_2X^4$. In embodiments, $R^4$ is independently $-C(O)R^{4A}$. In embodiments, $R^4$ is independently $-C(O)OR^{4A}$. In embodiments, $R^4$ is independently $-C(O)NR^{4A}R^{4B}$. In embodiments, $R^4$ is independently $-CH_3$. In embodiments, $R^4$ is independently $-CH_2CH_3$. In embodiments, $R^4$ is independently $-C(O)H$. In embodiments, $R^4$ is independently $-C(O)OH$. In embodiments, $R^4$ is independently $-C(O)NH_2$. In embodiments, $X^4$ is independently $-F$. In embodiments, $X^4$ is independently $-Cl$. In embodiments, $X^4$ is independently $-Br$. In embodiments, $X^4$ is independently $-I$.

In embodiments, $R^4$ is independently hydrogen, $-CX^4_3$, $-CHX^4_2$, $-CH_2X^4$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, $R^4$ is substituted (e.g., substituted with a substituent group, a size-limited substituent group, or lower substituent group) or unsubstituted alkyl. In embodiments, $R^4$ is substituted (e.g., substituted with a substituent group, a size-limited substituent group, or lower substituent group) alkyl. In embodiments, $R^4$ is unsubstituted alkyl. In embodiments, $R^4$ is substituted or unsubstituted alkyl (e.g., $C_1$-$C_8$, $C_1$-$C_6$, $C_1$-$C_4$, or $C_1$-$C_2$). In embodiments, $R^4$ is substituted alkyl (e.g., $C_1$-$C_8$, $C_1$-$C_6$, $C_1$-$C_4$, or $C_1$-$C_2$). In embodiments, $R^4$ is unsubstituted alkyl (e.g., $C_1$-$C_8$, $C_1$-$C_6$, $C_1$-$C_4$, or $C_1$-$C_2$).

In embodiments, $R^4$ is substituted (e.g., substituted with a substituent group, a size-limited substituent group, or lower substituent group) or unsubstituted heteroalkyl. In embodiments, $R^4$ is substituted (e.g., substituted with a substituent group, a size-limited substituent group, or lower substituent group) heteroalkyl. In embodiments, $R^4$ is unsubstituted heteroalkyl. In embodiments, $R^4$ is substituted or unsubstituted heteroalkyl (e.g., 2 to 8 membered, 2 to 6 membered, 4 to 6 membered, 2 to 3 membered, or 4 to 5 membered). In embodiments, $R^4$ is substituted heteroalkyl (e.g., 2 to 8 membered, 2 to 6 membered, 4 to 6 membered, 2 to 3 membered, or 4 to 5 membered). In embodiments, $R^4$ is an unsubstituted heteroalkyl (e.g., 2 to 8 membered, 2 to 6 membered, 4 to 6 membered, 2 to 3 membered, or 4 to 5 membered).

In embodiments, $R^4$ is substituted (e.g., substituted with a substituent group, a size-limited substituent group, or lower substituent group) or unsubstituted cycloalkyl. In embodiments, $R^4$ is substituted (e.g., substituted with a substituent group, a size-limited substituent group, or lower substituent group) cycloalkyl. In embodiments, $R^4$ is an unsubstituted cycloalkyl. In embodiments, $R^4$ is substituted or unsubstituted cycloalkyl (e.g., $C_3$-$C_8$, $C_3$-$C_6$, $C_4$-$C_6$, or $C_5$-$C_6$). In embodiments, $R^4$ is substituted cycloalkyl (e.g., $C_3$-$C_8$, $C_3$-$C_6$, $C_4$-$C_6$, or $C_5$-$C_6$). In embodiments, $R^4$ is unsubstituted cycloalkyl (e.g., $C_3$-$C_8$, $C_3$-$C_6$, $C_4$-$C_6$, or $C_5$-$C_6$).

In embodiments, $R^4$ is substituted (e.g., substituted with a substituent group, a size-limited substituent group, or lower substituent group) or unsubstituted heterocycloalkyl. In embodiments, $R^4$ is substituted (e.g., substituted with a substituent group, a size-limited substituent group, or lower substituent group) heterocycloalkyl. In embodiments, $R^4$ is an unsubstituted heterocycloalkyl. In embodiments, $R^4$ is substituted or unsubstituted heterocycloalkyl (e.g., 3 to 8 membered, 3 to 6 membered, 4 to 6 membered, 4 to 5 membered, or 5 to 6 membered). In embodiments, $R^4$ is substituted heterocycloalkyl (e.g., 3 to 8 membered, 3 to 6 membered, 4 to 6 membered, 4 to 5 membered, or 5 to 6 membered). In embodiments, $R^4$ an unsubstituted heterocycloalkyl (e.g., 3 to 8 membered, 3 to 6 membered, 4 to 6 membered, 4 to 5 membered, or 5 to 6 membered).

In embodiments, $R^4$ is substituted (e.g., substituted with a substituent group, a size-limited substituent group, or lower substituent group) or unsubstituted aryl. In embodiments, $R^4$ is substituted (e.g., substituted with a substituent group, a size-limited substituent group, or lower substituent group) aryl. In embodiments, $R^4$ is an unsubstituted aryl. In embodiments, $R^4$ is substituted or unsubstituted aryl (e.g., $C_6$-$C_{10}$ or phenyl). In embodiments, $R^4$ is substituted aryl (e.g., $C_6$-$C_{10}$ or phenyl). In embodiments, $R^4$ is an unsubstituted aryl (e.g., $C_6$-$C_{10}$ or phenyl).

In embodiments, $R^4$ is substituted (e.g., substituted with a substituent group, a size-limited substituent group, or lower substituent group) or unsubstituted heteroaryl. In embodiments, $R^4$ is substituted (e.g., substituted with a substituent group, a size-limited substituent group, or lower substituent group) heteroaryl. In embodiments, $R^4$ is an unsubstituted heteroaryl. In embodiments, $R^4$ is substituted or unsubstituted heteroaryl (e.g., 5 to 10 membered, 5 to 9 membered, or 5 to 6 membered). In embodiments, $R^4$ is substituted heteroaryl (e.g., 5 to 10 membered, 5 to 9 membered, or 5 to 6 membered). In embodiments, $R^4$ is an unsubstituted heteroaryl (e.g., 5 to 10 membered, 5 to 9 membered, or 5 to 6 membered).

In embodiments, each $R^{4A}$ and $R^{4B}$ is independently hydrogen, —$CX_3$, —CN, —COOH, —$CONH_2$, —$CHX_2$, —$CH_2X$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, each $R^{4A}$ and $R^{4B}$ is independently hydrogen. In embodiments, each $R^{4A}$ and $R^{4B}$ is independently —$CX_3$. In embodiments, each each $R^{4A}$ and $R^{4B}$ is independently —CN. In embodiments, each $R^{4A}$ and $R^{4B}$ is independently —COOH. In embodiments, each $R^{4A}$ and $R^{4B}$ is independently —$CONH_2$. In embodiments, each $R^{4A}$ and $R^{4B}$ is independently —$CHX_2$. In embodiments, each $R^{4A}$ and $R^{4B}$ is independently —$CH_2X$. In embodiments, each $R^{4A}$ and $R^{4B}$ is independently —$CH_3$. In embodiments, each $R^{4A}$ and $R^{4B}$ is independently —$CH_2CH_3$.

In embodiments, each $R^{4A}$ and $R^{4B}$ is independently hydrogen, —$CX_3$, —CN, —COOH, —$CONH_2$, —$CHX_2$, —$CH_2X$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^{4A}$ and $R^{4B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^{4A}$ and $R^{4B}$ substituents bonded to the same nitrogen atom may optionally be joined to independently form an unsubstituted heterocycloalkyl (e.g., 3 to 10 membered, 3 to 8 membered, 3 to 6 membered, 4 to 6 membered, 4 to 5 membered, or 5 to 6 membered) or unsubstituted heteroaryl (e.g., 5 to 12 membered, 5 to 10 membered, 5 to 9 membered, or 5 to 6 membered).

In embodiments, $L^4$-$R^5$ has the formula:

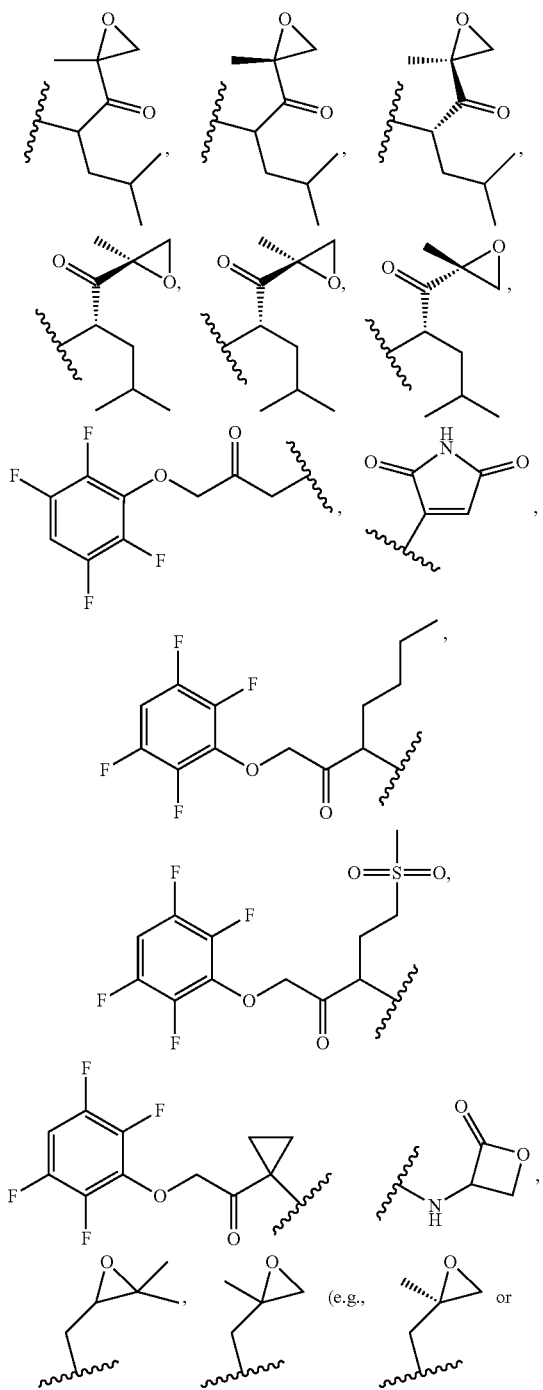

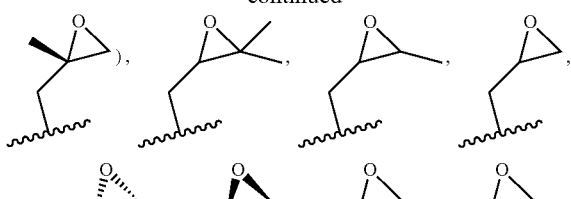
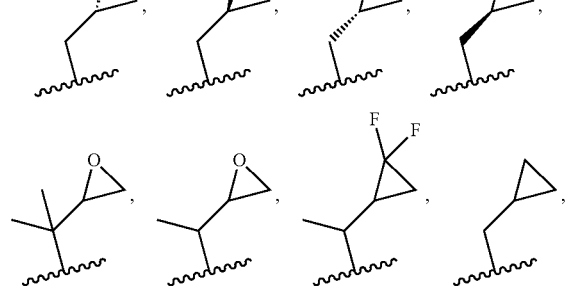
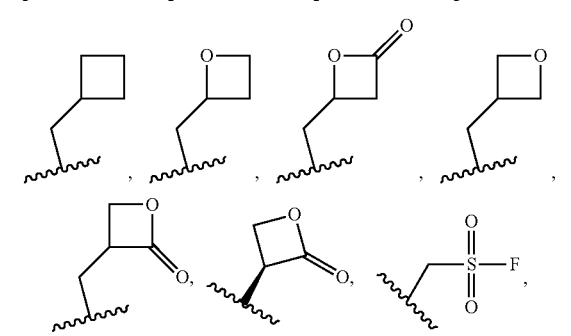
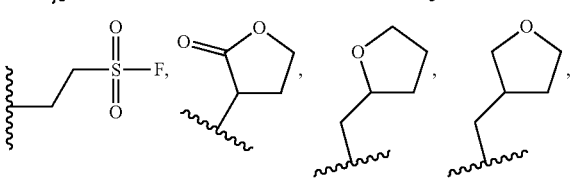
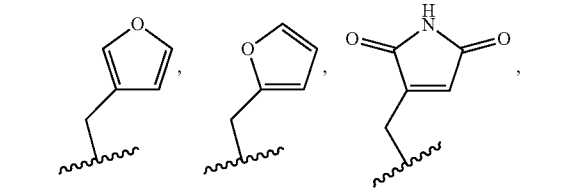
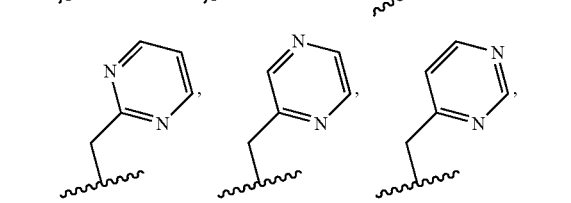
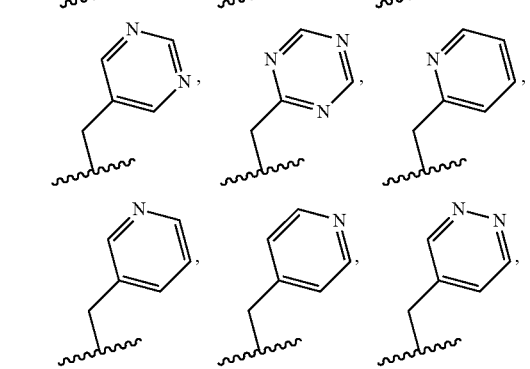
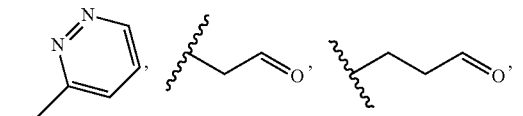
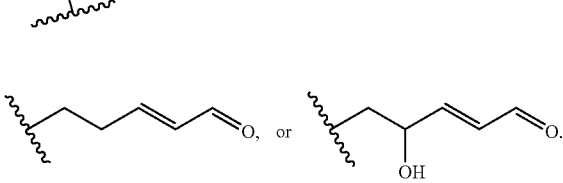
In embodiment, $L^4$-$R^5$ has the formula:
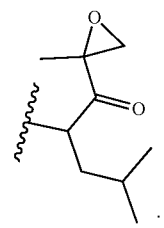 [SMILES: *C(CC(C)C)C(=O)C1(C)CO1]
In embodiment, $L^4$-$R^5$ has the formula:
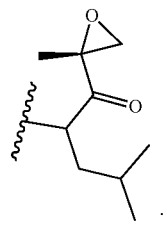 [SMILES: *C(CC(C)C)C(=O)[C@@]1(C)CO1]
In embodiment, $L^4$-$R^5$ has the formula:
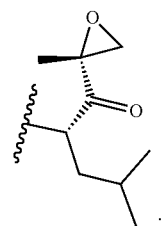 [SMILES: *[C@@H](CC(C)C)C(=O)[C@@]1(C)CO1]
In embodiment, $L^4$-$R^5$ has the formula:
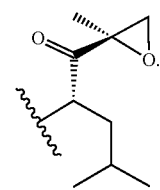

In embodiment, $L^4$-$R^5$ has the formula:

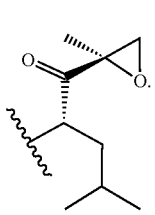 [SMILES: *[C@@H](CC(C)C)C(=O)[C@@]1(C)CO1]

In embodiment, $L^4$-$R^5$ has the formula:

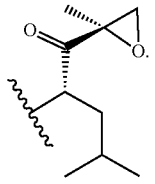 [SMILES: *[C@@H](CC(C)C)C(=O)[C@@]1(C)CO1]

In embodiment, $L^4$-$R^5$ has the formula:

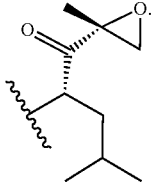 [SMILES: *[C@@H](CC(C)C)C(=O)[C@@]1(C)CO1]

In embodiment, $L^4$-$R^5$ has the formula:

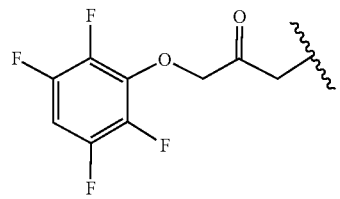

In embodiment, $L^4$-$R^5$ has the formula:

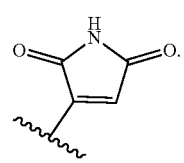 [SMILES: *C1=CC(=O)NC1=O]

In embodiment, $L^4$-$R^5$ has the formula:

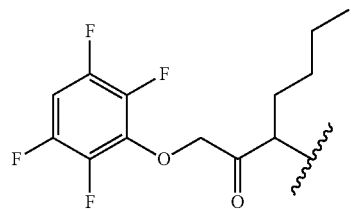

In embodiment, $L^4$-$R^5$ has the formula:

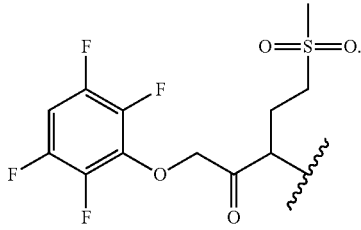 [SMILES: *C(CCS(C)(=O)=O)C(=O)COc1c(F)c(F)cc(F)c1F]

In embodiment, $L^4$-$R^5$ has the formula:

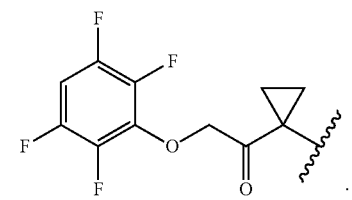 [SMILES: *C1(C(=O)COc2c(F)c(F)cc(F)c2F)CC1]

In embodiment, $L^4$-$R^5$ has the formula:

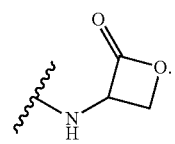

In embodiment, $L^4$-$R^5$ has the formula:

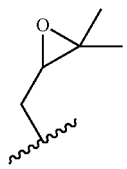

In embodiment, $L^4$-$R^5$ has the formula:

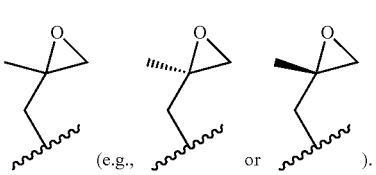

In embodiment, $L^4$-$R^5$ has the formula:

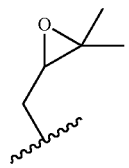

In embodiment, $L^4$-$R^5$ has the formula:

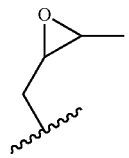

In embodiment, $L^4$-$R^5$ has the formula:

In embodiment, $L^4$-$R^5$ has the formula:


In embodiment, $L^4$-$R^5$ has the formula:

In embodiment, $L^4$-$R^5$ has the formula:

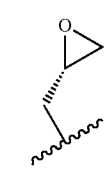

In embodiment, $L^4$-$R^5$ has the formula:

In embodiment, $L^4$-$R^5$ has the formula:

In embodiment, $L^4$-$R^5$ has the formula:

In embodiment, $L^4$-$R^5$ has the formula:

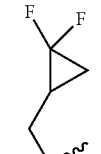

In embodiment, $L^4$-$R^5$ has the formula:

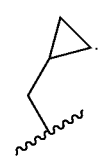

In embodiment, $L^4$-$R^5$ has the formula:

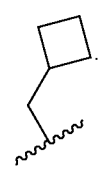

In embodiment, $L^4$-$R^5$ has the formula:

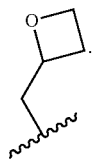

In embodiment, $L^4$-$R^5$ has the formula:

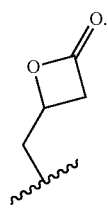 [SMILES: *CC1CC(=O)O1]

In embodiment, $L^4$-$R^5$ has the formula:

In embodiment, $L^4$-$R^5$ has the formula:

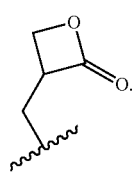 [SMILES: *CC1COC1=O]

In embodiment, $L^4$-$R^5$ has the formula:

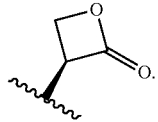 [SMILES: *[C@H]1COC1=O]

In embodiment, $L^4$-$R^5$ has the formula:

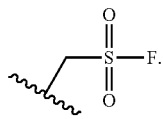 [SMILES: *CS(=O)(=O)F]

In embodiment, $L^4$-$R^5$ has the formula:

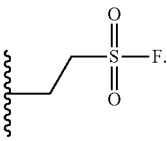

In embodiment, $L^4$-$R^5$ has the formula:

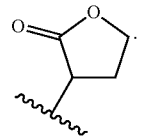 [SMILES: *C1CCOC1=O]

In embodiment, $L^4$-$R^5$ has the formula:

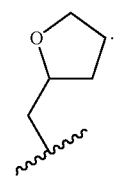 [SMILES: *CC1CCCO1]

In embodiment, $L^4$-$R^5$ has the formula:

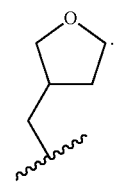 [SMILES: *CC1CCOC1]

In embodiment, $L^4$-$R^5$ has the formula:

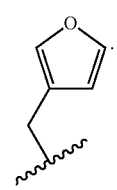 [SMILES: *Cc1ccoc1]

In embodiment, $L^4$-$R^5$ has the formula:


In embodiment, L⁴-R⁵ has the formula:

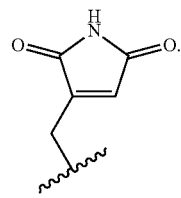 [SMILES: *CC1=CC(=O)NC1=O]

In embodiment L⁴-R⁵ has the formula:

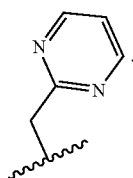

In embodiment, L⁴-R⁵ has the formula:

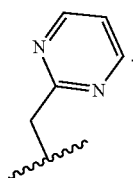

In embodiment, L⁴-R⁵ has the formula:

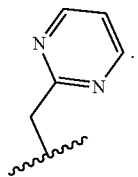 [SMILES: *Cc1ncccn1]

In embodiment, L⁴-R⁵ has the formula:

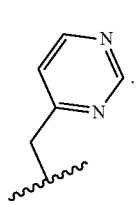 [SMILES: *Cc1ccncn1]

In embodiment, L⁴-R⁵ has the formula:

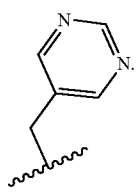 [SMILES: *Cc1cncnc1]

In embodiment, L⁴-R⁵ has the formula:

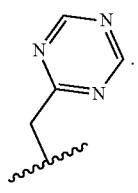 [SMILES: *Cc1ncncn1]

In embodiment, L⁴-R⁵ has the formula:

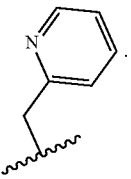 [SMILES: *Cc1ccccn1]

In embodiment, L⁴-R⁵ has the formula:

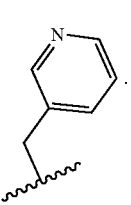 [SMILES: *Cc1cccnc1]

In embodiment, L⁴-R⁵ has the formula:

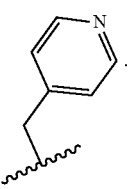 [SMILES: *Cc1ccncc1]

In embodiment, L⁴-R⁵ has the formula:

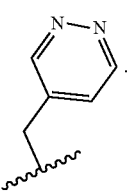 [SMILES: *Cc1ccnnc1]

In embodiment, L⁴-R⁵ has the formula:

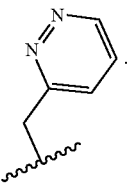 [SMILES: *Cc1cccnn1]

In embodiment, L⁴-R⁵ has the formula:

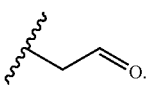 [SMILES: *CC=O]

In embodiment, $L^4$-$R^5$ has the formula:
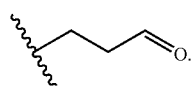
In embodiment, $L^4$-$R^5$ has the formula:
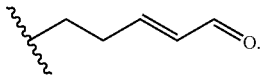 [SMILES: *CC/C=C/C=O]
In embodiment, $L^4$-$R^5$ has the formula:
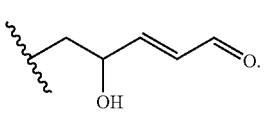 [SMILES: *CC(O)/C=C/C=O]
In embodiment, $L^4$-$R^5$ has the formula:
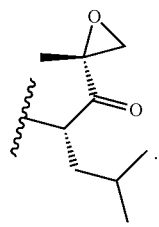 [SMILES: *[C@@H](CC(C)C)C(=O)[C@@]1(C)CO1]
In embodiments, $L^3$-$L^4$-$R^5$ has the formula:
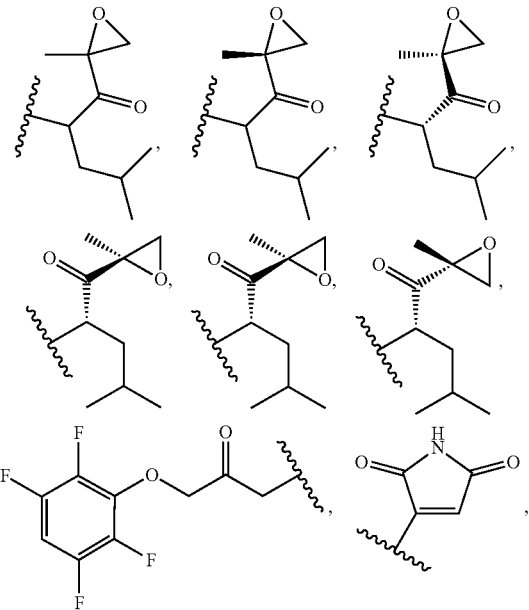
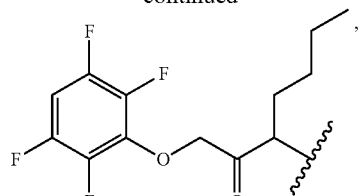
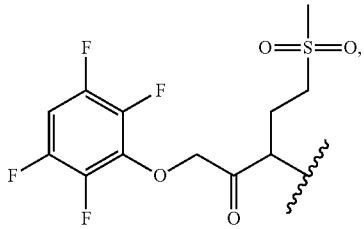
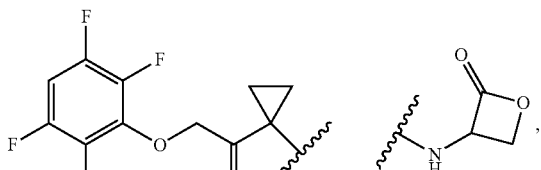
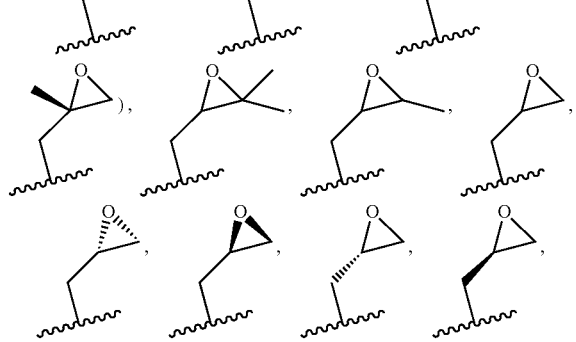
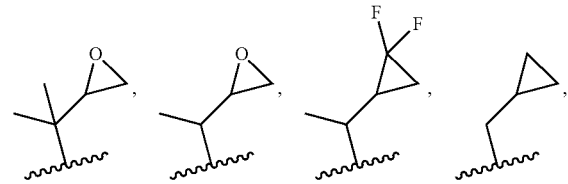
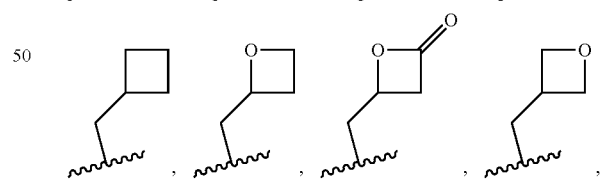
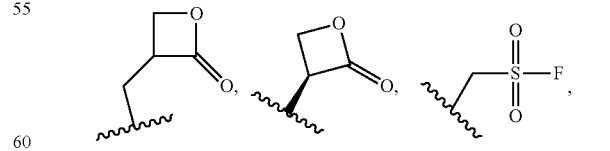
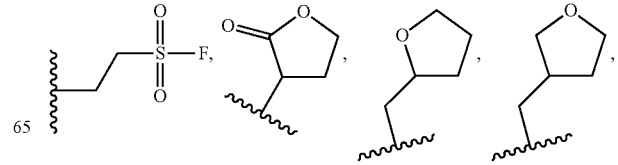

-continued
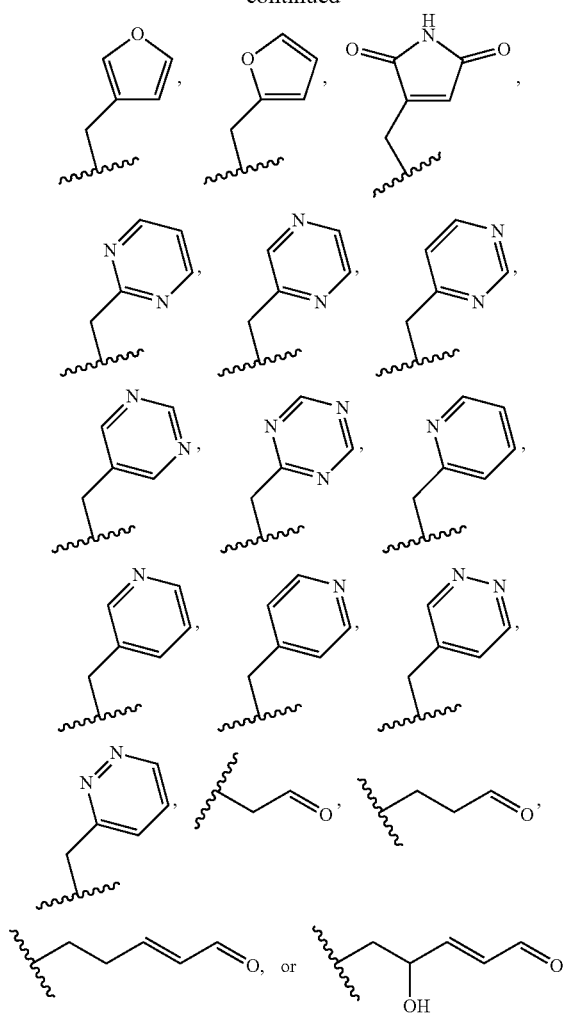
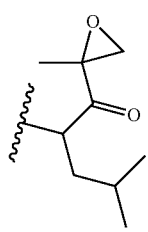
In embodiment, $L^3$-$L^4$-$R^5$ has the formula:
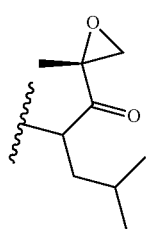
In embodiment, $L^3$-$L^4$-$R^5$ has the formula:
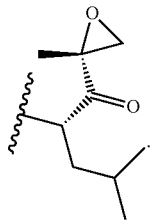 [SMILES: *[C@@H](CC(C)C)C(=O)[C@@]1(C)CO1]
In embodiment, $L^3$-$L^4$-$R^5$ has the formula:
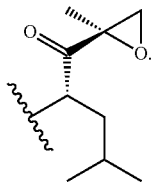 [SMILES: *[C@@H](CC(C)C)C(=O)[C@@]1(C)CO1]
In embodiment, $L^3$-$L^4$-$R^5$ has the formula:
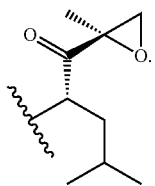 [SMILES: *[C@@H](CC(C)C)C(=O)[C@@]1(C)CO1]
In embodiment, $L^3$-$L^4$-$R^5$ has the formula:
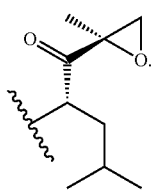 [SMILES: *[C@@H](CC(C)C)C(=O)[C@@]1(C)CO1]
In embodiment, $L^3$-$L^4$-$R^5$ has the formula:
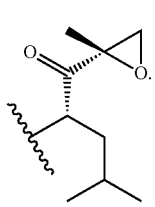 [SMILES: *[C@@H](CC(C)C)C(=O)[C@]1(C)CO1]
In embodiment, $L^3$-$L^4$-$R^5$ has the formula:
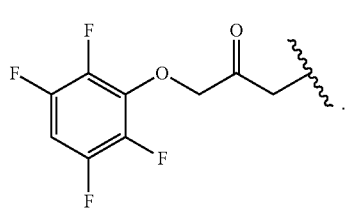 [SMILES: *CC(=O)COc1c(F)c(F)cc(F)c1F]

In embodiment $L^3$-$L^4$-$R^5$ has the formula:

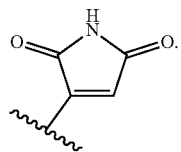 [SMILES: *C1=CC(=O)NC1=O]

In embodiment, $L^3$-$L^4$-$R^5$ has the formula:

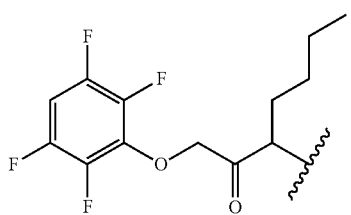

In embodiment, $L^3$-$L^4$-$R^5$ has the formula:

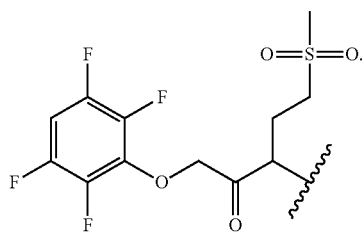 [SMILES: *C(CCS(C)(=O)=O)C(=O)COc1c(F)c(F)cc(F)c1F]

In embodiment, $L^3$-$L^4$-$R^5$ has the formula:

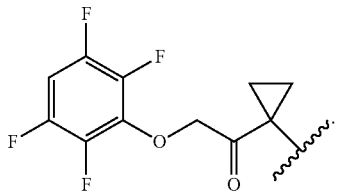 [SMILES: *C1(C(=O)COc2c(F)c(F)cc(F)c2F)CC1]

In embodiment, $L^3$-$L^4$-$R^5$ has the formula:

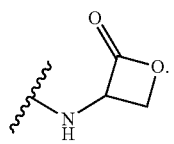 [SMILES: *NC1COC1=O]

In embodiment, $L^3$-$L^4$-$R^5$ has the formula:

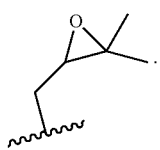

In embodiment, $L^3$-$L^4$-$R^5$ has the formula:

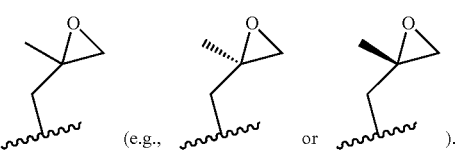

In embodiment, $L^3$-$L^4$-$R^5$ has the formula:

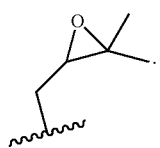 [SMILES: *CC1OC1(C)C]

In embodiment, $L^3$-$L^4$-$R^5$ has the formula:

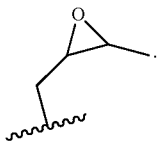 [SMILES: *CC1OC1C]

In embodiment, $L^3$-$L^4$-$R^5$ has the formula:

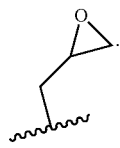 [SMILES: *CC1CO1]

In embodiment, $L^3$-$L^4$-$R^5$ has the formula:

In embodiment, $L^3$-$L^4$-$R^5$ has the formula:

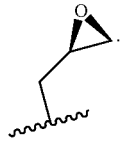

In embodiment, $L^3$-$L^4$-$R^5$ has the formula:

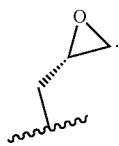 [SMILES: *C[C@H]1CO1]

In embodiment, $L^3$-$L^4$-$R^5$ has the formula:

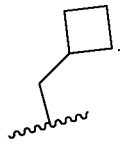

In embodiment, $L^3$-$L^4$-$R^5$ has the formula:

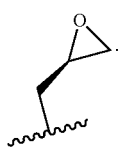 [SMILES: *C[C@@H]1CO1]

In embodiment, $L^3$-$L^4$-$R^5$ has the formula:

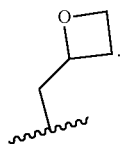

In embodiment, $L^3$-$L^4$-$R^5$ has the formula:

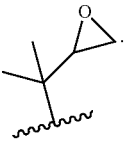 [SMILES: *C(C)(C)C1CO1]

In embodiment, $L^3$-$L^4$-$R^5$ has the formula:

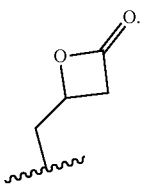 [SMILES: *CC1CC(=O)O1]

In embodiment, $L^3$-$L^4$-$R^5$ has the formula:

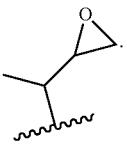

In embodiment, $L^3$-$L^4$-$R^5$ has the formula:

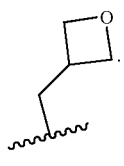 [SMILES: *CC1COC1]

In embodiment, $L^3$-$L^4$-$R^5$ has the formula:

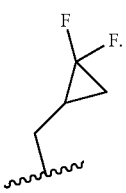

In embodiment, $L^3$-$L^4$-$R^5$ has the formula:

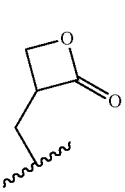

In embodiment, $L^3$-$L^4$-$R^5$ has the formula:

In embodiment, $L^3$-$L^4$-$R^5$ has the formula:

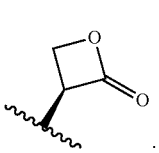 [SMILES: *[C@H]1COC1=O]

In embodiment, $L^3$-$L^4$-$R^5$ has the formula:

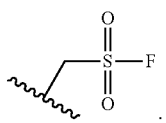 [SMILES: *CS(=O)(=O)F]

In embodiment, $L^3$-$L^4$-$R^5$ has the formula:

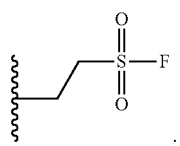

In embodiment, $L^3$-$L^4$-$R^5$ has the formula:

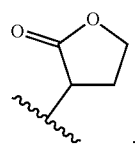

In embodiment, $L^3$-$L^4$-$R^5$ has the formula:

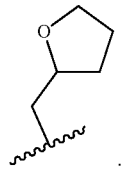

In embodiment, $L^3$-$L^4$-$R^5$ has the formula:

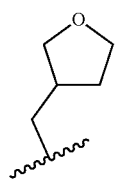

In embodiment, $L^3$-$L^4$-$R^5$ has the formula:

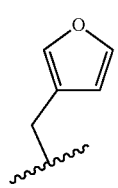

In embodiment, $L^3$-$L^4$-$R^5$ has the formula:

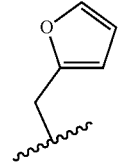

In embodiment, $L^3$-$L^4$-$R^5$ has the formula:

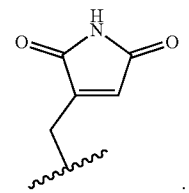 [SMILES: *CC1=CC(=O)NC1=O]

In embodiment, $L^3$-$L^4$-$R^5$ has the formula:

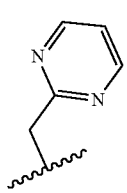

In embodiment, $L^3$-$L^4$-$R^5$ has the formula:

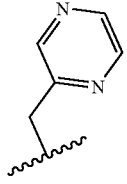

In embodiment, $L^3$-$L^4$-$R^5$ has the formula:

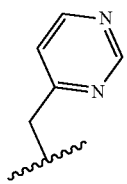

In embodiment $L^3$-$L^4$-$R^5$ has the formula:

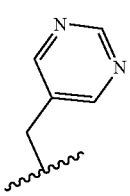

In embodiment, $L^3$-$L^4$-$R^5$ has the formula:

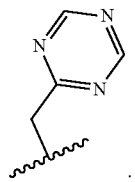 [SMILES: *Cc1ncncn1]

In embodiment, $L^3$-$L^4$-$R^5$ has the formula:

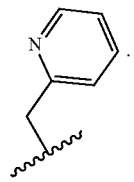

In embodiment, $L^3$-$L^4$-$R^5$ has the formula:

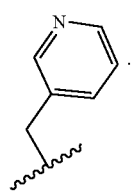 [SMILES: *Cc1cccnc1]

In embodiment, $L^3$-$L^4$-$R^5$ has the formula:

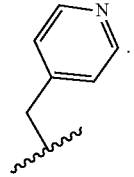

In embodiment, $L^3$-$L^4$-$R^5$ has the formula:

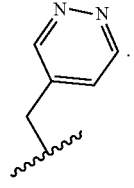 [SMILES: *Cc1ccnnc1]

In embodiment, $L^3$-$L^4$-$R^5$ has the formula:

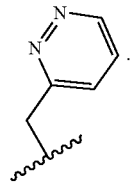

In embodiment, $L^3$-$L^4$-$R^5$ has the formula:

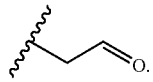 [SMILES: *CC=O]

In embodiment, $L^3$-$L^1$-$R^5$ has the formula:

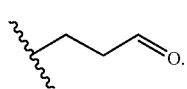 [SMILES: *CCC=O]

In embodiment, $L^3$-$L^4$-$R^5$ has the formula:

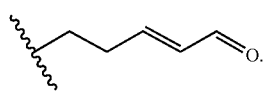 [SMILES: *CC/C=C/C=O]

In embodiment, $L^3$-$L^4$-$R^5$ has the formula:

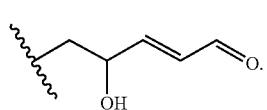 [SMILES: *CC(O)/C=C/C=O]

In embodiment, $L^3$-$L^4$-$R^5$ has the formula:

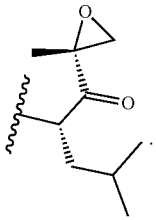 [SMILES: *[C@@H](CC(C)C)C(=O)[C@@]1(C)CO1]

In embodiments, $R^5$ is independently hydrogen, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered), or E.

In embodiments, $R^5$ is independently hydrogen, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, $R^5$ is independently substituted (e.g., substituted with a substituent group, a size-limited substituent group, or lower substituent group) or unsubstituted $C_1$-$C_6$ alkyl, substituted (e.g., substituted with a substituent group, a size-limited substituent group, or lower substituent group) or unsubstituted 2 to 6 membered heteroalkyl, substituted (e.g., substituted with a substituent group, a size-limited substituent group, or lower substituent group) or unsubstituted $C_3$-$C_6$ cycloalkyl, substituted (e.g., substituted with a substituent group, a size-limited substituent group, or lower substituent group) or unsubstituted 3 to 6 membered heterocycloalkyl, substituted (e.g., substituted with a substituent group, a size-limited substituent group, or lower substituent group) or unsubstituted phenyl, or substituted (e.g., substituted with a substituent group, a size-limited substituent group, or lower substituent group) or unsubstituted 5 to 6 membered heteroaryl.

In embodiments, $R^5$ is independently substituted (e.g., substituted with a substituent group, a size-limited substituent group, or lower substituent group) or unsubstituted 3 to 6 membered heterocycloalkyl or substituted (e.g., substituted with a substituent group, a size-limited substituent group, or lower substituent group) or unsubstituted 5 to 6 membered heteroaryl.

In embodiments, $R^5$ is independently 3 to 6 membered heterocycloalkyl or 5 to 6 membered heteroaryl; optionally substituted with one or more independent substituent groups, size-limited substituent groups, or lower substituent groups.

In embodiments, $R^5$ is substituted (e.g., substituted with a substituent group, a size-limited substituent group, or lower substituent group) or unsubstituted alkyl. In embodiments, $R^5$ is substituted (e.g., substituted with a substituent group, a size-limited substituent group, or lower substituent group) alkyl. In embodiments, $R^5$ is unsubstituted alkyl. In embodiments, $R^5$ is substituted or unsubstituted alkyl (e.g., $C_1$-$C_8$, $C_1$-$C_6$, $C_1$-$C_4$, or $C_1$-$C_2$). In embodiments, $R^5$ is substituted alkyl (e.g., $C_1$-$C_8$, $C_1$-$C_6$, $C_1$-$C_4$, or $C_1$-$C_2$). In embodiments, $R^5$ is unsubstituted alkyl (e.g., $C_1$-$C_8$, $C_1$-$C_6$, $C_1$-$C_4$, or $C_1$-$C_2$).

In embodiments, $R^5$ is substituted (e.g., substituted with a substituent group, a size-limited substituent group, or lower substituent group) or unsubstituted heteroalkyl. In embodiments, $R^5$ is substituted (e.g., substituted with a substituent group, a size-limited substituent group, or lower substituent group) heteroalkyl. In embodiments, $R^5$ is unsubstituted heteroalkyl. In embodiments, $R^5$ is substituted or unsubstituted heteroalkyl (e.g., 2 to 8 membered, 2 to 6 membered, 4 to 6 membered, 2 to 3 membered, or 4 to 5 membered). In embodiments, $R^5$ is substituted heteroalkyl (e.g., 2 to 8 membered, 2 to 6 membered, 4 to 6 membered, 2 to 3 membered, or 4 to 5 membered). In embodiments, $R^5$ is an unsubstituted heteroalkyl (e.g., 2 to 8 membered, 2 to 6 membered, 4 to 6 membered, 2 to 3 membered, or 4 to 5 membered).

In embodiments, $R^5$ is substituted (e.g., substituted with a substituent group, a size-limited substituent group, or lower substituent group) or unsubstituted cycloalkyl. In embodiments, $R^5$ is substituted (e.g., substituted with a substituent group, a size-limited substituent group, or lower substituent group) cycloalkyl. In embodiments, $R^5$ is an unsubstituted cycloalkyl. In embodiments, $R^5$ is substituted or unsubstituted cycloalkyl (e.g., $C_3$-$C_8$, $C_3$-$C_6$, $C_4$-$C_6$, or $C_5$-$C_6$). In embodiments, $R^5$ is substituted cycloalkyl (e.g., $C_3$-$C_8$, $C_3$-$C_6$, $C_4$-$C_6$, or $C_5$-$C_6$). In embodiments, $R^5$ is unsubstituted cycloalkyl (e.g., $C_3$-$C_8$, $C_3$-$C_6$, $C_4$-$C_6$, or $C_5$-$C_6$).

In embodiments, $R^5$ is substituted (e.g., substituted with a substituent group, a size-limited substituent group, or lower substituent group) or unsubstituted heterocycloalkyl. In embodiments, $R^5$ is substituted (e.g., substituted with a substituent group, a size-limited substituent group, or lower substituent group) heterocycloalkyl. In embodiments, $R^5$ is an unsubstituted heterocycloalkyl. In embodiments, $R^5$ is substituted or unsubstituted heterocycloalkyl (e.g., 3 to 8 membered, 3 to 6 membered, 4 to 6 membered, 4 to 5 membered, or 5 to 6 membered). In embodiments, $R^5$ is substituted heterocycloalkyl (e.g., 3 to 8 membered, 3 to 6 membered, 4 to 6 membered, 4 to 5 membered, or 5 to 6 membered). In embodiments, $R^5$ an unsubstituted heterocycloalkyl (e.g., 3 to 8 membered, 3 to 6 membered, 4 to 6 membered, 4 to 5 membered, or 5 to 6 membered).

In embodiments, $R^5$ is substituted (e.g., substituted with a substituent group, a size-limited substituent group, or lower substituent group) or unsubstituted aryl. In embodiments, $R^5$ is substituted (e.g., substituted with a substituent group, a size-limited substituent group, or lower substituent group) aryl. In embodiments, $R^5$ is an unsubstituted aryl. In embodiments, $R^5$ is substituted or unsubstituted aryl (e.g., $C_6$-$C_{10}$ or phenyl). In embodiments, $R^5$ is substituted aryl (e.g., $C_6$-$C_{10}$ or phenyl). In embodiments, $R^5$ is an unsubstituted aryl (e.g., $C_6$-$C_{10}$ or phenyl).

In embodiments, $R^5$ is substituted (e.g., substituted with a substituent group, a size-limited substituent group, or lower substituent group) or unsubstituted heteroaryl. In embodiments, $R^5$ is substituted (e.g., substituted with a substituent group, a size-limited substituent group, or lower substituent group) heteroaryl. In embodiments, $R^5$ is an unsubstituted heteroaryl. In embodiments, $R^5$ is substituted or unsubstituted heteroaryl (e.g., 5 to 10 membered, 5 to 9 membered, or 5 to 6 membered). In embodiments, $R^5$ is substituted heteroaryl (e.g., 5 to 10 membered, 5 to 9 membered, or 5 to 6 membered). In embodiments, $R^5$ is an unsubstituted heteroaryl (e.g., 5 to 10 membered, 5 to 9 membered, or 5 to 6 membered).

In embodiments, $R^5$ is independently $R^{13}$-substituted or unsubstituted alkyl (e.g., $C_1$-$C_8$ alkyl, $C_1$-$C_6$ alkyl, or $C_1$-$C_4$ alkyl), $R^{13}$-substituted or unsubstituted heteroalkyl (e.g., 2 to 8 membered heteroalkyl, 2 to 6 membered heteroalkyl, or 2 to 4 membered heteroalkyl), $R^{13}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{13}$-substituted or unsubstituted heterocycloalkyl (e.g., 3 to 8 membered heterocycloalkyl, 3 to 6 membered heterocycloalkyl, or 5 to 6 membered heterocycloalkyl), $R^{13}$-substituted or unsubstituted aryl (e.g., $C_6$-$C_{10}$ aryl, $C_{10}$ aryl, or phenyl), or $R^{13}$-substituted or unsubstituted heteroaryl (e.g., 5 to 10 membered heteroaryl, 5 to 9 membered heteroaryl, or 5 to 6 membered heteroaryl).

In embodiments, $R^5$ is $R^{13}$-substituted or unsubstituted alkyl (e.g., $C_1$-$C_8$ alkyl, $C_1$-$C_6$ alkyl, or $C_1$-$C_4$ alkyl). In embodiments, $R^5$ is $R^{13}$-substituted alkyl (e.g., $C_1$-$C_8$ alkyl, $C_1$-$C_6$ alkyl, or $C_1$-$C_4$ alkyl). In embodiments, $R^5$ is an unsubstituted alkyl (e.g., $C_1$-$C_8$ alkyl, $C_1$-$C_6$ alkyl, or $C_1$-$C_4$ alkyl).

In embodiments, $R^5$ is $R^{13}$-substituted or unsubstituted heteroalkyl (e.g., 2 to 8 membered heteroalkyl, 2 to 6 membered heteroalkyl, or 2 to 4 membered heteroalkyl). In embodiments, $R^5$ is $R^{13}$-substituted heteroalkyl (e.g., 2 to 8 membered heteroalkyl, 2 to 6 membered heteroalkyl, or 2 to 4 membered heteroalkyl). In embodiments, $R^5$ is an unsubstituted heteroalkyl (e.g., 2 to 8 membered heteroalkyl, 2 to 6 membered heteroalkyl, or 2 to 4 membered heteroalkyl).

In embodiments, $R^5$ is $R^{13}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is $R^{13}$-substituted cycloalkyl (e.g., $C_3$-$C_8$ cycloalkyl, $C_3$-$C_6$ cycloalkyl, or $C_5$-$C_6$ cycloalkyl). In embodiments, $R^5$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^5$ is $R^{13}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is $R^{13}$-substituted heterocycloalkyl (e.g., 3 to 8 membered heterocycloalkyl, 3 to 6 membered heterocycloalkyl, or 5 to 6 membered heterocycloalkyl). In embodiments, $R^5$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^5$ is $R^{13}$-substituted or unsubstituted aryl (e.g., $C_6$-$C_{10}$ aryl, $C_{10}$ aryl, or phenyl). In embodiments, $R^5$ is $R^{13}$-substituted aryl (e.g., $C_6$-$C_{10}$ aryl, $C_{10}$ aryl, or phenyl). In embodiments, $R^5$ is an unsubstituted aryl (e.g., $C_6$-$C_{10}$ aryl, $C_{10}$ aryl, or phenyl).

In embodiments, $R^5$ is $R^{13}$-substituted or unsubstituted heteroaryl (e.g., 5 to 10 membered heteroaryl, 5 to 9 membered heteroaryl, or 5 to 6 membered heteroaryl). In embodiments, $R^5$ is $R^{13}$-substituted heteroaryl (e.g., 5 to 10 membered heteroaryl, 5 to 9 membered heteroaryl, or 5 to 6 membered heteroaryl). In embodiments, $R^5$ is an unsubstituted heteroaryl (e.g., 5 to 10 membered heteroaryl, 5 to 9 membered heteroaryl, or 5 to 6 membered heteroaryl).

$R^{13}$ is independently hydrogen, oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$OR^{14}$, —$S(O)_2R^{14}$, $R^{14}$-substituted or unsubstituted alkyl (e.g., $C_1$-$C_8$ alkyl, $C_1$-$C_6$ alkyl, or $C_1$-$C_4$ alkyl), $R^{14}$-substituted or unsubstituted heteroalkyl (e.g., 2 to 8 membered heteroalkyl, 2 to 6 membered heteroalkyl, or 2 to 4 membered heteroalkyl), $R^{14}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{14}$-substituted or unsubstituted heterocycloalkyl (e.g., 3 to 8 membered heterocycloalkyl, 3 to 6 membered heterocycloalkyl, or 5 to 6 membered heterocycloalkyl), $R^{14}$-substituted or unsubstituted aryl (e.g., $C_6$-$C_{10}$ aryl, $C_{10}$ aryl, or phenyl), or $R^{14}$-substituted or unsubstituted heteroaryl (e.g., 5 to 10 membered heteroaryl, 5 to 9 membered heteroaryl, or 5 to 6 membered heteroaryl). In embodiments, $R^{13}$ is independently oxo, halogen (e.g., —F), unsubstituted methyl, unsubstituted ethyl, unsubstituted propyl, unsubstituted butyl, unsubstituted $C_5$ alkyl, or unsubstituted $C_6$ alkyl. In embodiments, $R^{13}$ is independently oxo. In embodiments, $R^{13}$ is independently halogen (e.g., —F). In embodiments, $R^{13}$ is independently unsubstituted methyl. In embodiments, $R^{13}$ is independently unsubstituted ethyl. In embodiments, $R^{13}$ is independently unsubstituted propyl. In embodiments, $R^{13}$ is independently unsubstituted butyl. In embodiments, $R^{13}$ is independently unsubstituted $C_5$ alkyl. In embodiments, $R^{13}$ is independently unsubstituted $C_6$ alkyl.

$R^{14}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{15}$-substituted or unsubstituted alkyl (e.g., $C_1$-$C_8$ alkyl, $C_1$-$C_6$ alkyl, or $C_1$-$C_4$ alkyl), $R^{15}$-substituted or unsubstituted heteroalkyl (e.g., 2 to 8 membered heteroalkyl, 2 to 6 membered heteroalkyl, or 2 to 4 membered heteroalkyl), $R^{15}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{15}$-substituted or unsubstituted heterocycloalkyl (e.g., 3 to 8 membered heterocycloalkyl, 3 to 6 membered heterocycloalkyl, or 5 to 6 membered heterocycloalkyl), $R^{15}$-substituted or unsubstituted aryl (e.g., $C_6$-$C_{10}$ aryl, $C_{10}$ aryl, or phenyl), or $R^{15}$-substituted or unsubstituted heteroaryl (e.g., 5 to 10 membered heteroaryl, 5 to 9 membered heteroaryl, or 5 to 6 membered heteroaryl).

$R^{15}$ is independently hydrogen, oxo, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^5$ is

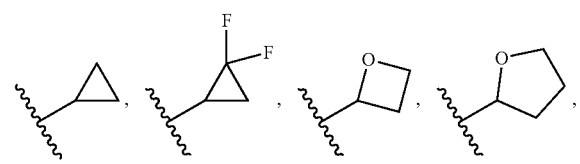

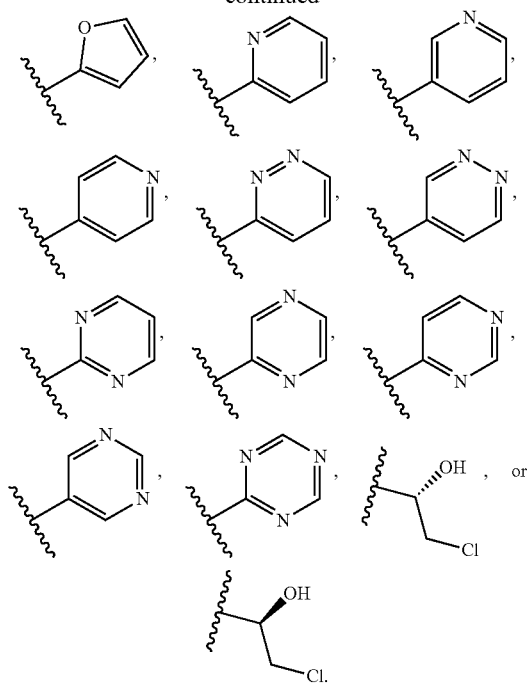
In embodiments, R⁵ is
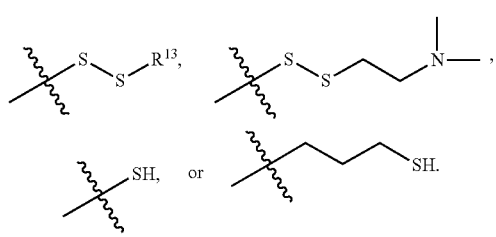
In embodiments, R⁵ is
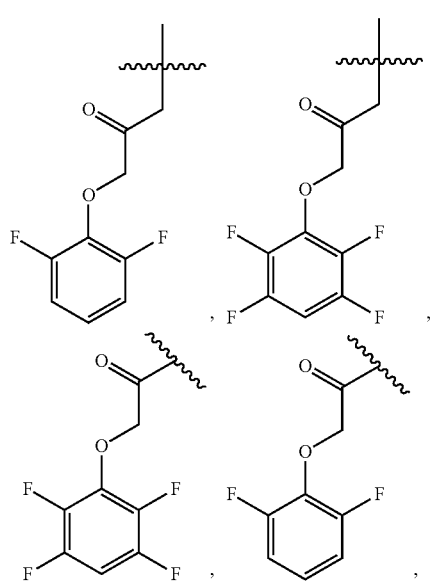
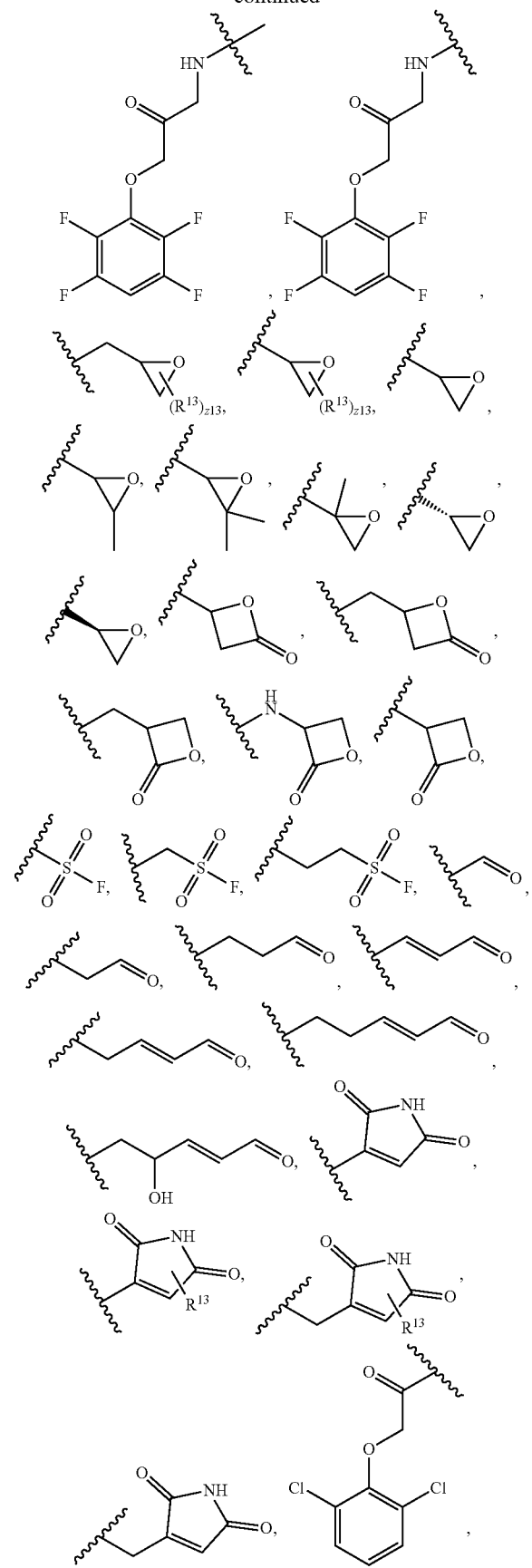

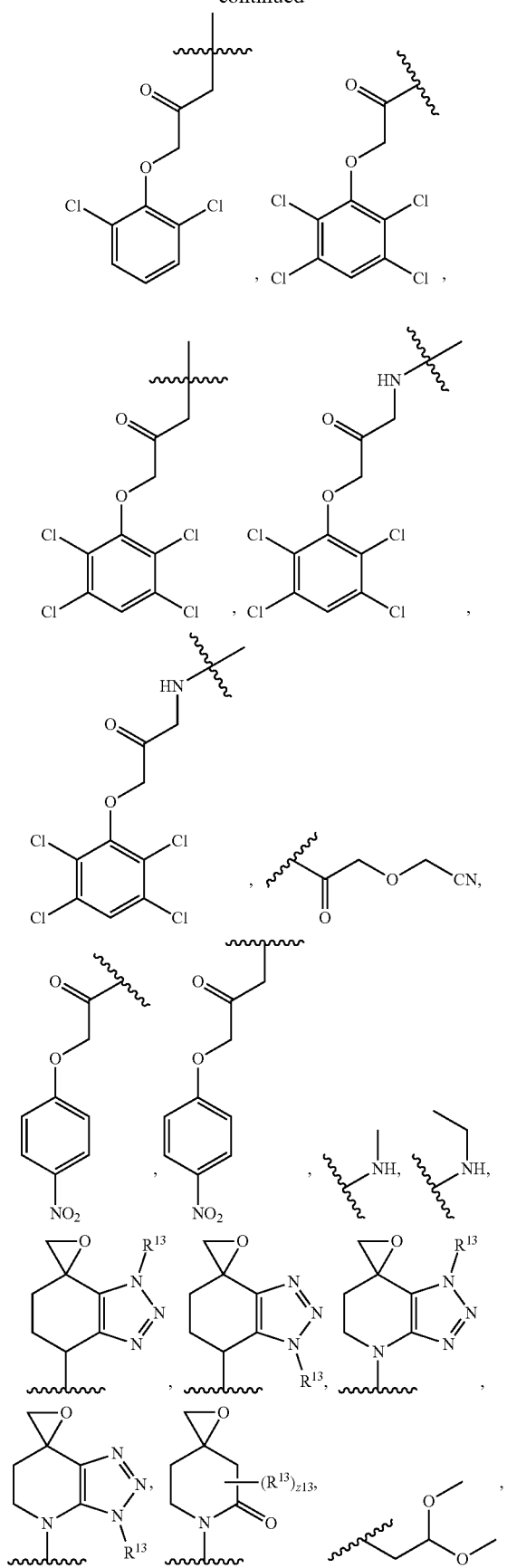
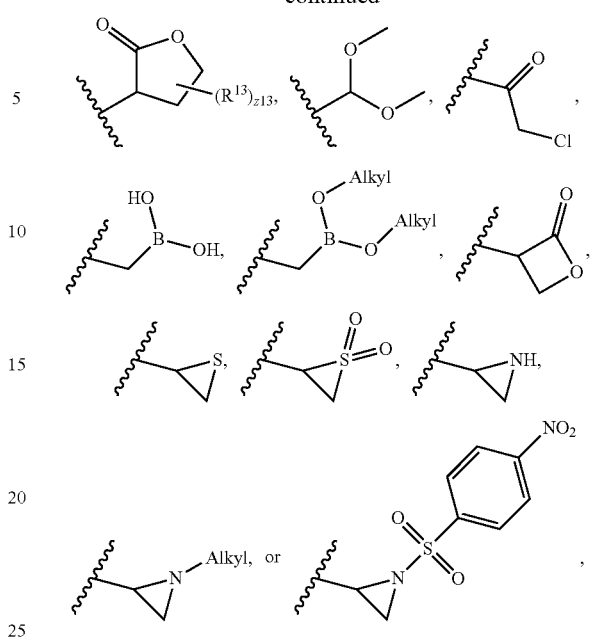
wherein z13 is an integer from 0 to 12. In embodiments, z13 is 0. In embodiments, z13 is 1. In embodiments, z13 is 2.
In embodiments, $R^5$ is
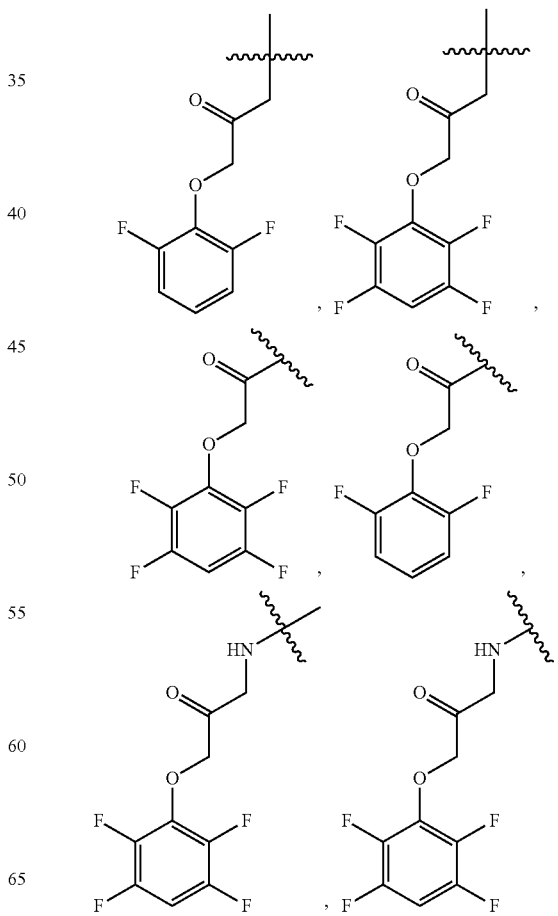

-continued
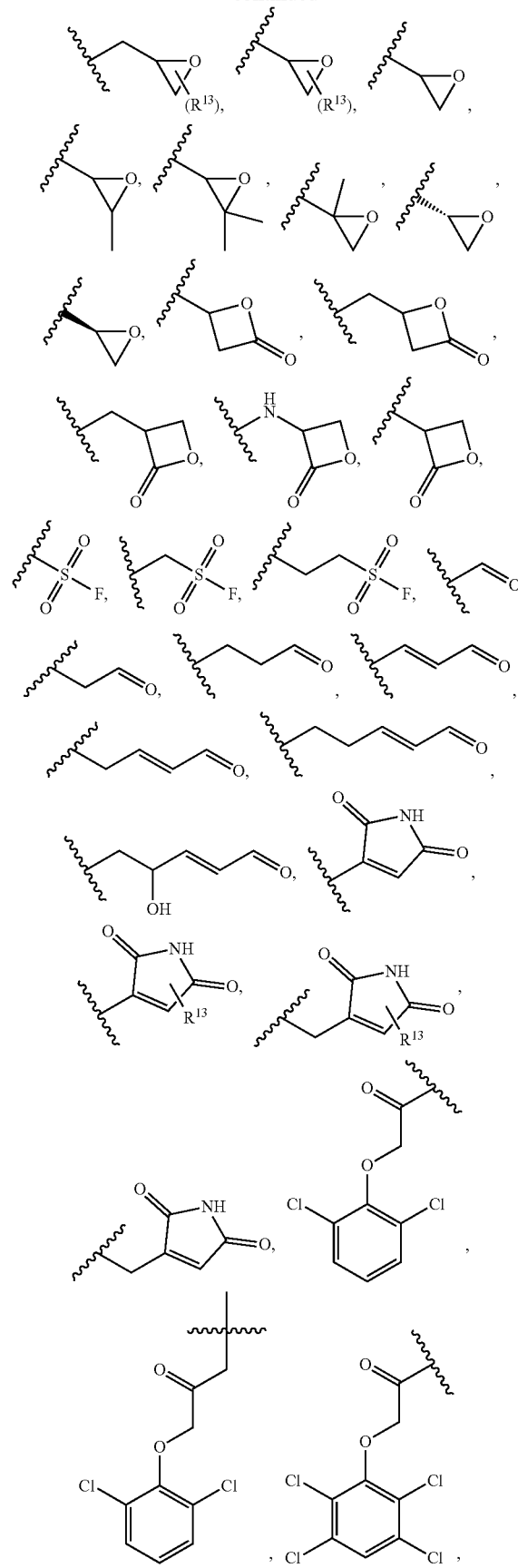
-continued
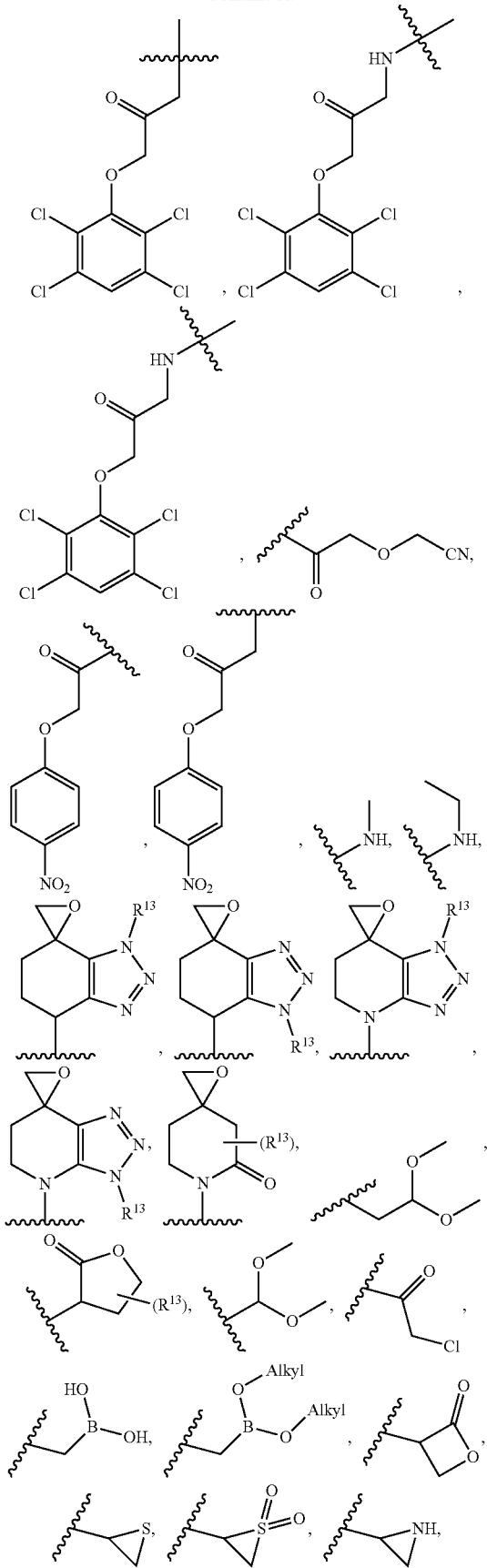

-continued
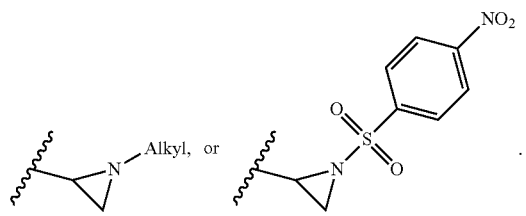 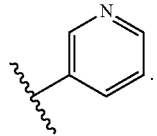
In embodiments, $R^5$ is
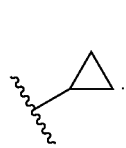
In embodiments, $R^5$ is
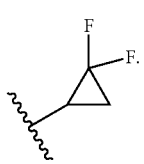 [SMILES: *C1CC1(F)F]
In embodiments, $R^5$ is
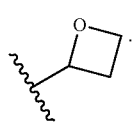
In embodiments, $R^5$ is
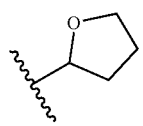
In embodiments, $R^5$ is
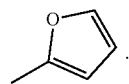
In embodiments, $R^5$ is
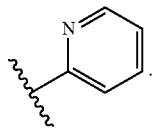
In embodiments, $R^5$ is
In embodiments, $R^5$ is
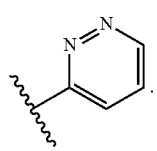
In embodiments, $R^5$ is
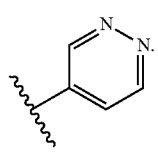 [SMILES: *c1ccnnc1]
In embodiments, $R^5$ is
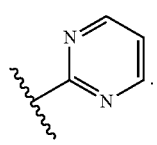
In embodiments, $R^5$ is
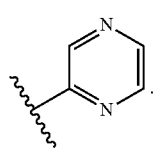
In embodiments, $R^5$ is
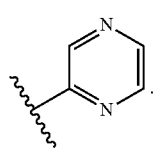
In embodiments, $R^5$ is
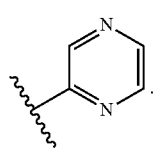

In embodiments, R⁵ is
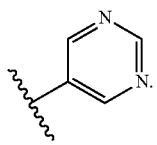 [SMILES: *c1cncnc1]
In embodiments, R⁵ is
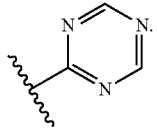
In embodiments, R⁵ is
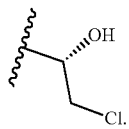
In embodiments, R⁵ is
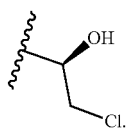 [SMILES: *[C@@H](O)CCl]
In embodiments, R⁵ is
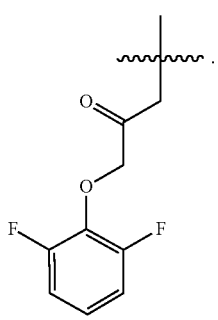
In embodiments, R⁵ is
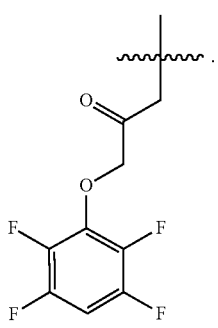 [SMILES: *CC(=O)COc1c(F)c(F)cc(F)c1F]
In embodiments, R⁵ is
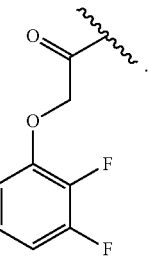
In embodiments, R⁵ is
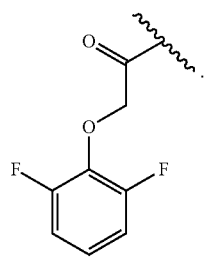
In embodiments, R⁵ is
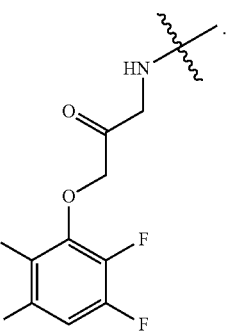
In embodiments, R⁵ is
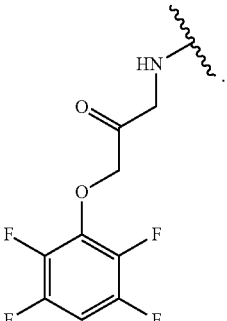
In embodiments, R⁵ is
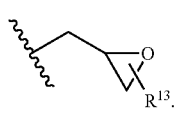

In embodiments, R⁵ is
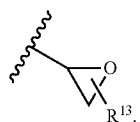
In embodiments, R⁵ is
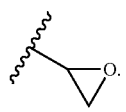 [SMILES: *C1CO1]
In embodiments, R⁵ is
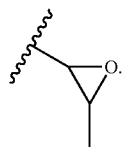
In embodiments, R⁵ is
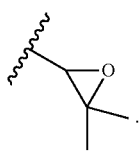 [SMILES: *C1OC1(C)C]
In embodiments, R⁵ is
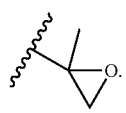
In embodiments, R⁵ is
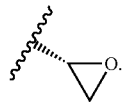
In embodiments, R⁵ is
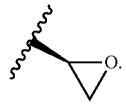
In embodiments, R⁵ is
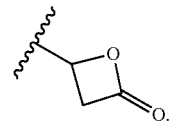 [SMILES: *C1CC(=O)O1]
In embodiments, R⁵ is
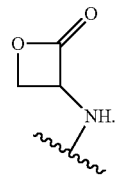
In embodiments, R⁵ is
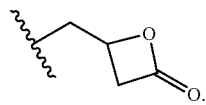 [SMILES: *CC1CC(=O)O1]
In embodiments, R⁵ is
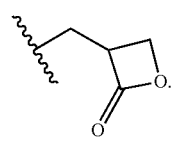 [SMILES: *CC1COC1=O]
In embodiments, R⁵ is
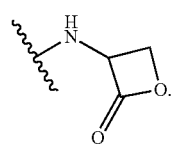 [SMILES: *NC1COC1=O]
In embodiments, R⁵ is
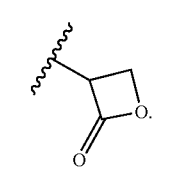 [SMILES: *C1COC1=O]
In embodiments, R⁵ is
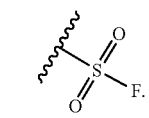

In embodiments, R⁵ is
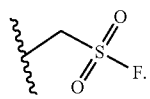
In embodiments, R⁵ is
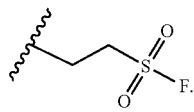
In embodiments, R⁵ is
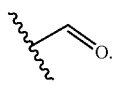
In embodiments, R⁵ is
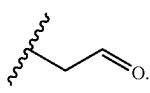 [SMILES: *CC=O]
In embodiments, R⁵ is
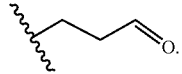
In embodiments, R⁵ is
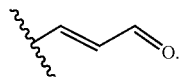 [SMILES: */C=C/C=O]
In embodiments, R⁵ is
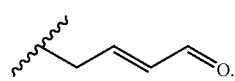 [SMILES: *C/C=C/C=O]
In embodiments, R⁵ is
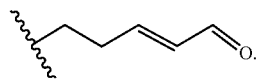 [SMILES: *CC/C=C/C=O]
In embodiments, R⁵ is
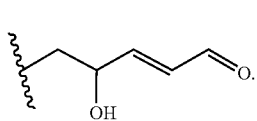 [SMILES: *CC(O)/C=C/C=O]
In embodiments, R⁵ is
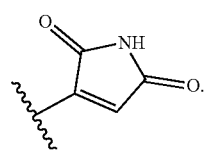 [SMILES: *C1=CC(=O)NC1=O]
In embodiments, R⁵ is
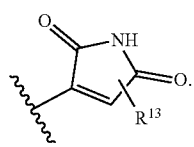
In embodiments, R⁵ is
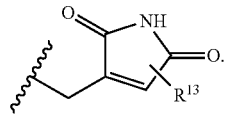
In embodiments, R⁵ is
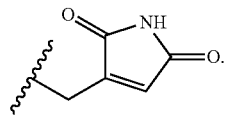 [SMILES: *CC1=CC(=O)NC1=O]
In embodiments, R⁵ is
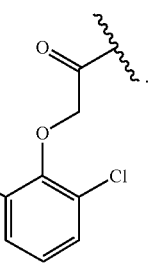

In embodiments, $R^5$ is
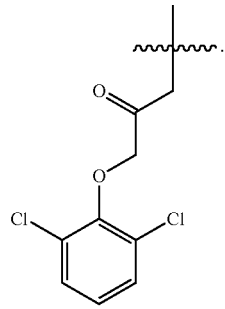 [SMILES: *CC(=O)COc1c(Cl)cccc1Cl]
In embodiments, $R^5$ is
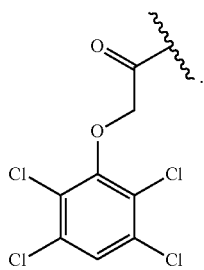 [SMILES: *C(=O)COc1c(Cl)c(Cl)cc(Cl)c1Cl]
In embodiments, $R^5$ is
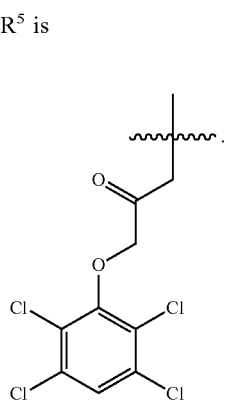
In embodiments, $R^5$ is
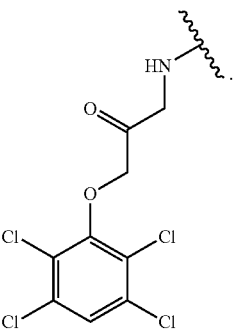 [SMILES: *NCC(=O)COc1c(Cl)c(Cl)cc(Cl)c1Cl]
In embodiments, $R^5$ is
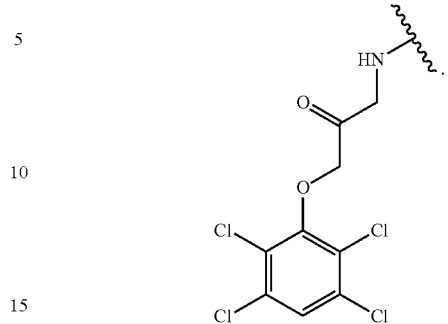
In embodiments, $R^5$ is
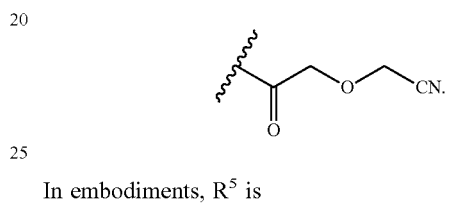
In embodiments, $R^5$ is
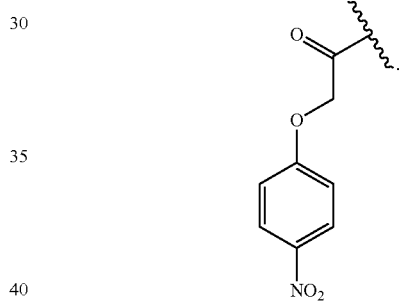
In embodiments, $R^5$ is
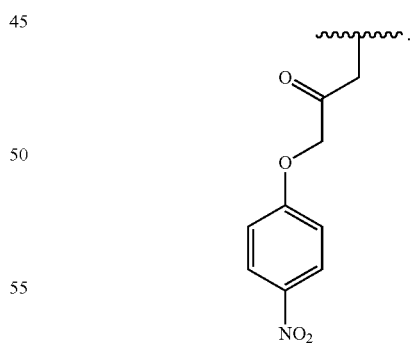
In embodiments, $R^5$ is

In embodiments, R⁵ is
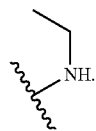
In embodiments, R⁵ is
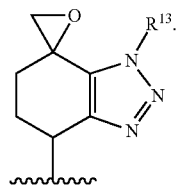
In embodiments, R⁵ is
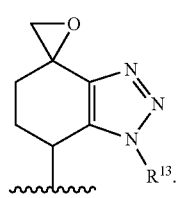
In embodiments, R⁵ is
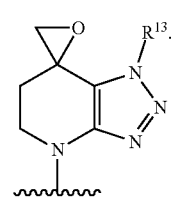
In embodiments, R⁵ is
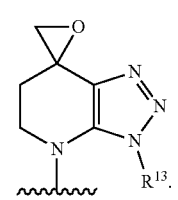
In embodiments, R⁵ is
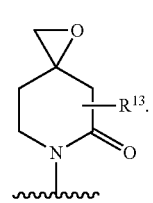
In embodiments, R⁵ is
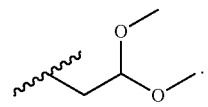 [SMILES: *CC(OC)OC]
In embodiments, R⁵ is
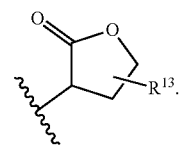
In embodiments, R⁵ is
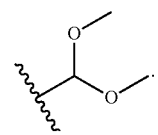 [SMILES: *C(OC)OC]
In embodiments, R⁵ is
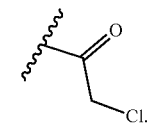 [SMILES: *C(=O)CCl]
In embodiments, R⁵ is
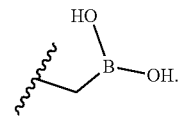
In embodiments, R⁵ is
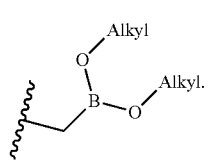
In embodiments, R⁵ is
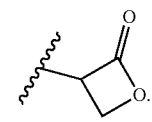

In embodiments, R⁵ is
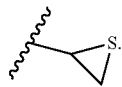
In embodiments, R⁵ is
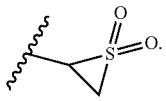 [SMILES: *C1CS1(=O)=O]
In embodiments, R⁵ is
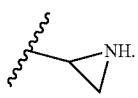
In embodiments, R⁵ is
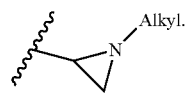
In embodiments, R⁵ is
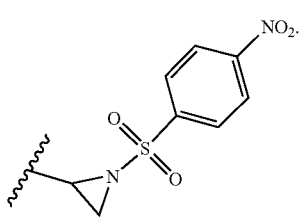 [SMILES: *C1CN1S(=O)(=O)c1ccc([N+](=O)[O-])cc1]
In embodiments, R⁵ is
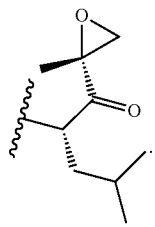 [SMILES: *[C@@H](CC(C)C)C(=O)[C@@]1(C)CO1]
In embodiments, R⁵ is
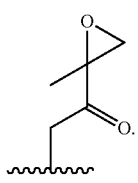 [SMILES: *CC(=O)C1(C)CO1]
In embodiments, R⁵ is
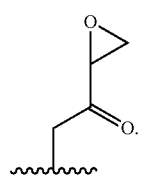 [SMILES: *CC(=O)C1CO1]
In embodiments, R⁵ is
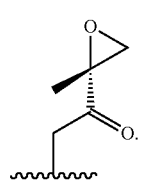 [SMILES: *CC(=O)[C@@]1(C)CO1]
In embodiments, R⁵ is
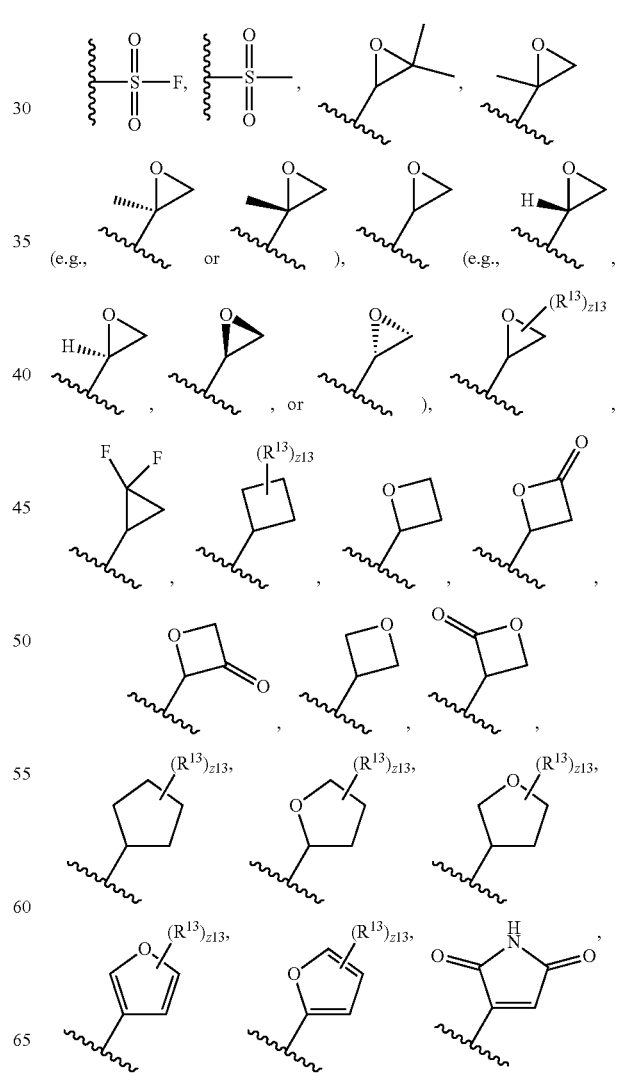

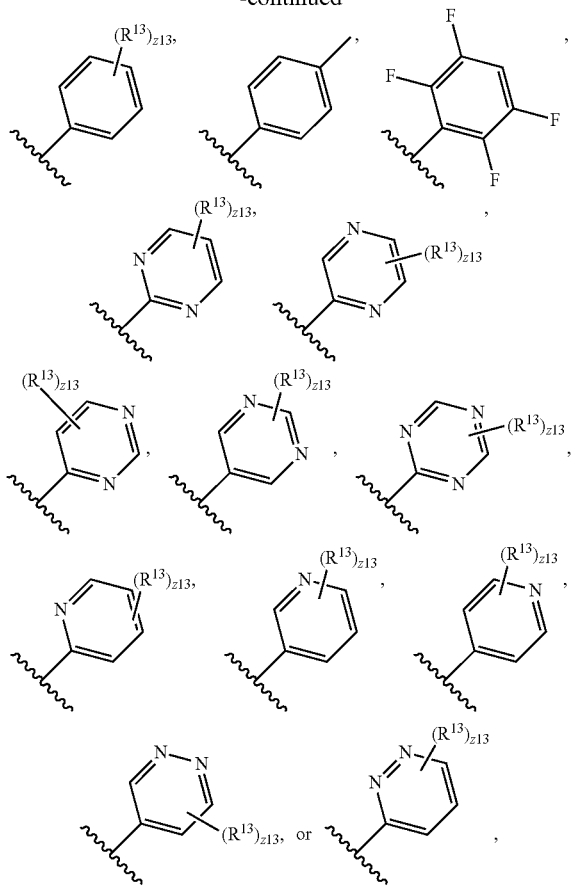
wherein $R^{13}$ and z13 are as described herein, including embodiments.
In embodiments, $R^5$ is
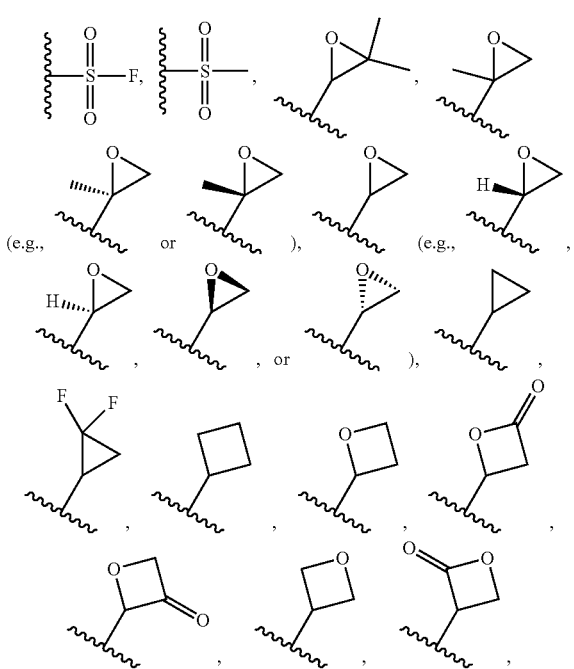
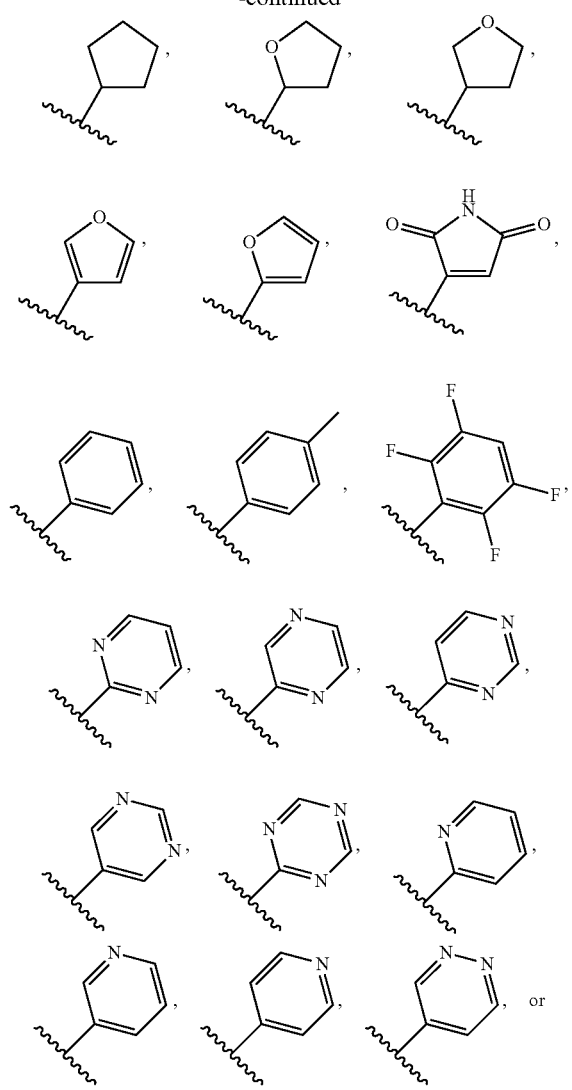
In embodiments, $R^5$ is
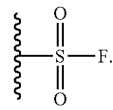 [SMILES: *S(=O)(=O)F]
In embodiments, $R^5$ is
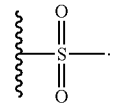

In embodiments, R⁵ is
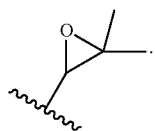 [SMILES: *C1OC1(C)C]
In embodiments, R⁵ is
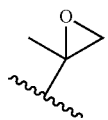
(e.g., or ).
In embodiments, R⁵ is
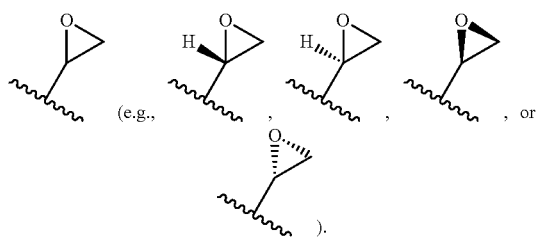
(e.g., , , , or ).
In embodiments, R⁵ is
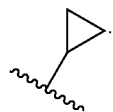
In embodiments, R⁵ is
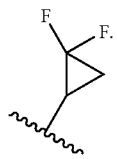 [SMILES: *C1CC1(F)F]
In embodiments, R⁵ is
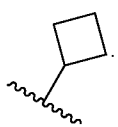 [SMILES: *C1CCC1]
In embodiments, R⁵ is
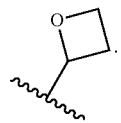
In embodiments, R⁵ is
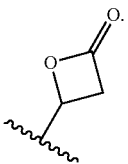 [SMILES: *C1CC(=O)O1]
In embodiments, R⁵ is
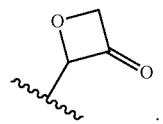 [SMILES: *C1OCC1=O]
In embodiments, R⁵ is
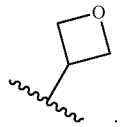 [SMILES: *C1COC1]
In embodiments, R⁵ is
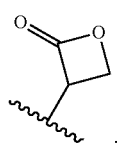
In embodiments, R⁵ is
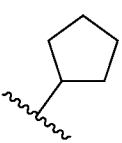
In embodiments, R⁵ is
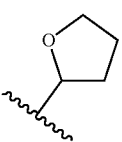

In embodiments, $R^5$ is
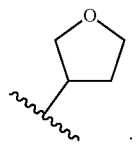
In embodiments, $R^5$ is
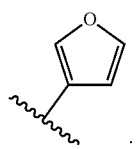
In embodiments, $R^5$ is
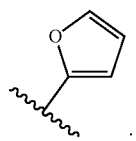
In embodiments, $R^5$ is
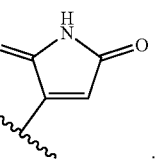
In embodiments, $R^5$ is
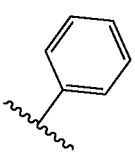
In embodiments, $R^5$ is
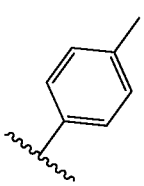
In embodiments, $R^5$ is
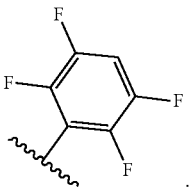 [SMILES: *c1c(F)c(F)cc(F)c1F]
In embodiments, $R^5$ is
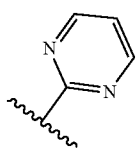
In embodiments, $R^5$ is
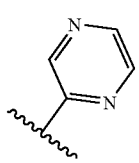
In embodiments, $R^5$ is
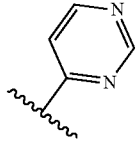
In embodiments, $R^5$ is
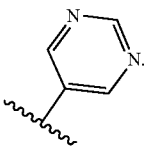 [SMILES: *c1cncnc1]
In embodiments, $R^5$ is
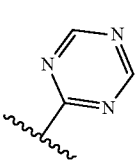

In embodiments, R⁵ is

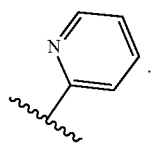 [SMILES: *c1ccccn1]

In embodiments, R⁵ is

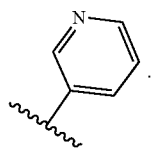 [SMILES: *c1cccnc1]

In embodiments, R⁵ is

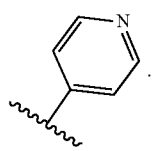 [SMILES: *c1ccncc1]

In embodiments, R⁵ is

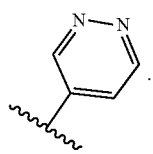 [SMILES: *c1ccnnc1]

In embodiments, R⁵ is

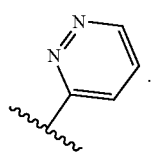 [SMILES: *c1cccnn1]

In embodiments, R⁵ is substituted or unsubstituted oziranyl, substituted or unsubstituted oxetanyl, substituted or unsubstituted furanyl, substituted or unsubstituted pyrazinyl, substituted or unsubstituted pyrimidinyl, substituted or unsubstituted triazinyl, substituted or unsubstituted pyridazinyl, substituted or unsubstituted pyridinyl, substituted or unsubstituted phenyl, —SO₂F, —COH,

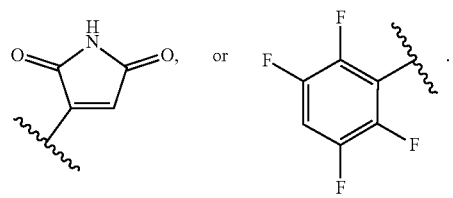 [SMILES: *C1=CC(=O)NC1=O ; *c1c(F)c(F)cc(F)c1F]

In embodiments, R⁵ is substituted oziranyl, substituted oxetanyl, substituted furanyl, substituted pyrazinyl, substituted pyrimidinyl, substituted triazinyl, substituted pyridazinyl, substituted pyridinyl, substituted phenyl, —SO₂F, —COH,

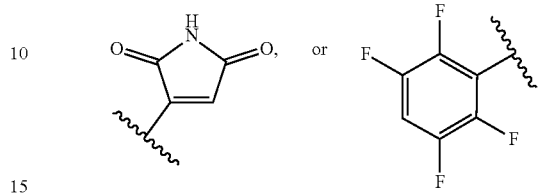

In embodiments, R⁵ is unsubstituted oziranyl, unsubstituted oxetanyl, unsubstituted furanyl, unsubstituted pyrazinyl, unsubstituted pyrimidinyl, unsubstituted triazinyl, unsubstituted pyridazinyl, unsubstituted pyridinyl, unsubstituted phenyl, —SO₂F, —COH,

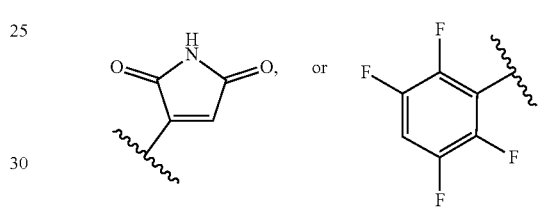

In embodiments, R⁵ is E. In embodiments, E is a covalent histidine binding moiety.

In embodiments, E is

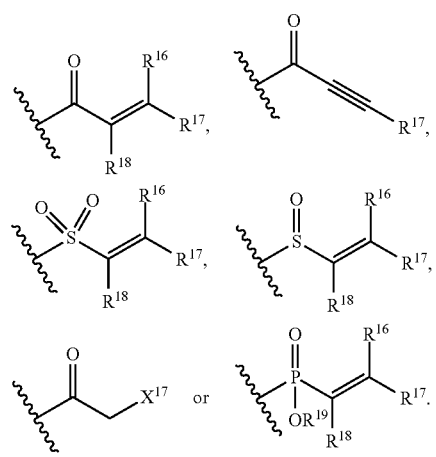

In embodiments, E is

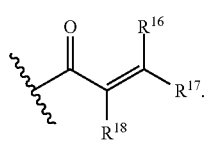

In embodiments, E is

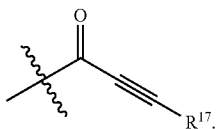

In embodiments, E is

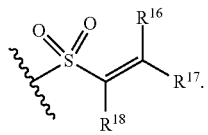

In embodiments, E is

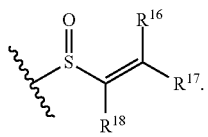

In embodiments, E is

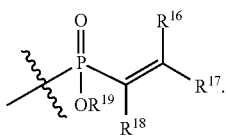

In embodiments, E is

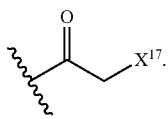

In embodiments, E is

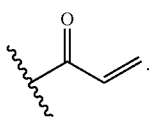

In embodiments, E is

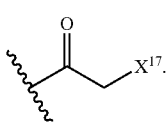

In embodiments, E is

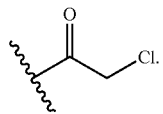 [SMILES: *C(=O)CCl]

$R^{16}$ is independently hydrogen, halogen, $CX^{16}_3$, —$CHX^{16}_2$, —$CH_2X^{16}$, —CN, —$SO_2Cl$, —$SO_{n16}R^{16D}$, —$SO_{v16}NR^{16A}R^{16B}$, —$NHNR^{16A}R^{16B}$, —$ONR^{16A}R^{16B}$, —NHC=(O)NHNR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, —OCX$^{16}_3$, —OCHX$^{16}_2$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

$R^{17}$ is independently hydrogen, halogen, $CX^{17}_3$, —$CHX^{17}_2$, —$CH_2X^{17}$, —CN, —$SO_2Cl$, —$SO_{n17}R^{17D}$, —$SO_{v17}NR^{17A}R^{17B}$, —$NHNR^{17A}R^{17B}$, —$ONR^{17A}R^{17B}$, —NHC=(O)NHNR$^{17A}$R$^{17B}$, —NHC(O)NR$^{17A}$R$^{17B}$, —N(O)$_{m17}$, —NR$^{17A}$R$^{17B}$, C(O)R$^{17C}$, —C(O)—OR$^{17C}$, C(O)NR$^{17A}$R$^{17B}$, —OR$^{17D}$, —NR$^{17A}$SO$_2$R$^{17D}$, —NR$^{17A}$C(O)R$^{17C}$, —NR$^{17A}$C(O)OR$^{17C}$, —NR$^{17A}$OR$^{17C}$, —OCX$^{17}_3$, —OCHX$^{17}_2$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

$R^{18}$ is independently hydrogen, halogen, $CX^{18}_3$, —$CHX^{18}_2$, —$CH_2X^{18}$, —CN, —$SO_2Cl$, —$SO_{n18}R^{18D}$, —$SO_{v18}NR^{18A}R^{18B}$, —$NHNR^{18A}R^{18B}$, —$ONR^{18A}R^{18B}$, —NHC=(O)NHNR$^{18A}$R$^{18B}$, —NHC(O)NR$^{18A}$R$^{18B}$, —N(O)$_{m18}$, —NR$^{18A}$R$^{18B}$, —C(O)R$^{18C}$, —C(O)—OR$^{18C}$, —C(O)NR$^{18A}$R$^{18B}$, —OR$^{18D}$, —NR$^{18A}$SO$_2$R$^{18D}$, —NR$^{18A}$C(O)R$^{18C}$, —NR$^{18A}$C(O)OR$^{8C}$, —NR$^{18A}$OR$^{18C}$, —OCX$^{18}_3$, —OCHX$^{18}_2$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

$R^{19}$ is independently hydrogen, halogen, $CX^{19}_3$, —$CHX^{19}_2$, —$CH_2X^{19}$, —CN, —$SO_2Cl$, —$SO_{n19}R^{19D}$, —$SO_{v19}NR^{19A}R^{19B}$, —$NHNR^{19A}R^{19B}$, —$ONR^{19A}R^{19B}$, —NHC=(O)NHNR$^{19A}$R$^{19B}$, —NHC(O)NR$^{19A}$R$^{19B}$, —N(O)$_{m19}$, —NR$^{19A}$R$^{19B}$, —C(O)R$^{19C}$, —C(O)—OR$^{19C}$, —C(O)NR$^{19A}$R$^{19B}$, —OR$^{19D}$, NR$^{19A}$SO$_2$R$^{19D}$, —NR$^{19A}$C(O)R$^{19C}$, —NR$^{19A}$C(O)OR$^{19C}$, —NR$^{19A}$OR$^{19C}$, —OCX$^{19}_3$, —OCHX$^{19}_2$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$, and $R^{19D}$ are independently hydrogen, halogen, —$CX_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCX_3$, —$OCHX_2$, —$CHX_2$, —$CH_2X$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

$R^{16A}$ and $R^{16B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered); $R^{17A}$ and $R^{17B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered); $R^{18A}$ and $R^{18B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered); $R^{19A}$ and $R^{19B}$ substituents bonded to the same nitrogen atom may optionally be joined to form a substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered) or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

Each X, $X^{16}$, $X^{17}$, $X^{18}$ and $X^{19}$ is independently —F, —Cl, —Br, or —I. The symbols n16, n17, n18, n19, v16, v17, v18, and v19 are independently an integer from 0 to 4. The symbols m16, m17, m18, and m19 are independently an integer from 1 to 2. In embodiments, $R^{18}$ is —CN. In embodiments, $R^{16}$ is unsubstituted methyl. In embodiments, $R^{17}$ is unsubstituted methyl. In embodiments, $R^{18}$ is unsubstituted methyl. In embodiments, $R^{19}$ is unsubstituted methyl. In embodiments, $R^{18}$ is hydrogen. In embodiments, $R^{16}$ is hydrogen. In embodiments, $R^{17}$ is hydrogen. In embodiments, $R^{19}$ is hydrogen.

X may independently be —F. X may independently be —Cl. X may independently be —Br. X may independently be —I. $X^{16}$ may independently be —F. $X^{16}$ may independently be —Cl. $X^{16}$ may independently be —Br. $X^{16}$ may independently be —I. $X^{17}$ may independently be —F. $X^{17}$ may independently be —Cl. $X^{17}$ may independently be —Br. $X^{17}$ may independently be —I. $X^{18}$ may independently be —F. $X^{18}$ may independently be —Cl. $X^{18}$ may independently be —Br. $X^{18}$ may independently be —I. $X^{19}$ may independently be —F. $X^{19}$ may independently be —Cl. $X^{19}$ may independently be —Br. $X^{19}$ may independently be —I.

n16 may independently be 0. n16 may independently be 1. n16 may independently be 2. n16 may independently be 3. n16 may independently be 4. n17 may independently be 0. n17 may independently be 1. n17 may independently be 2. n17 may independently be 3. n17 may independently be 4. n18 may independently be 0. n18 may independently be 1. n18 may independently be 2. n18 may independently be 3. n18 may independently be 4. n19 may independently be 0. n19 may independently be 1. n19 may independently be 2. n19 may independently be 3. n19 may independently be 4.

v16 may independently be 0. v16 may independently be 1. v16 may independently be 2. v16 may independently be 3. v16 may independently be 4. v17 may independently be 0. v17 may independently be 1. v17 may independently be 2. v17 may independently be 3. v17 may independently be 4. v18 may independently be 0. v18 may independently be 1. v18 may independently be 2. v18 may independently be 3. v18 may independently be 4. v19 may independently be 0. v19 may independently be 1. v19 may independently be 2. v19 may independently be 3. v19 may independently be 4.

m16 may independently be 1. m16 may independently be 2. m17 may independently be 1. m17 may independently be 2. m18 may independently be 1. m18 may independently be 2. m19 may independently be 1. m19 may independently be 2.

In embodiments, $R^{16}$ is hydrogen. In embodiments, $R^{16}$ is halogen. In embodiments, $R^{16}$ is unsubstituted tert-butyl. In embodiments, $R^{16}$ is —$CH_2Ph$. In embodiments, $R^{16}$ is independently unsubstituted methyl. In embodiments, $R^{16}$ is independently unsubstituted ethyl. In embodiments, $R^{16}$ is independently unsubstituted propyl. In embodiments, $R^{16}$ is independently unsubstituted n-propyl. In embodiments, $R^{16}$ is independently unsubstituted isopropyl. In embodiments, $R^{16}$ is independently unsubstituted butyl. In embodiments, $R^{16}$ is independently unsubstituted n-butyl. In embodiments, $R^{16}$ is independently unsubstituted isobutyl. In embodiments, $R^{16}$ is independently unsubstituted tert-butyl. In embodiments, $R^{16}$ is independently unsubstituted pentyl. In embodiments, $R^{16}$ is independently unsubstituted hexyl. In embodiments, $R^{16}$ is independently unsubstituted heptyl. In embodiments, $R^{16}$ is independently unsubstituted octyl. In embodiments, $R^{16}$ is independently —F. In embodiments, $R^{16}$ is independently —Cl. In embodiments, $R^{16}$ is independently —Br. In embodiments, $R^{16}$ is independently —I. In embodiments, $R^{16}$ is independently unsubstituted methoxy. In embodiments, $R^{16}$ is independently unsubstituted ethoxy. In embodiments, $R^{16}$ is independently —$CF_3$. In embodiments, $R^{16}$ is independently —$CCl_3$. In embodiments, $R^{16}$ is an unsubstituted isopropyl. In embodiments, $R^{16}$ is an unsubstituted phenyl. In embodiments, $R^{16}$ is an unsubstituted pyridyl. In embodiments, $R^{16}$ is independently halogen. In embodiments, $R^{16}$ is independently —$CX^{16}_3$. In embodiments, $R^{16}$ is independently —$CHX^{16}_2$. In embodiments, $R^{16}$ is independently —$CH_2X^{1.6}$. In embodiments, $R^{16}$ is independently —CN. In embodiments, $R^{16}$ is independently —OH. In embodiments, $R^{16}$ is independently —$NH_2$. In embodiments, $R^{16}$ is independently —COOH. In embodiments, $R^{16}$ is independently —$CONH_2$. In embodiments, $R^{16}$ is independently —$NO_2$. In embodiments, $R^{16}$ is independently —SH. In embodiments, $R^{16}$ is independently —$SO_3H$. In embodiments, $R^{16}$ is independently —$SO_4H$. In embodiments, $R^{16}$ is independently —$SO_2NH_2$. In embodiments, $R^{16}$ is independently —$NHNH_2$. In embodiments, $R^{16}$ is independently —$ONH_2$. In embodiments, $R^{16}$ is independently —$NHC(O)NHNH_2$. In embodiments, $R^{16}$ is independently —$NHC(O)NH_2$. In embodiments, $R^{16}$ is independently —$NHSO_2H$. In embodiments, $R^{16}$ is independently —NHC(O)H. In embodiments, $R^{16}$ is independently —NHC(O)OH. In embodiments, $R^{16}$ is independently —NHOH. In embodiments, $R^{16}$ is independently —$OCX^{16}_3$. In embodiments, $R^{16}$ is independently —$OCHX^{16}_2$.

In embodiments, $R^{16A}$ is hydrogen. In embodiments, $R^{16A}$ is —$CX_3$. In embodiments, $R^{16A}$ is —CN. In embodiments, $R^{16A}$ is —COOH. In embodiments, $R^{16A}$ is —$CONH_2$. In embodiments, $R^{16A}$ is —$CHX_2$. In embodiments, $R^{16A}$ is —$CH_2X$. In embodiments, $R^{16A}$ is unsubstituted methyl. In embodiments, $R^{16A}$ is unsubstituted ethyl. In embodiments, $R^{16A}$ is unsubstituted propyl. In embodiments, $R^{16A}$ is unsubstituted isopropyl. In embodiments, $R^{16A}$ is unsubstituted butyl. In embodiments, $R^{16A}$ is unsubstituted tert-butyl.

In embodiments, $R^{16B}$ is hydrogen. In embodiments, $R^{16B}$ is —$CX_3$. In embodiments, $R^{16B}$ is —CN. In embodiments, $R^{16B}$ is —COOH. In embodiments, $R^{16B}$ is —$CONH_2$. In embodiments, $R^{16B}$ is —$CHX_2$. In embodiments, $R^{16B}$ is —$CH_2X$. In embodiments, $R^{16B}$ is unsubstituted methyl. In embodiments, $R^{16B}$ is unsubstituted ethyl. In embodiments, $R^{16B}$ is unsubstituted propyl. In embodiments, $R^{16B}$ is unsubstituted isopropyl. In embodiments, $R^{16B}$ is unsubstituted butyl. In embodiments, $R^{16B}$ is unsubstituted tert-butyl.

In embodiments, $R^{16C}$ is hydrogen. In embodiments, $R^{16C}$ is —$CX_3$. In embodiments, $R^{16C}$ is —CN. In embodiments, $R^{16C}$ is —COOH. In embodiments, $R^{16C}$ is —$CONH_2$. In embodiments, $R^{16C}$ is —$CHX_2$. In embodiments, $R^{16C}$ is —$CH_2X$. In embodiments, $R^{16C}$ is unsubstituted methyl. In embodiments, $R^{16C}$ is unsubstituted ethyl. In embodiments, $R^{16C}$ is unsubstituted propyl. In embodiments, $R^{16C}$ is unsubstituted isopropyl. In embodiments, $R^{16C}$ is unsubstituted butyl. In embodiments, $R^{16C}$ is unsubstituted tert-butyl.

In embodiments, $R^{16D}$ is hydrogen. In embodiments, $R^{16D}$ is —$CX_3$. In embodiments, $R^{16D}$ is —CN. In embodiments, $R^{16D}$ is —COOH. In embodiments, $R^{16D}$ is —$CONH_2$. In embodiments, $R^{16D}$ is —$CHX_2$. In embodiments, $R^{16D}$ is —$CH_2X$. In embodiments, $R^{16D}$ is unsubstituted methyl. In embodiments, $R^{16D}$ is unsubstituted ethyl. In embodiments, $R^{16D}$ is unsubstituted propyl. In embodiments, $R^{16D}$ is unsubstituted isopropyl. In embodiments, $R^{16D}$ is unsubstituted butyl. In embodiments, $R^{16D}$ is unsubstituted tert-butyl.

In embodiments, $R^{17}$ is hydrogen. In embodiments, $R^{17}$ is halogen. In embodiments, $R^{17}$ is unsubstituted tert-butyl. In embodiments, $R^{17}$ is —CH$_2$Ph. In embodiments, $R^{17}$ is independently unsubstituted methyl. In embodiments, $R^{17}$ is independently unsubstituted ethyl. In embodiments, $R^{17}$ is independently unsubstituted propyl. In embodiments, $R^{17}$ is independently unsubstituted n-propyl. In embodiments, $R^{17}$ is independently unsubstituted isopropyl. In embodiments, $R^{17}$ is independently unsubstituted butyl. In embodiments, $R^{17}$ is independently unsubstituted n-butyl. In embodiments, $R^{17}$ is independently unsubstituted isobutyl. In embodiments, $R^{17}$ is independently unsubstituted tert-butyl. In embodiments, $R^{17}$ is independently unsubstituted pentyl. In embodiments, $R^{17}$ is independently unsubstituted hexyl. In embodiments, $R^{17}$ is independently unsubstituted heptyl. In embodiments, $R^{17}$ is independently unsubstituted octyl. In embodiments, $R^{17}$ is independently —F. In embodiments, $R^{17}$ is independently —Cl. In embodiments, $R^{17}$ is independently —Br. In embodiments, $R^{17}$ is independently —I. In embodiments, $R^{17}$ is independently unsubstituted methoxy. In embodiments, $R^{17}$ is independently unsubstituted ethoxy. In embodiments, $R^{17}$ is independently —CF$_3$. In embodiments, $R^{17}$ is independently —CCl$_3$. In embodiments, $R^{17}$ is an unsubstituted isopropyl. In embodiments, $R^{17}$ is an unsubstituted phenyl. In embodiments, $R^{17}$ is an unsubstituted pyridyl. In embodiments, $R^{17}$ is independently halogen. In embodiments, $R^{17}$ is independently —CX$^{17}_3$. In embodiments, $R^{17}$ is independently —CHX$^{17}_2$. In embodiments, $R^{17}$ is independently —CH$_2$X$^{1.7}$. In embodiments, $R^{17}$ is independently —CN. In embodiments, $R^{17}$ is independently —OH. In embodiments, $R^{17}$ is independently —NH$_2$. In embodiments, $R^{17}$ is independently —COOH. In embodiments, $R^{17}$ is independently —CONH$_2$. In embodiments, $R^{17}$ is independently —NO$_2$. In embodiments, $R^{17}$ is independently —SH. In embodiments, $R^{17}$ is independently —SO$_3$H. In embodiments, $R^{17}$ is independently —SO$_4$H. In embodiments, $R^{17}$ is independently —SO$_2$NH$_2$. In embodiments, $R^{17}$ is independently —NHNH$_2$. In embodiments, $R^{17}$ is independently —ONH$_2$. In embodiments, $R^{17}$ is independently —NHC(O)NHNH$_2$. In embodiments, $R^{17}$ is independently —NHC(O)NH$_2$. In embodiments, $R^{17}$ is independently —NHSO$_2$H. In embodiments, $R^{17}$ is independently —NHC(O)H. In embodiments, $R^{17}$ is independently —NHC(O)OH. In embodiments, $R^{17}$ is independently —NHOH. In embodiments, $R^{17}$ is independently —OCX$^{17}_3$. In embodiments, $R^{17}$ is independently —OCHX$^{17}_2$.

In embodiments, $R^{17A}$ is hydrogen. In embodiments, $R^{17A}$ is —CX$_3$. In embodiments, $R^{17A}$ is —CN. In embodiments, $R^{17A}$ is —COOH. In embodiments, $R^{17A}$ is —CONH$_2$. In embodiments, $R^{17A}$ is —CHX$_2$. In embodiments, $R^{17A}$ is —CH$_2$X. In embodiments, $R^{17A}$ is unsubstituted methyl. In embodiments, $R^{17A}$ is unsubstituted ethyl. In embodiments, $R^{17A}$ is unsubstituted propyl. In embodiments, $R^{17A}$ is unsubstituted isopropyl. In embodiments, $R^{17A}$ is unsubstituted butyl. In embodiments, $R^{17A}$ is unsubstituted tert-butyl.

In embodiments, $R^{17B}$ is hydrogen. In embodiments, $R^{17B}$ is —CX$_3$. In embodiments, $R^{17B}$ is —CN. In embodiments, $R^{17B}$ is —COOH. In embodiments, $R^{17B}$ is —CONH$_2$. In embodiments, $R^{17B}$ is —CHX$_2$. In embodiments, $R^{17B}$ is —CH$_2$X. In embodiments, $R^{17B}$ is unsubstituted methyl. In embodiments, $R^{17B}$ is unsubstituted ethyl. In embodiments, $R^{17B}$ is unsubstituted propyl. In embodiments, $R^{17B}$ is unsubstituted isopropyl. In embodiments, $R^{17B}$ is unsubstituted butyl. In embodiments, $R^{17B}$ is unsubstituted tert-butyl.

In embodiments, $R^{17C}$ is hydrogen. In embodiments, $R^{17C}$ is —CX$_3$. In embodiments, $R^{17C}$ is —CN. In embodiments, $R^{17C}$ is —COOH. In embodiments, $R^{17C}$ is —CONH$_2$. In embodiments, $R^{17C}$ is —CHX$_2$. In embodiments, $R^{17C}$ is —CH$_2$X. In embodiments, $R^{17C}$ is unsubstituted methyl. In embodiments, $R^{17C}$ is unsubstituted ethyl. In embodiments, $R^{17C}$ is unsubstituted propyl. In embodiments, $R^{17C}$ is unsubstituted isopropyl. In embodiments, $R^{17C}$ is unsubstituted butyl. In embodiments, $R^{17C}$ is unsubstituted tert-butyl.

In embodiments, $R^{17D}$ is hydrogen. In embodiments, $R^{17D}$ is —CX$_3$. In embodiments, $R^{17D}$ is —CN. In embodiments, $R^{17D}$ is —COOH. In embodiments, $R^{17D}$ is —CONH$_2$. In embodiments, $R^{17D}$ is —CHX$_2$. In embodiments, $R^{17D}$ is —CH$_2$X. In embodiments, $R^{17D}$ is unsubstituted methyl. In embodiments, $R^{17D}$ is unsubstituted ethyl. In embodiments, $R^{17D}$ is unsubstituted propyl. In embodiments, $R^{17D}$ is unsubstituted isopropyl. In embodiments, $R^{17D}$ is unsubstituted butyl. In embodiments, $R^{17D}$ is unsubstituted tert-butyl.

In embodiments, $R^{18}$ is hydrogen. In embodiments, $R^{18}$ is halogen. In embodiments, $R^{18}$ is unsubstituted tert-butyl. In embodiments, $R^{18}$ is —CH$_2$Ph. In embodiments, $R^{18}$ is independently unsubstituted methyl. In embodiments, $R^{18}$ is independently unsubstituted ethyl. In embodiments, $R^{18}$ is independently unsubstituted propyl. In embodiments, $R^{18}$ is independently unsubstituted n-propyl. In embodiments, $R^{18}$ is independently unsubstituted isopropyl. In embodiments, $R^{18}$ is independently unsubstituted butyl. In embodiments, $R^{18}$ is independently unsubstituted n-butyl. In embodiments, $R^{18}$ is independently unsubstituted isobutyl. In embodiments, $R^{18}$ is independently unsubstituted tert-butyl. In embodiments, $R^{18}$ is independently unsubstituted pentyl. In embodiments, $R^{18}$ is independently unsubstituted hexyl. In embodiments, $R^{18}$ is independently unsubstituted heptyl. In embodiments, $R^{18}$ is independently unsubstituted octyl. In embodiments, $R^{18}$ is independently —F. In embodiments, $R^{18}$ is independently —Cl. In embodiments, $R^{18}$ is independently —Br. In embodiments, $R^{18}$ is independently —I. In embodiments, $R^{18}$ is independently unsubstituted methoxy. In embodiments, $R^{18}$ is independently unsubstituted ethoxy. In embodiments, $R^{18}$ is independently —CF$_3$. In embodiments, $R^{18}$ is independently —CCl$_3$. In embodiments, $R^{18}$ is an unsubstituted isopropyl. In embodiments, $R^{18}$ is an unsubstituted phenyl. In embodiments, $R^{18}$ is an unsubstituted pyridyl. In embodiments, $R^{18}$ is independently halogen. In embodiments, $R^{18}$ is independently —CX$^{18}_3$. In embodiments, $R^{18}$ is independently —CHX$^{18}_2$. In embodiments, $R^{18}$ is independently —CH$_2$X$^{18}$. In embodiments, $R^{18}$ is independently —CN. In embodiments, $R^{18}$ is independently —OH. In embodiments, $R^{18}$ is independently —NH$_2$. In embodiments, $R^{18}$ is independently —COOH. In embodiments, $R^{18}$ is independently —CONH$_2$. In embodiments, $R^{18}$ is independently —NO$_2$. In embodiments, $R^{18}$ is independently —SH. In embodiments, $R^{18}$ is independently —SO$_3$H. In embodiments, $R^{18}$ is independently —SO$_4$H. In embodiments, $R^{18}$ is independently —SO$_2$NH$_2$. In embodiments, $R^{18}$ is independently —NHNH$_2$. In embodiments, $R^{18}$ is independently —ONH$_2$. In embodiments, $R^{18}$ is independently —NHC(O)NHNH$_2$. In embodiments, $R^{18}$ is independently —NHC(O)NH$_2$. In embodiments, $R^{18}$ is independently —NHSO$_2$H. In embodiments, $R^{18}$ is independently —NHC(O)H. In embodiments, $R^{18}$ is independently —NHC(O)OH. In embodiments, $R^{18}$ is independently —NHOH. In embodiments, $R^{18}$ is independently —OCX$^{18}_3$. In embodiments, $R^{18}$ is independently —OCHX$^{18}_2$.

In embodiments, $R^{18A}$ is hydrogen. In embodiments, $R^{18A}$ is —CX$_3$. In embodiments, $R^{18A}$ is —CN. In embodiments, $R^{18A}$ is —COOH. In embodiments, $R^{18A}$ is —CONH$_2$. In embodiments, $R^{18A}$ is —CHX$_2$. In embodiments, $R^{18A}$ is —CH$_2$X. In embodiments, $R^{18A}$ is unsubstituted methyl. In embodiments, $R^{18A}$ is unsubstituted ethyl. In embodiments, $R^{18A}$ is unsubstituted propyl. In embodiments, $R^{18A}$ is unsubstituted isopropyl. In embodiments, $R^{18A}$ is unsubstituted butyl. In embodiments, $R^{18A}$ is unsubstituted tert-butyl.

In embodiments, $R^{18B}$ is hydrogen. In embodiments, $R^{18B}$ is —CX$_3$. In embodiments, $R^{18B}$ is —CN. In embodiments, $R^{18B}$ is —COOH. In embodiments, $R^{18B}$ is —CONH$_2$. In embodiments, $R^{18B}$ is —CHX$_2$. In embodiments, $R^{18B}$ is —CH$_2$X. In embodiments, $R^{18B}$ is unsubstituted methyl. In embodiments, $R^{18B}$ is unsubstituted ethyl. In embodiments, $R^{18B}$ is unsubstituted propyl. In embodiments, $R^{18B}$ is unsubstituted isopropyl. In embodiments, $R^{18B}$ is unsubstituted butyl. In embodiments, $R^{18B}$ is unsubstituted tert-butyl.

In embodiments, $R^{18C}$ is hydrogen. In embodiments, $R^{18C}$ is —CX$_3$. In embodiments, $R^{18C}$ is —CN. In embodiments, $R^{18C}$ is —COOH. In embodiments, $R^{18C}$ is —CONH$_2$. In embodiments, $R^{18C}$ is —CHX$_2$. In embodiments, $R^{18C}$ is —CH$_2$X. In embodiments, $R^{18C}$ is unsubstituted methyl. In embodiments, $R^{18C}$ is unsubstituted ethyl. In embodiments, $R^{18C}$ is unsubstituted propyl. In embodiments, $R^{18C}$ is unsubstituted isopropyl. In embodiments, $R^{18C}$ is unsubstituted butyl. In embodiments, $R^{18C}$ is unsubstituted tert-butyl.

In embodiments, $R^{18D}$ is hydrogen. In embodiments, $R^{18D}$ is —CX$_3$. In embodiments, $R^{18D}$ is —CN. In embodiments, $R^{18D}$ is —COOH. In embodiments, $R^{18D}$ is —CONH$_2$. In embodiments, $R^{18D}$ is —CHX$_2$. In embodiments, $R^{18D}$ is —CH$_2$X. In embodiments, $R^{18D}$ is unsubstituted methyl. In embodiments, $R^{18D}$ is unsubstituted ethyl. In embodiments, $R^{18D}$ is unsubstituted propyl. In embodiments, $R^{18D}$ is unsubstituted isopropyl. In embodiments, $R^{18D}$ is unsubstituted butyl. In embodiments, $R^{18D}$ is unsubstituted tert-butyl.

In embodiments, $R^{19}$ is hydrogen. In embodiments, $R^{19}$ is halogen. In embodiments, $R^{19}$ is unsubstituted tert-butyl. In embodiments, $R^{19}$ is —CH$_2$Ph. In embodiments, $R^{19}$ is independently unsubstituted methyl. In embodiments, $R^{19}$ is independently unsubstituted ethyl. In embodiments, $R^{19}$ is independently unsubstituted propyl. In embodiments, $R^{19}$ is independently unsubstituted n-propyl. In embodiments, $R^{19}$ is independently unsubstituted isopropyl. In embodiments, $R^{19}$ is independently unsubstituted butyl. In embodiments, $R^{19}$ is independently unsubstituted n-butyl. In embodiments, $R^{19}$ is independently unsubstituted isobutyl. In embodiments, $R^{19}$ is independently unsubstituted tert-butyl. In embodiments, $R^{19}$ is independently unsubstituted pentyl. In embodiments, $R^{19}$ is independently unsubstituted hexyl. In embodiments, $R^{19}$ is independently unsubstituted heptyl. In embodiments, $R^{19}$ is independently unsubstituted octyl. In embodiments, $R^{19}$ is independently —F. In embodiments, $R^{19}$ is independently —Cl. In embodiments, $R^{19}$ is independently —Br. In embodiments, $R^{19}$ is independently —I. In embodiments, $R^{19}$ is independently unsubstituted methoxy. In embodiments, $R^{19}$ is independently unsubstituted ethoxy. In embodiments, $R^{19}$ is independently —CF$_3$. In embodiments, $R^{19}$ is independently —CCl$_3$. In embodiments, $R^{19}$ is an unsubstituted isopropyl. In embodiments, $R^{19}$ is an unsubstituted phenyl. In embodiments, $R^{19}$ is an unsubstituted pyridyl. In embodiments, $R^{19}$ is independently halogen. In embodiments, $R^{19}$ is independently —CX$^{19}_3$. In embodiments, $R^{19}$ is independently —CHX$^{19}_2$. In embodiments, $R^{19}$ is independently —CH$_2$X$^{19}$. In embodiments, $R^{19}$ is independently —CN. In embodiments, $R^{19}$ is independently —OH. In embodiments, $R^{19}$ is independently —NH$_2$. In embodiments, $R^{19}$ is independently —COOH. In embodiments, $R^{19}$ is independently —CONH$_2$. In embodiments, $R^{19}$ is independently —NO$_2$. In embodiments, $R^{19}$ is independently —SH. In embodiments, $R^{19}$ is independently —SO$_3$H. In embodiments, $R^{19}$ is independently —SO$_4$H. In embodiments, $R^{19}$ is independently —SO$_2$NH$_2$. In embodiments, $R^{19}$ is independently —NHNH$_2$. In embodiments, $R^{19}$ is independently —ONH$_2$. In embodiments, $R^{19}$ is independently —NHC(O)NHNH$_2$. In embodiments, $R^{19}$ is independently —NHC(O)NH$_2$. In embodiments, $R^{19}$ is independently —NHSO$_2$H. In embodiments, $R^{19}$ is independently —NHC(O)H. In embodiments, $R^{19}$ is independently —NHC(O)OH. In embodiments, $R^{19}$ is independently —NHOH. In embodiments, $R^{19}$ is independently —OCX$^{19}_3$. In embodiments, $R^{19}$ is independently —OCHX$^{19}_2$.

In embodiments, $R^{19A}$ is hydrogen. In embodiments, $R^{19A}$ is —CX$_3$. In embodiments, $R^{19A}$ is —CN. In embodiments, $R^{19A}$ is —COOH. In embodiments, $R^{19A}$ is —CONH$_2$. In embodiments, $R^{19A}$ is —CHX$_2$. In embodiments, $R^{19A}$ is —CH$_2$X. In embodiments, $R^{19A}$ is unsubstituted methyl. In embodiments, $R^{19A}$ is unsubstituted ethyl. In embodiments, $R^{19A}$ is unsubstituted propyl. In embodiments, $R^{19A}$ is unsubstituted isopropyl. In embodiments, $R^{19A}$ is unsubstituted butyl. In embodiments, $R^{19A}$ is unsubstituted tert-butyl.

In embodiments, $R^{19B}$ is hydrogen. In embodiments, $R^{19B}$ is —CX$_3$. In embodiments, $R^{19B}$ is —CN. In embodiments, $R^{19B}$ is —COOH. In embodiments, $R^{19B}$ is —CONH$_2$. In embodiments, $R^{19B}$ is —CHX$_2$. In embodiments, $R^{19B}$ is —CH$_2$X. In embodiments, $R^{19B}$ is unsubstituted methyl. In embodiments, $R^{19B}$ is unsubstituted ethyl. In embodiments, $R^{19B}$ is unsubstituted propyl. In embodiments, $R^{19B}$ is unsubstituted isopropyl. In embodiments, $R^{19B}$ is unsubstituted butyl. In embodiments, $R^{19B}$ is unsubstituted tert-butyl.

In embodiments, $R^{19C}$ is hydrogen. In embodiments, $R^{19C}$ is —CX$_3$. In embodiments, $R^{19C}$ is —CN. In embodiments, $R^{19C}$ is —COOH. In embodiments, $R^{19C}$ is —CONH$_2$. In embodiments, $R^{19C}$ is —CHX$_2$. In embodiments, $R^{19C}$ is —CH$_2$X. In embodiments, $R^{19C}$ is unsubstituted methyl. In embodiments, $R^{19C}$ is unsubstituted ethyl. In embodiments, $R^{19C}$ is unsubstituted propyl. In embodiments, $R^{19C}$ is unsubstituted isopropyl. In embodiments, $R^{19C}$ is unsubstituted butyl. In embodiments, $R^{19C}$ is unsubstituted tert-butyl.

In embodiments, $R^{19D}$ is hydrogen. In embodiments, $R^{19D}$ is —CX$_3$. In embodiments, $R^{19D}$ is —CN. In embodiments, $R^{19D}$ is —COOH. In embodiments, $R^{19D}$ is —CONH$_2$. In embodiments, $R^{19D}$ is —CHX$_2$. In embodiments, $R^{19D}$ is —CH$_2$X. In embodiments, $R^{19D}$ is unsubstituted methyl. In embodiments, $R^{19D}$ is unsubstituted ethyl. In embodiments, $R^{19D}$ is unsubstituted propyl. In embodiments, $R^{19D}$ is unsubstituted isopropyl. In embodiments, $R^{19D}$ is unsubstituted butyl. In embodiments, $R^{19D}$ is unsubstituted tert-butyl.

In embodiments, E includes a substituted (e.g., substituted with a substituent group, a size-limited substituent group, or lower substituent group) or unsubstituted vinyl sulfone moiety, substituted (e.g., substituted with a substituent group, a size-limited substituent group, or lower substituent group) or unsubstituted vinyl sulfonamide moiety, substituted (e.g., substituted with a substituent group, a size-limited substituent group, or lower substituent group) or unsubstituted fluoro($C_1$-$C_4$)alkylketone moiety, substituted (e.g., substituted with a substituent group, a size-limited substituent group, or lower substituent group) or unsubstituted chloro($C_1$-$C_4$)alkylketone moiety, substituted (e.g., substituted with a substituent group, a size-limited substituent group, or lower substituent group) or unsubstituted acrylamide moiety, substituted (e.g., substituted with a substituent group, a size-limited substituent group, or lower substituent group) or unsubstituted disulfide moiety, substituted (e.g., substituted with a substituent group, a size-limited substituent group, or lower substituent group) or unsubstituted thiol moiety, substituted (e.g., substituted with a substituent group, a size-limited substituent group, or lower substituent group) or unsubstituted phosphonate moiety, substituted (e.g., substituted with a substituent group, a size-limited substituent group, or lower substituent group) or unsubstituted aldehyde moiety, substituted (e.g., substituted with a substituent group, a size-limited substituent group, or lower substituent group) or unsubstituted enone moiety, substituted (e.g., substituted with a substituent group, a size-limited substituent group, or lower substituent group) or unsubstituted diazomethylketone moiety, substituted (e.g., substituted with a substituent group, a size-limited substituent group, or lower substituent group) or unsubstituted diazomethylamide moiety, substituted (e.g., substituted with a substituent group, a size-limited substituent group, or lower substituent group) or unsubstituted cyanocyclopropyl carboxamide moiety, substituted (e.g., substituted with a substituent group, a size-limited substituent group, or lower substituent group) or unsubstituted epoxide moiety, substituted (e.g., substituted with a substituent group, a size-limited substituent group, or lower substituent group) or unsubstituted epoxyketone moiety, substituted (e.g., substituted with a substituent group, a size-limited substituent group, or lower substituent group) or unsubstituted epoxyamide moiety, substituted (e.g., substituted with a substituent group, a size-limited substituent group, or lower substituent group) or unsubstituted aryl aldehyde moiety, substituted (e.g., substituted with a substituent group, a size-limited substituent group, or lower substituent group) or unsubstituted aryl dialdehyde moiety, substituted (e.g., substituted with a substituent group, a size-limited substituent group, or lower substituent group) or unsubstituted dialdehyde moiety, substituted (e.g., substituted with a substituent group, a size-limited substituent group, or lower substituent group) or unsubstituted nitrogen mustard moiety, substituted (e.g., substituted with a substituent group, a size-limited substituent group, or lower substituent group) or unsubstituted propargyl moiety, substituted (e.g., substituted with a substituent group, a size-limited substituent group, or lower substituent group) or unsubstituted propargylamide moiety,

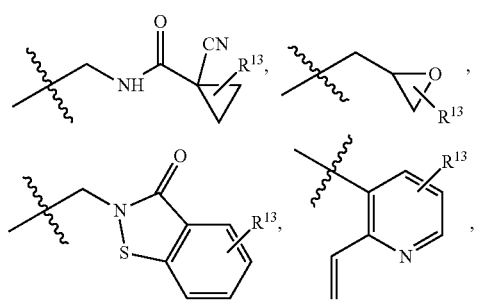

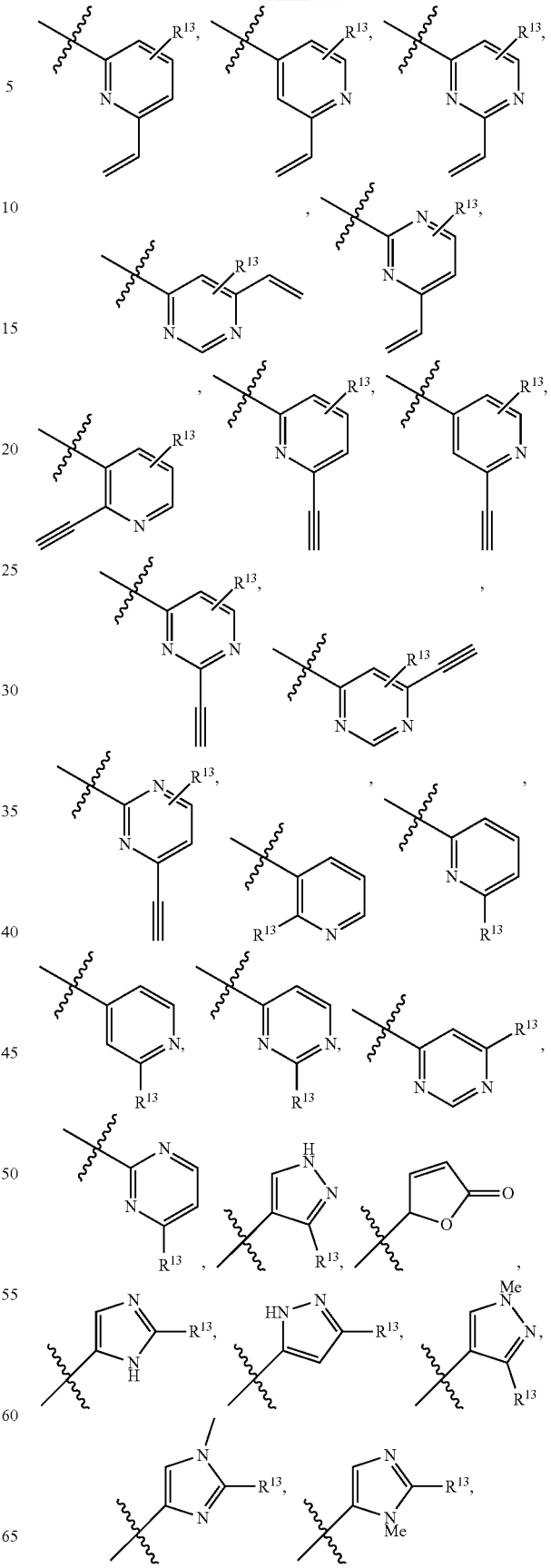

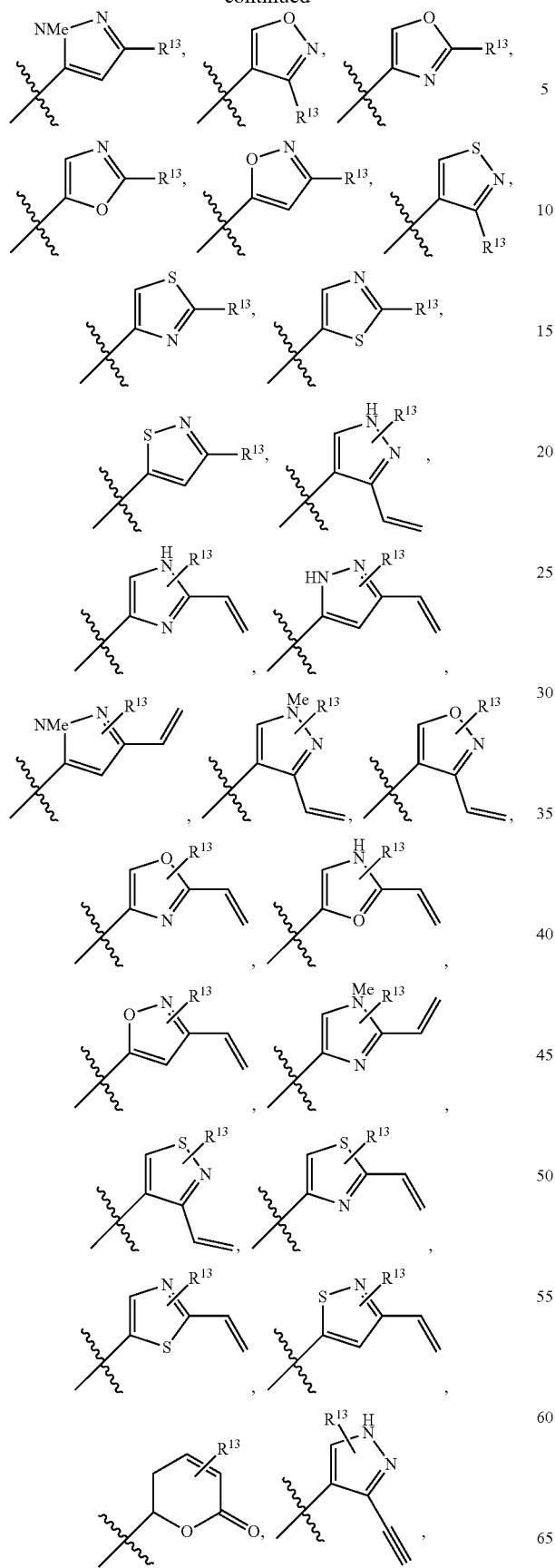
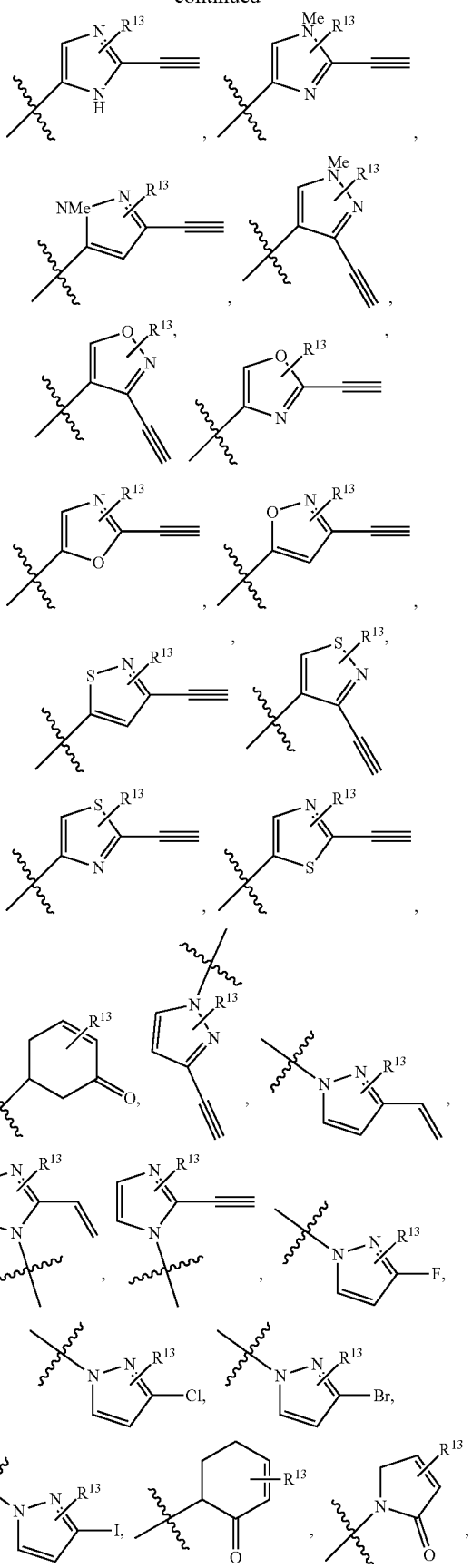

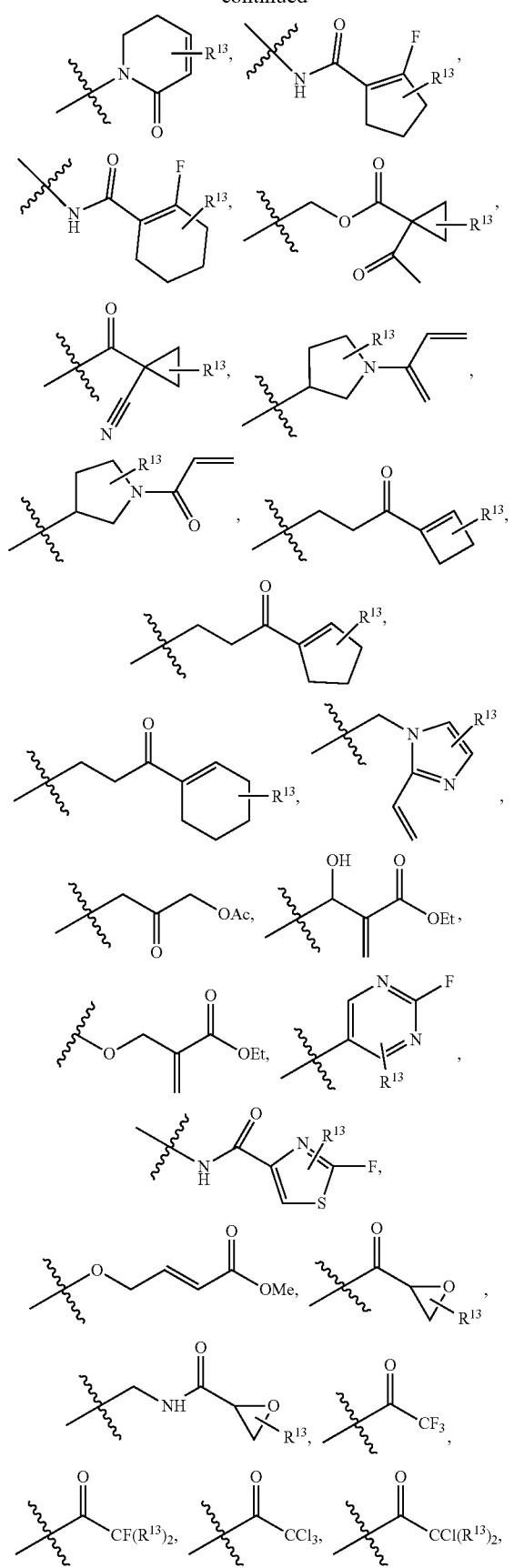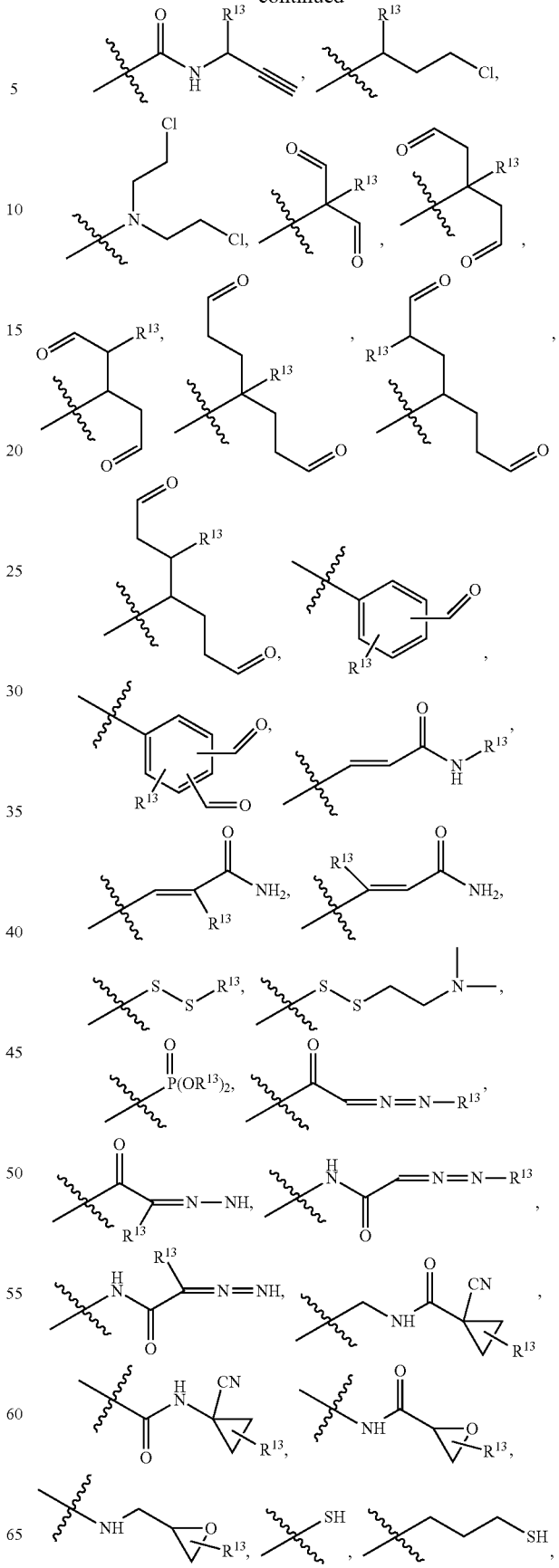

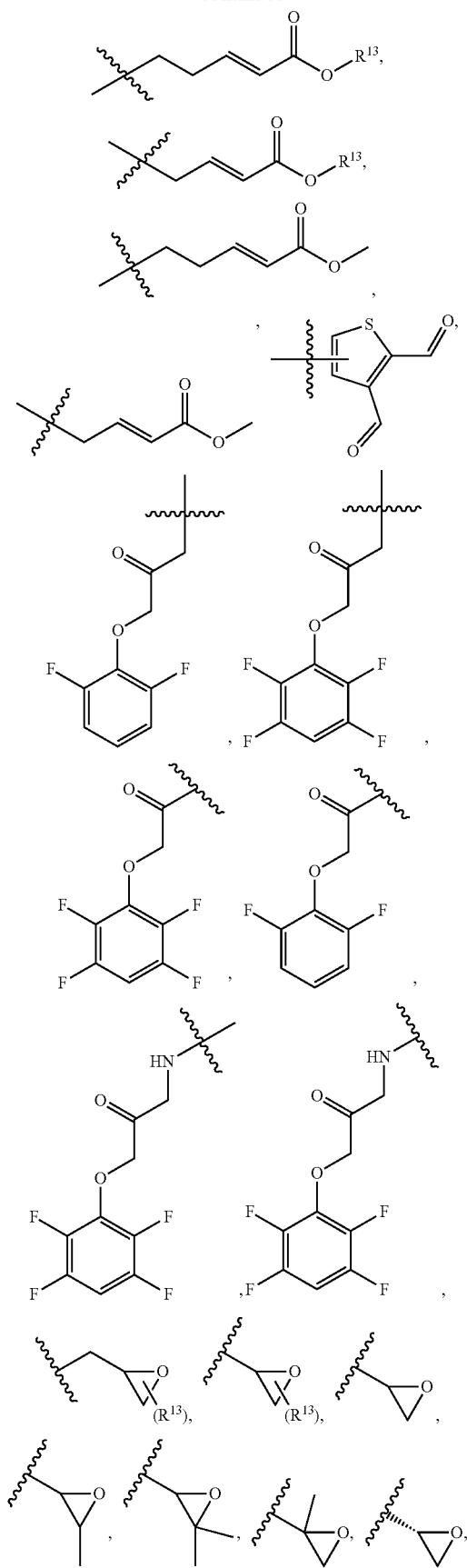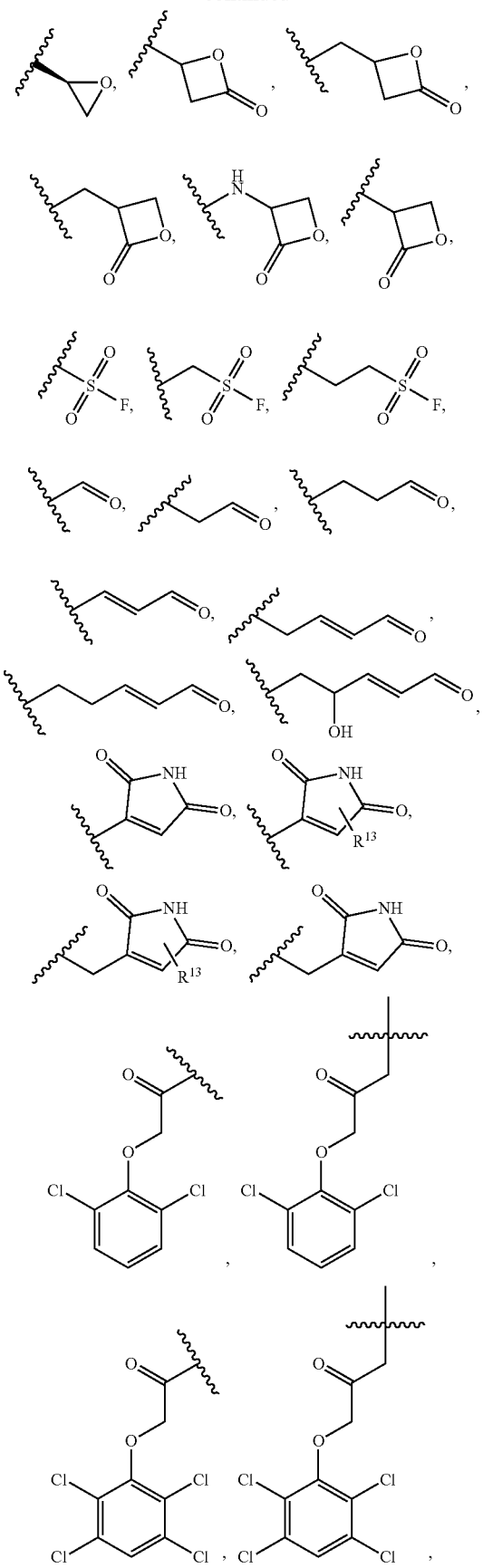

-continued

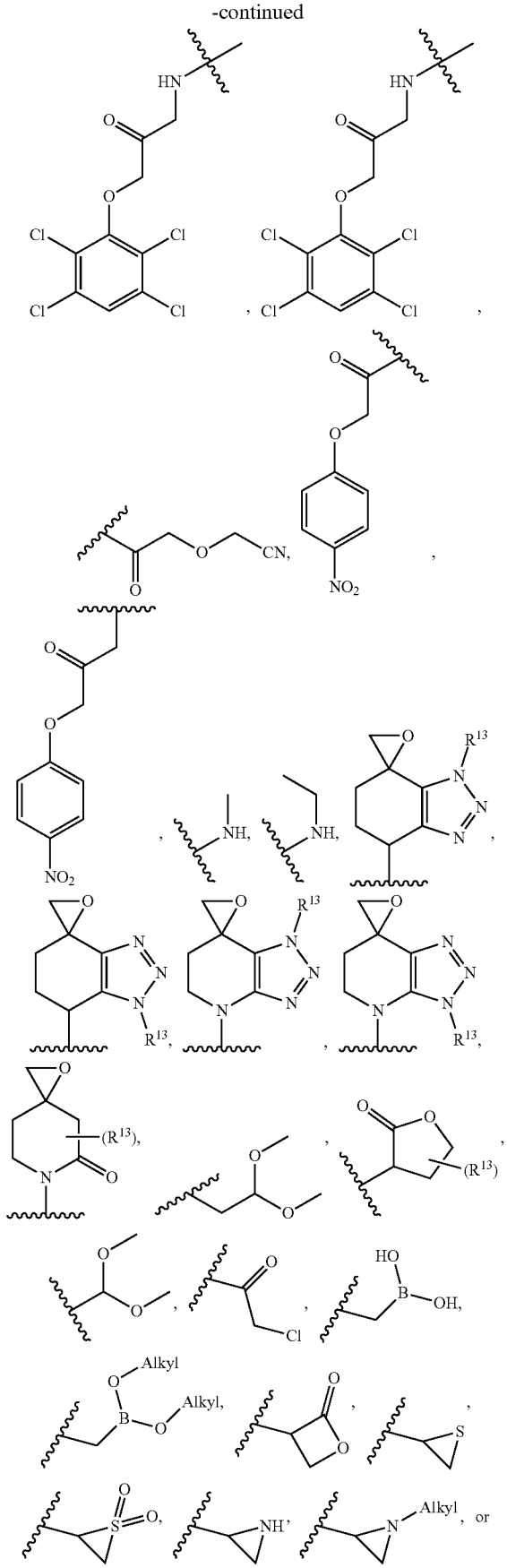

-continued

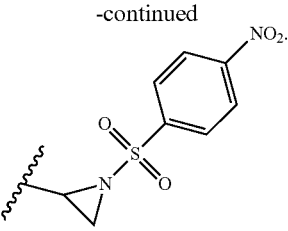

In embodiments, E is a substituted (e.g., substituted with a substituent group, a size-limited substituent group, or lower substituent group) or unsubstituted vinyl sulfone moiety, substituted (e.g., substituted with a substituent group, a size-limited substituent group, or lower substituent group) or unsubstituted vinyl sulfonamide moiety, substituted (e.g., substituted with a substituent group, a size-limited substituent group, or lower substituent group) or unsubstituted fluoro($C_1$-$C_4$)alkylketone moiety, substituted (e.g., substituted with a substituent group, a size-limited substituent group, or lower substituent group) or unsubstituted chloro($C_1$-$C_4$)alkylketone moiety, substituted (e.g., substituted with a substituent group, a size-limited substituent group, or lower substituent group) or unsubstituted acrylamide moiety, substituted (e.g., substituted with a substituent group, a size-limited substituent group, or lower substituent group) or unsubstituted disulfide moiety, substituted (e.g., substituted with a substituent group, a size-limited substituent group, or lower substituent group) or unsubstituted thiol moiety, substituted (e.g., substituted with a substituent group, a size-limited substituent group, or lower substituent group) or unsubstituted phosphonate moiety, substituted (e.g., substituted with a substituent group, a size-limited substituent group, or lower substituent group) or unsubstituted aldehyde moiety, substituted (e.g., substituted with a substituent group, a size-limited substituent group, or lower substituent group) or unsubstituted enone moiety, substituted (e.g., substituted with a substituent group, a size-limited substituent group, or lower substituent group) or unsubstituted diazomethylketone moiety, substituted (e.g., substituted with a substituent group, a size-limited substituent group, or lower substituent group) or unsubstituted diazomethylamide moiety, substituted (e.g., substituted with a substituent group, a size-limited substituent group, or lower substituent group) or unsubstituted cyanocyclopropyl carboxamide moiety, substituted (e.g., substituted with a substituent group, a size-limited substituent group, or lower substituent group) or unsubstituted epoxide moiety, substituted (e.g., substituted with a substituent group, a size-limited substituent group, or lower substituent group) or unsubstituted epoxyketone moiety, substituted (e.g., substituted with a substituent group, a size-limited substituent group, or lower substituent group) or unsubstituted epoxyamide moiety, substituted (e.g., substituted with a substituent group, a size-limited substituent group, or lower substituent group) or unsubstituted aryl aldehyde moiety, substituted (e.g., substituted with a substituent group, a size-limited substituent group, or lower substituent group) or unsubstituted aryl dialdehyde moiety, substituted (e.g., substituted with a substituent group, a size-limited substituent group, or lower substituent group) or unsubstituted dialdehyde moiety, substituted (e.g., substituted with a substituent group, a size-limited substituent group, or lower substituent group) or unsubstituted nitrogen mustard moiety, substituted (e.g., substituted with a substituent group, a size-limited substituent group, or lower substituent group) or unsubstituted propargyl moiety, substituted (e.g., substituted with a substituent group, a size-limited substituent group, or lower substituent group) or unsubstituted propargylamide moiety,
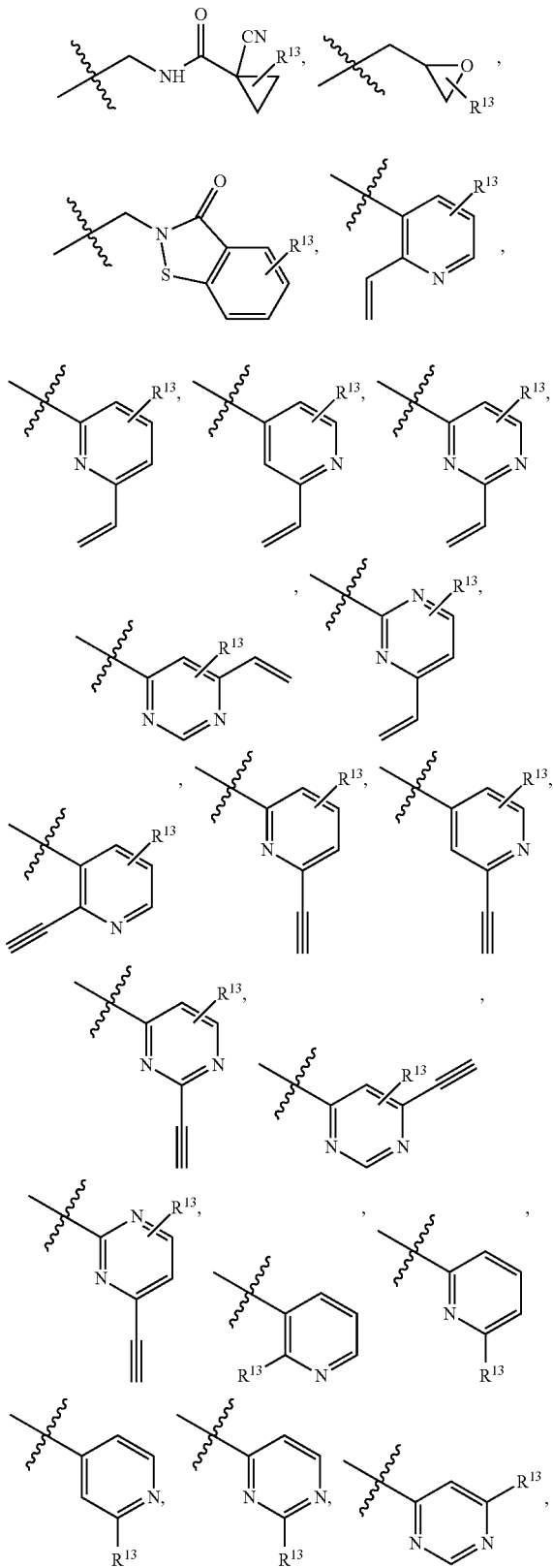
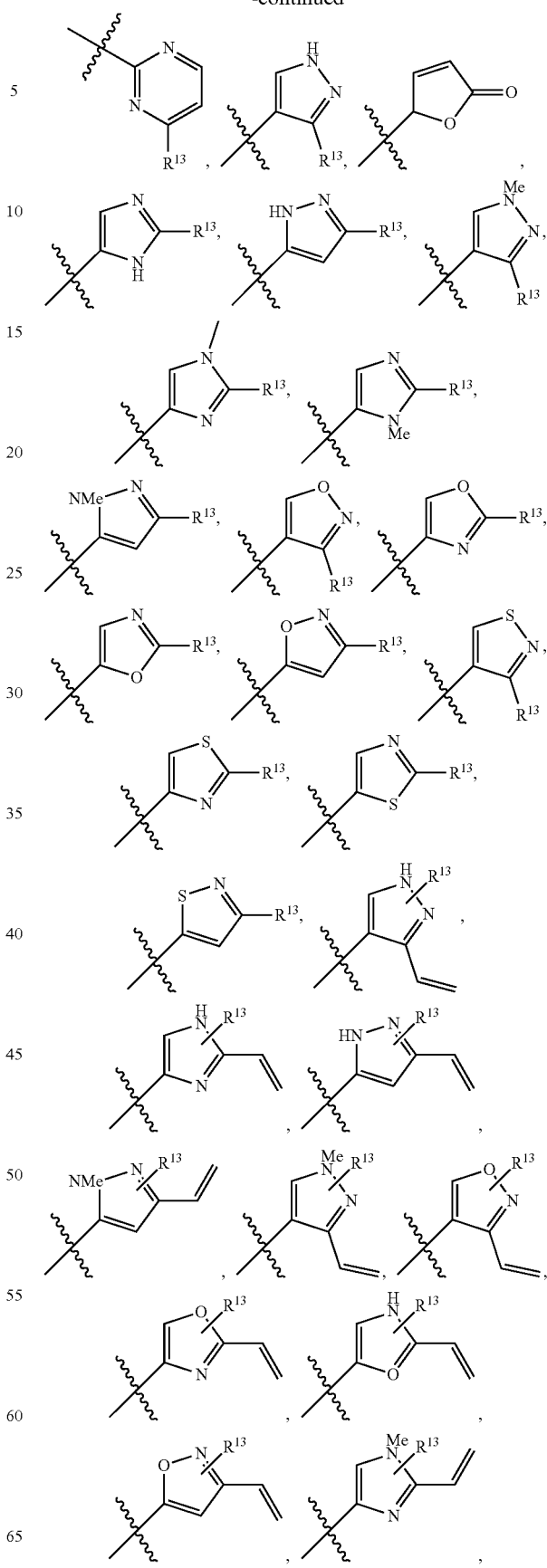

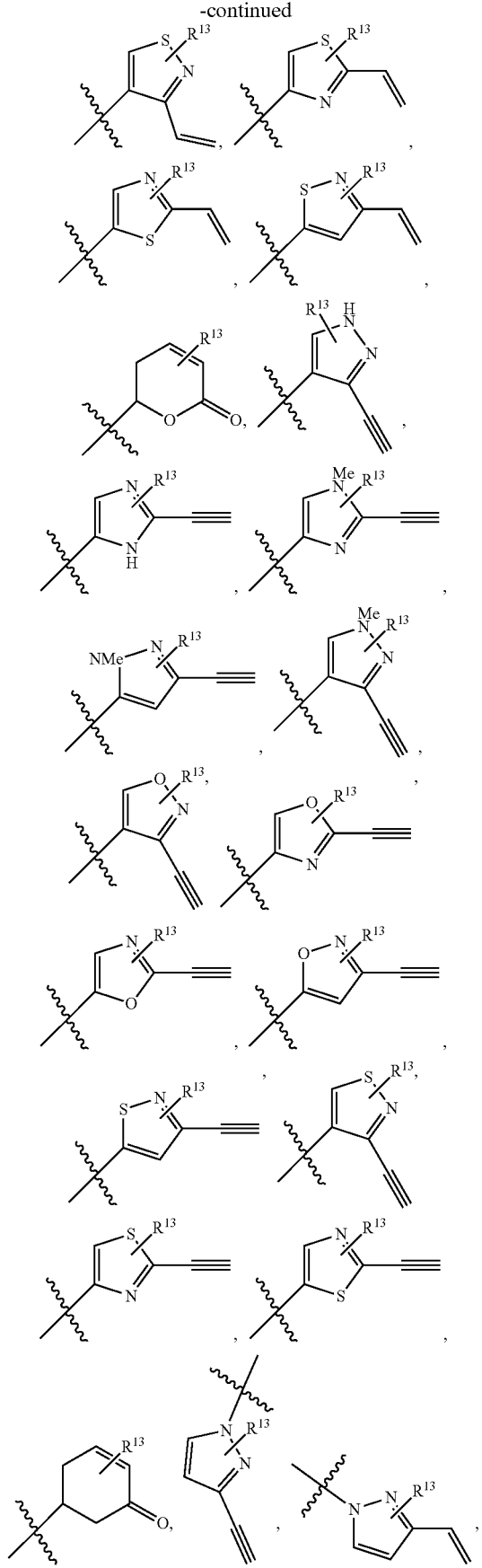
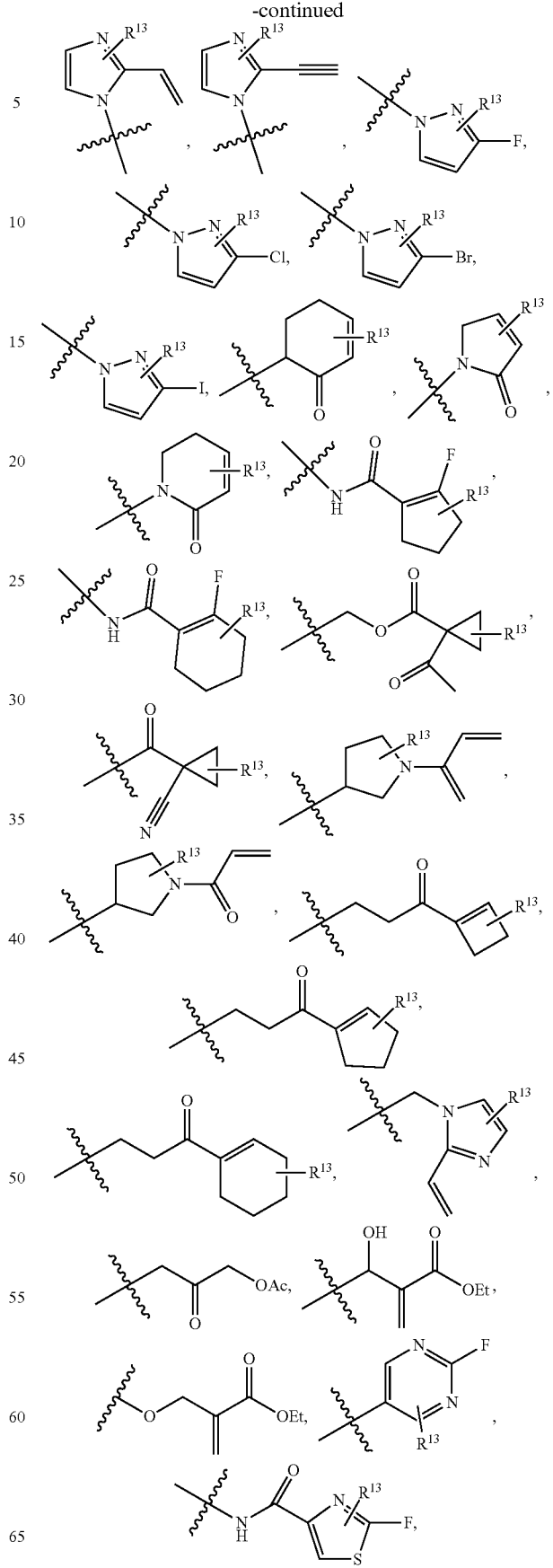

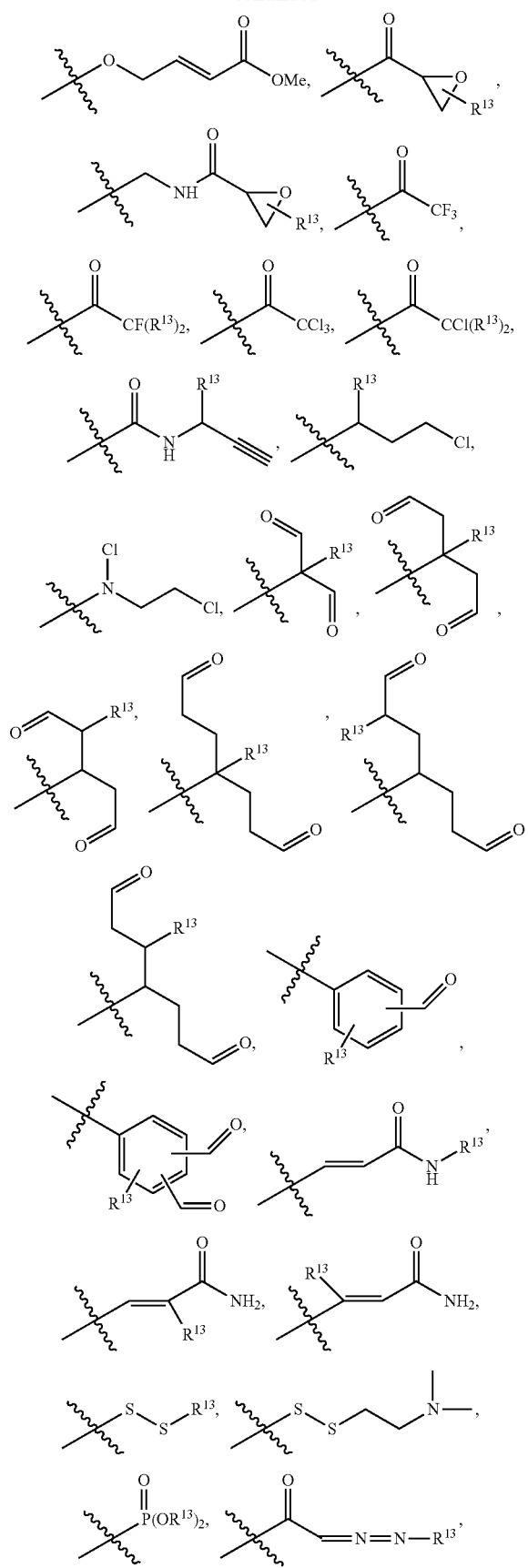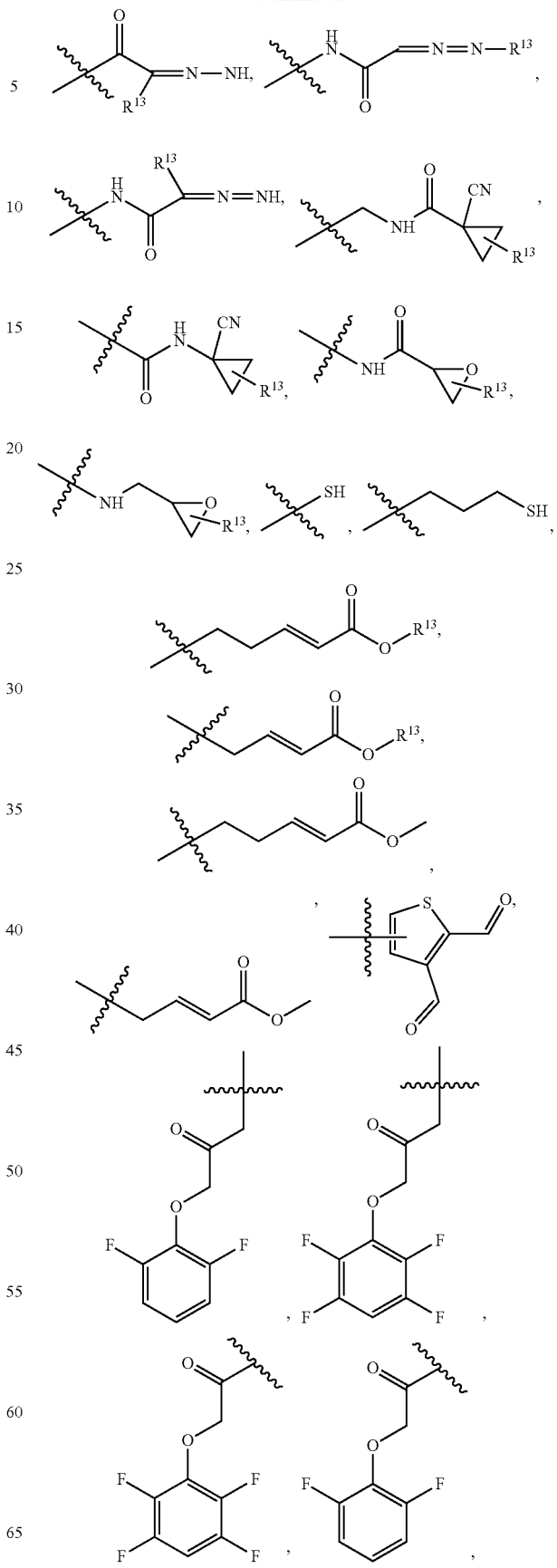

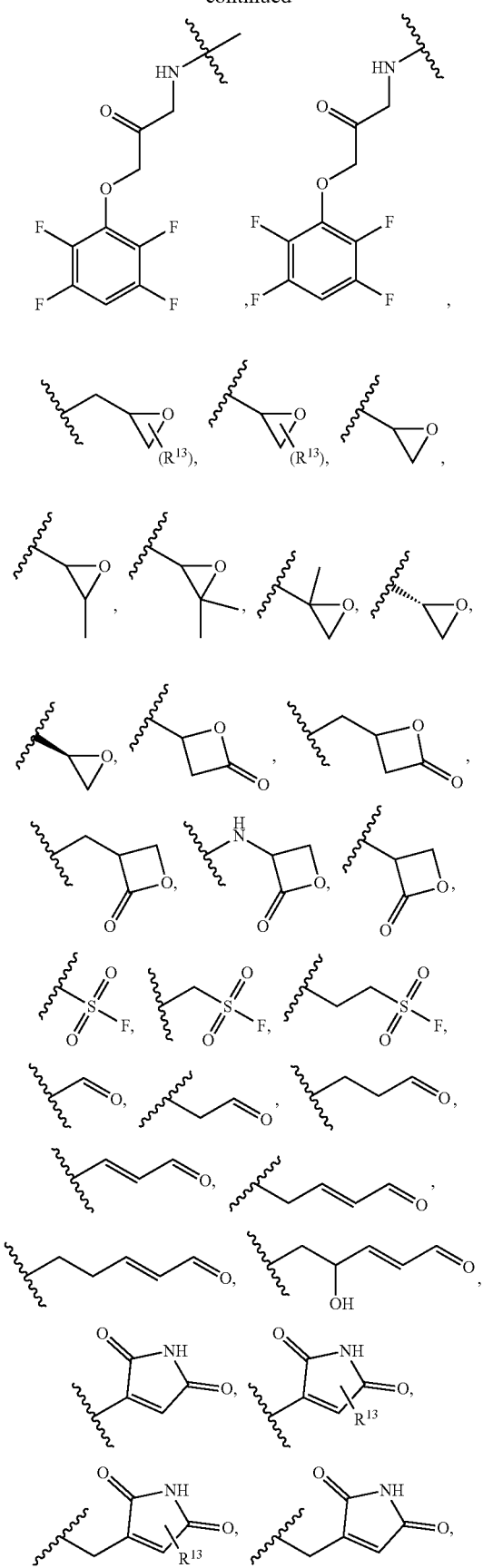
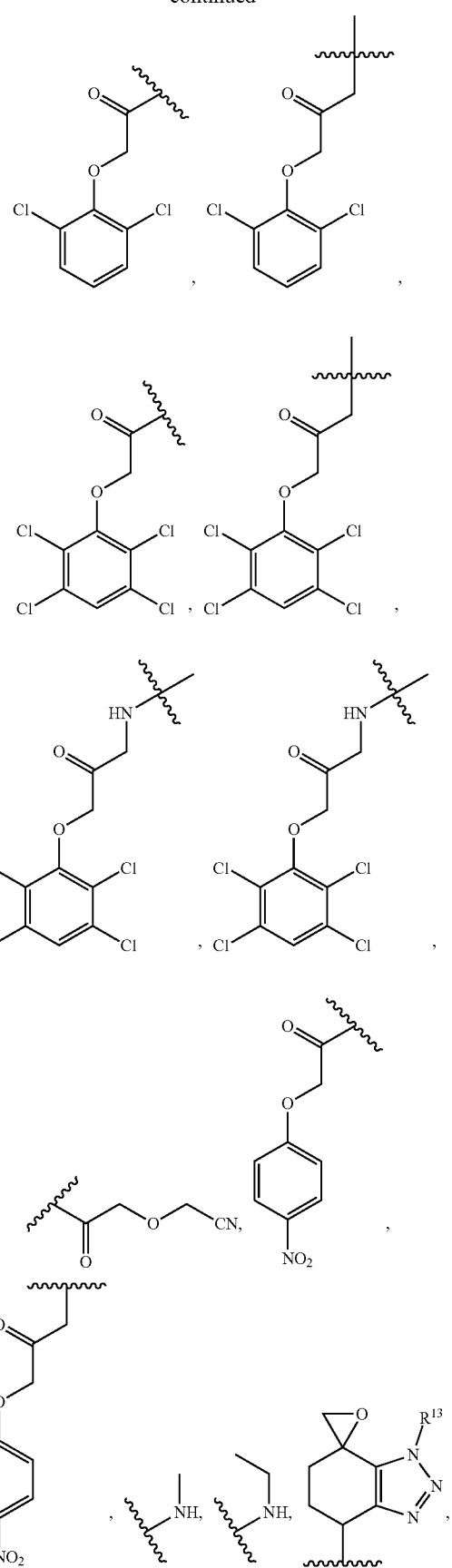

-continued

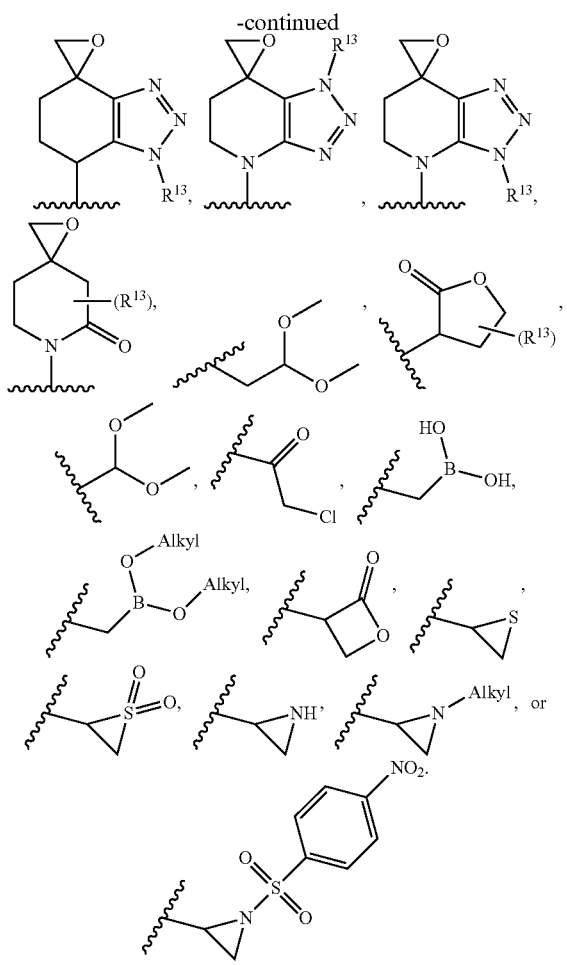

In embodiments, E is an unsubstituted vinyl sulfone moiety, unsubstituted vinyl sulfonamide moiety, unsubstituted fluoro($C_1$-$C_4$)alkylketone moiety, unsubstituted chloro ($C_1$-$C_4$)alkylketone moiety, unsubstituted acrylamide moiety, unsubstituted disulfide moiety, unsubstituted thiol moiety, unsubstituted phosphonate moiety, unsubstituted aldehyde moiety, unsubstituted enone moiety, unsubstituted diazomethylketone moiety, unsubstituted diazomethylamide moiety, unsubstituted cyanocyclopropyl carboxamide moiety, unsubstituted epoxide moiety, unsubstituted epoxyketone moiety, unsubstituted epoxyamide moiety, unsubstituted aryl aldehyde moiety, unsubstituted aryl dialdehyde moiety, unsubstituted dialdehyde moiety, unsubstituted nitrogen mustard moiety, unsubstituted propargyl moiety, or unsubstituted propargylamide moiety.

$R^{13}$ is independently hydrogen, a substituent group, a size-limited substituent group, or a lower substituent group. In embodiments, $R^{13}$ is independently hydrogen.

In embodiments, the compound is

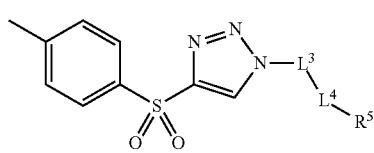

wherein $L^3$, $L^4$, and $R^5$ are as described herein. In embodiments, the compound is

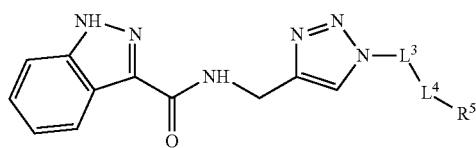

wherein $L^3$, $L^4$, and $R^5$ are as described herein. In embodiments, the compound is

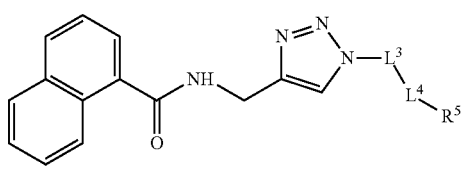

wherein $L^3$, $L^4$, and $R^5$ are as described herein. In embodiments, the compound is

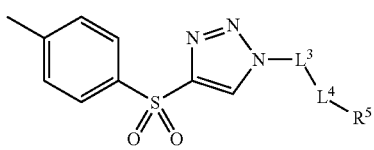

wherein $L^3$, $L^4$, and $R^5$ are as described herein. In embodiments, the compound is

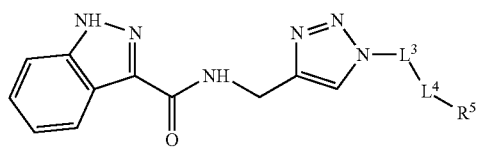

wherein $L^3$, $L^4$ and $R^5$ are as described herein. In embodiments, the compound is

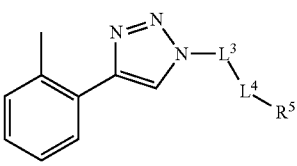

wherein $L^3$, $L^4$, and $R^5$ are as described herein. In embodiments, the compound is

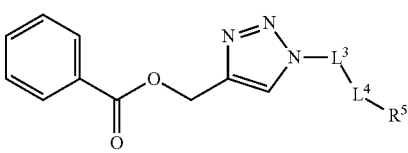

wherein $L^3$, $L^4$, and $R^5$ are as described herein. In embodiments, the compound is

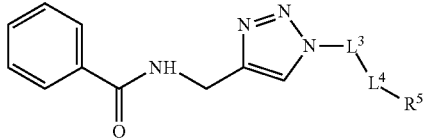

wherein $L^3$, $L^4$, and $R^5$ are as described herein. In embodiments, the compound is

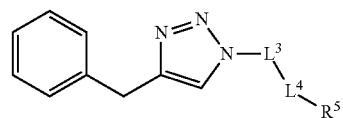

wherein $L^3$, $L^4$, and $R^5$ are as described herein. In embodiments, the compound is

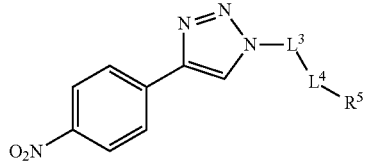

wherein $L^3$, $L^4$, and $R^5$ are as described herein. In embodiments, the compound is

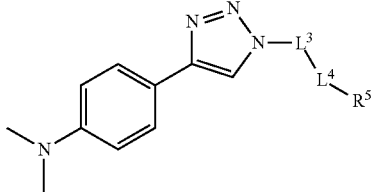

wherein $L^3$, $L^4$, and $R^5$ are as described herein. In embodiments, the compound is

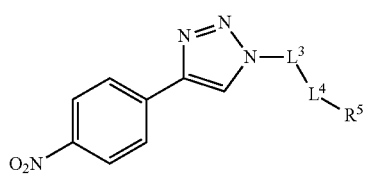

wherein $L^3$, $L^4$, and $R^5$ are as described herein.

In embodiments, the compound is

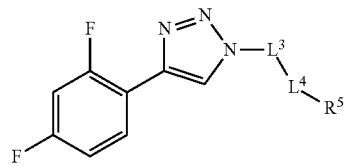

wherein $L^3$, $L^4$, and $R^5$ are as described herein. In embodiments, the compound is

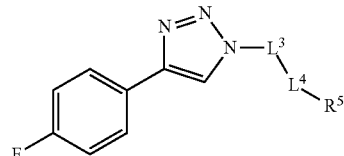

wherein $L^3$, $L^4$, and $R^5$ are as described herein. In embodiments, the compound is

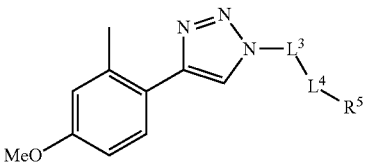

wherein $L^3$, $L^4$, and $R^5$ are as described herein. In embodiments, the compound is

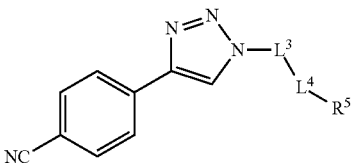

wherein $L^3$, $L^4$, and $R^5$ are as described herein. In embodiments, the compound is

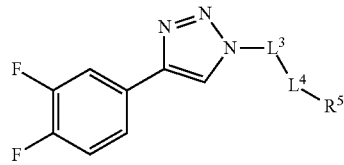

wherein $L^3$, $L^4$, and $R^5$ are as described herein. In embodiments, the compound is

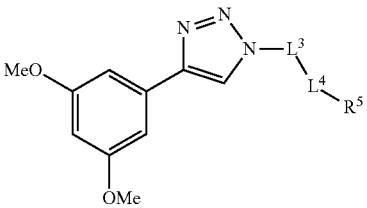

wherein L³, L⁴, and R⁵ are as described herein. In embodiments, the compound is

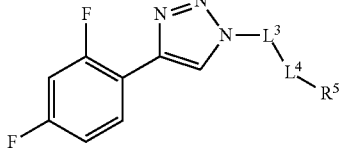

wherein L³, L⁴, and R⁵ are as described herein. In embodiments, the compound is

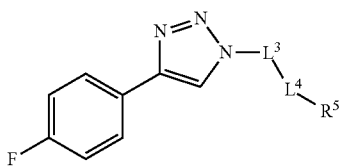

wherein L³, L⁴, and R⁵ are as described herein. In embodiments, the compound is

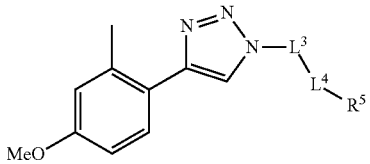

wherein L³, L⁴, and R⁵ are as described herein. In embodiments, the compound is

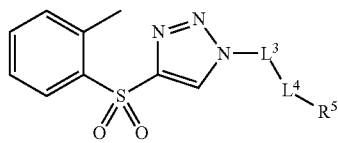

wherein L³, L⁴, and R⁵ are as described herein. In embodiments, the compound is

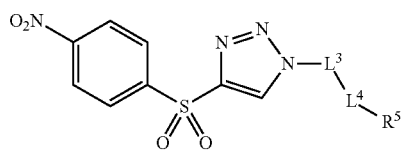

wherein L³, L⁴, and R⁵ are as described herein. In embodiments, the compound is

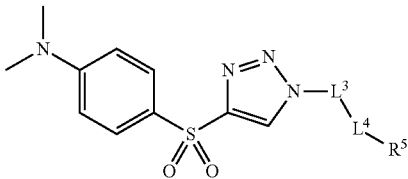

wherein L⁴, L⁴, and R⁵ are as described herein. In embodiments, the compound is

wherein L³, L⁴, and R⁵ are as described herein. In embodiments, the compound is

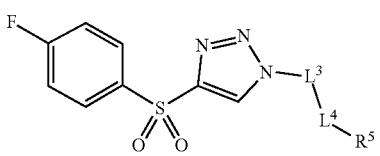

wherein L³, L⁴, and R⁵ are as described herein. In embodiments, the compound is

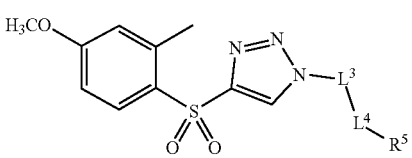

wherein L³, L⁴, and R⁵ are as described herein. In embodiments, the compound is

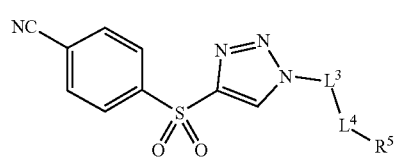

wherein L³, L⁴, and R⁵ are as described herein. In embodiments, the compound is

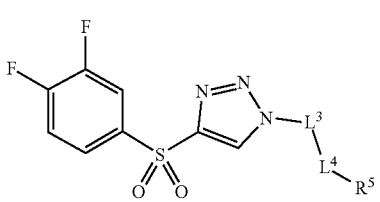

wherein $L^3$, $L^4$, and $R^5$ are as described herein. In embodiments, the compound is

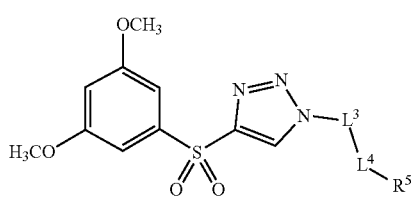

wherein $L^3$, $L^4$, and $R^5$ are as described herein. In embodiments, the compound is

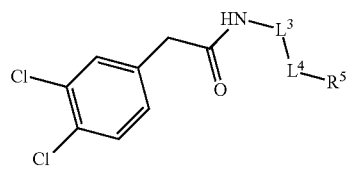

wherein $L^3$, $L^4$, and $R^5$ are as described herein. In embodiments, the compound is

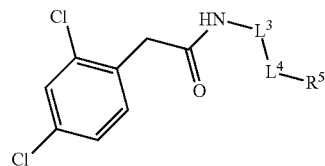

wherein $L^3$, $L^4$, and $R^5$ are as described herein. In embodiments, the compound is

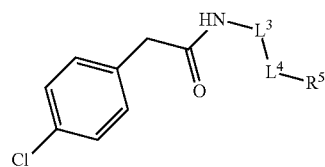

wherein $L^3$, $L^4$, and $R^5$ are as described herein. In embodiments, the compound is

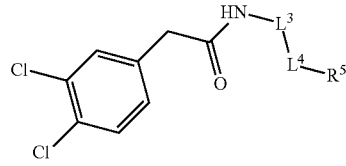

wherein $L^3$, $L^4$, and $R^5$ are as described herein. In embodiments, the compound is

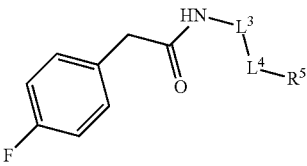

wherein $L^3$, $L^4$, and $R^5$ are as described herein. In embodiments, the compound is

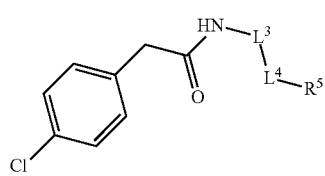

wherein $L^3$, $L^4$, and $R^5$ are as described herein. In embodiments, the compound is

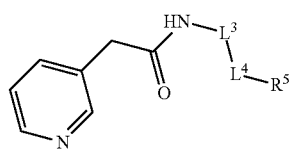

wherein $L^3$, $L^4$, and $R^5$ are as described herein. In embodiments, the compound is

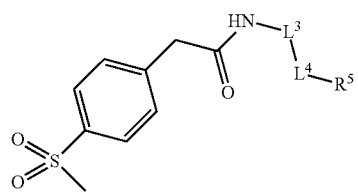

wherein $L^3$, $L^4$, and $R^5$ are as described herein. In embodiments, the compound is

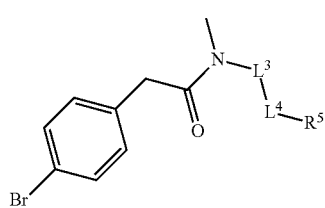

wherein $L^3$, $L^4$, and $R^5$ are as described herein. In embodiments, the compound is

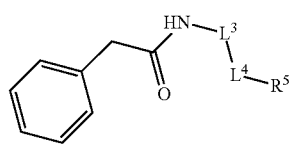

wherein $L^3$, $L^4$, and $R^5$ are as described herein. In embodiments, the compound is

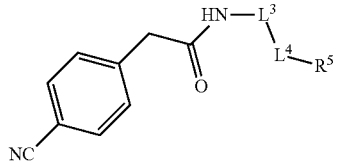

wherein $L^3$, $L^4$, and $R^5$ are as described herein. In embodiments, the compound is

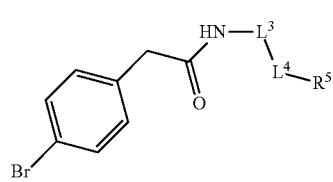

wherein $L^3$, $L^4$, and $R^5$ are as described herein. In embodiments, the compound is

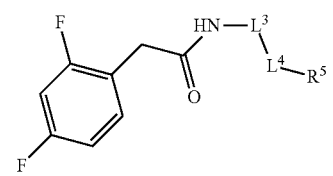

wherein $L^3$, $L^4$, and $R^5$ are as described herein. In embodiments, the compound is

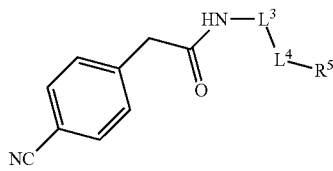

wherein $L^3$, $L^4$, and $R^5$ are as described herein. In embodiments, the compound is

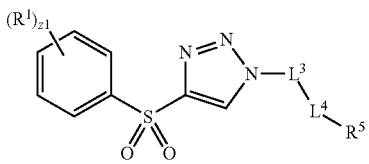

wherein $R^1$, z1, $L^3$, $L^4$, and $R^5$ are as described herein. In embodiments, the compound is

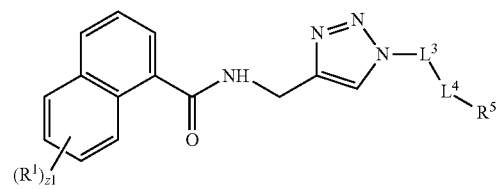

wherein $R^1$, z1, $L^3$, $L^4$, and $R^5$ are as described herein. In embodiments, the compound is

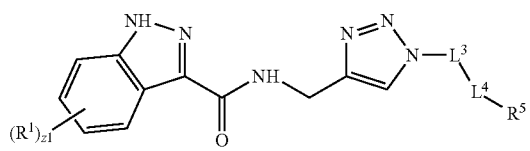

wherein $R^1$, z1, $L^3$, $L^4$, and $R^5$ are as described herein. In embodiments, the compound is

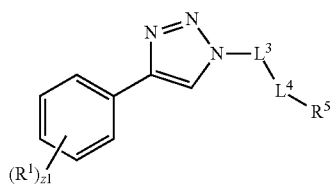

wherein $R^1$, z1, $L^3$, $L^4$, and $R^5$ are as described herein. In embodiments, the compound is

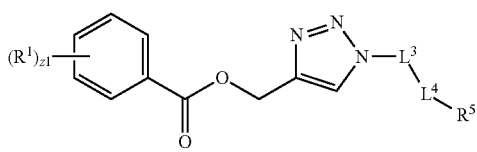

wherein $R^1$, z1, $L^3$, $L^4$, and $R^5$ are as described herein. In embodiments, the compound is

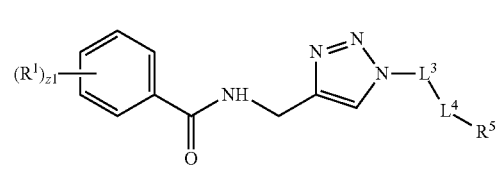

wherein $R^1$, z1, $L^3$, $L^4$, and $R^5$ are as described herein. In embodiments, the compound is

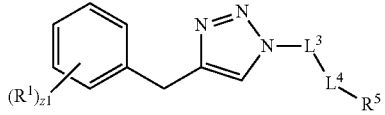

wherein $R^1$, z1, $L^3$, $L^4$, and $R^5$ are as described herein. In embodiments, the compound is

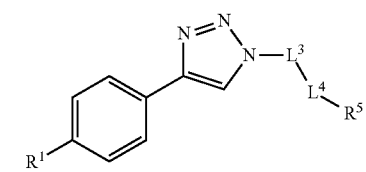

wherein $R^1$, $L^3$, $L^4$, and $R^5$ are as described herein. In embodiments, the compound is

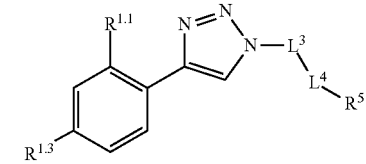

wherein $R^{1.3}$, $R^{1.1}$, $R^{1.3}$, $L^3$, $L^4$, and $R^5$ $L^3$, $L^4$, and $R^5$ are as described herein. In embodiments, the compound is

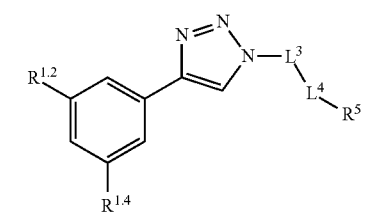

wherein $R^{1.2}$, $R^{1.4}$, $L^3$, $L^4$, and $R^5$ are as described herein. In embodiments, the compound is

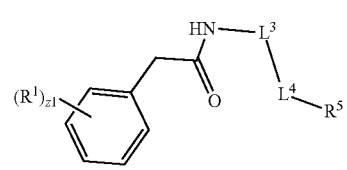

wherein $R^1$, z1, $L^3$, $L^4$, and $R^5$ are as described herein. In embodiments, the compound is

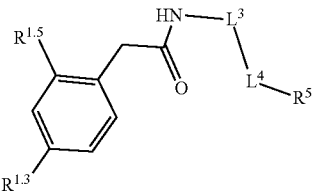

wherein $R^{1.3}$, $R^{1.5}$, $L^3$, $L^4$, and $R^5$ are as described herein. In embodiments, the compound is

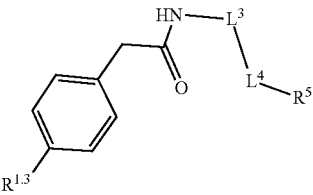

wherein $R^{1.3}$, $L^3$, $L^4$, and $R^5$ are as described herein. In embodiments, the compound is

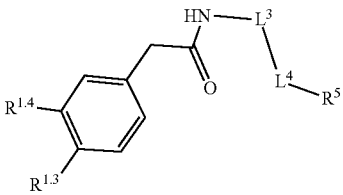

wherein $R^{1.3}$, $R^{1.4}$, $L^3$, $L^4$, and $R^5$ are as described herein. In embodiments, the compound is

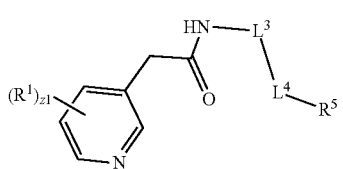

wherein $R^1$, z1, $L^3$, $L^4$, and $R^5$ are as described herein. In embodiments, the compound is

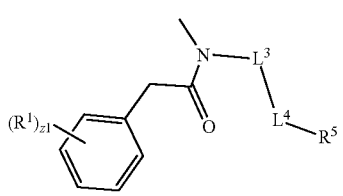

wherein $R^1$, z1, $L^3$, $L^4$, and $R^5$ are as described herein.

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer.

In embodiments, the compound inhibits proliferation of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under serum deprivation conditions relative to the absence of the compound. In embodiments, the compound inhibits proliferation of cancer cells under serum deprivation conditions relative to the absence of the compound. In embodiments, the compound inhibits growth of cancer cells under conditions (e.g. local cell environment in a patient) mimicking serum deprivation relative to the absence of the compound. In embodiments, the compound inhibits proliferation of cancer cells under conditions (e.g. local cell environment in a patient) mimicking serum deprivation relative to the absence of the compound.

In some embodiments, the compound is any one of the compounds described herein (e.g., in an aspect, embodiment, claim, figure, table, or example).

In some embodiments, a compound as described herein may include multiple instances of $R^1$ and/or other variables. In such embodiments, each variable may optional be different and be appropriately labeled to distinguish each group for greater clarity. For example, where each $R^1$, is different, they may be referred to, for example, as $R^{1.1}$, $R^{1.2}$, $R^{1.3}$, $R^{1.4}$, $R^{1.5}$, respectively, wherein the definition of $R^1$ is assumed by $R^{1.1}$, $R^{1.2}$, $R^{1.3}$, $R^{1.4}$, $R^{1.5}$.

The variables used within a definition of $R^1$ and/or other variables that appear at multiple instances and are different may similarly be appropriately labeled to distinguish each group for greater clarity.

In embodiments, the compound is 966844. In embodiments, the compound is 966854. In embodiments, the compound is 917181. In embodiments, the compound is 917105. In embodiments, the compound is 960005. In embodiments, the compound is 917332. In embodiments, the compound is 916860. In embodiments, the compound is 916929. In embodiments, the compound is 917680. In embodiments, the compound is 917876. In embodiments, the compound is 957805. In embodiments, the compound is 966844. In embodiments, the compound is 966849. In embodiments, the compound is 966794. In embodiments, the compound is 966854. In embodiments, the compound is 957833. In embodiments, the compound is 916860. In embodiments, the compound is 917105. In embodiments, the compound is 917181. In embodiments, the compound is 966976. In embodiments, the compound is 917162. In embodiments, the compound is 916929. In embodiments, the compound is 957805. In embodiments, the compound is 916960. In embodiments, the compound is 996844. In embodiments, the compound is 996849. In embodiments, the compound is 996854. In embodiments, the compound is 717105. In embodiments, the compound is 916929. In embodiments, the compound is 966844. In embodiments, the compound is 966854. In embodiments, the compound is 966849. In embodiments, the compound is 917105. In embodiments, the compound is 916929. In embodiments, the compound is FNL-002. In embodiments, the compound is FNL-0006. In embodiments, the compound is FNL-0007. In embodiments, the compound is FNL-0008. In embodiments, the compound is FNL-0004. In embodiments, the compound is FNL-0005. In embodiments, the compound is FNL-0009. In embodiments, the compound is FNL-0001. In embodiments, the compound is FNL-0013. In embodiments, the compound is FNL-00014. In embodiments, the compound is FNL-0015. In embodiments, the compound is FNL-0024. In embodiments, the compound is FNL-0026. In embodiments, the compound is FNL-0016. In embodiments, the compound is FNL-0010. In embodiments, the compound is FNL-0012. In embodiments, the compound is FNL-0030. In embodiments, the compound is FNL-0036. In embodiments, the compound is FNL-0037. In embodiments, the compound is FNL-0038.

In embodiments, the compound is SMDC 917105. In embodiments, the compound is SMDC 917102. In embodiments, the compound is SMDC 916899. In embodiments, the compound is SMDC 917181. In embodiments, the compound is SMDC 916860. In embodiments, the compound is SMDC 916860. In embodiments, the compound is SMDC 966906. In embodiments, the compound is SMDC 917138. In embodiments, the compound is SMDC 960055. In embodiments, the compound is SMDC 966921. In embodiments, the compound is SMDC 966976. In embodiments, the compound is SMDC 917632. In embodiments, the compound is SMDC917192. In embodiments, the compound is SMDC 966938. In embodiments, the compound is SMDC 957780. In embodiments, the compound is SMDC 966844. In embodiments, the compound is SMDC 966854. In embodiments, the compound is SMDC 966782. In embodiments, the compound is SMDC 966849. In embodiments, the compound is SMDC 966859. In embodiments, the compound is SMDC 966539. In embodiments, the compound is SMDC 966781. In embodiments, the compound is SMDC 966846. In embodiments, the compound is SMDC 957828. In embodiments, the compound is SMDC 966783. In embodiments, the compound is SMDC966536. In embodiments, the compound is SMDC 966541. In embodiments, the compound is SMDC 966794. In embodiments, the compound is SMDC 966793. In embodiments, the compound is SMDC 966785. In embodiments, the compound is SMDC 966538. In embodiments, the compound is SMDC 966858. In embodiments, the compound is SMDC 966857. In embodiments, the compound is SMDC 966789. In embodiments, the compound is SMDC 957835. In embodiments, the compound is SMDC 957827. In embodiments, the compound is SMDC 966844. In embodiments, the compound is SMDC 916860. In embodiments, the compound is SMDC 917162. In embodiments, the compound is SMDC 966849. In embodiments, the compound is SMDC 917105. In embodiments, the compound is SMDC 916929. In embodiments, the compound is SMDC 996794. In embodiments, the compound is SMDC 917181. In embodiments, the compound is SMDC 966854. In embodiments, the compound is SMDC 966976. In embodiments, the compound is SMDC 957805. In embodiments, the compound is SMDC 957833. In embodiments, the compound is SMDC 916960.

In embodiments, the compound is not a compound described in an example, figure, table, or scheme. In embodiments, the compound is not a compound described in WO 2016/179558, which is incorporated by reference for any purpose.

In embodiments, R⁵ is not

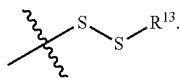

In embodiments, R⁵ does not include a disulfide bridge moiety. In embodiments, R⁵ is not

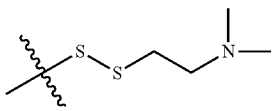 [SMILES: *SSCCN(C)C]

In embodiments, R⁵ is not

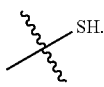

In embodiments, R⁵ is not

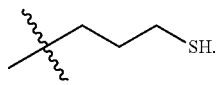 [SMILES: *CCCS]

In embodiments, -L³-L⁴-R⁵ is not

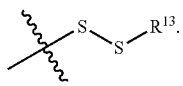

In embodiments, -L³-L⁴-R⁵ is not

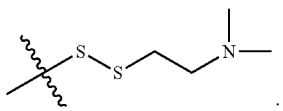

In embodiments, -L³-L⁴-R⁵ is not

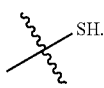

In embodiments, -L³-L⁴-R⁵ is not

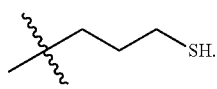 [SMILES: *CCCS]

In embodiments, -L³-L⁴-R⁵ is not

In embodiments, -L³-L⁴-R⁵ is not

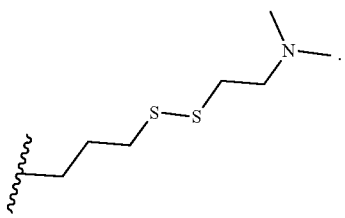 [SMILES: *CCCSSCCN(C)C]

In embodiments, E is not

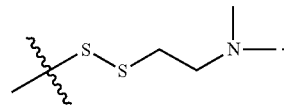

In embodiments, E does not include a disulfide bridge moiety. In embodiments, E is not

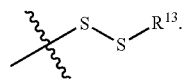

In embodiments, E is not

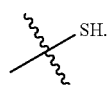

In embodiments, E is not

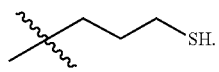

In embodiments, -L³-L⁴-E is not

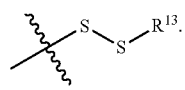

In embodiments, -L³-L⁴-E is not

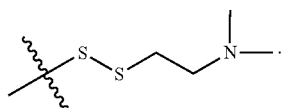 [SMILES: *SSCCN(C)C]

In embodiments, -L³-L⁴-E is not

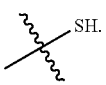

In embodiments, -L³-L⁴-E is not

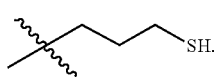

In embodiments, -L³-L⁴E is not

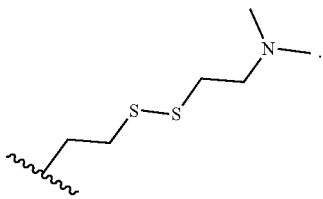 [SMILES: *CCSSCCN(C)C]

In embodiments, -L³-L⁴-E is not

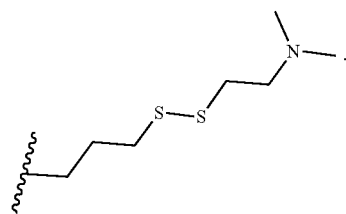 [SMILES: *CCCSSCCN(C)C]

In embodiments, the compound is not

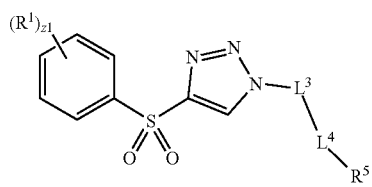

wherein R¹, z1, L³, L⁴, and R⁵ are as described herein. In embodiments, the compound is not

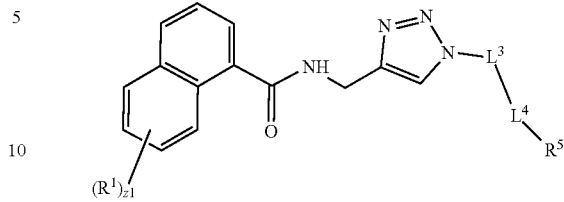

wherein R¹, z1, L³, L⁴, and R⁵ are as described herein. In embodiments, the compound is not

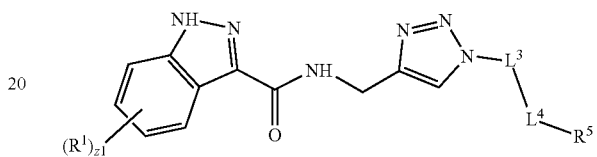

wherein R¹, z1, L³, L⁴, and R⁵ are as described herein. In embodiments, the compound is not

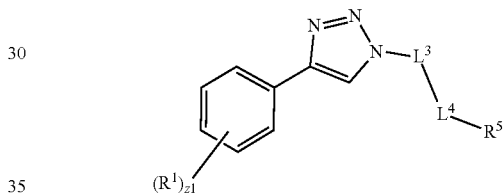

wherein R¹, z1, L³, L⁴, and R⁵ are as described herein. In embodiments, the compound is not

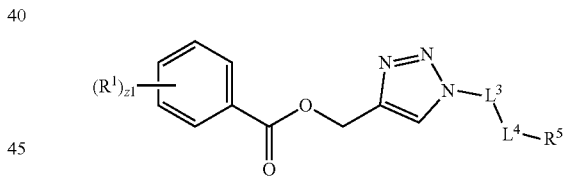

wherein R¹, z1, L³, L⁴, and R⁵ are as described herein. In embodiments, the compound is not

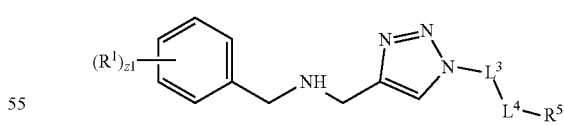

wherein R¹, z1, L³, L⁴, and R⁵ are as described herein. In embodiments, the compound is not

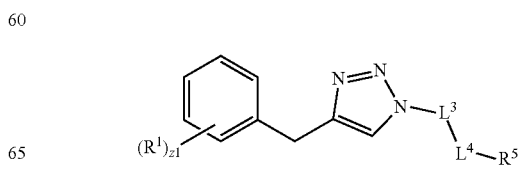

wherein $R^1$, z1, $L^3$, $L^4$, and $R^5$ are as described herein. In embodiments, the compound is not

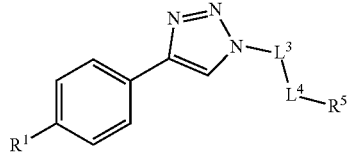

wherein $R^1$, $L^3$, $L^4$, and $R^5$ are as described herein. In embodiments, the compound is not

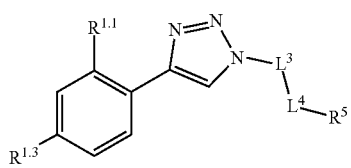

wherein $R^{1.3}$, $R^{1.1}$, $R^{1.3}$, $L^3$, $L^4$, and $R^5$ $L^3$, $L^4$, and $R^5$ are as described herein. In embodiments, the compound is not wherein $R^{1.2}$, $R^{1.4}$, $L^3$, $L^4$, and $R^5$ are as described herein. In embodiments, the compound is not wherein $R^1$, z1, $L^3$, $L^4$, and $R^5$ are as described herein. In embodiments, the compound is not wherein $R^{1.3}$, $R^{1.5}$, $L^3$, $L^4$, and $R^5$ are as described herein. In embodiments, the compound is not

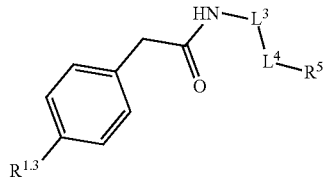

wherein $R^{1.3}$, $R^{1.5}$, $L^3$, $L^4$, and $R^5$ are as described herein. In embodiments, the compound is not

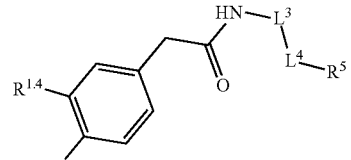

wherein $R^{1.3}$, $R^{1.4}$, $L^3$, $L^4$, and $R^5$ are as described herein. In embodiments, the compound is not

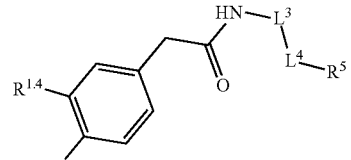

wherein $R^1$, z1, $L^3$, $L^4$, and $R^5$ are as described herein. In embodiments, the compound is not wherein $R^1$, z1, $L^3$, $L^4$, and $R^5$ are as described herein. In embodiments, the compound is not wherein R¹ and z1 are as described herein. In embodiments, the compound is not

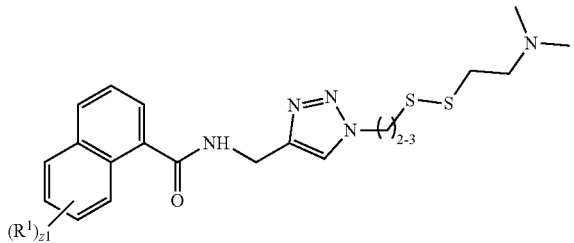

wherein R¹ and z1 are as described herein. In embodiments, the compound is not

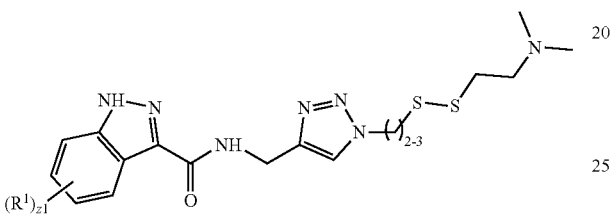

wherein R¹ and z1 are as described herein. In embodiments, the compound is not

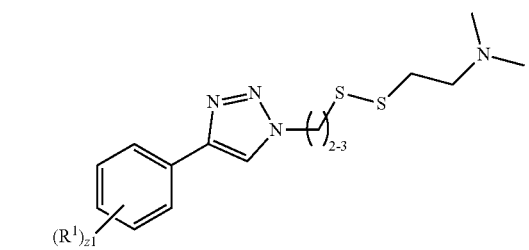

wherein R¹ and z1 are as described herein. In embodiments, the compound is not

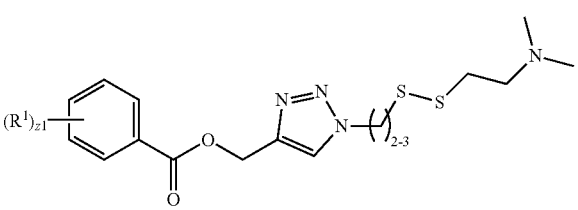

wherein R¹ and z1 are as described herein. In embodiments, the compound is not

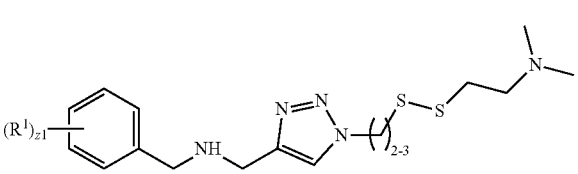

wherein R¹ and z1 are as described herein. In embodiments, the compound is not

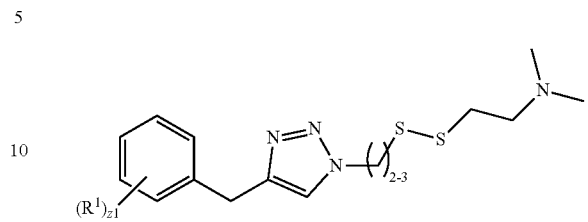

wherein R¹ and z1 are as described herein. In embodiments, the compound is not

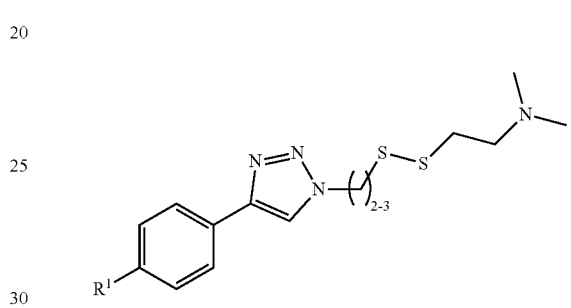

wherein R¹ is as described herein. In embodiments, the compound is not wherein $R^{1.1}$ and $R^{1.3}$ are as described herein. In embodiments, the compound is not wherein $R^{1.2}$ and $R^{1.4}$ are as described herein.

In embodiments, the compound is not

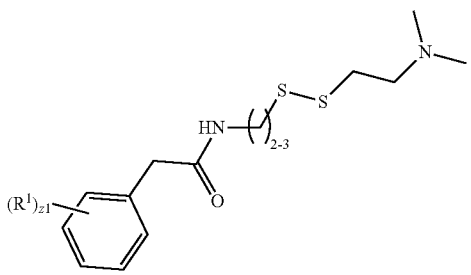

wherein $R^1$ and z1 are as described herein. In embodiments, the compound is not

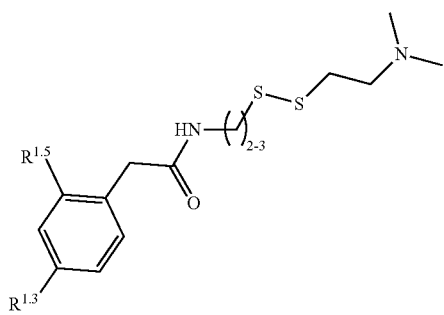

wherein $R^{1.3}$ and $R^{1.5}$ are as described herein. In embodiments, the compound is not

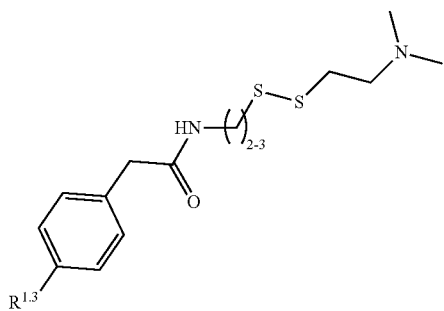

$R^{1.3}$ wherein $R^{1.3}$ is as described herein. In embodiments, the compound is not

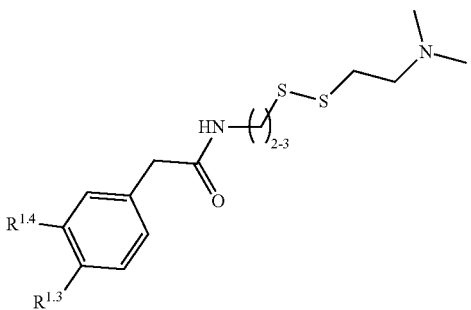

wherein $R^{1.3}$ and $R^{1.4}$ are as described herein. In embodiments, the compound is not

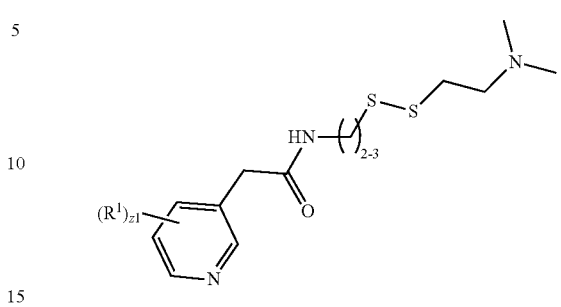

wherein $R^1$ and z1 are as described herein. In embodiments, the compound is not

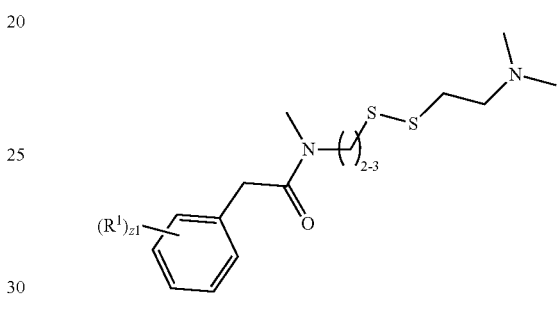

wherein $R^1$ and z1 are as described herein.

In embodiments, the compound is not 966844. In embodiments, the compound is not 966854. In embodiments, the compound is not 917181. In embodiments, the compound is not 917105. In embodiments, the compound is not 960005. In embodiments, the compound is not 917332. In embodiments, the compound is not 916860. In embodiments, the compound is not 916929. In embodiments, the compound is not 917680. In embodiments, the compound is not 917876. In embodiments, the compound is not 957805. In embodiments, the compound is not 966844. In embodiments, the compound is not 966849. In embodiments, the compound is not 966794. In embodiments, the compound is not 966854. In embodiments, the compound is not 957833. In embodiments, the compound is not 916860. In embodiments, the compound is not 917105. In embodiments, the compound is not 917181. In embodiments, the compound is not 966976. In embodiments, the compound is not 917162. In embodiments, the compound is not 916929. In embodiments, the compound is not 957805. In embodiments, the compound is not 916960. In embodiments, the compound is not 996844. In embodiments, the compound is not 996849. In embodiments, the compound is not 996854. In embodiments, the compound is not 717105. In embodiments, the compound is not 916929. In embodiments, the compound is not 966844. In embodiments, the compound is not 966854. In embodiments, the compound is not 966849. In embodiments, the compound is not 917105. In embodiments, the compound is not 916929. In embodiments, the compound is not FNL-002. In embodiments, the compound is not FNL-0006. In embodiments, the compound is not FNL-0007. In embodiments, the compound is not FNL-0008. In embodiments, the compound is not FNL-0004. In embodiments, the compound is not FNL-0005. In embodiments, the compound is not FNL-0009. In embodiments, the compound is not FNL- 0001. In embodiments, the compound is not FNL-0013. In embodiments, the compound is not FNL-00014. In embodiments, the compound is not FNL-0015. In embodiments, the compound is not FNL-0024. In embodiments, the compound is not FNL-0026. In embodiments, the compound is not FNL-0016. In embodiments, the compound is not FNL-0010. In embodiments, the compound is not FNL-0012. In embodiments, the compound is not FNL-0030. In embodiments, the compound is not FNL-0036. In embodiments, the compound is not FNL-0037. In embodiments, the compound is not FNL-0038.

In embodiments, the compound is not 966844 or an analog or prodrug thereof. In embodiments, the compound is not 966854 or an analog or prodrug thereof. In embodiments, the compound is not 917181 or an analog or prodrug thereof. In embodiments, the compound is not 917105 or an analog or prodrug thereof. In embodiments, the compound is not 960005 or an analog or prodrug thereof. In embodiments, the compound is not 917332 or an analog or prodrug thereof. In embodiments, the compound is not 916860 or an analog or prodrug thereof. In embodiments, the compound is not 916929 or an analog or prodrug thereof. In embodiments, the compound is not 917680 or an analog or prodrug thereof. In embodiments, the compound is not 917876 or an analog or prodrug thereof. In embodiments, the compound is not 957805 or an analog or prodrug thereof. In embodiments, the compound is not 966844 or an analog or prodrug thereof. In embodiments, the compound is not 966849 or an analog or prodrug thereof. In embodiments, the compound is not 966794 or an analog or prodrug thereof. In embodiments, the compound is not 966854 or an analog or prodrug thereof. In embodiments, the compound is not 957833 or an analog or prodrug thereof. In embodiments, the compound is not 916860 or an analog or prodrug thereof. In embodiments, the compound is not 917105 or an analog or prodrug thereof. In embodiments, the compound is not 917181 or an analog or prodrug thereof. In embodiments, the compound is not 966976 or an analog or prodrug thereof. In embodiments, the compound is not 917162 or an analog or prodrug thereof. In embodiments, the compound is not 916929 or an analog or prodrug thereof. In embodiments, the compound is not 957805 or an analog or prodrug thereof. In embodiments, the compound is not 916960 or an analog or prodrug thereof. In embodiments, the compound is not 996844 or an analog or prodrug thereof. In embodiments, the compound is not 996849 or an analog or prodrug thereof. In embodiments, the compound is not 996854 or an analog or prodrug thereof. In embodiments, the compound is not 717105 or an analog or prodrug thereof. In embodiments, the compound is not 916929 or an analog or prodrug thereof. In embodiments, the compound is not 966844 or an analog or prodrug thereof. In embodiments, the compound is not 966854 or an analog or prodrug thereof. In embodiments, the compound is not 966849 or an analog or prodrug thereof. In embodiments, the compound is not 917105 or an analog or prodrug thereof. In embodiments, the compound is not 916929 or an analog or prodrug thereof. In embodiments, the compound is not FNL-002 or an analog or prodrug thereof. In embodiments, the compound is not FNL-0006 or an analog or prodrug thereof. In embodiments, the compound is not FNL-0007 or an analog or prodrug thereof. In embodiments, the compound is not FNL-0008 or an analog or prodrug thereof. In embodiments, the compound is not FNL-0004 or an analog or prodrug thereof. In embodiments, the compound is not FNL-0005 or an analog or prodrug thereof. In embodiments, the compound is not FNL-0009 or an analog or prodrug thereof. In embodiments, the compound is not FNL-0001 or an analog or prodrug thereof. In embodiments, the compound is not FNL-0013 or an analog or prodrug thereof. In embodiments, the compound is not FNL-00014 or an analog or prodrug thereof. In embodiments, the compound is not FNL-0015 or an analog or prodrug thereof. In embodiments, the compound is not FNL-0024 or an analog or prodrug thereof. In embodiments, the compound is not FNL-0026 or an analog or prodrug thereof. In embodiments, the compound is not FNL-0016 or an analog or prodrug thereof. In embodiments, the compound is not FNL-0010 or an analog or prodrug thereof. In embodiments, the compound is not FNL-0012 or an analog or prodrug thereof. In embodiments, the compound is not FNL-0030 or an analog or prodrug thereof. In embodiments, the compound is not FNL-0036 or an analog or prodrug thereof. In embodiments, the compound is not FNL-0037 or an analog or prodrug thereof. In embodiments, the compound is not FNL-0038 or an analog or prodrug thereof.

In embodiments, the compound is not SMDC 917105. In embodiments, the compound is not SMDC 917102. In embodiments, the compound is not SMDC 916899. In embodiments, the compound is not SMDC 917181. In embodiments, the compound is not SMDC 916860. In embodiments, the compound is not SMDC 916860. In embodiments, the compound is not SMDC 966906. In embodiments, the compound is not SMDC 917138. In embodiments, the compound is not SMDC 960055. In embodiments, the compound is not SMDC 966921. In embodiments, the compound is not SMDC 966976. In embodiments, the compound is not SMDC 917632. In embodiments, the compound is not SMDC917192. In embodiments, the compound is not SMDC 966938. In embodiments, the compound is not SMDC 957780. In embodiments, the compound is not SMDC 966844. In embodiments, the compound is not SMDC 966854. In embodiments, the compound is not SMDC 966782. In embodiments, the compound is not SMDC 966849. In embodiments, the compound is not SMDC 966859. In embodiments, the compound is not SMDC 966539. In embodiments, the compound is not SMDC 966781. In embodiments, the compound is not SMDC 966846. In embodiments, the compound is not SMDC 957828. In embodiments, the compound is not SMDC 966783. In embodiments, the compound is not SMDC966536. In embodiments, the compound is not SMDC 966541. In embodiments, the compound is not SMDC 966794. In embodiments, the compound is not SMDC 966793. In embodiments, the compound is not SMDC 966785. In embodiments, the compound is not SMDC 966538. In embodiments, the compound is not SMDC 966858. In embodiments, the compound is not SMDC 966857. In embodiments, the compound is not SMDC 966789. In embodiments, the compound is not SMDC 957835. In embodiments, the compound is not SMDC 957827. In embodiments, the compound is not SMDC 966844. In embodiments, the compound is not SMDC 916860. In embodiments, the compound is not SMDC 917162. In embodiments, the compound is not SMDC 966849. In embodiments, the compound is not SMDC 917105. In embodiments, the compound is not SMDC 916929. In embodiments, the compound is not SMDC 996794. In embodiments, the compound is not SMDC 917181. In embodiments, the compound is not SMDC 966854. In embodiments, the compound is not SMDC 966976. In embodiments, the compound is not SMDC 957805. In embodiments, the compound is not SMDC 957833. In embodiments, the compound is not SMDC 916960.

In embodiments, the compound is not SMDC 917105 or an analog or prodrug thereof. In embodiments, the compound is not SMDC 917102 or an analog or prodrug thereof. In embodiments, the compound is not SMDC 916899 or an analog or prodrug thereof. In embodiments, the compound is not SMDC 917181 or an analog or prodrug thereof. In embodiments, the compound is not SMDC 916860 or an analog or prodrug thereof. In embodiments, the compound is not SMDC 916860 or an analog or prodrug thereof. In embodiments, the compound is not SMDC 966906 or an analog or prodrug thereof. In embodiments, the compound is not SMDC 917138 or an analog or prodrug thereof. In embodiments, the compound is not SMDC 960055 or an analog or prodrug thereof. In embodiments, the compound is not SMDC 966921 or an analog or prodrug thereof. In embodiments, the compound is not SMDC 966976 or an analog or prodrug thereof. In embodiments, the compound is not SMDC 917632 or an analog or prodrug thereof. In embodiments, the compound is not SMDC917192 or an analog or prodrug thereof. In embodiments, the compound is not SMDC 966938 or an analog or prodrug thereof. In embodiments, the compound is not SMDC 957780 or an analog or prodrug thereof. In embodiments, the compound is not SMDC 966844 or an analog or prodrug thereof. In embodiments, the compound is not SMDC 966854 or an analog or prodrug thereof. In embodiments, the compound is not SMDC 966782 or an analog or prodrug thereof. In embodiments, the compound is not SMDC 966849 or an analog or prodrug thereof. In embodiments, the compound is not SMDC 966859 or an analog or prodrug thereof. In embodiments, the compound is not SMDC 966539 or an analog or prodrug thereof. In embodiments, the compound is not SMDC 966781 or an analog or prodrug thereof. In embodiments, the compound is not SMDC 966846 or an analog or prodrug thereof. In embodiments, the compound is not SMDC 957828 or an analog or prodrug thereof. In embodiments, the compound is not SMDC 966783 or an analog or prodrug thereof. In embodiments, the compound is not SMDC 966536 or an analog or prodrug thereof. In embodiments, the compound is not SMDC 966541 or an analog or prodrug thereof. In embodiments, the compound is not SMDC 966794 or an analog or prodrug thereof. In embodiments, the compound is not SMDC 966793 or an analog or prodrug thereof. In embodiments, the compound is not SMDC 966785 or an analog or prodrug thereof. In embodiments, the compound is not SMDC 966538 or an analog or prodrug thereof. In embodiments, the compound is not SMDC 966858 or an analog or prodrug thereof. In embodiments, the compound is not SMDC 966857 or an analog or prodrug thereof. In embodiments, the compound is not SMDC 966789 or an analog or prodrug thereof. In embodiments, the compound is not SMDC 957835 or an analog or prodrug thereof. In embodiments, the compound is not SMDC 957827 or an analog or prodrug thereof. In embodiments, the compound is not SMDC 966844 or an analog or prodrug thereof. In embodiments, the compound is not SMDC 916860 or an analog or prodrug thereof. In embodiments, the compound is not SMDC 917162 or an analog or prodrug thereof. In embodiments, the compound is not SMDC 966849 or an analog or prodrug thereof. In embodiments, the compound is not SMDC 917105 or an analog or prodrug thereof. In embodiments, the compound is not SMDC 916929 or an analog or prodrug thereof. In embodiments, the compound is not SMDC 996794 or an analog or prodrug thereof. In embodiments, the compound is not SMDC 917181 or an analog or prodrug thereof. In embodiments, the compound is not SMDC 966854 or an analog or prodrug thereof. In embodiments, the compound is not SMDC 966976 or an analog or prodrug thereof. In embodiments, the compound is not SMDC 957805 or an analog or prodrug thereof. In embodiments, the compound is not SMDC 957833 or an analog or prodrug thereof. In embodiments, the compound is not SMDC 916960 or an analog or prodrug thereof.

III. PHARMACEUTICAL COMPOSITIONS

In an aspect is provided a pharmaceutical composition including a compound described herein and a pharmaceutically acceptable excipient.

In embodiments, the pharmaceutical composition includes an effective amount of the compound. In embodiments, the pharmaceutical composition includes a therapeutically effective amount of the compound. In embodiments, the pharmaceutical composition includes a second agent (e.g., an anti-cancer agent). In embodiments of the pharmaceutical compositions, the pharmaceutical composition includes a second agent in a therapeutically effective amount. In embodiments, the anti-cancer agent is an EGFR inhibitor (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, or BMS-599626). In embodiments, the anti-cancer agent is erlotinib. In embodiments, the anti-cancer agent is gefitinib. In embodiments, the anti-cancer agent is lapatinib. In embodiments, the anti-cancer agent is panitumumab.

The pharmaceutical compositions may include optical isomers, diastereomers, or pharmaceutically acceptable salts of the modulators disclosed herein. The compound included in the pharmaceutical composition may be covalently attached to a carrier moiety. Alternatively, the compound included in the pharmaceutical composition is not covalently linked to a carrier moiety.

IV. METHODS FOR TREATING CANCER

In another aspect, is provided a method of treating cancer in a subject in need of such treatment (patient). The method including administering a therapeutically effective amount of a compound described herein (including embodiments, examples, figures, tables) to the subject. In some embodiments, the cancer is lung cancer, colorectal cancer, colon cancer, pancreatic cancer, breast cancer, or leukemia. In some embodiments, the cancer is lung cancer. In some embodiments, the cancer is non-small cell lung cancer. In some embodiments, the cancer is colon cancer. In some embodiments, the cancer is colorectal cancer. In some embodiments, the cancer is breast cancer. In some embodiments, the cancer is leukemia. In some embodiments, the cancer is pancreatic cancer. In some embodments, the cancer is a cancer associated with aberrant K-Ras. In some embodiments, the cancer is a cancer associated with a mutant K-Ras. In some embodiments, the cancer is a cancer associated with K-Ras G12C. In some embodiments, the cancer is a cancer associated with K-Ras G12D. In some embodiments, the cancer is a cancer associated with K-Ras G12V. In some embodiments, the cancer is a cancer associated with K-Ras G12S. In some embodiments, the cancer is a cancer associated with K-Ras G13C. In some embodiments, the cancer is a cancer associated with K-Ras G13D. In embodiments, the treating does not include preventing.

The compounds of the invention (i.e. compounds described herein, including in embodiments, examples, figures, tables) can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation or anti-cancer agents). In embodiments, the anti-cancer agent is an EGFR inhibitor (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, or BMS-599626). In embodiments, the anti-cancer agent is erlotinib. In embodiments, the anti-cancer agent is gefitinib. In embodiments, the anti-cancer agent is lapatinib. In embodiments, the anti-cancer agent is panitumumab.

V. METHODS OF MODULATING ACTIVITY

In an aspect is provided a method of reducing the level of activity of a K-Ras (e.g., human K-Ras 4A and/or human K-Ras 4B) protein, the method including contacting the K-Ras (e.g., human K-Ras 4A and/or human K-Ras 4B) protein with a compound described herein (including in embodiments, examples, figures, and tables). In some embodiments, the activity of the K-Ras (e.g., human K-Ras 4A and/or human K-Ras 4B) protein is it's GTPase activity, nucleotide exchange, differential GDP or GTP binding, effector protein binding, effector protein activation, guanine exchange factor (GEF) binding, GEF-facilitated nucleotide exchange, phosphate release, nucleotide release, nucleotide binding, K-Ras (e.g., human K-Ras 4A and/or human K-Ras 4B) subcellular localization, K-Ras (e.g., human K-Ras 4A and/or human K-Ras 4B) post-translational processing, K-Ras (e.g., human K-Ras 4A and/or human K-Ras 4B) post-translational modifications, prenylation, or a GTP bound K-Ras (e.g., human K-Ras 4A and/or human K-Ras 4B) signaling pathway. In some embodiments, the activity of the K-Ras (e.g., human K-Ras 4A and/or human K-Ras 4B) protein is its GTPase activity, nucleotide exchange, effector protein binding, effector protein activation, guanine exchange factor (GEF) binding, GEF-facilitated nucleotide exchange, phosphate release, nucleotide release, nucleotide binding, or the activity of a GTP bound K-Ras (e.g., human K-Ras 4A and/or human K-Ras 4B) signaling pathway. In some embodiments, the activity of the K-Ras (e.g., human K-Ras 4A and/or human K-Ras 4B) protein is the activity of a signaling pathway activated by GTP bound K-Ras (e.g., human K-Ras 4A and/or human K-Ras 4B) (i.e., the method reduces the activity of the signaling pathway activated by GTP bound K-Ras (e.g., human K-Ras 4A and/or human K-Ras 4B). In some embodiments, the modulating is increasing the activity of the K-Ras (e.g., human K-Ras 4A and/or human K-Ras 4B) protein. In some embodiments, the modulating is reducing the activity of the K-Ras (e.g., human K-Ras 4A and/or human K-Ras 4B) protein. In some embodiments, the K-Ras (e.g., human K-Ras 4A and/or human K-Ras 4B) protein is a human K-Ras protein. In some embodiments, the human K-Ras protein includes a G12C mutation. In some embodiments, the human K-Ras protein includes a G12V mutation. In some embodiments, the human K-Ras protein includes a G12S mutation. In some embodiments, the human K-Ras protein includes a G12D mutation. In some embodiments, the human K-Ras protein includes a G13C mutation. In some embodiments, the human K-Ras protein includes a G13D mutation. In some embodiments, the K-Ras protein is a human K-Ras4A protein. In some embodiments, the K-Ras protein is a human K-Ras4B protein. In some embodiments, the K-Ras (e.g., human K-Ras 4A and/or human K-Ras 4B) protein is a mutant K-Ras (e.g., human K-Ras 4A and/or human K-Ras 4B) protein. In some embodiments, the K-Ras (e.g., human K-Ras 4A and/or human K-Ras 4B) protein is an activated K-Ras (e.g., human K-Ras 4A and/or human K-Ras 4B) protein. In some embodiments, the K-Ras (e.g., human K-Ras 4A and/or human K-Ras 4B) protein is within a biological cell (e.g., a cancer cell). In some embodiments, the biological cell forms part of an organism. In some embodiments of the method of modulating the activity of a K-Ras (e.g., human K-Ras 4A and/or human K-Ras 4B) protein including contacting the K-Ras (e.g., human K-Ras 4A and/or human K-Ras 4B) protein with an effective amount of a compound described herein (including in embodiments, examples, figures, and tables), the compound is less effective at modulating the activity of an H-Ras protein (e.g., compared to the level of modulation of K-Ras (e.g., human K-Ras 4A and/or human K-Ras 4B)). In some embodiments of the method, the compound modulates the activity of K-Ras (e.g., human K-Ras 4A and/or human K-Ras 4B) at least two-fold more than it modulates the activity of H-Ras. In some embodiments of the method, the compound modulates the activity of K-Ras (e.g., human K-Ras 4A and/or human K-Ras 4B) at least five-fold more than it modulates the activity of H-Ras. In some embodiments of the method, the compound modulates the activity of K-Ras (e.g., human K-Ras 4A and/or human K-Ras 4B) at least ten-fold more than it modulates the activity of H-Ras. In some embodiments of the method, the compound modulates the activity of K-Ras (e.g., human K-Ras 4A and/or human K-Ras 4B) at least fifty-fold more than it modulates the activity of H-Ras. In some embodiments of the method of modulating the activity of a K-Ras (e.g., human K-Ras 4A and/or human K-Ras 4B) protein including contacting the K-Ras (e.g., human K-Ras 4A and/or human K-Ras 4B) protein with an effective amount of a compound described herein (including embodiments, examples, figures, and tables), the compound is less effective at modulating the activity of an N-Ras protein. In some embodiments of the method, the compound modulates the activity of K-Ras (e.g., human K-Ras 4A and/or human K-Ras 4B) at least two-fold more than it modulates the activity of N-Ras. In some embodiments of the method, the compound modulates the activity of K-Ras (e.g., human K-Ras 4A and/or human K-Ras 4B) at least five-fold more than it modulates the activity of N-Ras. In some embodiments of the method, the compound modulates the activity of K-Ras (e.g., human K-Ras 4A and/or human K-Ras 4B) at least ten-fold more than it modulates the activity of N-Ras. In some embodiments of the method, the compound modulates the activity of K-Ras (e.g., human K-Ras 4A and/or human K-Ras 4B) at least fifty-fold more than it modulates the activity of N-Ras. In embodiments, the compound contacts the K-Ras amino acid corresponding to H95 of human K-Ras (e.g., human K-Ras 4A and/or human K-Ras 4B). In embodiments, compound covalently binds the K-Ras amino acid corresponding to H95 of human K-Ras (e.g., human K-Ras 4A and/or human K-Ras 4B). In embodiments, the compound contacts H95 of human K-Ras 4A. In embodiments, the compound contacts H95 of human K-Ras 4B. In embodiments, the compound contacts H95 of both human K-Ras 4A and human K-Ras 4B. In embodiments, the compound inhibits the activity of human K-Ras 4A. In embodiments, the compound inhibits the activity of human K-Ras 4B. In embodiments, the compound inhibits the activity of both human K-Ras 4A and human K-Ras 4B. In embodiments, the compound is capable of inhibiting the activity of human K-Ras 4A. In embodiments, the compound is capable of inhibiting the activity of human K-Ras 4B. In embodiments, the compound is capable of inhibiting the activity of both human K-Ras 4A and human K-Ras 4B. In embodiments, the compound inhibits K-Ras (e.g., human K-Ras 4A and/or human K-Ras 4B) binding to a second protein. In embodiments, the compound inhibits K-Ras (e.g., human K-Ras 4A and/or human K-Ras 4B) binding to a second protein and does not inhibit K-Ras (e.g., human K-Ras 4A and/or human K-Ras 4B) GTPase activity (e.g., intrinsic GTPase activity). In embodiments, the compound inhibits K-Ras (e.g., human K-Ras 4A and/or human K-Ras 4B) downstream pathway activity activated by GTP bound K-Ras (e.g., human K-Ras 4A and/or human K-Ras 4B). In embodiments, the compound inhibits K-Ras (e.g., human K-Ras 4A and/or human K-Ras 4B) downstream pathway activity activated by GTP bound K-Ras (e.g., human K-Ras 4A and/or human K-Ras 4B) and does not inhibit K-Ras (e.g., human K-Ras 4A and/or human K-Ras 4B) GTPase activity (e.g., intrinsic GTPase activity). In embodiments, the compound reduces GTP bound K-Ras (e.g., human K-Ras 4A and/or human K-Ras 4B) contact with a protein (e.g., effector or downstream component of pathway) and does not inhibit K-Ras (e.g., human K-Ras 4A and/or human K-Ras 4B) GTPase activity (e.g., intrinsic GTPase activity).

In another aspect, a method of modulating a K-Ras (e.g., human K-Ras 4A and/or human K-Ras 4B) protein is provided. The method including contacting the K-Ras (e.g., human K-Ras 4A and/or human K-Ras 4B) protein with an effective amount of a compound described herein (including in embodiments, examples, figures, and tables). In some embodiments, the K-Ras (e.g., human K-Ras 4A and/or human K-Ras 4B) protein is modulated (e.g., inhibited relative to absence of the compound) in K-Ras (e.g., human K-Ras 4A and/or human K-Ras 4B) subcellular localization, K-Ras (e.g., human K-Ras 4A and/or human K-Ras 4B) post-translational processing, K-Ras (e.g., human K-Ras 4A and/or human K-Ras 4B) post-translational modifications, or a GTP bound K-Ras (e.g., human K-Ras 4A and/or human K-Ras 4B) signaling pathway. In some embodiments, the modulating is increasing the post-translational processing or modifications of the K-Ras (e.g., human K-Ras 4A and/or human K-Ras 4B) protein. In some embodiments, the modulating is reducing the post-translational processing or modifications of the K-Ras (e.g., human K-Ras 4A and/or human K-Ras 4B) protein. In some embodiments, the K-Ras (e.g., human K-Ras 4A and/or human K-Ras 4B) protein is a human K-Ras protein. In some embodiments, the human K-Ras protein contains a G12C mutation. In some embodiments, the human K-Ras protein contains a G12V mutation. In some embodiments, the human K-Ras protein contains a G12S mutation. In some embodiments, the human K-Ras protein contains a G12D mutation. In some embodiments, the human K-Ras protein contains a G13C mutation. In some embodiments, the human K-Ras protein contains a G13D mutation. In some embodiments, the K-Ras protein is a human K-Ras4A protein. In some embodiments, the K-Ras protein is a human K-Ras4B protein. In some embodiments, the K-Ras (e.g., human K-Ras 4A and/or human K-Ras 4B) protein is a mutant K-Ras (e.g., human K-Ras 4A and/or human K-Ras 4B) protein. In some embodiments, the K-Ras (e.g., human K-Ras 4A and/or human K-Ras 4B) protein is an activated K-Ras protein. In some embodiments, the K-Ras (e.g., human K-Ras 4A and/or human K-Ras 4B) protein is within a biological cell. In some embodiments, the biological cell forms part of an organism. In embodiments, compound (e.g., compound described herein) modulates the stability of the K-Ras (e.g., human K-Ras 4A and/or human K-Ras 4B) protein. In embodiments, compound (e.g., compound described herein) reduces the stability of the K-Ras (e.g., human K-Ras 4A and/or human K-Ras 4B) protein relative to the absence of the compound. In embodiments, compound (e.g., compound described herein) increases the rate of degradation of the K-Ras (e.g., human K-Ras 4A and/or human K-Ras 4B) protein relative to the absence of the compound.

In embodiments, the compound (e.g., compound described herein) contacts the amino acid corresponding to His95 in K-Ras (e.g., human K-Ras 4A (SEQ ID NO:4) and/or human K-Ras 4B (SEQ ID NO:5). In embodiments, the compound (e.g., compound described herein) reacts with His95 in K-Ras (e.g., human K-Ras 4A (SEQ ID NO:4) and/or human K-Ras 4B (SEQ ID NO:5). In embodiments, the compound (e.g., compound described herein) covalently binds to the amino acid corresponding to His95 in K-Ras (e.g., human K-Ras 4A (SEQ ID NO:4) and/or human K-Ras 4B (SEQ ID NO:5). In embodiments, the compound (e.g., compound described herein) covalently reacts with His95 in K-Ras (e.g., human K-Ras 4A (SEQ ID NO:4) and/or human K-Ras 4B (SEQ ID NO:5). In embodiments, the compound (e.g., compound described herein) is capable of binding to the amino acid corresponding to His95 of K-Ras (e.g., human K-Ras 4A (SEQ ID NO:4) and/or human K-Ras 4B (SEQ ID NO:5). In embodiments, the compound (e.g., compound described herein) is capable of reacting with His95 of K-Ras (e.g., human K-Ras 4A (SEQ ID NO:4) and/or human K-Ras 4B (SEQ ID NO:5).

In embodiments, the compound (e.g., compound described herein) binds to the amino acid corresponding to His95 in K-Ras (e.g., human K-Ras 4A and/or human K-Ras 4B) protein when the K-Ras (e.g., human K-Ras 4A (SEQ ID NO:4) and/or human K-Ras 4B (SEQ ID NO:5) protein Cys185 (or amino acid corresponding to Cys185 of K-Ras 4B, SEQ ID NO:5) is covalently modified (e.g., prenylated, farnesylated). In embodiments, the compound (e.g., compound described herein) binds to the amino acid corresponding to H95 in K-Ras (e.g., human K-Ras 4A (SEQ ID NO:4) and/or human K-Ras 4B (SEQ ID NO:5) protein following protein synthesis, when the K-Ras (e.g., human K-Ras 4A (SEQ ID NO:4) and/or human K-Ras 4B (SEQ ID NO:5) protein Cys185 (or amino acid corresponding to Cys185 of K-Ras 4B SEQ ID NO:5) has not yet been covalently modified (e.g., prenylated, farnesylated).

In embodiments, the compound prevents productive folding of K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound. In embodiments, the compound increases misfolding of K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound. In embodiments, the compound increases unfolding of K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound. In embodiments, the compound increases degradation of K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound. In embodiments, the compound reduces GTP binding to K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound. In embodiments, the compound decreases GDP release by K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound. In embodiments, the compound decreases interactions of a second protein (e.g., pathway component, effector) with K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound. In embodiments, the compound decreases prenylation (e.g., farnesylation, geranylgeranylation) of K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound. In embodiments, the compound decreases degradation of K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound. In embodiments, the compound stabilizes the conformation of K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound. In embodiments, the compound stabilizes a conformation of K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound. In embodiments, the compound reduces protein flexibility of K-Ras (e.g., human K-Ras 4A and/or human K-Ras 4B) protein (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound.

In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) function in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than about 1 hour (e.g., less than about 1, 2, 3, 4, 5, 6, 7, 8, 9, 10, 20, 30, 40, or 50 minutes). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) function in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than 1 hour (e.g., less than 1, 2, 3, 4, 5, 6, 7, 8, 9, 10, 20, 30, 40, or 50 minutes). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) function in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than about 1 day (e.g., less than about 1, 2, 3, 4, 5, 6, 7, 8, 9, 10, 11, 12, 13, 14, 15, 16, 17, 18, 19, 20, 21, 22, or 23 hours). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) function in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than 1 day (e.g., less than 1, 2, 3, 4, 5, 6, 7, 8, 9, 10, 11, 12, 13, 14, 15, 16, 17, 18, 19, 20, 21, 22, or 23 hours). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) function in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than about 1 month (e.g., less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) function in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than 1 month (e.g., less than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days). In embodiments, the compound binds to K-Ras (e.g., only K-Ras 4B, only K-Ras 4A, or both K-Ras 4A and K-Ras 4B). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) function in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than 48 hours (e.g., less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) protein in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than 48 hours (e.g., less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) function in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than 72 hours (e.g., less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) protein in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than 72 hours (e.g., less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) function in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than 100 hours (e.g., less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 hours). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras (e.g., human K-Ras 4A and/or human K-Ras 4B) protein in a cell (e.g., by binding to K-Ras (e.g., human K-Ras 4A and/or human K-Ras 4B) protein, by contacting the amino acid corresponding to His95 of K-Ras (e.g., human K-Ras 4A and/or human K-Ras 4B)) relative to the absence of the compound, in less than 100 hours (e.g., less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 hours).

VI. EXAMPLES

The development of small-molecule inhibitors that directly target Ras is highly desirable, but has proven to be a major challenge. All isoforms of the Ras protein (HRas, NRas and KRas) play essential roles in normal cells. Therefore, one desirable Ras-targeting drug would specifically target the oncogenic form of the protein. However, targeting K-Ras (without distinguishing between wildtype and mutant protein) could be an effective approach, since all isoforms are redundant in normal tissues, and eliminating one is expected to be tolerable.

Recently, we discovered that histidine 95 (H95) in KRas—a residue that was not previously considered as a potential drug target in KRas, could be covalently modified by electrophiles. The importance of this discovery is that H95 is unique for KRas, (Q in HRas and L in NRas, FIG. 1). This creates the opportunity for direct drug-targeting of this unique site. Moreover, targeting H95 as it is in a G-domain, would affect both Kras4A and 4B splice variants of KRas. The covalently (e.g., irreversibly) modified KRas protein could be sent for degradation, or—since H95 resides in helix 3 near switch II—this modification could impair effector(s) binding. We have since utilized H95C mutant protein and disulfide tethering to find small molecule fragments that bind at this location. These studies led to the discovery of two hit-series with demonstrable SAR: triazoles and phenylacetamides. Through an iterative approach we followed up functionalizing selected hits with irreversible electrophilic groups. One of these irreversible electrophiles—a triazole with an epoxide moiety, growth arrested KRas-driven mouse embryonic fibroblasts (MEFs), but not BRAF-driven MEFs. This compound (FNL-0012) covalently modified H95C KRas protein; however, caused minimal modification to C185 in KRas WT protein, and did not modify FMe-KRas protein in vitro. In cell culture, this compound caused growth arrest within 24 h and a decrease in MEK phosphorylation 1 h after treatment was initiated, both in KRas MEFs and in pancreatic cancer cell lines, and not in BRAF MEFs. This compound may function through noncovalent binding to KRas protein. To investigate the role of the epoxide oxygen a cyclopropyl control compound was prepared. This analogue did not cause growth arrest or any perturbations in MAPK signaling. FNL-0012 may bind KRas non-covalently by virtue of a H-bonding interaction between the epoxide oxygen and the H95 sidechain. FNL-0012 may bind in a pocket nearby H95, influencing Switch2/effector(s) binding to KRas.

Example 1. Tethering Screen

Disulfide tethering is a site-directed fragment-based approach to drug-discovery, which allows the screening low-affinity disulfide containing fragments against a native or introduced cysteine residue of a target protein. Fragment binding is reversible, and can be tuned to favor detection of only the strongest bound fragments through the use of increasing concentrations of a reductant (typically β-mecaptoethanol). This binding is not purely driven by reactivity; it is influenced by protein/ligand interactions and is independent of pKa or surface exposure. Bound fragments are detected by mass spectrometry and provide a lead into the drug discovery process.

To target H95 specifically, we generated Kras4b H95C (1-169) mutant protein, and used it (GppNHp-loaded), to search for compounds that could bind to active KRas in close proximity to H95. We performed a tethering screen of a disulfide containing fragment library at the University of California San Francisco. The initial screen consisted of >1600 fragments and resulted in a number of hits. We selected 52 compounds representative of this data-set for further evaluation in a dose response screen.

Example 2. Compounds Including Phenylacetamide

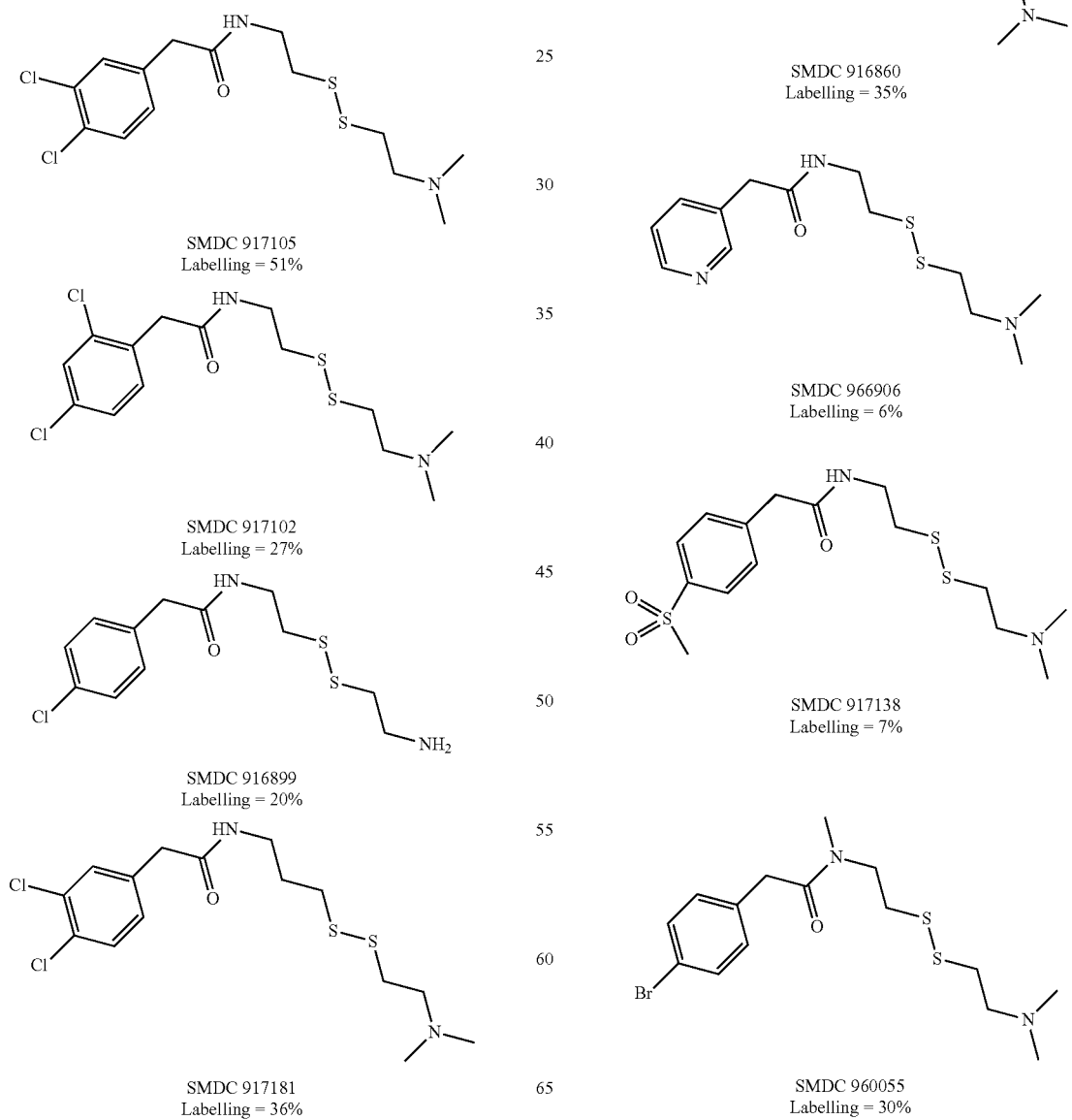

SMDC 917105
Labelling = 51%

SMDC 917102
Labelling = 27%

SMDC 916899
Labelling = 20%

SMDC 917181
Labelling = 36%

SMDC 916860
Labelling = 27%

SMDC 916860
Labelling = 35%

SMDC 966906
Labelling = 6%

SMDC 917138
Labelling = 7%

SMDC 960055
Labelling = 30%

217
-continued
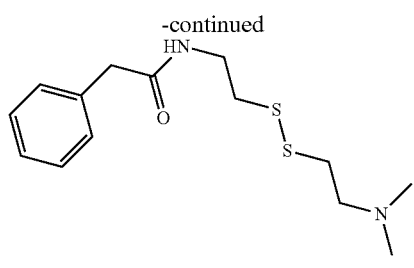
SMDC 966921
Labelling = 5%
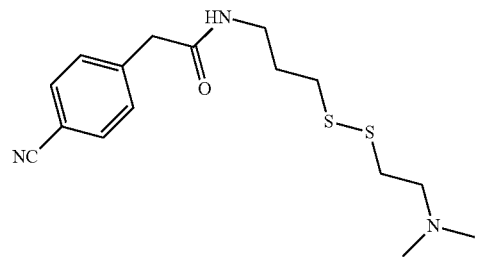
SMDC 966975
Labelling = 36%
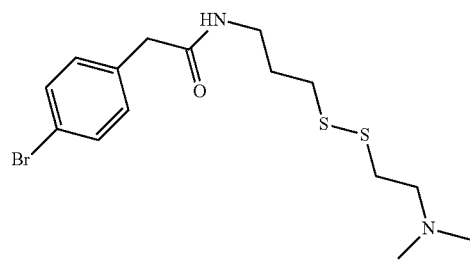
SMDC 917632
Labelling = 35%
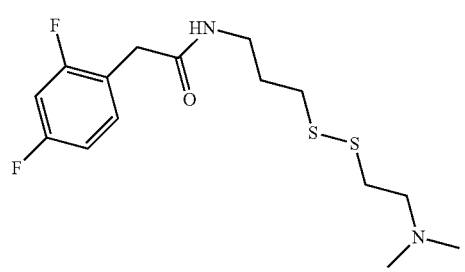
SMDC 917192
Labelling = 17%
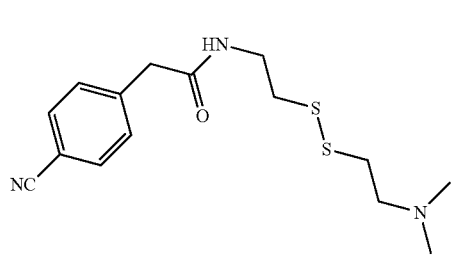
SMDC 966938
Labelling = 5%
218
-continued
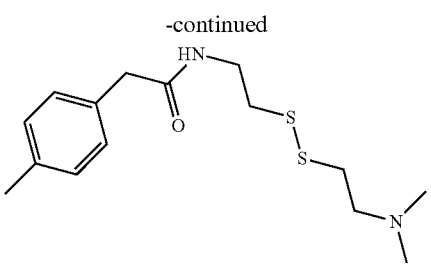
SMDC 957780
Labelling = 34%
Example 3. Compounds Including Triazole
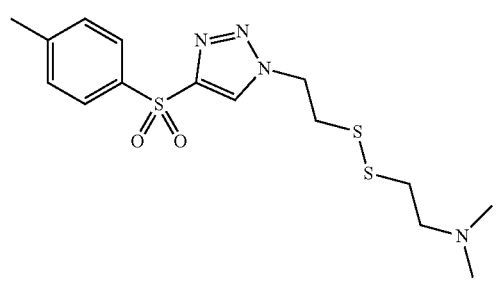
SMDC 966844
Labelling = 62%
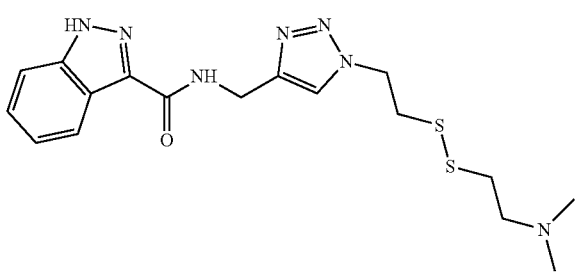
SMDC 966854
Labelling = 62%
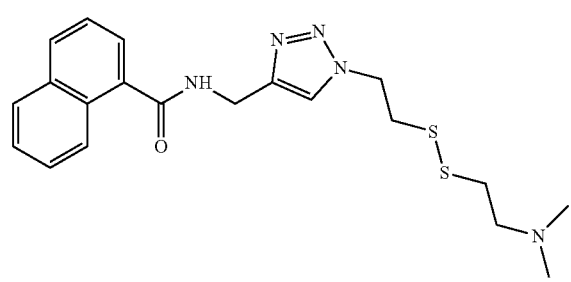
SMDC 966782
Labelling = 32%

-continued
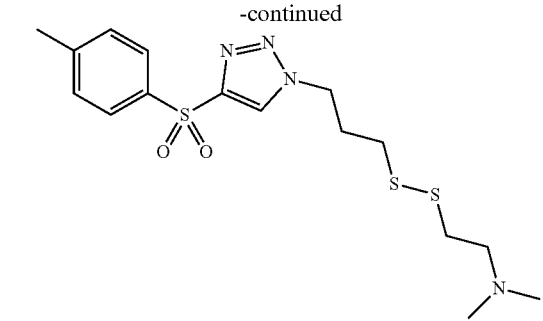
SMDC 966849
Labelling = 29%
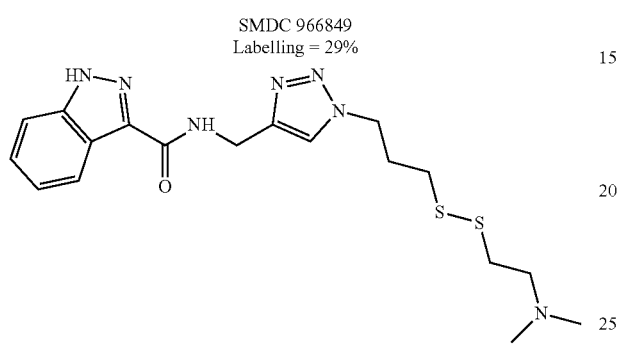
SMDC 966859
Labelling = 26%
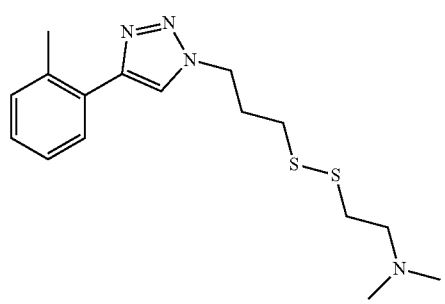
SMDC 966539
Labelling = 39%
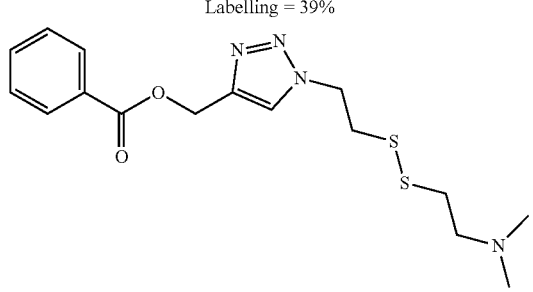
SMDC 966781
Labelling = 35%
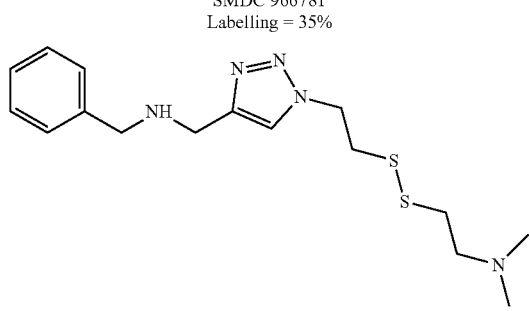
SMDC 966846
Labelling = 26%
-continued
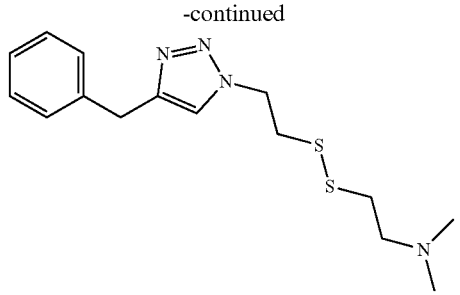
SMDC 957828
Labelling = 24%
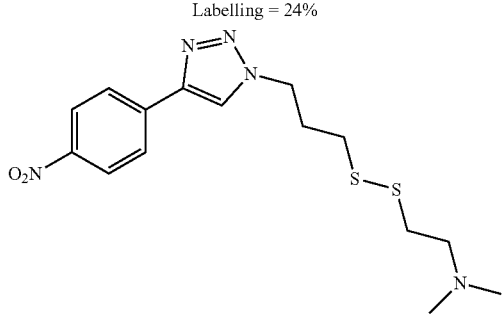
SMDC 966783
Labelling = 30%
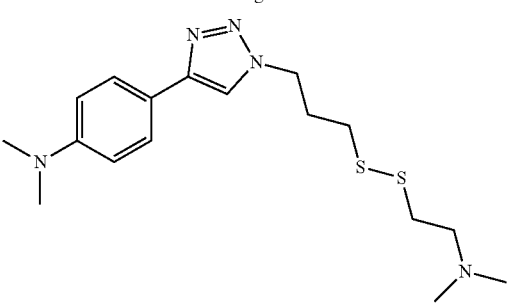
SMDC 966536
Labelling = 2%
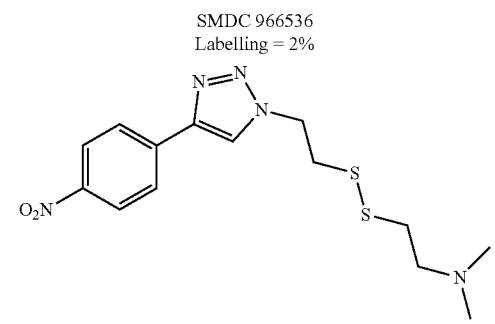
SMDC 966541
Labelling = 6%
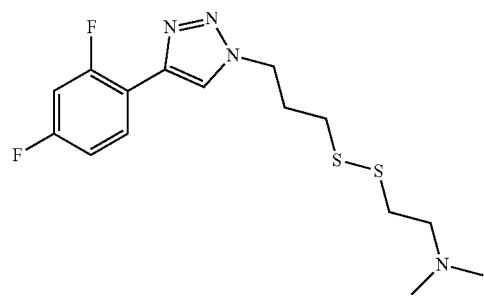
SMDC 966794
Labelling = 43%

-continued
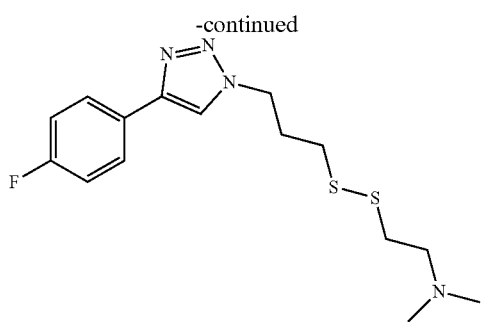
SMDC 966793
Labelling = 34%
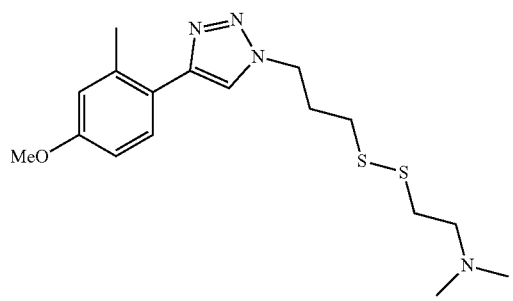
SMDC 966785
Labelling = 35%
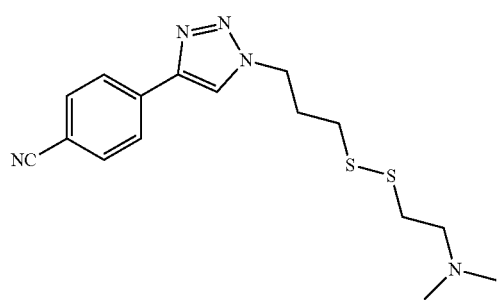
SMDC 966538
Labelling = 26%
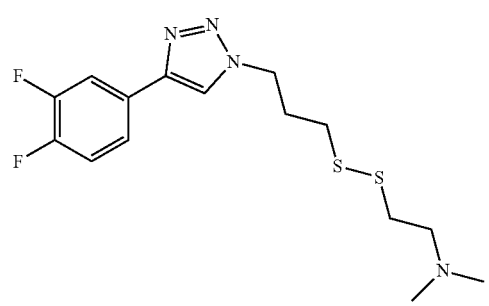
SMDC 966858
Labelling = 31%
-continued
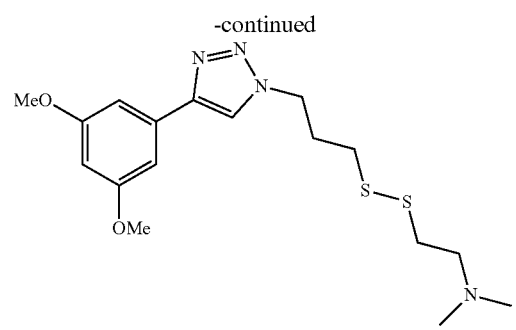
SMDC 966857
Labelling = 13%
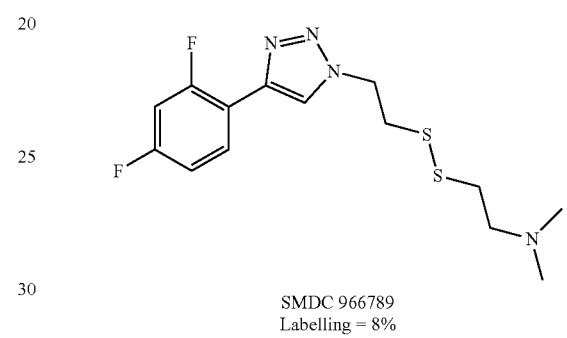
SMDC 966789
Labelling = 8%
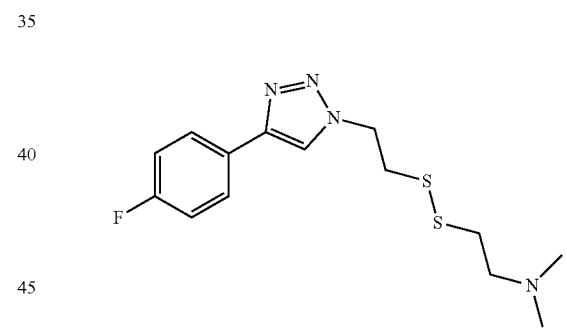
SMDC 966835
Labelling = 7%
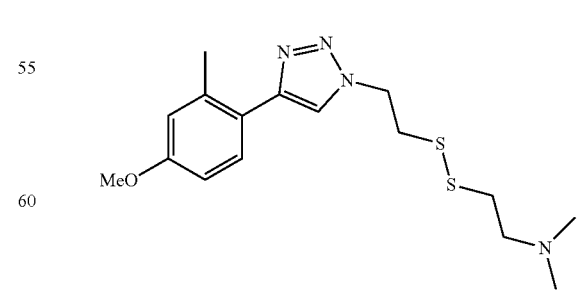
SMDC 957827
Labelling = 8%

Example 4. Additional Binding Compounds
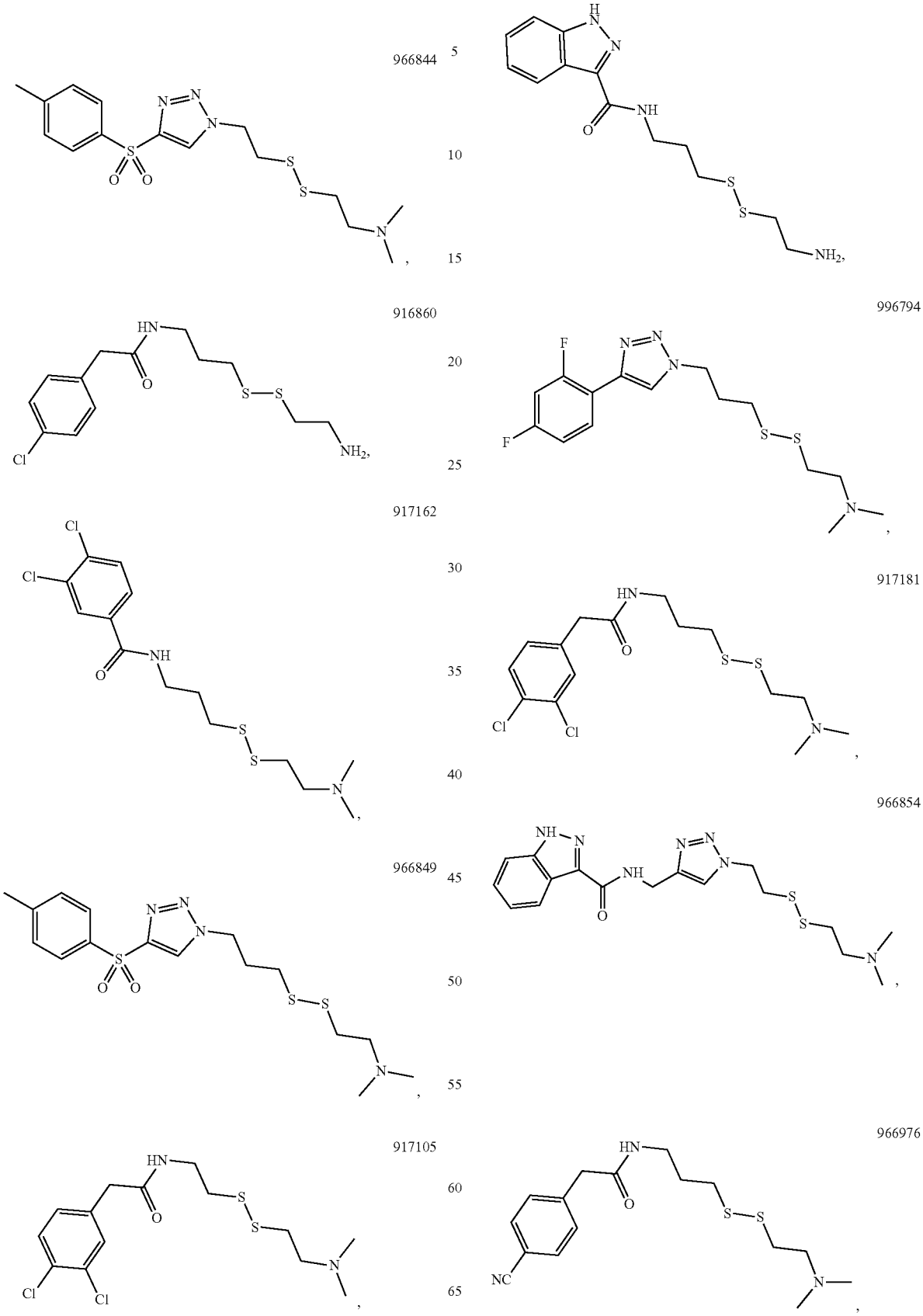

-continued

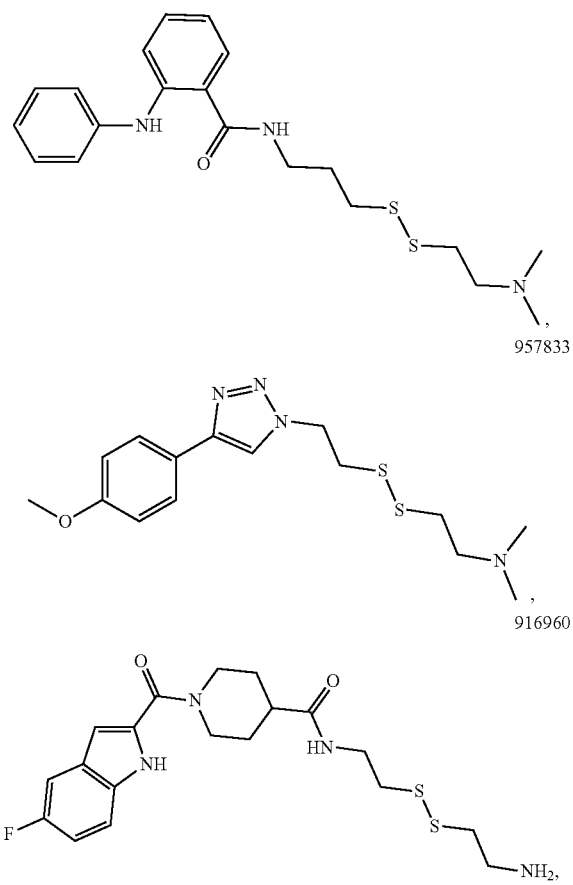

Figure 5:
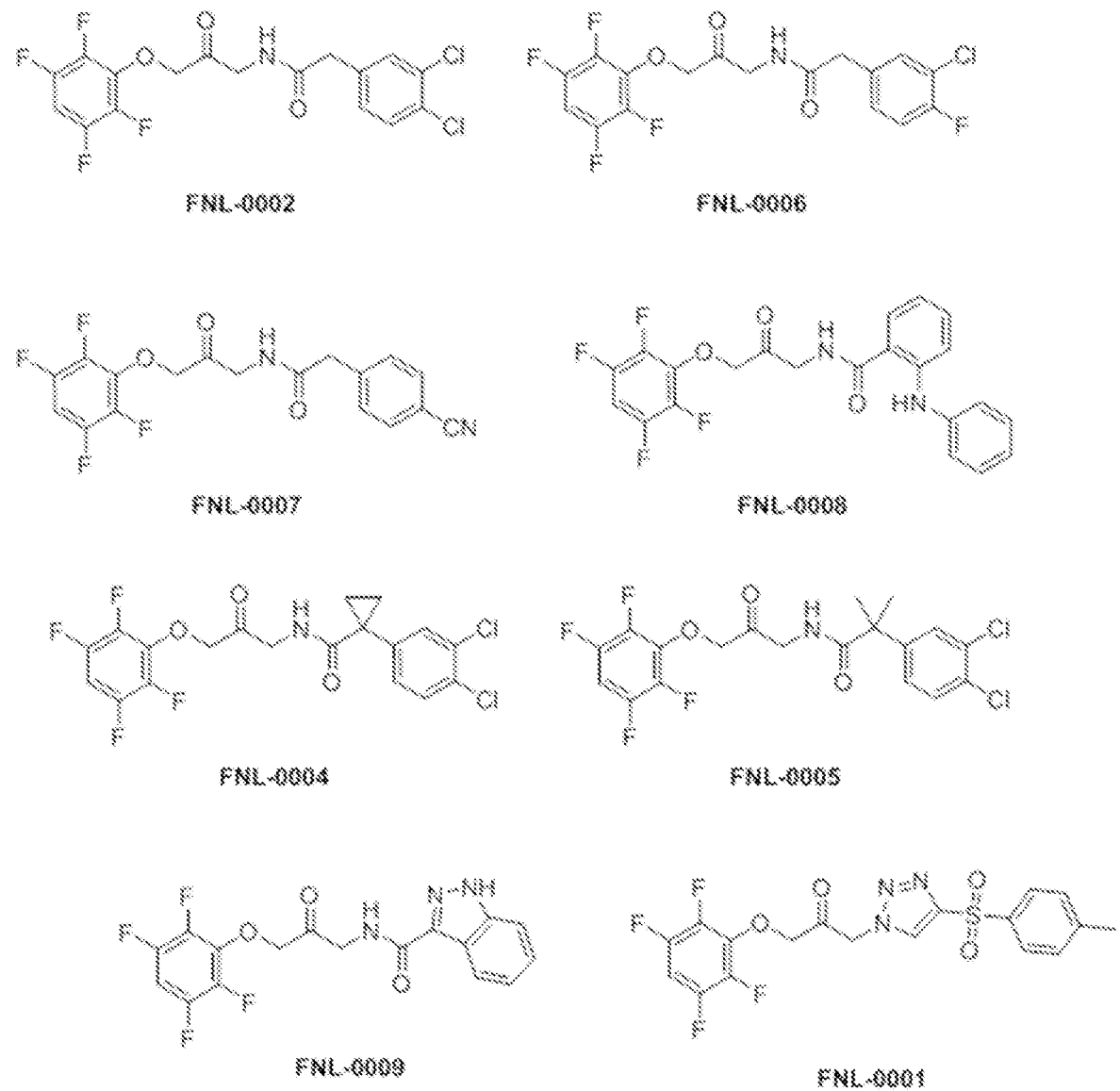
FIG. 5. Tetrafluorophenoxyketone analogues of H95C tethering screen hits.
Figure 6:
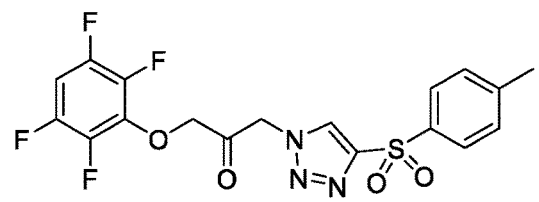
FIG. 6. Compounds with linker substitutions.
Figure 6:
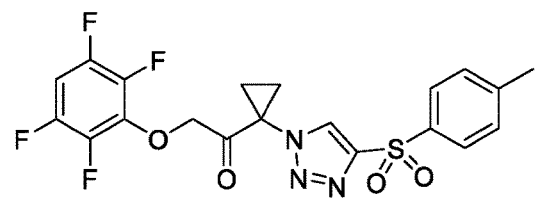
Figure 6:
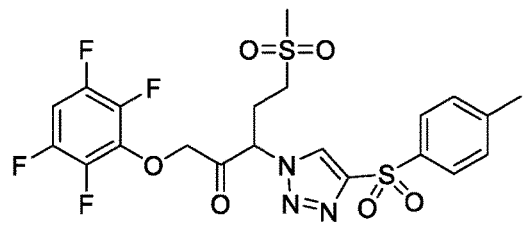
Figure 6:
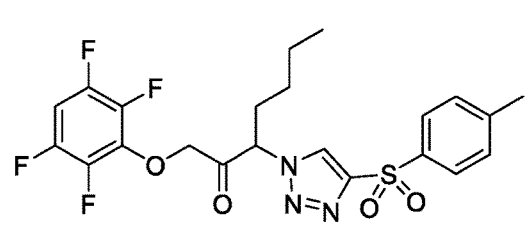

Example 5. Modification of Disulfide Moieties to Alternative Electrophilic Moieties Chemistry efforts focused upon functionalizing selected hits with electrophilic (e.g., irreversible) moieties (FIG. 5). These covalent compounds were initially screened for K-Ras binding affinity using mass spectrometry/biophysical/biochemical methods, which were followed up with cell-based experiments. We modified 966844, 966854, and 917105 with a tetrafluorophenoxymethyl ketone electrophilic moiety to generate covalent analogues of the original hits (FIG. 5), then investigated substitutions of the linker group (FIG. 5), and the introduction of alternative electrophiles (FIG. 5).

Example 6. Biological Characterization

We used mouse embryo fibroblasts (MEFs) that have been rescued by KRas4b G12D or BRAF V600E that are essential for proliferation of these cells (Drosten et al. EMBO Journal, 2010). Inhibition of KRas/MAPK pathway in these cells results in growth arrest, making these KRas- or BRAF-driven MEFs a useful tool in Ras-drug discovery.

Figure 8A:
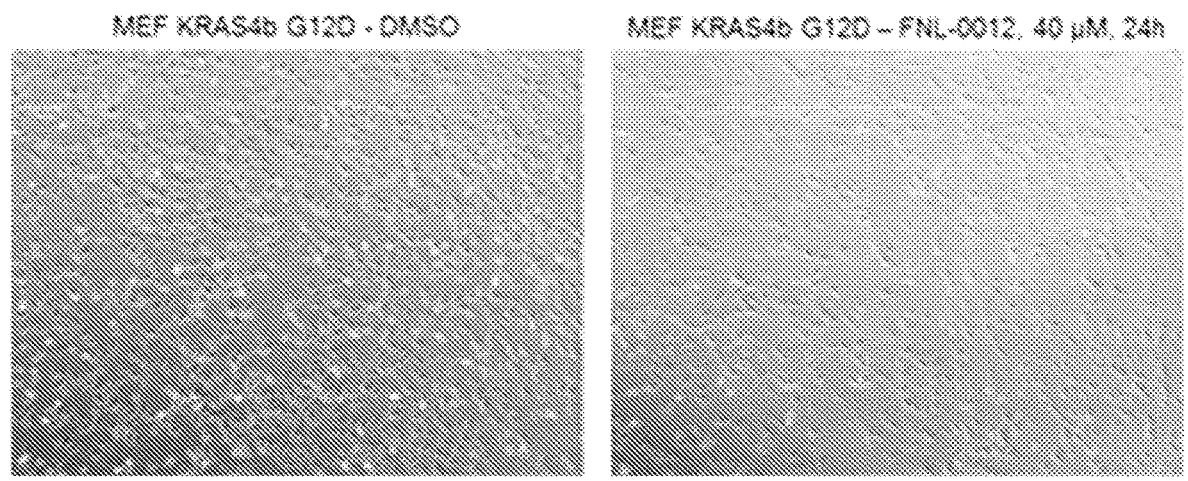
FIGS. 8A-8F. FNL-0012 causes growth arrest and downregulation of MAPK signaling in KRas-driven mouse embryonic fibroblasts (MEFs) and in malignant cell lines.
Figure 8B:
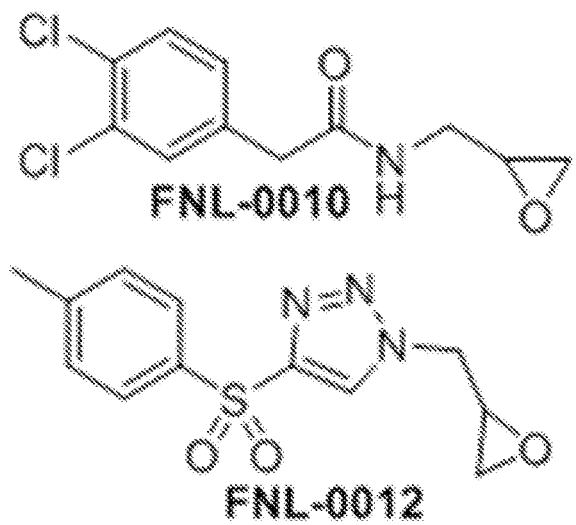
Figure 8C:
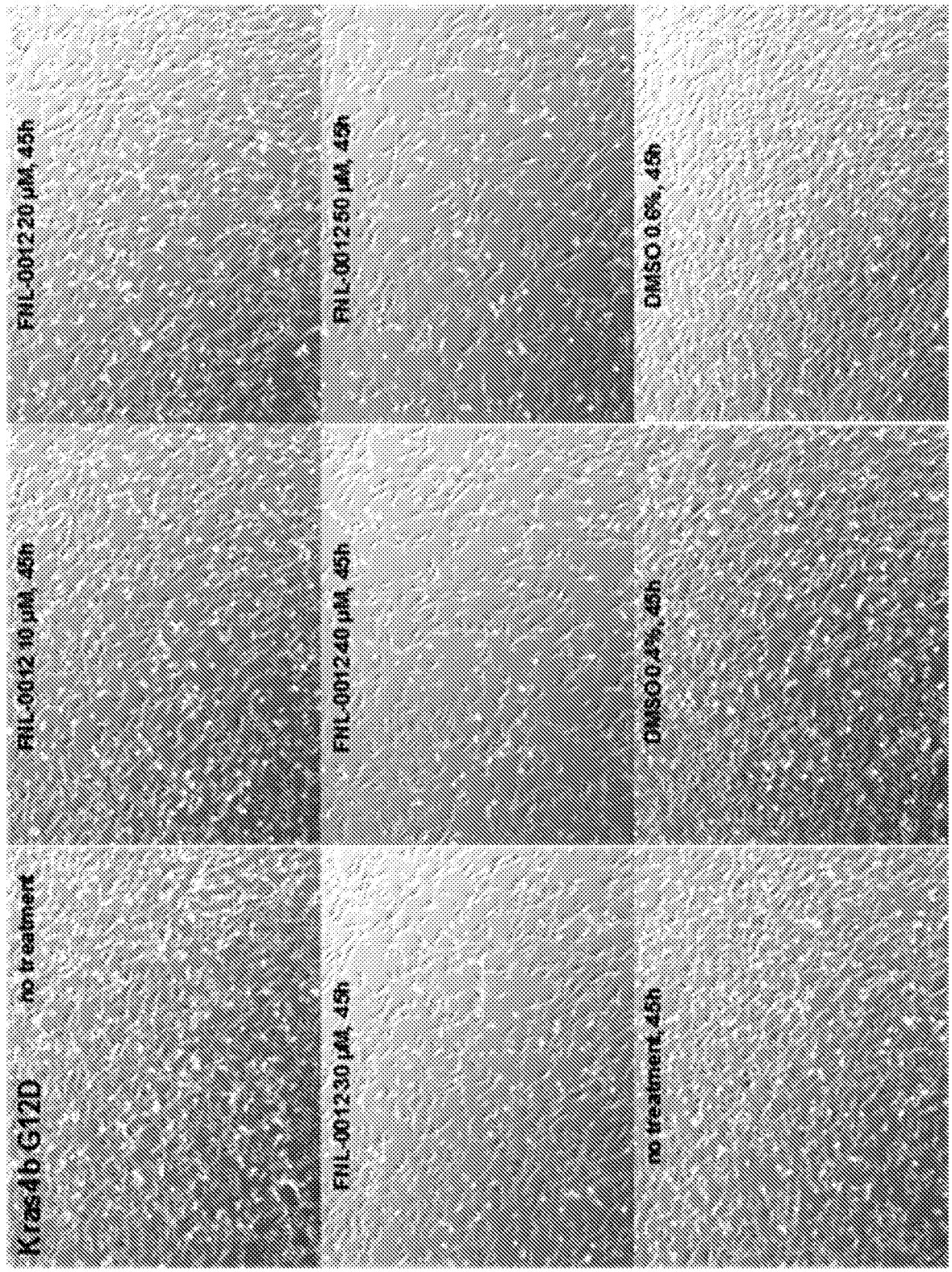
Figure 8D:
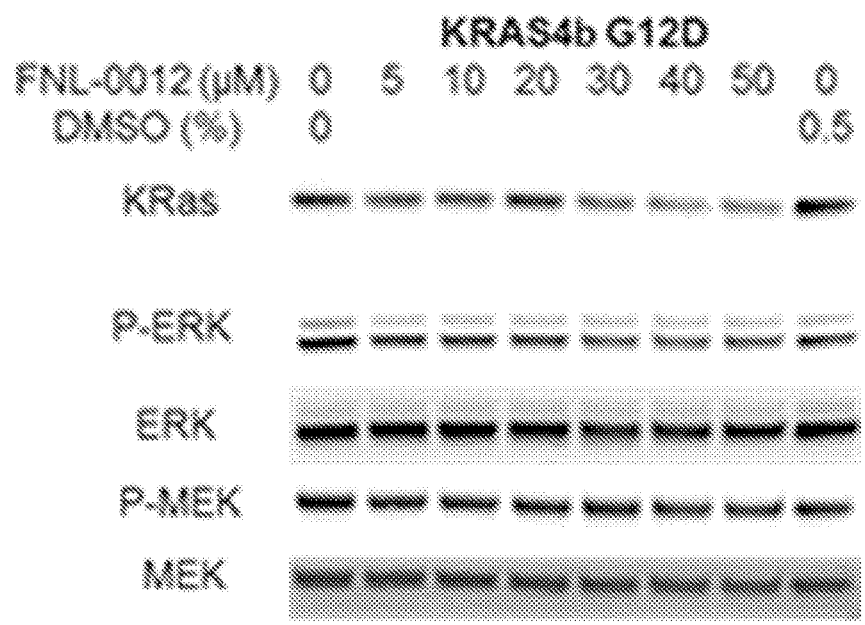
Figure 8E:
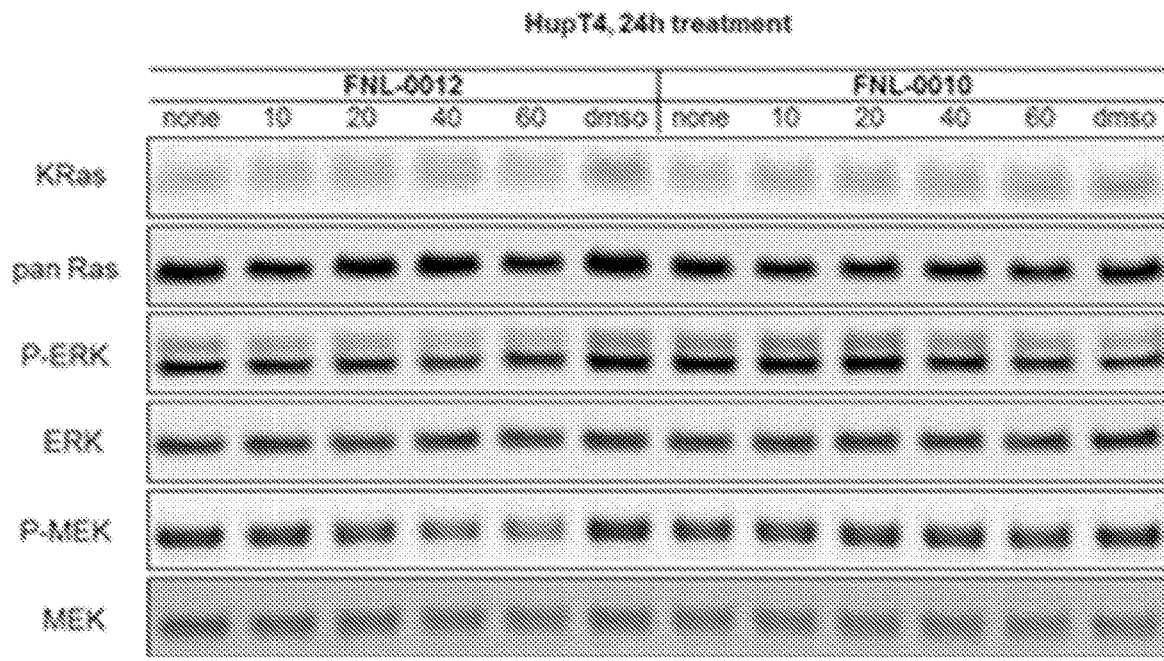

Compound FNL-0012 (epoxide derivative of 966844) showed dose-dependent growth arrest in KRAS4b G12D MEFs, without signs of toxicity, suggesting a direct inhibitory effect on KRAS. Growth arrest was observed within 24 h after treatment was initiated (FIG. 8A), and was very clearly dose-dependent after 45 h, without toxicity up to 50 µM (FIG. 8C). Decrease in KRas level was seen after 45 h of treatment, but not within 24 h.

Figure 7:
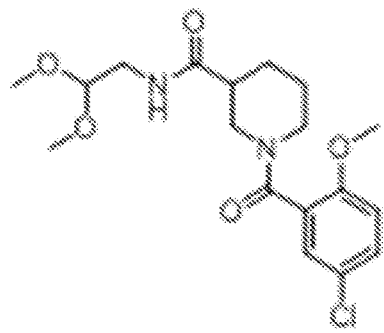
FIG. 7. Electrophilic moiety substitutions.
Figure 7:
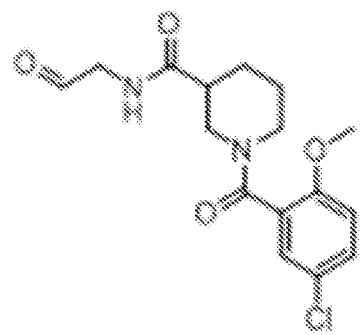
Figure 7:
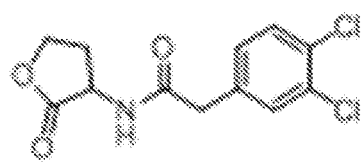
Figure 7:
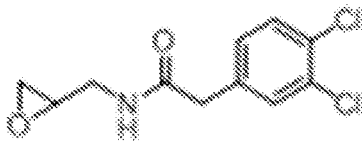
Figure 7:
Figure 8F:
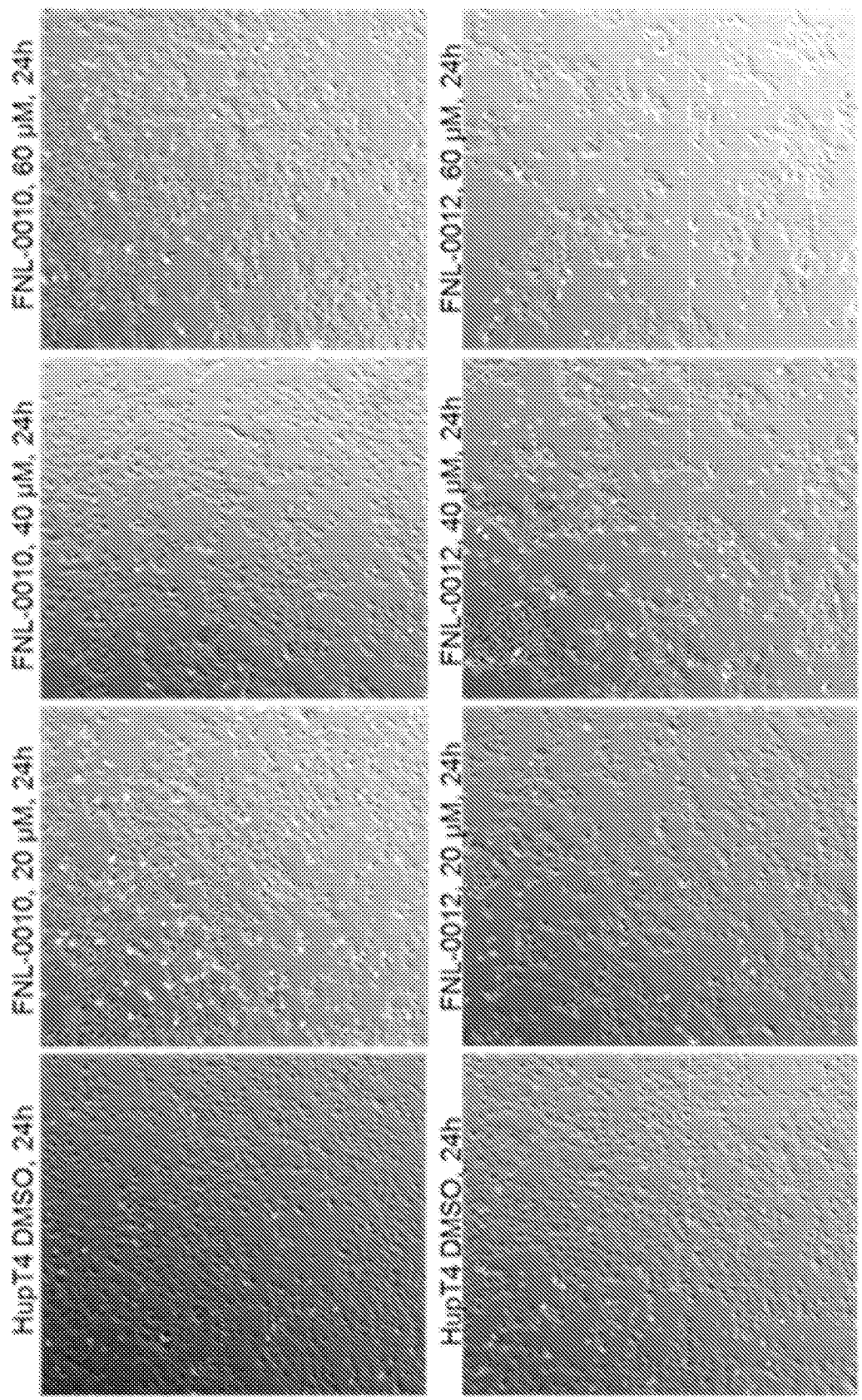

Next, we treated pancreas carcinoma cells HupT4 with FNL-0012, and FNL-0010—an epoxide derivative of fragment 917105, for 24 h. FNL-0012 growth arrested these cells within 24 h, a weaker binder (based on tethering screen dose-response data) FNL-0010 did not affect cell proliferation in this assay (FIG. 8F). Analysis of MAPK signaling in HupT4 revealed downregulation of P-MEK, and to lesser extend P-Erk after 24 h treatment with FNL-0012, but not with FNL-0010 in this assay (FIG. 7E).

Example 7. Covalent Modification of K-Ras

Figure 9:
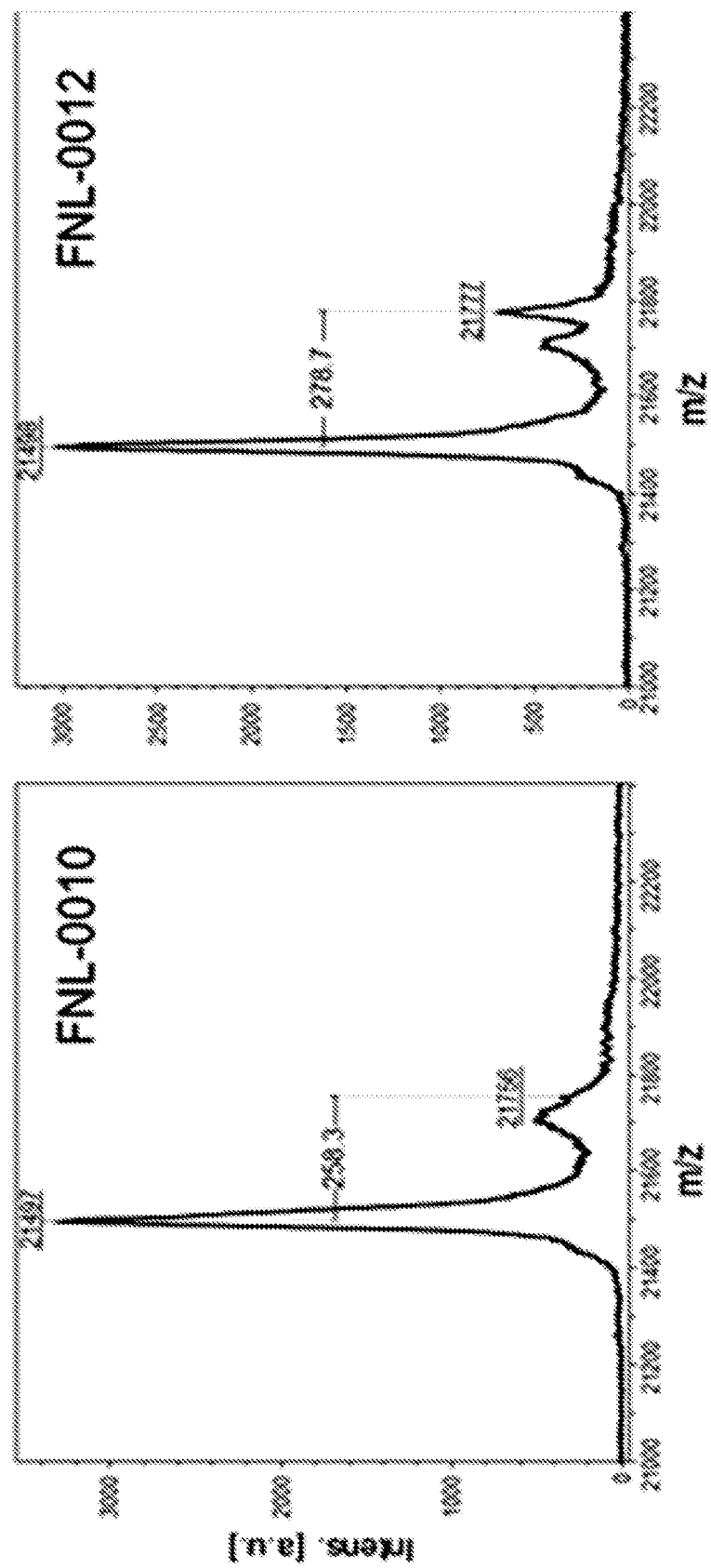
FIG. 9. MALDI-TOF analysis of KRas4b (1-188) reacted with FNL-0010 and FNL-0012 for 24 h.

Both FNL-0012 and FNL-0010 did not label fully processed (farnesylated and carboxymethylated KRas(FMe-KRas) (MALDI-TOF analysis), and when reacted with full length 1-188 KRas protein minimal modification to C185 with FNL-0012 was observed after 24 h (FIG. 9). This level of modification is too small to justify the degree of growth arrest observed in MEFs within 24 h of treatment with this compound.

Figure 10A:
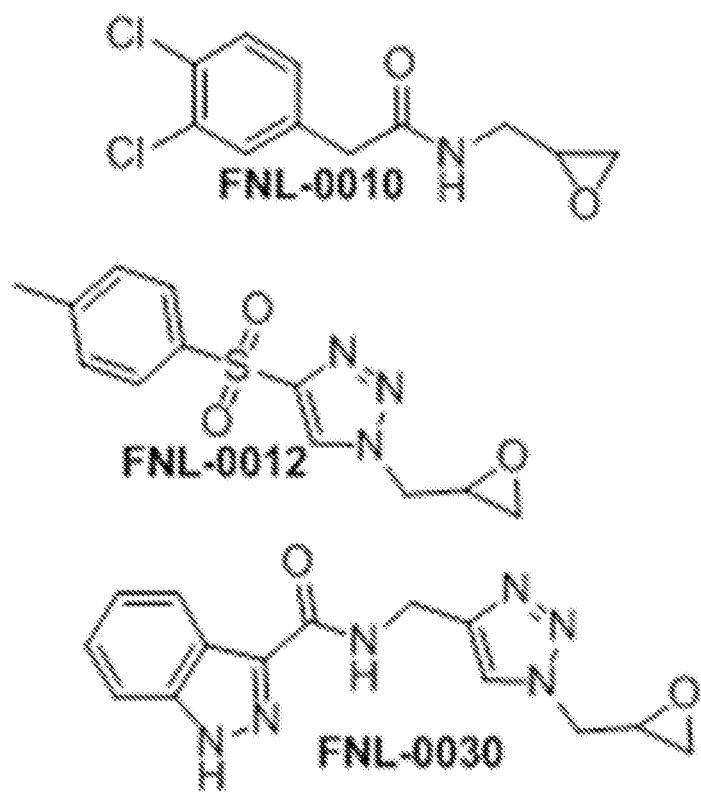
FIGS. 10A-10B.
Figure 10B:
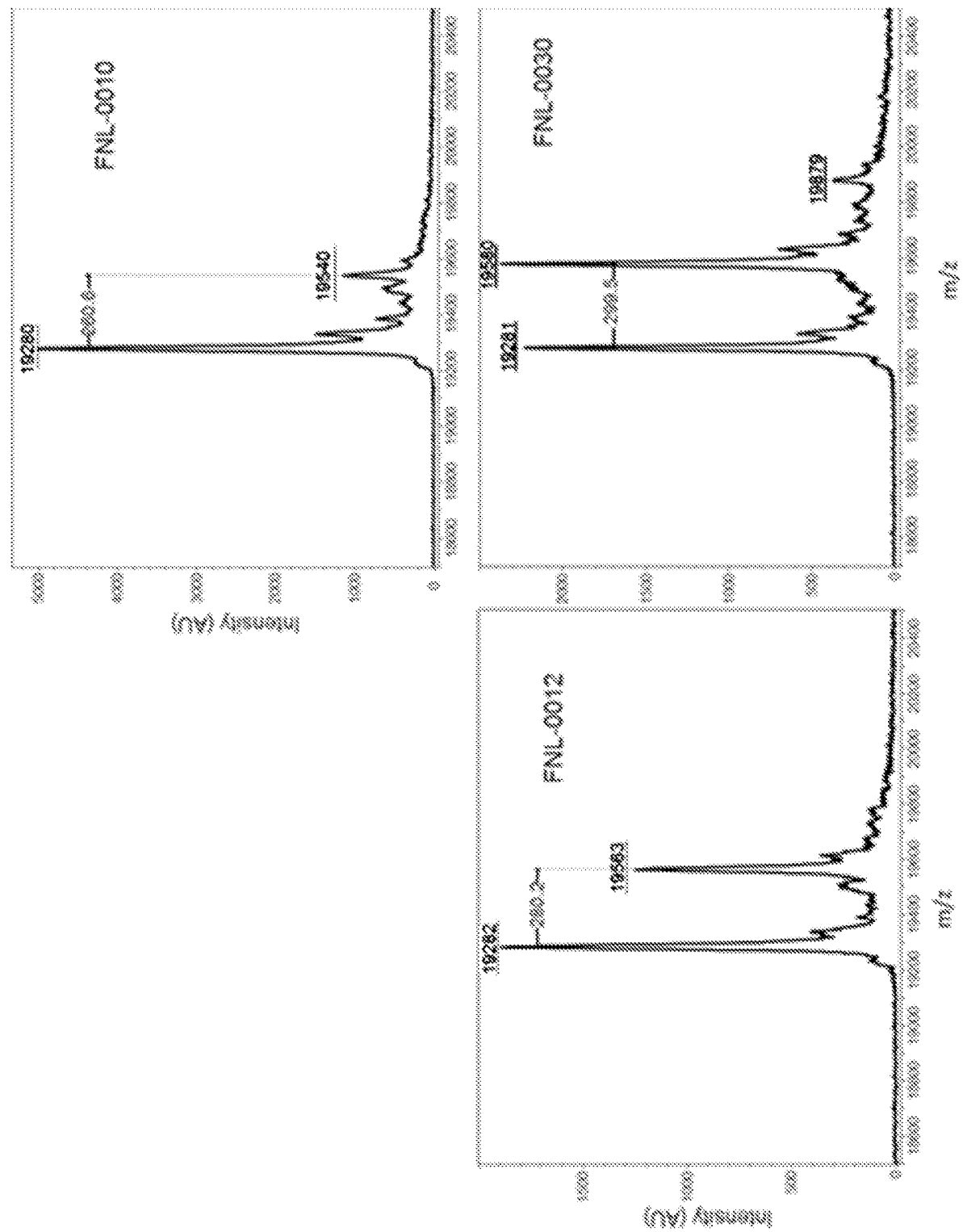

Next, we reacted all three epoxides synthesized (structures depicted in FIG. 10A) with KRas H95C (1-169) to investigate reactivity at that site. All three compounds covalently labeled C95, but level of modification to this cysteine by derivatives of two strong binding fragments from the tethering screen (FNL-0012 and -0030) was significantly higher (FIG. 10B) than that of the weaker binder FNL-0010.

Example 8. Further Biological Characterization

Figure 11A:
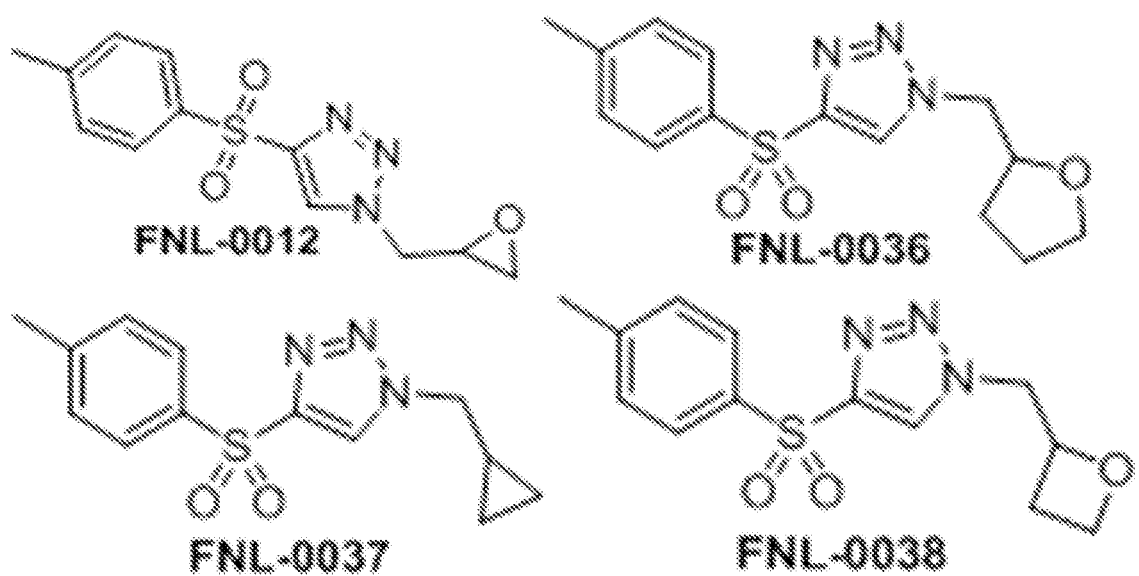
FIGS. 11A-11C.
Figure 11B:
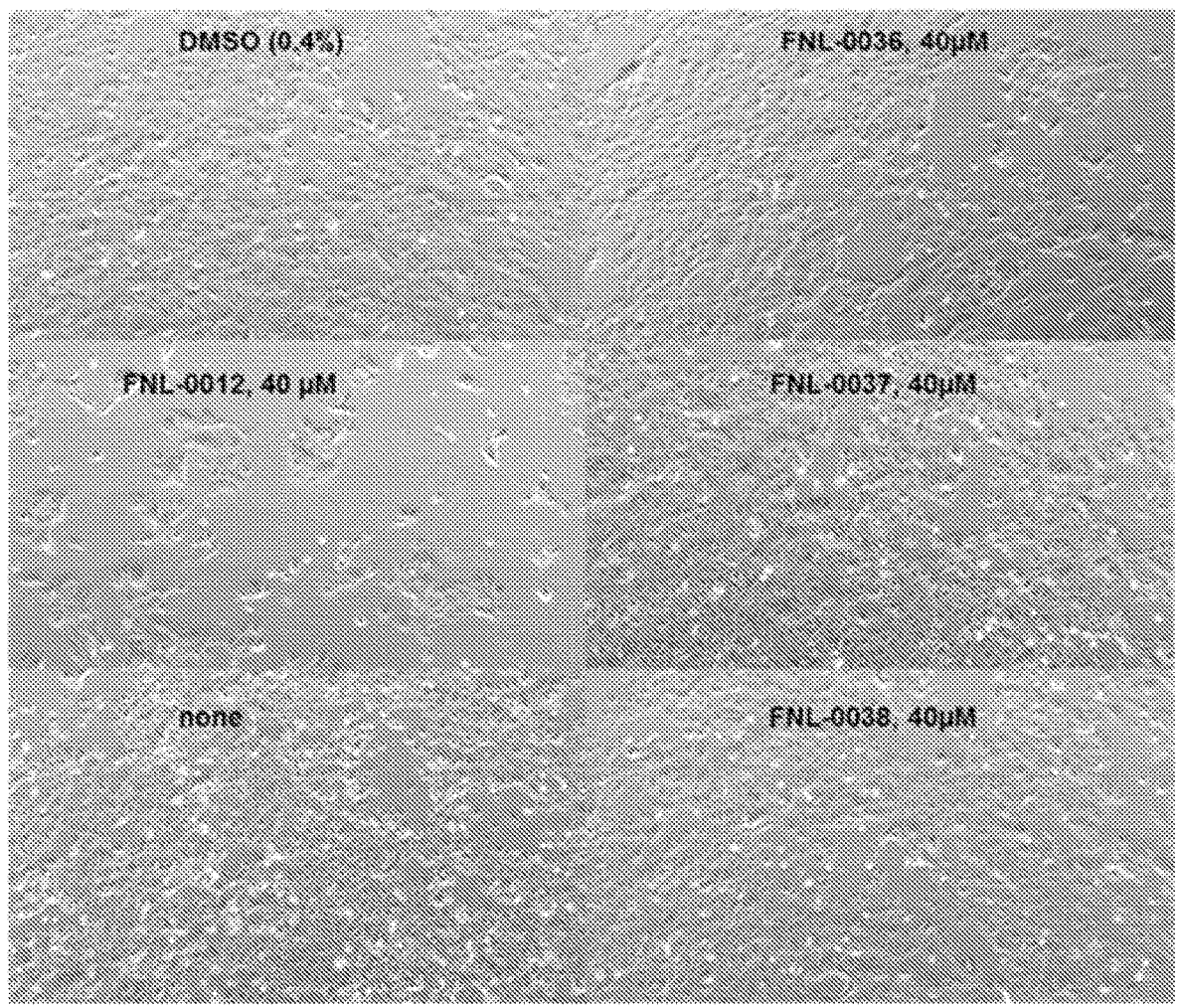
Figure 11C:
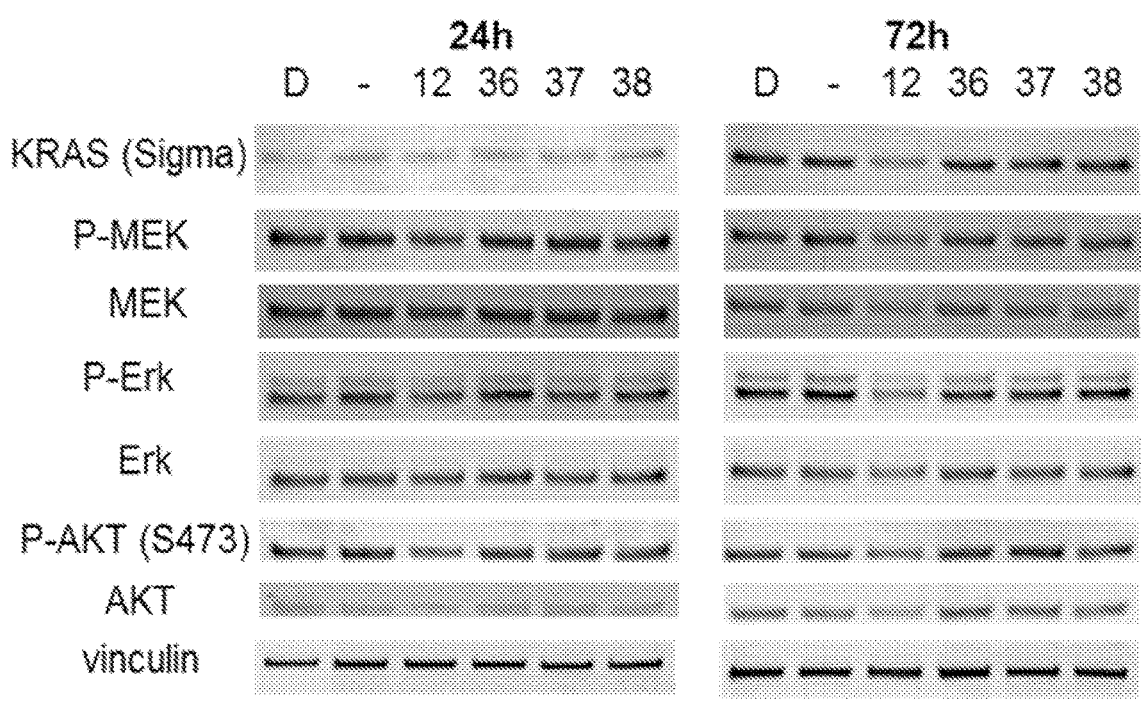

Derivatives of FNL-0012 shown in FIG. 11A were synthesized to be used as controls in biochemical and cell-based experiments: tetrahydrofuran (FNL-0036), cyclopropyl (FNL-0037), and oxetane (FNL-0038). HupT4 pancreas carcinoma cells treated with FNL-0012 or the above control compounds responded with growth arrest to FNL-0012 only (FIG. 11B). There was a decrease in MAPK signaling with FNL-0012 only at 24 h, and in KRas protein and MAPK signaling after 72 h (FIG. 11C).

Example 9. Biological Characterization in BRAF V600E, Ras Independent Cells

Figure 12A:
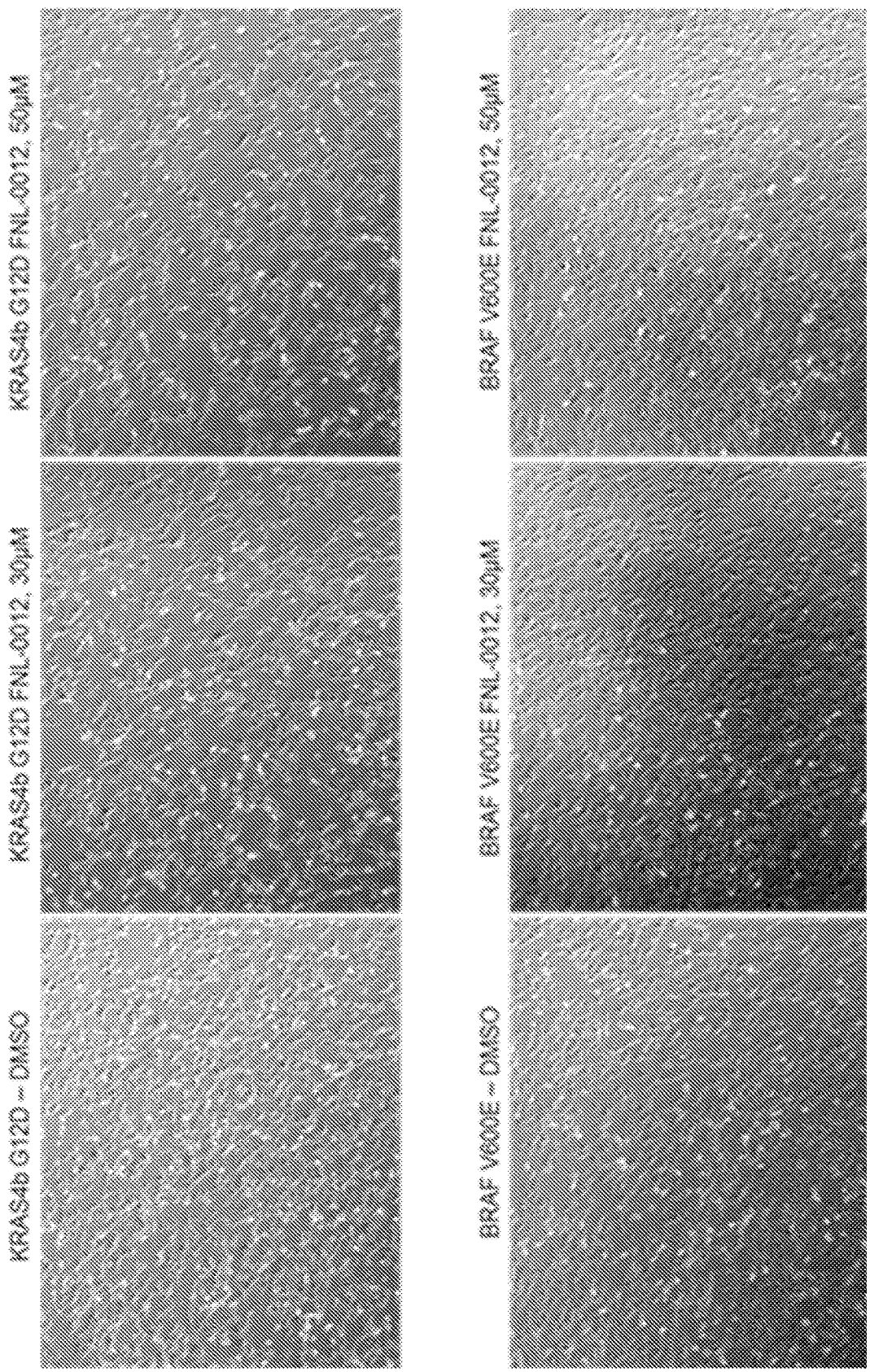
FIGS. 12A-12B.
Figure 12B:
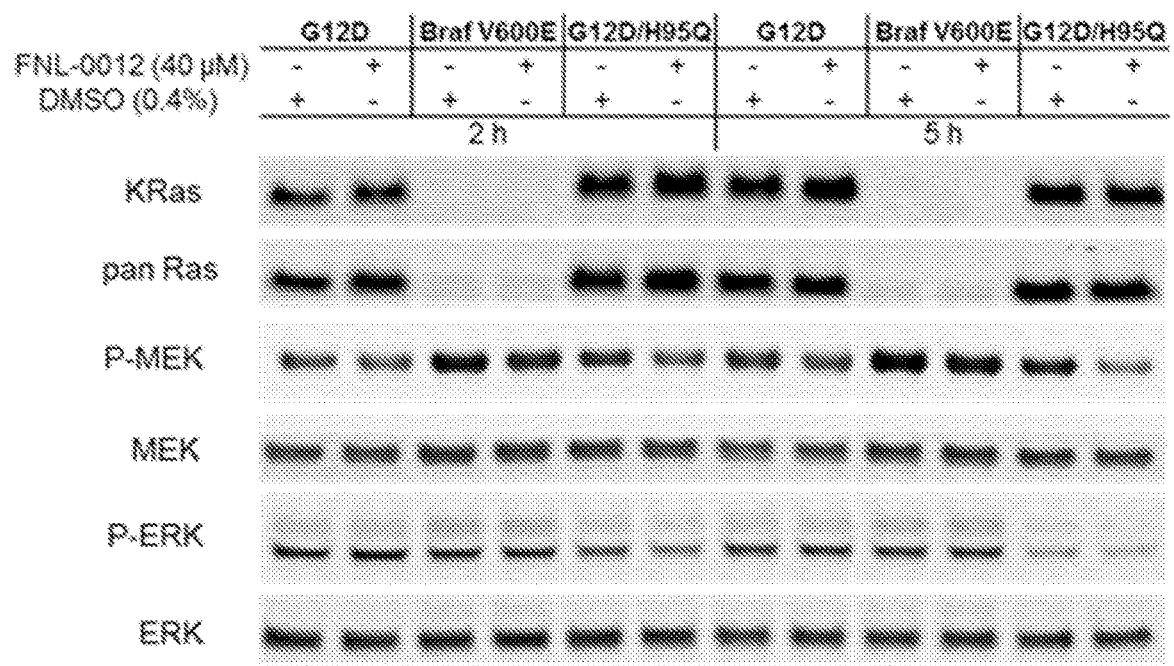

We investigated effects of FNL-0012 in BRAF V600E-driven MEFs that are Ras-independent. FNL-0012 did not cause growth arrest in BRAF V600E MEFs, nor decrease in MEK phosphorylation (FIG. 12A-12B).

Example 10. Ongoing Compound Derivatization

We are investigating alternative electrophiles and developing a histidine-specific warhead. For this purpose, we generated MEF cell lines expressing Kras H95Q. We will use these two pairs of Kras MEFs: G12D vs G12D/H95Q, and WT vs WT/H95Q to investigate compounds' effectiveness against K-ras, and H95-binding specificity.

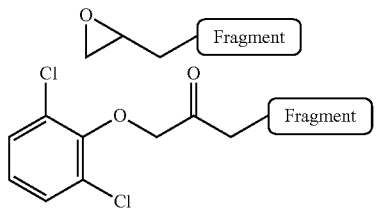

227
-continued

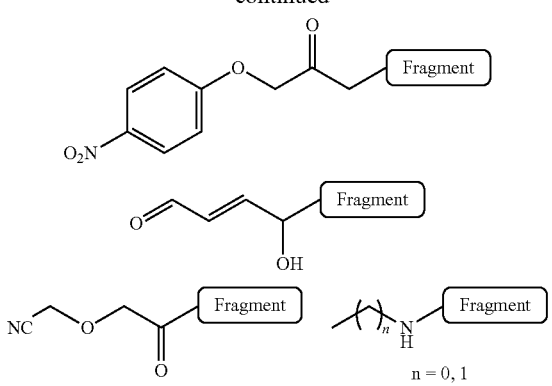

R = Et, ᵗBu, Ph
X = NH or O

Fumagillin-like spiroepoxytriazoles irreversibly inhibit methinonine aminopeptidate 2 (MetAP2) with potent cellular activity through covalent modification of His231 (Morgen et al. 2016 (DOI: 10.1021/acschembio.5b00755), incorporated herein by reference for all purposes). Ongoing efforts are incorporating similar electrophiles into compounds described herein, which specifically target Kras H95.

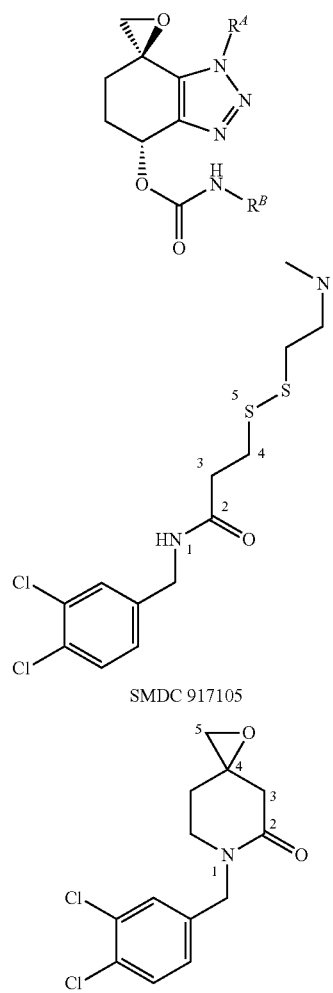

SMDC 917105

228
-continued

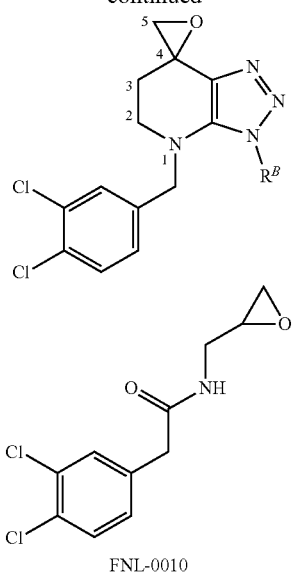

FNL-0010

To further investigate the role of the epoxide group in K-Ras inhibition we are synthesizing a number of analogues of FNL-0010, -0012, and -0030. Initially, we are exploring the effect of steric hindrance on epoxide binding. We are also examining a number of heterocyclic compounds with an aim of mimicking the proposed H-bond interaction of the epoxide oxygen with H95. Finally, we are investigating alternative electrophilic groups for covalent modification of H95.

R =

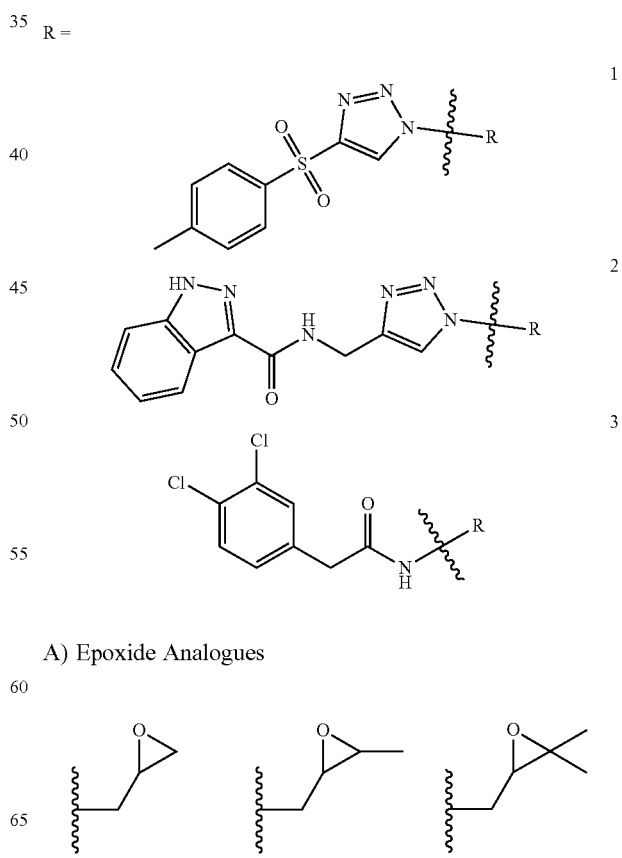

A) Epoxide Analogues

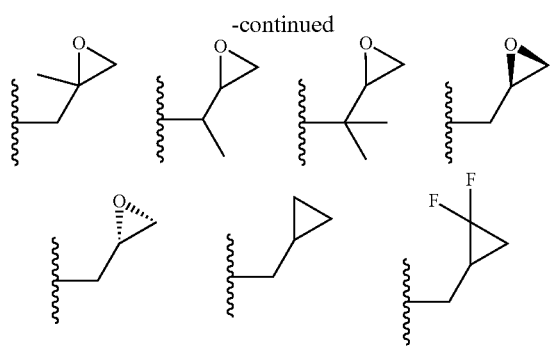

B) Alternative Heterocycles

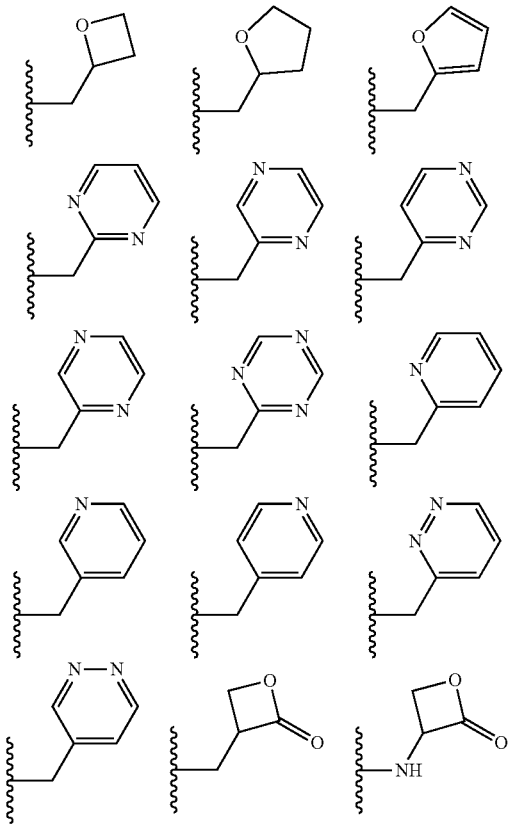

C) Alternative Electrophiles

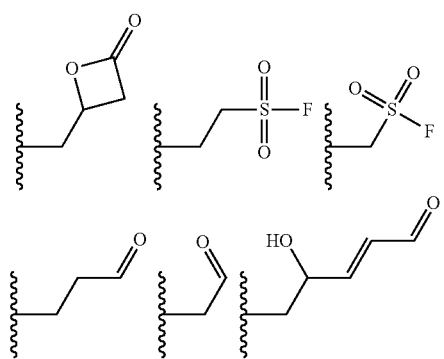

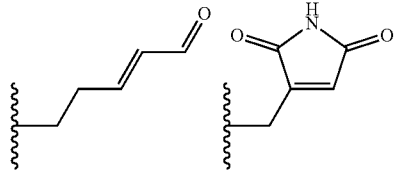

We are investigating derivatives of compound FNL-0030.

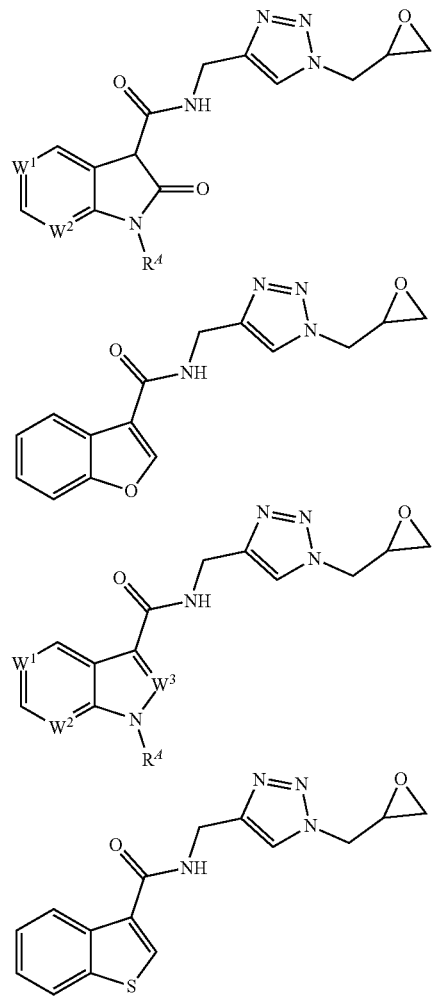

$R^A$ = H, Alkyl
$W^3$ = N, CH
$W^2$ = CH, N
$W^1$ = CH, N

Example 11: Further In Vitro Characterization

Figure 13:
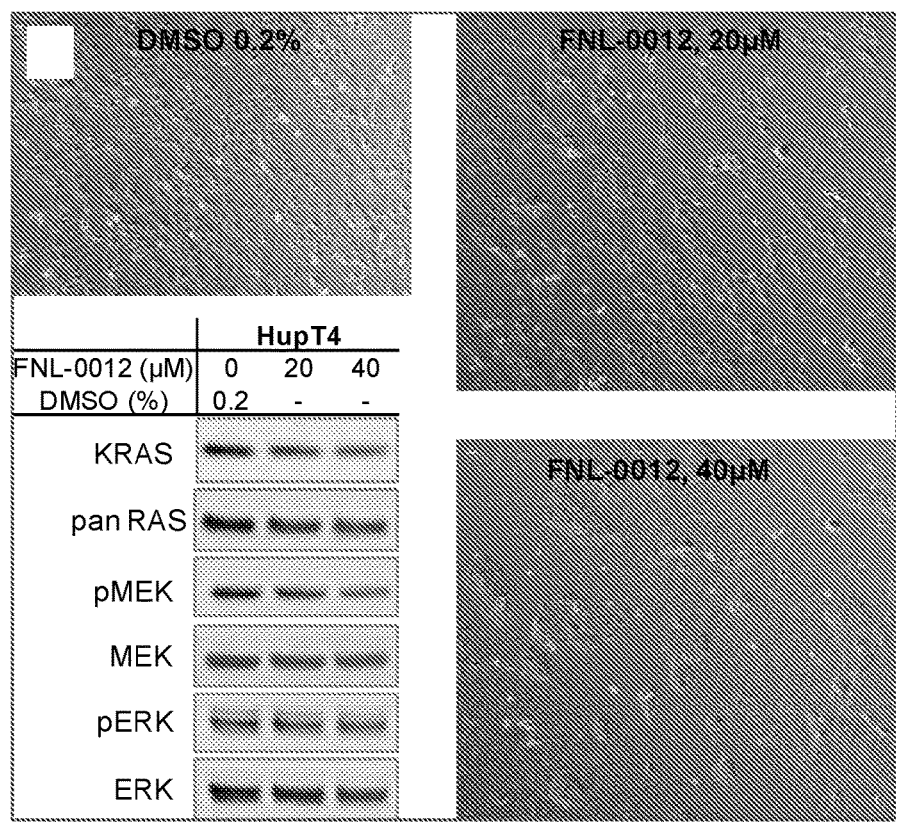
FIG. 13. Dose-dependent growth arrest and downregulation of MAPK signaling in HupT4 cells treated with compound FNL-0012.

In an experiment similar to Example 6, a HupT4 pancreas cancer cell line harboring KRAS G12V mutation and considered RAS-dependent showed growth arrest and dose-dependent decrease in KRAS level and MAPK signaling associated with treatment with FNL-0012 (FIG. 13).

Example 12: Characterization of Selected Enantiomers

Figures 14A, 14B:
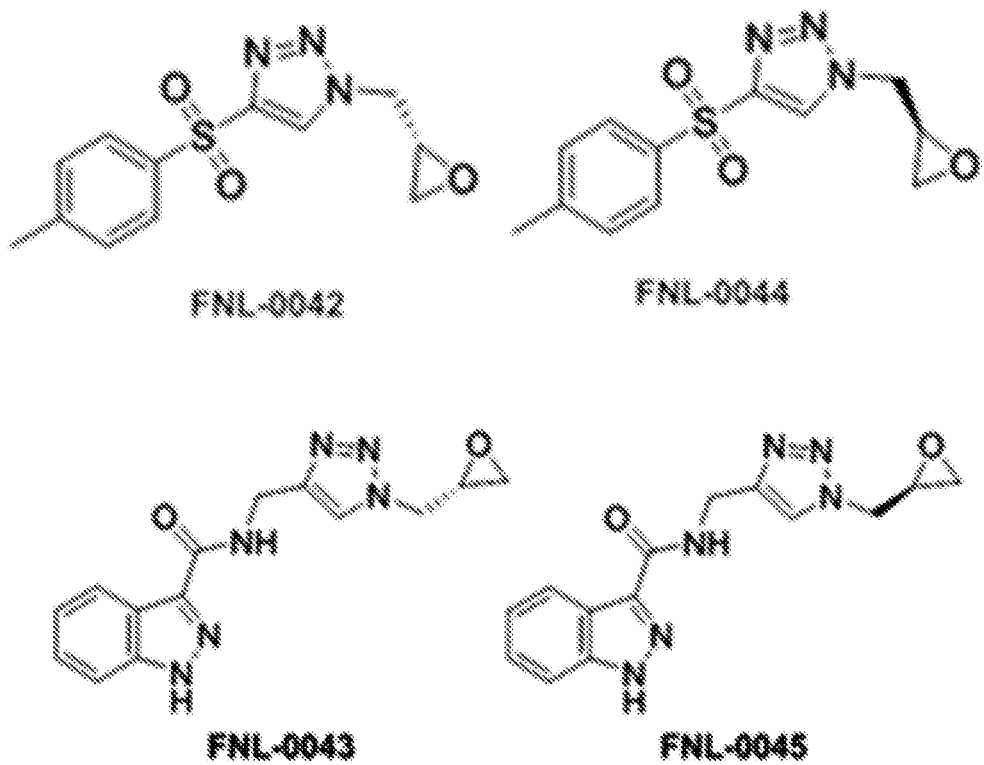
FIGS. 14A-14C.
Figure 14C:
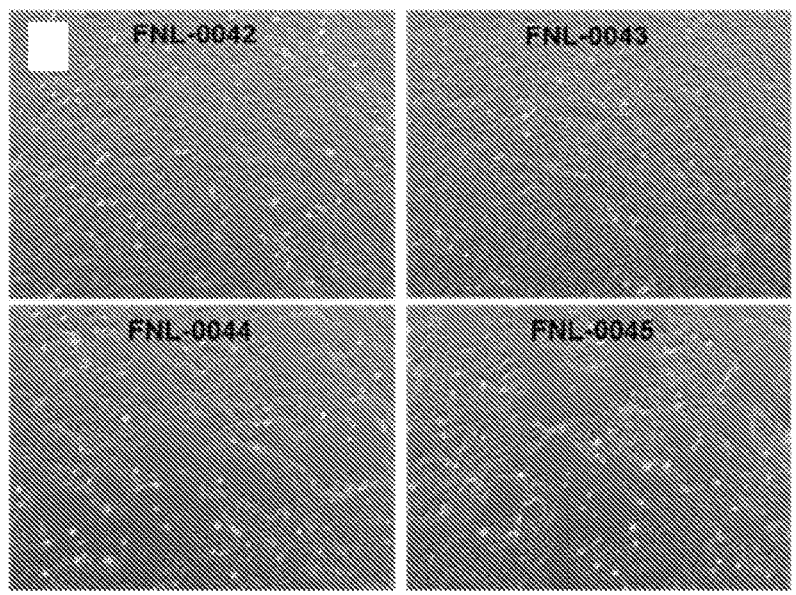

Single enantiomers of FNL-0012, compounds FNL-004.2 (S) and FNL-0044 (R), then corresponding single enantiomers of FNL-0030, compounds FNL-0043 (S) and FNL-0045 (R), were synthesized (FIG. 14A). These enantiomers were investigated using a MALDI-TOF MS screen using KRAS4b (1-169) H95C, and also cell-based assays. The level of covalent modification to KRAS4b H95C was significantly higher in the (R) enantiomer compared to the (S) counterpart (FIG. 14B). This also translated to antiproliferative activity of (R) isomers, with (S) being inactive (FIG. 14C).

Example 13: Analogues of FNL-0045

Figure 15A:
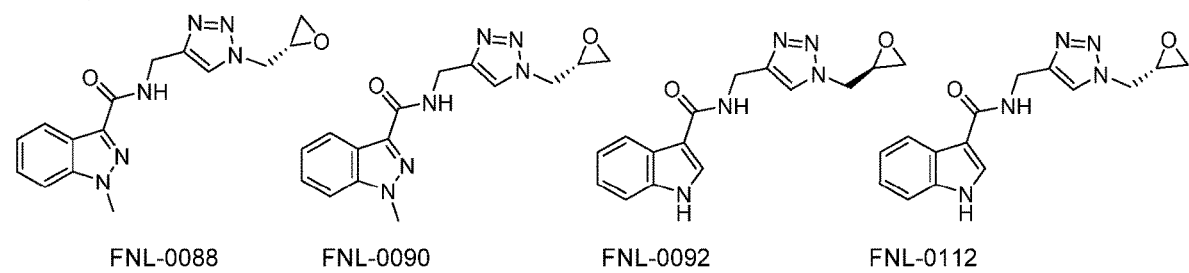
FIGS. 15A-15B.
Figure 15B:
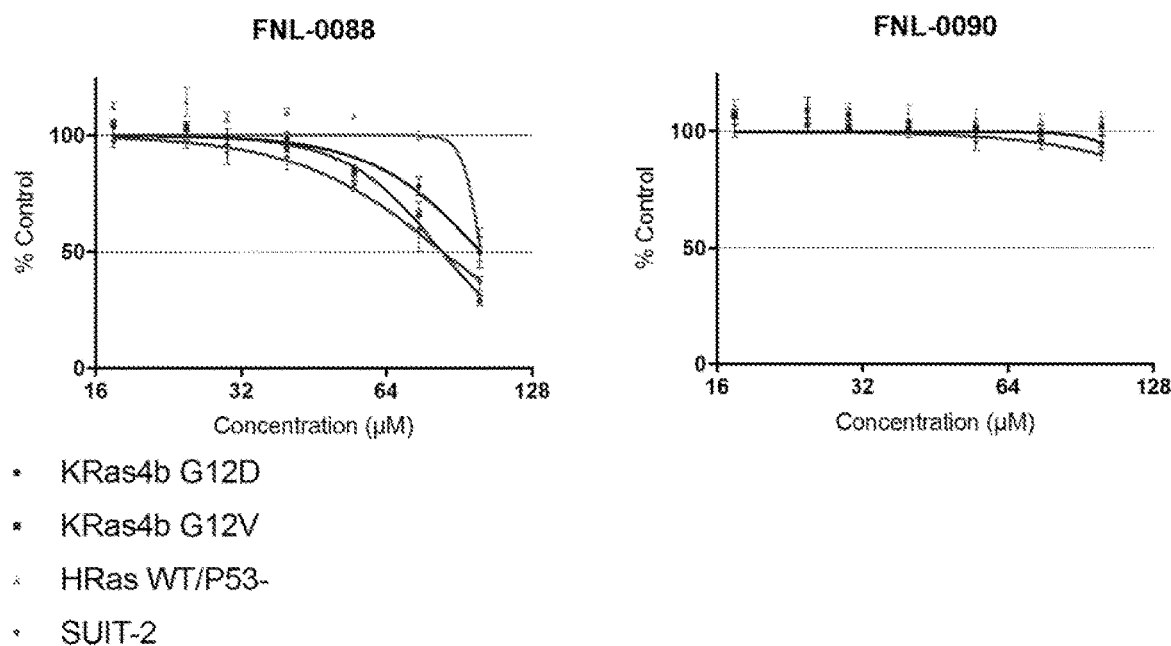

Analogues of compound FNL-0045 (FIG. 15A) were synthesized and assessed. Methyl substitution converting the imidazole to indole increased stability of the compound and prevented dimer formation. FIG. 15B demonstrates that compound FNL-0088 (R enantiomer) compared favorably in the proliferation assay with the (S) enantiomer, compound FNL-0090.

Example 14: Additional Compounds

Table 1 is a table summarizing levels of covalent labeling to C95 as analyzed by MALDI-TOF MS for a series of synthesized compounds. Recombinant KRAS4b H95C/C118S protein was used in a GDP-loaded (inactive) form, or nucleotide exchange was performed as described in Experimental Section below. Both species, GDP or nonhydrolyzable analogue of GTP—GppNHp-loaded KRAS4b H95C/C118S, were then reacted with a panel of epoxides and analyzed by MALDI-TOF MS to assess level of covalent modification to C95 after 3 h, 6 h, or 24 h of incubation with the protein. All R isomers show enhanced activity compared to S isomers. Protein in a GDP state shows higher level of covalent modification than the GppNHp-loaded protein.

TABLE 1

| Compound | GDP | | | GppNHp | | |
| --- | --- | --- | --- | --- | --- | --- |
|  | 3 h | 6 h | 24 h | 3 h | 6 h | 24 h |
| 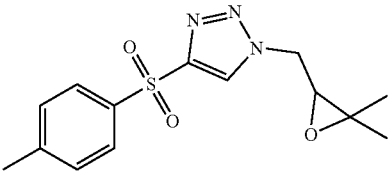 FNL-0058 | 0 | 0 | 0 | 0 | 0 | 0 |
| 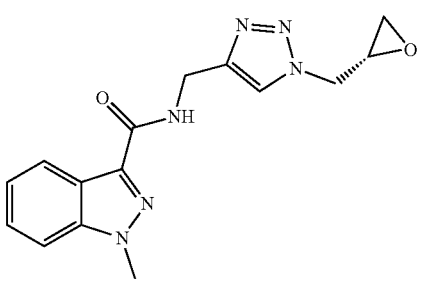 FNL-0088 | 3 | 9 | 38 | 0 | 3 | 13 |
| 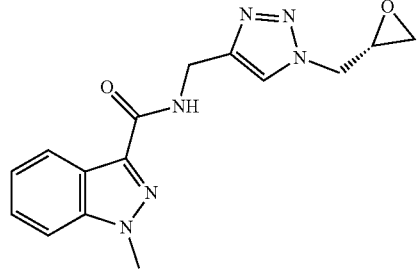 FNL-0090 | 0 | 0 | 0 | 0 | 0 | 0 |

TABLE 1-continued
| Compound | GDP | | | GppNHp | | |
|---|---|---|---|---|---|---|
| | 3 h | 6 h | 24 h | 3 h | 6 h | 24 h |
| 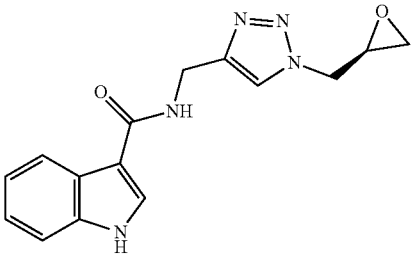 FNL-0092 | 7 | 18 | 72 | 2 | 4 | 25 |
| 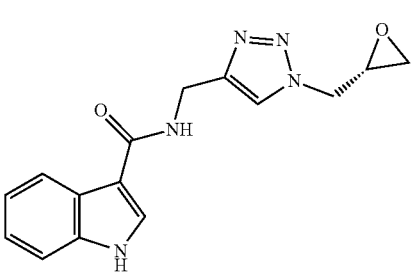 FNL-0112 | 0 | 5 | 31 | 0 | 2 | 11 |
| 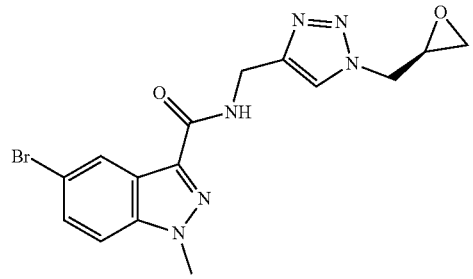 FNL-0119 | 23 | 52 | 96 | 0 | 4 | 19 |
| 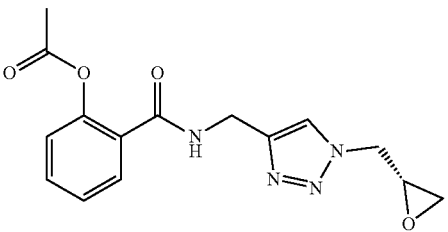 FNL-0120 | 5 | 12 | 45 | 2 | 3 | 14 |
| 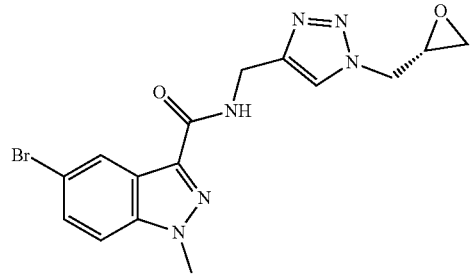 FNL-0121 | 3 | 10 | 49 | 0 | 2 | 10 |

TABLE 1-continued
| Compound | GDP | | | GppNHp | | |
|---|---|---|---|---|---|---|
| | 3 h | 6 h | 24 h | 3 h | 6 h | 24 h |
| 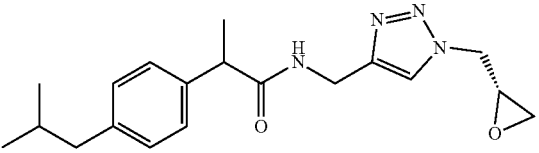 FNL-0126 | 36 | 73 | 98 | 0 | 2 | 17 |
| 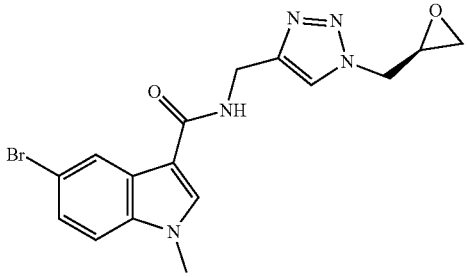 FNL-0139 | 19 | 42 | 91 | 3 | 4 | 22 |
| 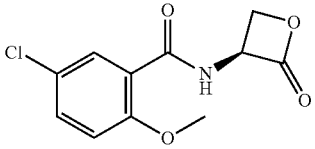 FNL-0173 | 87 | 91 | 89 | 76 | 81 | 78 |
| 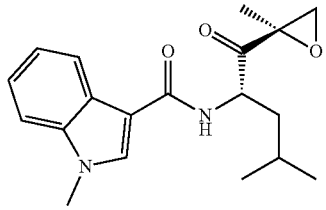 FNL-0178 | 0 | 0 | 0 | 0 | 0 | 0 |
| 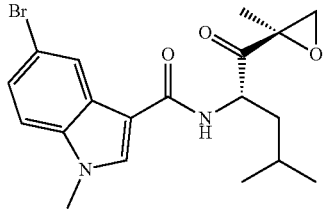 FNL-0179 | 0 | 0 | 0 | 0 | 0 | 0 |
| 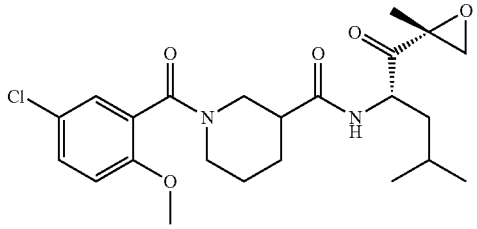 FNL-0194 | 0 | 0 | 0 | 0 | 0 | 0 |

Example 15: Cell Proliferation Assays

Cell viability in the presence of compounds (discussed in examples above) was measured using CellTiter-Glo (Promega). Cells were plated in black-walled 384-well plates (Greiner, 781091) at densities in accordance with their doubling time (for MEFs typically 1,000 cells/well in 20 μl), using the Multidrop Combi Reagent Dispenser (Thermo). They were then incubated overnight at 37° C. in a humidified atmosphere of 5% $CO_2$ prior to compound addition.

Compound and dimethylsulfoxide (DMSO) addition to microplates was performed using the Access Laboratory Workstation (Labcyte) and Echo 555 (Labcyte) liquid handler. Source plates with compounds and DMSO were prepared and the Echo 555 was used to transfer 50 nL of compound, DMSO, or both to the appropriate wells. Five L of complete culture medium was added to all wells of the microplate after compound addition. The highest final concentration in each assay was 100 μM or 50 μM with between seven to 12 dilutions. The final DMSO concentration in all wells was 0.2%.

Cells were incubated with compounds for 72 h. All conditions were done in triplicates and experiments performed at least thrice. Cellular ATP levels (an indicator of cell count) were determined with CellTiter-Glo (CTG, Promega G7573) luminescence assay, using an EnVision Plate Reader (PerkinElmer).

Plates were harvested at two time points. At the time of drug addition, one plate for each cell line with no compounds added received 5 μL of media and were harvested to represent a measurement of the cell population at the time of compound addition (T0). After 72 h incubation, the compound treated plates were harvested using CTG reagent and luminescence read using the EnVision giving control growth (C) and compound treated well (T72) measurements. Growth inhibition was calculated by:

$$\frac{T72 - T0}{C - T0} \times 100$$

Dose-response curves were generated using Prism 7 software (GraphPad).

Example 16: Immunoblot Analysis

For immunoblot analysis experiments, cells rinsed trice with ice-cold phosphate-buffered saline (PBS) were lysed on ice, with ice-cold TNE buffer, supplemented with Halt protease and phosphatase inhibitors (Thermo Scientific), and centrifuged at 15,000 g for 15 minutes to collect whole-cell lysates. Protein concentration was measured with the BCA protein assay (Pierce). Thirty micrograms of total protein per sample were loaded into 4%-12% NuPAGE Bis-Tris gradient gels (Life Technologies) and separated by SDS-PAGE. Proteins were transferred to polyvinylidene difluoride (PVDF) membranes. The following antibodies were used for immunoblotting: mouse monoclonal anti-KRAS (Sigma WH0003845M1, clone 3B10-2F2), mouse anti-RAS (Thermo 1862335), rabbit anti-pERK1/2 (T202/Y204; Cell Signaling Technology 4370), mouse anti-ERK1/2 (Cell Signaling Technology 4696), rabbit anti-p-MEK1/2 (S217/221; Cell Signaling Technology 9154), mouse anti-MEK1/2 (Cell Signaling Technology 4694), rabbit anti-p-AKT (S473; Cell Signaling Technology 4060), mouse anti-AKT (Cell Signaling Technology 2920). Vinculin (rabbit anti-vinculin, Cell Signaling Technology 4650) was used as a loading control. Primary antibodies were detected with fluorescence-conjugated (LI-COR) secondary antibodies.

Example 17: GppNHp Nucleotide Exchange Protocol for GDP KRAS Proteins 150 to 300 μM solution of GDP loaded protein in KRAS buffer was prepared (20 mM HEPES, 150 mM NaCl, 1 mM $MgCl_2$, 0.05 mM TCEP, pH 7.3). To this was added vigorously 1500×molar excess of 1 M ammonium sulfate in KRAS buffer, and the combination mixed gently by inverting tube. Next was prepared 250 mM solution of GppNHp (150 molar excess of GppNHp to protein; keep it on ice). To the protein was pipetted 10% of prepared GppNHp solution, then suspension of alkaline phosphatase from calf intestine on agarose was added (Sigma-Aldrich, P0726) to have 2 units of enzyme per each mg of protein. The reaction mixture was incubated at room temperature, rotating end-over for 1 h 30 min. The alkaline phosphatase was removed on agarose beads by filtering solution to a new vial using Millex-GP syringe filter. Remaining solution of GppNHp was added and incubated for additional 45 min. At the end of the exchange the protein was filtered again, placed on ice, and purified on NGC medium-pressure chromatography system (Bio-Rad). Five in-lane connected desalting columns (5×GE Healthcare HiTrap Desalting columns 5 ml, 17-1408-01) were used with isocratic elution of KRAS buffer at 4 ml/min. The protein elution was monitored at 280 nm. The concentration of final protein was evaluated by NanoDrop 2000 spectrophotometer (Thermo Fisher) using molar attenuation coefficient $\varepsilon=19685 \, l \cdot mol^{-1} \cdot cm^{-1}$. The quality of the protein was confirmed by MALDI and the exchange rate was assessed by HPLC based assay.

Example 18: Percentage Labeling Determination for Compounds Targeting KRAS4b Residue 95 by Matrix Assisted Laser Desorption Ionization-Time of Flight Mass Spectrometry (MALDI-TOF)

Proteins:
The assay uses four tool proteins:
Guanosine diphosphate (GDP) loaded KRAS4b(1-169) H95C/C118S mutant
5'-Guanylyl imidodiphosphate (GppNHp) loaded KRAS4b(1-169) H95C/C118S mutant
GDP loaded KRAS4b(1-169) C118S mutant
GppNHp loaded KRAS4b(1-169) C118S mutant
Reaction:
20 μM Solution of protein in 20 mM HEPES, 150 mM NaCl, 1 mM $MgCl_2$, pH 7.3 buffer was prepared freshly before assay. 20 μl Aliquots of protein were dispensed on 384 well polypropylene plate, then tested compounds (0.8 μl, 10 mM in DMSO) were added to appropriate wells. For each reaction/assay three blank and three control samples were prepared by mixing 20 μl of protein solution with 0.8 μl DMSO or 10 mM standards (compounds 994566 and FB9). The wells content was carefully mixed by aspiration, then plate was sealed by adhesive cover, centrifuged at 2000 g for 1 minute and kept in dark at room temperature for 3, 6 (or 8) and 24 h.

MALDI Target Pre-Treatment:
Before each assay MALDI target (Bruker MPT 384 ground steel BC) was pre-treated by pipetting on each spot 1 μl of saturated sinapinic acid in acetonitrile (ACN). This step significantly improves uniformity of sample crystallization across the plate resulting in better assay sensitivity.

MALDI Sample Preparation:

After 24 h reaction, 2 μl of reaction mixtures were pipetted out into 20 μl MALDI matrix solution (saturated solution of sinapinic acid in 1:1 ACN:water solution containing 0.75% trifluoroacetic acid (TFA)) deposited on 384 well polypropylene plate. Resulting solution was mixed by aspiration, centrifuged at 2000 g for 1 minute, then 2 μl aliquots were dispensed on pre-treated MALDI target using Beckman Coulter Biomek FX$^P$ 96/Span-8 Laboratory Automation Workstation. Finally, the MALDI target was dried under mild vacuum to produce spots with fine crystalline structure.

MALDI Measurements:

MALDI-TOF measurements were performed on Bruker Daltonics ultraflex III TOF-TOF mass spectrometer using linear mode and mass range from 5 to 45 kDa. Detector gain was set to ×9 (1734 V), sample rate to 1 GS/s, smart beam parameter set: 3_medium was used, and the laser frequency was 66.7 Hz. Spectra were automatically collected using custom AutoXecute method. Laser power was auto-adjusted using fuzzy control. The peak selection range was set to be between 19000 and 20200 Da. Peak evaluation uses half width parameter set to be smaller than 30 Da. Fuzzy control used Proteins/Oligonucleotides protocol with minimum half width ⅙ times above threshold. Up to 1500 shots were collected in 500 shot steps. Dynamic termination was implemented to finish data collection when peak intensity was reaching value of 1200 [a.u.].

Spectra Processing:

Spectra were smoothed by SavitzkyGolay algorithm using 5 m/z width and three cycles. Centroid peak detection algorithm was used with signal to noise threshold set to 4, relative intensity threshold 2%, minimum intensity threshold 20 [a.u.], peak width 10 m/z and TopHat baseline subtraction. Peak intensity and area under the peak were evaluated and recorded for all peaks between 19248 Da and 20500 Da for H95/C118 mutant and 19285 Da and 20500 Da for C118 mutant respectively.

Calculation:

Percent of labeling was calculated using followed equation:

$$\% \text{ modification} = \frac{\text{modified protein peak height}}{\text{modified protein peak height} + \text{unmodified protein peak height}} \times 100\%$$

Similar results were obtained when peak area instead of peak height was used for calculations, however peak height method produced more reliable data in case of poor quality spectra.

Tables summarizing protein labeling over time by different compounds provided herein are presented in Table 1.

Example 19: Synthesis of 4-Benzene Sulfonyl Triazole Compounds

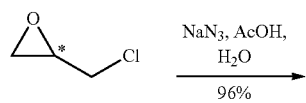

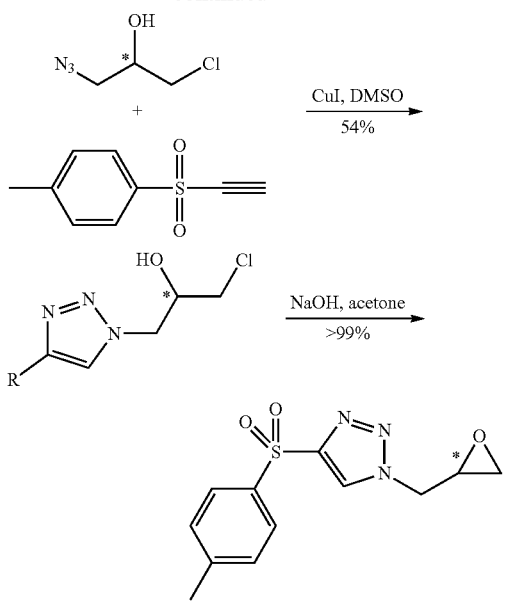

* = R or S

The compound 1-(oxiran-2-ylmethyl)-4-tosyl-1H-1,2,3-triazole was synthesized according to the above scheme. Certain compounds comprising a sulfonyl triazole moiety were synthesized following an analogous route. In the first step, 2-(chloromethyl)oxirane was combined with NaN$_3$, acetic acid (AcOH), and water, and the mixture stirred at room temperature to produce 1-azido-3-chloropropan-2-ol. This compound was then combined with ethynyl p-tolyl sulfone, CuI (0.05%) in dimethyl sulfoxide (DMSO) and stirred at room temperature for 18 hours to produce a triazole compound. This triazole was combined with NaOH (1N), and acetone, and the mixture stirred at room temperature for 1 h to produce 1-(oxiran-2-ylmethyl)-4-tosyl-1H-1,2,3-triazole.

Example 20: Synthesis of 4-Methylamido Triazole Compounds

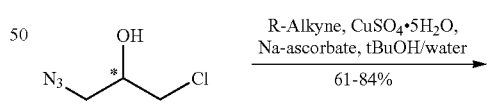

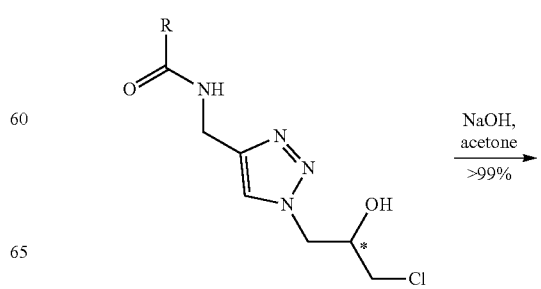

-continued

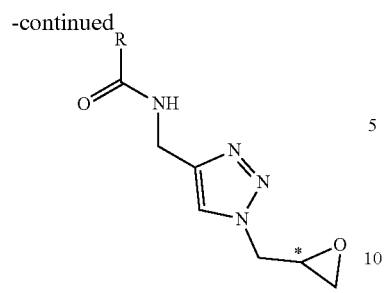

* = R or S

Certain compounds comprising a 4-methylamido triazole moiety were synthesized according to the above scheme. In the first step, 1-azido-3-chloropropan-2-ol is combined with an R-alkyne reactant, CuSO$_4$·5H$_2$O (10%), Na-ascorbate (30%), a mixture of t-butanol and water (tBuOH/water (1:1)), and the mixture stirred at 50° C. for 18 h to produce a compound comprising a triazole moiety and a 3-chloropropan-2-ol moiety. This is then reacted with NaOH (1N) and acetone at room temperature for 1 hour to produce the compound comprising a 4-methylamido triazole moiety.

Example 21: Synthesis of Compounds with an Amide Moiety

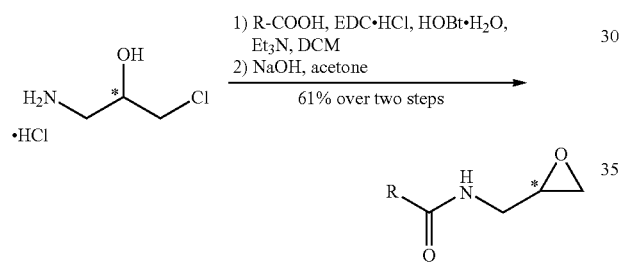

* = R or S

Certain compounds disclosed herein with an amide moiety, without a triazole moiety, were synthesized according to the above scheme, over two steps. In the first step, 1-amino-3-chloropropan-2-ol hydrochloride was combined with R—COOH, 1-ethyl-3-(3-dimethylaminopropyl)carbodiimide hydrochloride (EDC.HCl), hydroxybenzotriazole hydrate (HOBt.H$_2$O), triethylamine (Et$_3$N), and dichloromethane (DCM), and the mixture stirred at room temperature for 18 h. In the second step, the product from the first step was reacted with NaOH (1N) and acetone at room temperature for 30 minutes to produce the final compound comprising an amide moiety, without a triazole.

The following compounds were synthesized, for example in some instances by following synthetic schemes analogous to those shown in Examples 19-21 above:

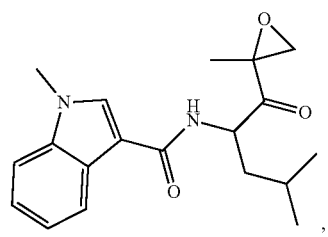

-continued

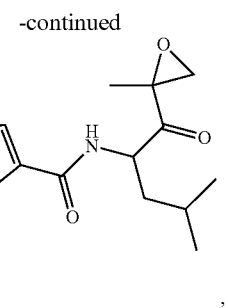

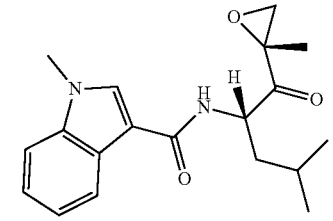

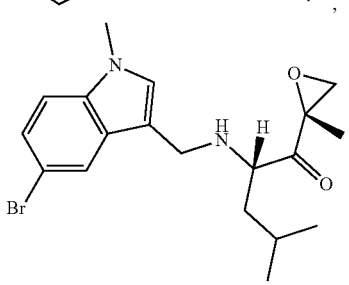

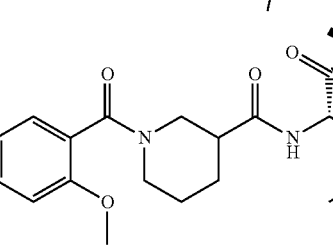

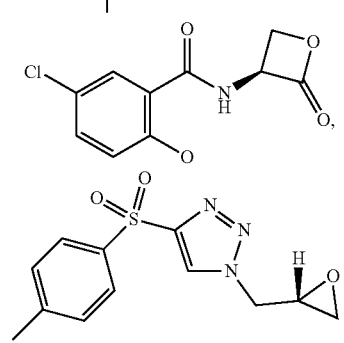

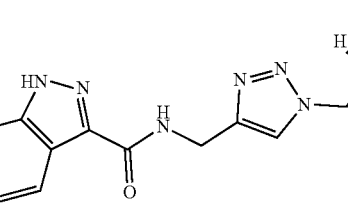

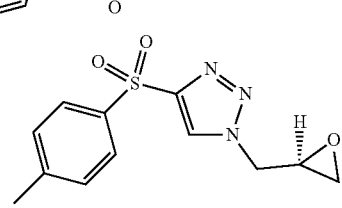

243
-continued
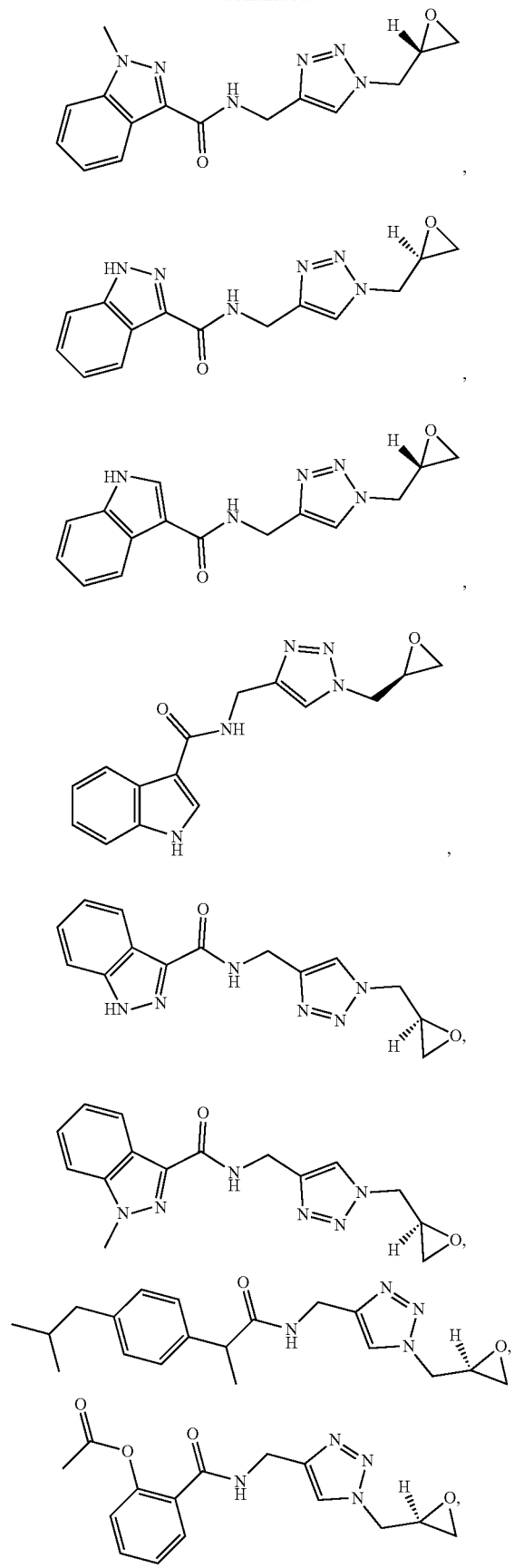
244
-continued
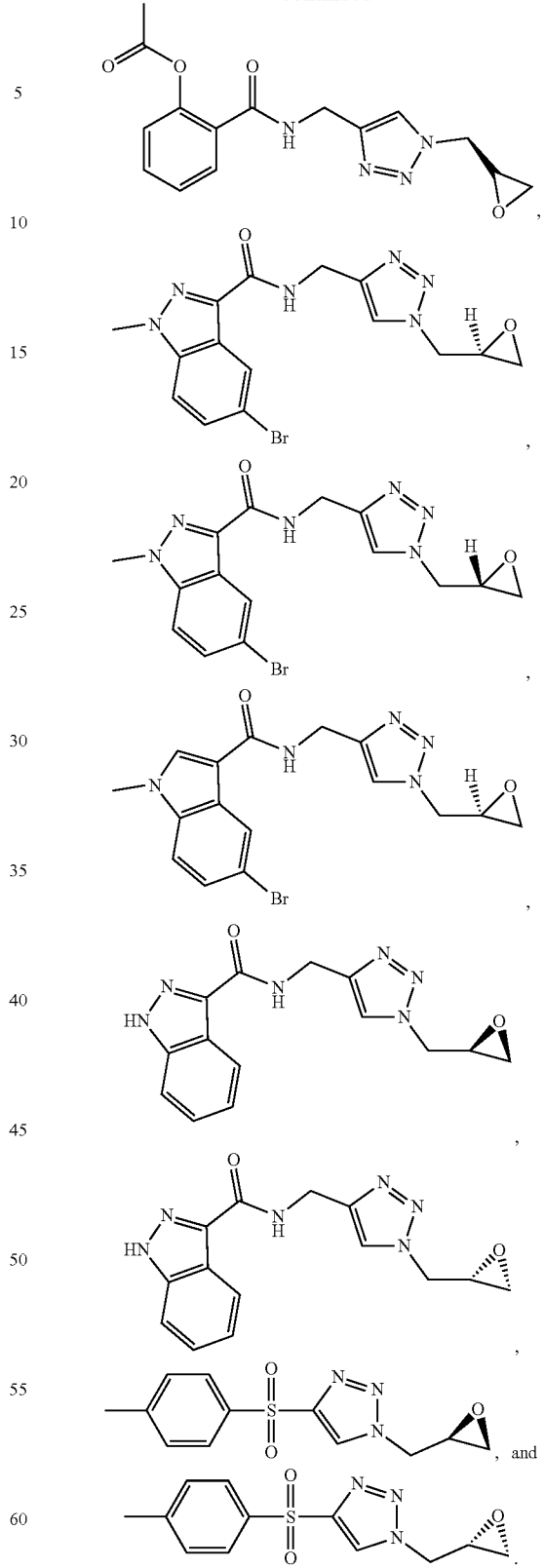
It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Enumerated Embodiments

Embodiment I-1. A compound having the formula:

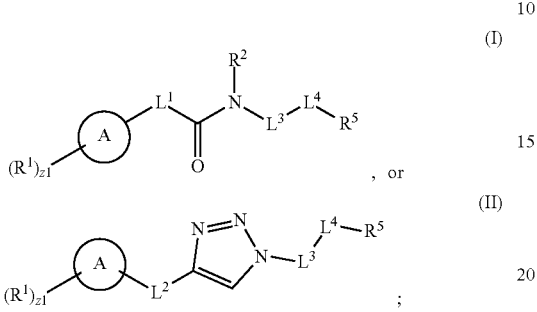

wherein, ring A is an aryl or heteroaryl;

$R^1$ is independently halogen, $-CX^1_3$, $-CHX^1_2$, $-CH_2X^1$, $-CN$, $-SO_{n1}R^{1D}$, $-SO_{v1}NR^{1A}R^{1B}$, $-NHNR^{1A}R^{1B}$, $-ONR^{1A}R^{1B}$, $-NHC=(O)NHNR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;

$R^2$ is independently hydrogen, $-CX^2_3$, $-CHX^2_2$, $-CH_2X^2$, $-C(O)R^{2A}$, $-C(O)OR^{2A}$, $-C(O)NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$L^1$ is a bond, substituted or unsubstituted alkylene, substituted or unsubstituted cycloalkylene, or

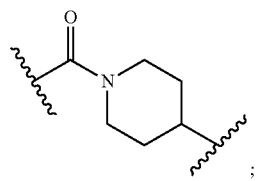 [SMILES: *C(=O)N1CCC(*)CC1]

$L^2$ is a bond, $-O-$, $-C(O)-$, $-C(O)O-$, $-OC(O)-$, $-S-$, $-SO-$, $-S(O)_2-$, $-NH-$, $-NHC(O)-$, $-C(O)NH-$, $-SO_2NH-$, $-NHSO_2-$, $-OC(O)NH-$, $-NHC(O)O-$, $-NHC(O)NH-$, $-C(O)OCH_2-$, $-CH_2OC(O)-$, $-C(O)NHCH_2-$, $-CH_2NHC(O)-$, $-CH_2NHCH_2-$, substituted or unsubstituted alkylene, or substituted or unsubstituted heteroalkylene;

$L^3$ is a bond, $-S(O)_2-$, $-N(R^3)-$, $-O-$, $-S-$, $-C(O)-$, $-C(O)N(R^3)-$, $-N(R^3)C(O)-$, $-N(R^3)C(O)NH-$, $-NHC(O)N(R^3)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently hydrogen, $-CX^3_3$, $-CHX^3_2$, $-CH_2X^3$, $-C(O)R^{3A}$, $-C(O)OR^{3A}$, $-C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^4$ is a bond, $-S(O)_2-$, $-N(R^4)-$, $-O-$, $-S-$, $-C(O)-$, $-C(O)N(R^4)-$, $-N(R^4)C(O)-$, $-N(R^4)C(O)NH-$, $-NHC(O)N(R^4)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^4$ is independently hydrogen, $-CX^4_3$, $-CHX^4_2$, $-CH_2X^4$, $-C(O)R^{4A}$, $-C(O)OR^{4A}$, $-C(O)NR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or E;

E is a histidine binding moiety;

each $R^{1A}$, $R^{1B}$, $R^{1C}$, $R^{1D}$, $R^{2A}$, $R^{2B}$, $R^{3A}$, $R^{3B}$, $R^{4A}$, and $R^{4B}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl;

each X, $X^1$, $X^2$, $X^3$, and $X^4$ is independently $-F$, $-Cl$, $-Br$, or $-I$;

n1 is independently an integer from 0 to 4; and m1 and v1 are independently 1 or 2.

Embodiment I-2. The compound of embodiment I-1, having the formula:

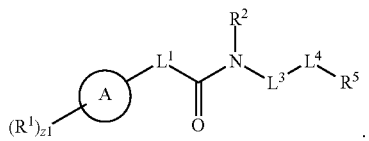

Embodiment I-3. The compound of embodiment I-2, wherein
Ring A is an aryl or heteroaryl;
$R^1$ is independently halogen, $-CX^1_3$, $-CHX^1_2$, $-CH_2X^1$, $-CN$, $-SR^{1D}$, $-SO_2R^{1D}$, $-NHC(O)NR^{1A}R^{1B}$, $-N(O)_2$, $-NR^{1A}R^{1B}$, $-C(O)R^{1C}$, $-C(O)OR^{1C}$, $-C(O)NR^{1A}R^{1B}$, $-OR^{1D}$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;
z1 is an integer from 0 to 4;
$R^2$ is independently hydrogen or unsubstituted alkyl;
$L^1$ is a bond, unsubstituted alkylene, or unsubstituted cycloalkylene;
each $R^{1A}$, $R^{1B}$, $R^{1C}$, $R^{1D}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; and
each $X^1$ is independently $-F$, $-Cl$, $-Br$, or $-I$.

Embodiment I-4. The compound of one of embodiments I-2 to I-3, wherein Ring A is phenyl or 5 to 9 membered heteroaryl.

Embodiment I-5. The compound of one of embodiments I-2 to I-3, wherein Ring A is phenyl.

Embodiment I-6. The compound of one of embodiments I-2 to I-3, wherein Ring A is 5 to 9 membered heteroaryl.

Embodiment I-7. The compound of one of embodiments I-2 to I-3, wherein Ring A is pyridyl.

Embodiment I-8. The compound of one of embodiments I-2 to I-3, wherein Ring A is indazolyl.

Embodiment I-9. The compound of one of embodiments I-2 to I-8, wherein $R^1$ is independently halogen, $-CX^1_3$, $-CHX^1_2$, $-CH_2X^1$, $-CN$, $-SR^{1D}$, $-SO_2R^{1D}$, $-NR^{1A}R^{1B}$, $-OR^{1D}$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; each $R^{1A}$, $R^{1B}$, $R^{1C}$, $R^{1D}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; $R^{1A}$ and $R^{1B}$ substituents bonded to the same nitrogen atom may optionally be joined to form an unsubstituted 3 to 6 membered heterocycloalkyl or unsubstituted 5 to 6 membered heteroaryl.

Embodiment I-10. The compound of one of embodiments I-2 to I-8, wherein $R^1$ is independently halogen, $-CX^1_3$, $-CHX^1_2$, $-CH_2X^1$, $-CN$, $-SO_2CH_3$, $-NHPh$, $-CH_3$, or $-CH_2CH_3$.

Embodiment I-11. The compound of one of embodiments I-2 to I-10, wherein z1 is 0.

Embodiment I-12. The compound of one of embodiments I-2 to I-10, wherein z1 is 1.

Embodiment I-13. The compound of one of embodiments I-2 to I-10, wherein z1 is 2.

Embodiment I-14. The compound of one of embodiments I-2 to I-13, wherein $R^2$ is hydrogen.

Embodiment I-15. The compound of one of embodiments I-2 to I-13, wherein $R^2$ is $-CH_3$.

Embodiment I-16. The compound of one of embodiments I-2 to I-15, wherein $L^1$ is a bond.

Embodiment I-17. The compound of one of embodiments I-2 to I-15, wherein $L^1$ is $-CH_2-$.

Embodiment I-18. The compound of one of embodiments I-2 to I-15, wherein $L^1$ is $-C(CH_3)_2-$.

Embodiment I-19. The compound of one of embodiments I-2 to I-15, wherein $L^1$ is unsubstituted cyclopropylene.

Embodiment I-20. The compound of embodiment I-1, having the formula

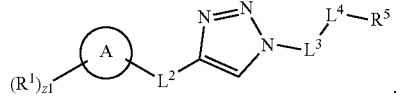

Embodiment I-21. The compound of embodiment I-20, wherein
ring A is an aryl or heteroaryl;
$R^1$ is independently halogen, $-CX^1_3$, $-CHX^1_2$, $-CH_2X^1$, $-CN$, $-SR^{1D}$, $-SO_2R^{1D}$, $-NHC(O)NR^{1A}R^{1B}$, $-N(O)_2$, $-NR^{1A}R^{1B}$, $-C(O)R^{1C}$, $-C(O)OR^{1C}$, $-C(O)NR^{1A}R^{1B}$, $-OR^{1D}$, $-OCX^{13}$, $-OCHX^1_2$, $-OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;
z1 is an integer from 0 to 4;
$L^2$ is a bond, $-O-$, $-C(O)-$, $-C(O)O-$, $-OC(O)-$, $-S-$, $-SO-$, $-S(O)_2-$, $-NH-$, $-NHC(O)-$, $-C(O)NH-$, $-SO_2NH-$, $-NHSO_2-$, $-OC(O)NH-$, $-NHC(O)O-$, $-NHC(O)NH-$, $-C(O)OCH_2-$, $-CH_2OC(O)-$, $-C(O)NHCH_2-$, $-CH_2NHC(O)-$, $-CH_2NHCH_2-$, substituted or unsubstituted alkylene, or substituted or unsubstituted heteroalkylene;
each $R^{1A}$, $R^{1B}$, $R^{1C}$, $R^{1D}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; and
each $X^1$ is independently $-F$, $-Cl$, $-Br$, or $-I$.

Embodiment I-22. The compound of one of embodiments I-20 to I-21, wherein Ring A is $C_6$-$C_{10}$ aryl or 5 to 9 membered heteroaryl.

Embodiment I-23. The compound of one of embodiments I-20 to I-21, wherein Ring A is phenyl.

Embodiment I-24. The compound of one of embodiments I-20 to I-21, wherein Ring A is naphthyl.

Embodiment I-25. The compound of one of embodiments I-20 to I-21, wherein Ring A is 5 to 9 membered heteroaryl.

Embodiment I-26. The compound of one of embodiments I-20 to I-21, wherein Ring A is indazolyl.

Embodiment I-27. The compound of one of embodiments I-20 to I-26, wherein $R^1$ is independently halogen, —$CX^1_3$, —$CHX^1_2$, —$CH_2X^1$, —CN, —$SR^{1D}$, —$N(O)_2$, —$SO_2R^{1D}$, —$NR^{1A}R^{1B}$, —$OR^{1D}$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; each $R^{1A}$, $R^{1B}$, $R^{1C}$, $R^{1D}$ is independently hydrogen, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl; $R^{1A}$ and $R^{1B}$ substituents bonded to the same nitrogen atom may optionally be joined to form an unsubstituted 3 to 6 membered heterocycloalkyl or unsubstituted 5 to 6 membered heteroaryl.

Embodiment I-28. The compound of one of embodiments I-20 to I-26, wherein $R^1$ is independently halogen, —$CX^1_3$, —$CHX^1_2$, —$CH_2X^1$, —$OCX^1_3$, —$OCHX^1_2$, —$OCH_2X^1$, —CN, —$N(O)_2$, —$SO_2CH_3$, —$N(CH_3)_2$, —$OCH_3$, —$OCH_2CH_3$, —$CH_3$, or —$CH_2CH_3$.

Embodiment I-29. The compound of one of embodiments I-20 to I-28, wherein z1 is 0.

Embodiment I-30. The compound of one of embodiments I-20 to I-28, wherein z1 is 1.

Embodiment I-31. The compound of one of embodiments I-20 to I-28, wherein z1 is 2.

Embodiment I-32. The compound of one of embodiments I-20 to I-31, wherein $L^2$ is a bond, —$S(O)_2$—, —$C(O)OCH_2$—, —$CH_2OC(O)$—, —$C(O)NHCH_2$—, —$CH_2NHC(O)$—, —$CH_2NHCH_2$—, or —$CH_2$—.

Embodiment I-33. The compound of one of embodiments I-20 to I-31, wherein $L^2$ is a bond.

Embodiment I-34. The compound of one of embodiments I-20 to I-31, wherein $L^2$ is a —$S(O)_2$—.

Embodiment I-35. The compound of one of embodiments I-20 to I-31, wherein $L^2$ is a —$C(O)OCH_2$—.

Embodiment I-36. The compound of one of embodiments I-20 to I-31, wherein $L^2$ is a —$C(O)NHCH_2$—.

Embodiment I-37. The compound of one of embodiments I-20 to I-31, wherein $L^2$ is a —$CH_2NHCH_2$—.

Embodiment I-38. The compound of one of embodiments I-20 to I-31, wherein $L^2$ is a —$CH_2$—.

Embodiment I-39. The compound of one of embodiments I-1 to I-38, wherein $L^3$ is a bond, —$S(O)_2$—, —$N(R^3)$—, —O—, —S—, —$C(O)$—, —$C(O)N(R^3)$—, —$N(R^3)C(O)$—, —$N(R^3)C(O)NH$—, —$NHC(O)N(R^3)$—, —$C(O)O$—, —$OC(O)$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^3$ is independently hydrogen, —$CX^3_3$, —$CHX^3_2$, —$CH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and each $X^3$ is independently —F, —Cl, —Br, or —I.

Embodiment I-40. The compound of one of embodiments I-1 to I-38, wherein $L^3$ is a bond, —$S(O)_2$—, —NH—, —$C(O)NH$—, —$NHC(O)$—, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenylene, or substituted or unsubstituted 5 to 6 membered heteroarylene.

Embodiment I-41. The compound of one of embodiments I-1 to I-38, wherein $L^3$ is a bond.

Embodiment I-42. The compound of one of embodiments I-1 to I-38, wherein $L^3$ is substituted or unsubstituted methylene.

Embodiment I-43. The compound of one of embodiments I-1 to I-38, wherein $L^3$ is

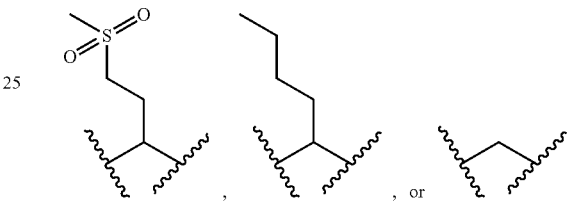

Embodiment I-44. The compound of one of embodiments I-1 to I-38, wherein $L^3$ is unsubstituted methylene.

Embodiment I-45. The compound of one of embodiments I-1 to I-38, wherein $L^3$ is

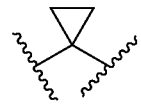

Embodiment I-46. The compound of one of embodiments I-1 to I-45, wherein $L^4$ is a bond, —$S(O)_2$—, —$N(R^4)$—, —O—, —S—, —$C(O)$—, —$C(O)N(R^4)$—, —$N(R^4)C(O)$—, —$N(R^4)C(O)NH$—, —$NHC(O)N(R^4)$—, —$C(O)O$—, —$OC(O)$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^4$ is independently hydrogen, —$CX^4_3$, —$CHX^4_2$, —$CH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
each $X^4$ is independently —F, —Cl, —Br, or —I.

Embodiment I-47. The compound of one of embodiments I-1 to I-45, wherein $L^4$ is a bond, —$S(O)_2$—, —NH—, —$C(O)NH$—, —$NHC(O)$—, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenylene, or substituted or unsubstituted 5 to 6 membered heteroarylene.

Embodiment I-48. The compound of one of embodiments I-1 to I-45, wherein $L^4$ is a bond.

Embodiment I-49. The compound of one of embodiments I-1 to I-45, wherein $L^4$ is substituted or unsubstituted methylene.

Embodiment I-50. The compound of one of embodiments I-1 to I-45, wherein $L^4$ is

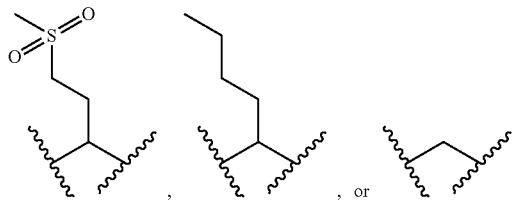

Embodiment I-51. The compound of one of embodiments I-1 to I-45, wherein $L^4$ is unsubstituted methylene.

Embodiment I-52. The compound of one of embodiments I-1 to I-45, wherein $L^4$ is

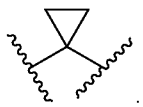 [SMILES: *C1(*)CC1]

Embodiment I-53. The compound of one of embodiments I-1 to I-52, wherein $R^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

Embodiment I-54. The compound of one of embodiments I-1 to I-52, wherein $R^5$ is independently substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment I-55. The compound of one of embodiments I-1 to I-52, wherein $R^5$ is independently substituted or unsubstituted 3 to 6 membered heterocycloalkyl or substituted or unsubstituted 5 to 6 membered heteroaryl.

Embodiment I-56. The compound of one of embodiments I-1 to I-52, wherein $R^5$ is independently 3 to 6 membered heterocycloalkyl or 5 to 6 membered heteroaryl; optionally substituted with one or more independent substituent groups, a size-limited substituent groups, or lower substituent groups.

Embodiment I-57. The compound of one of embodiments I-1 to I-52, wherein $R^5$ is

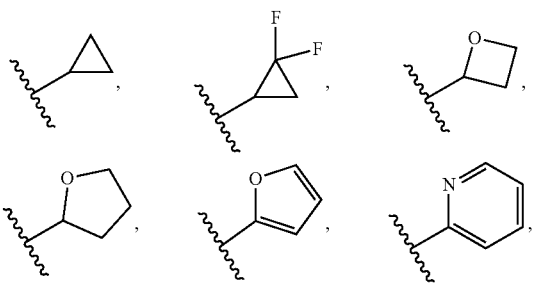

Embodiment I-58. The compound of one of embodiments I-1 to I-52, wherein $R^5$ is E.

Embodiment I-59. The compound of embodiment I-58, wherein E is a covalent histidine binding moiety.

Embodiment I-60. The compound embodiment I-59, wherein E is

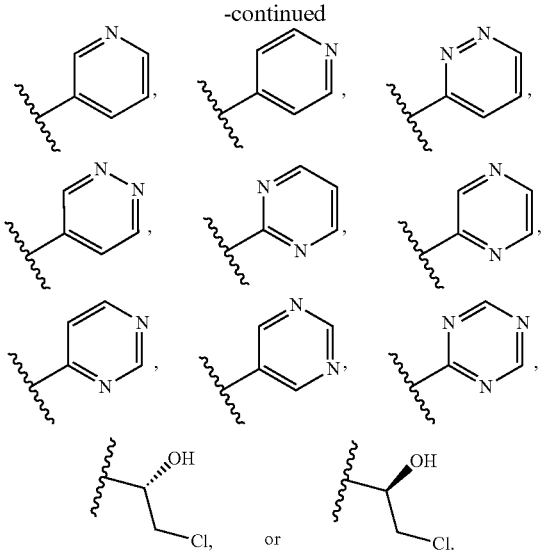

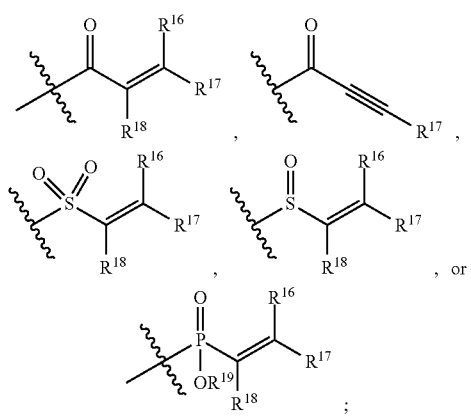

wherein $R^{16}$ is independently hydrogen, halogen, $CX^{16}_3$, $-CHX^{16}_2$, $-CH_2X^{16}$, $-CN$, $-SO_{n16}R^{16D}$, $-SO_{v16}NR^{16A}R^{16B}$, $-NHNR^{16A}R^{16B}$, $-ONR^{16A}R^{16B}$, $-NHC=(O)NHNR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$ $-NR^{16A}C(O)R^{16C}$, $-NR^{16A}C(O)OR^{16C}$, $-NR^{16A}OR^{16C}$, $-OCX^{16}_3$, $-OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is independently hydrogen, halogen, $CX^{17}_3$, $-CHX^{17}_2$, $-CH_2X^{17}$, $-CN$, $-SO_{n17}R^{17D}$, $-SO_7NR^{17A}R^{17B}$, $-NHNR^{17A}R^{17B}$, $-ONR^{17A}R^{17B}$, $-NHC=(O)NHNR^{17A}R^{17B}$, $-NHC(O)NR^{17A}R^{17B}$, $-N(O)_{m17}$, $-NR^{17A}R^{17B}$, $C(O)R^{17C}$, $-C(O)-OR^{17C}$, $C(O)NR^{17A}R^{17B}$, $-OR^{17D}$, $-NR^{17A}SO_2R^{17D}$, —NR$^{17A}$C(O)R$^{17C}$, —NR$^{17A}$C(O)OR$^{17C}$, —NR$^{17A}$OR$^{17C}$, —OCX$^{17}_3$, —OCHX$^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{18}$ is independently hydrogen, halogen, CX$^{18}_3$, —CHX$^{18}_2$, —CH$_2$X$^{18}$, —CN, —SO$_{n18}$R$^{18D}$, —SO$_{v18}$NR$^{18A}$R$^{18B}$, —NHNR$^{18A}$R$^{18B}$, —ONR$^{18A}$R$^{18B}$, —NHC=(O)NHNR$^{18A}$R$^{18B}$, —NHC(O)NR$^{18A}$R$^{18B}$, —N(O)$_{m18}$, —NR$^{18A}$R$^{18B}$, —C(O)R$^{18C}$, —C(O)—OR$^{18C}$, —C(O)NR$^{18A}$R$^{18B}$, —OR$^{18D}$, —NR$^{18A}$SO$_2$R$^{18D}$, —NR$^{18A}$C(O)R$^{18C}$, —NR$^{18A}$C(O)OR$^{18C}$, —NR$^{18A}$OR$^{18C}$, —OCX$^{18}_3$, —OCHX$^{18}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{19}$ is independently hydrogen, halogen, CX$^{19}_3$, —CHX$^{19}_2$, —CH$_2$X$^{19}$, —CN, —SO$_{n19}$R$^{19D}$, —SO$_{v19}$NR$^{19A}$R$^{19B}$, —NHNR$^{19A}$R$^{19B}$, —ONR$^{19A}$R$^{19B}$, —NHC=(O)NHNR$^{19A}$R$^{19B}$, —NHC(O)NR$^{19A}$R$^{19B}$, —N(O)$_{m19}$, —NR$^{19A}$R$^{19B}$, —C(O)R$^{19C}$, —C(O)—OR$^{19C}$, —C(O)NR$^{19A}$R$^{19B}$, —OR$^{19D}$—NR$^{19A}$SO$_2$R$^{19D}$—NR$^{19A}$C(O)R$^{19C}$, —NR$^{19A}$C(O)OR$^{19C}$, —NR$^{19A}$OR$^{19C}$, —OCX$^{19}_3$, —OCHX$^{19}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{16A}$, R$^{16B}$, R$^{16C}$, R$^{16D}$, R$^{17A}$, R$^{17B}$, R$^{17C}$, R$^{17D}$, R$^{18A}$, R$^{18B}$, R$^{18C}$, R$^{18D}$, R$^{19A}$, R$^{19B}$, R$^{19C}$, R$^{19D}$, are independently hydrogen, halogen, —CX$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$_3$, —OCHX$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{16A}$ and R$^{16B}$ substituents bonded to the same nitrogen atom may optionally be joined to form a substituted or unsubstituted heterocycloalkyl or substituted or unsubstituted heteroaryl; R$^{17A}$ and R$^{17B}$ substituents bonded to the same nitrogen atom may optionally be joined to form a substituted or unsubstituted heterocycloalkyl or substituted or unsubstituted heteroaryl; R$^{18A}$ and R$^{18B}$ substituents bonded to the same nitrogen atom may optionally be joined to form a substituted or unsubstituted heterocycloalkyl or substituted or unsubstituted heteroaryl; R$^{19A}$ and R$^{19B}$ substituents bonded to the same nitrogen atom may optionally be joined to form a substituted or unsubstituted heterocycloalkyl or substituted or unsubstituted heteroaryl; each X, X$^{16}$, X$^{17}$, X$^{18}$ and X$^{19}$ is independently —F, —Cl, —Br, or —I; n16, n17, n18, n19, v16, v17, v18, and v19 are independently an integer from 0 to 4; and m16, m17, m18, and m19 are independently an integer from 1 to 2.

Embodiment I-61. The compound embodiment I-59, wherein E is

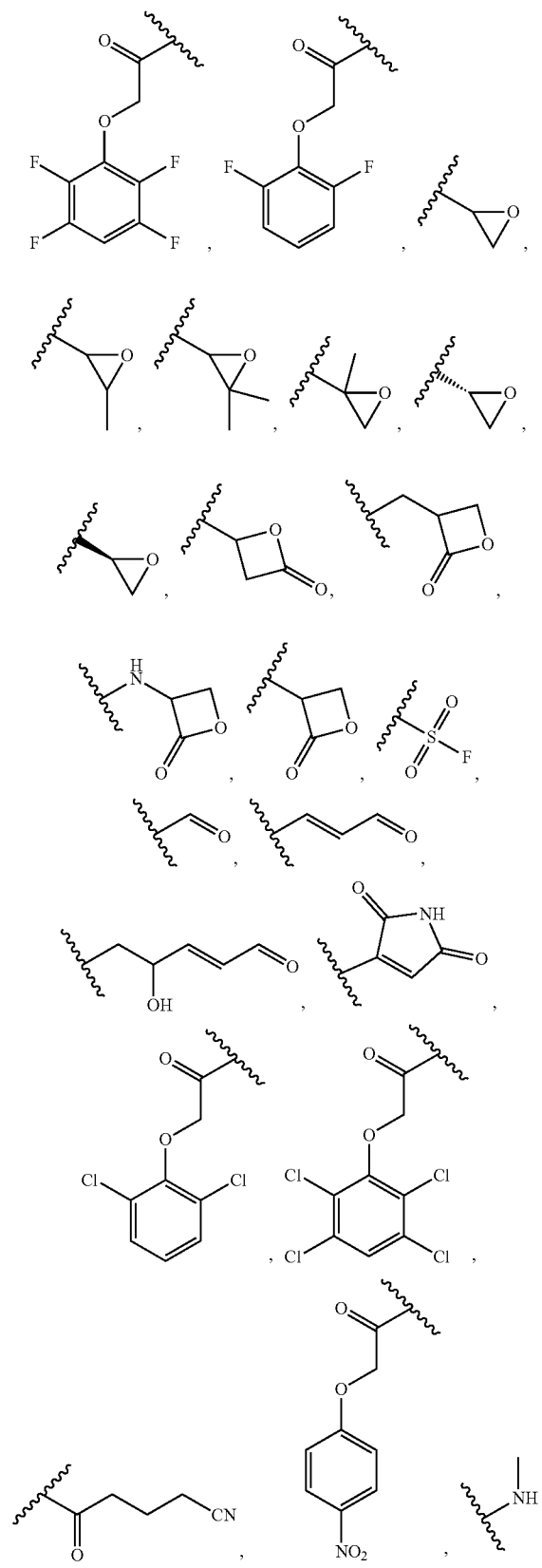

-continued

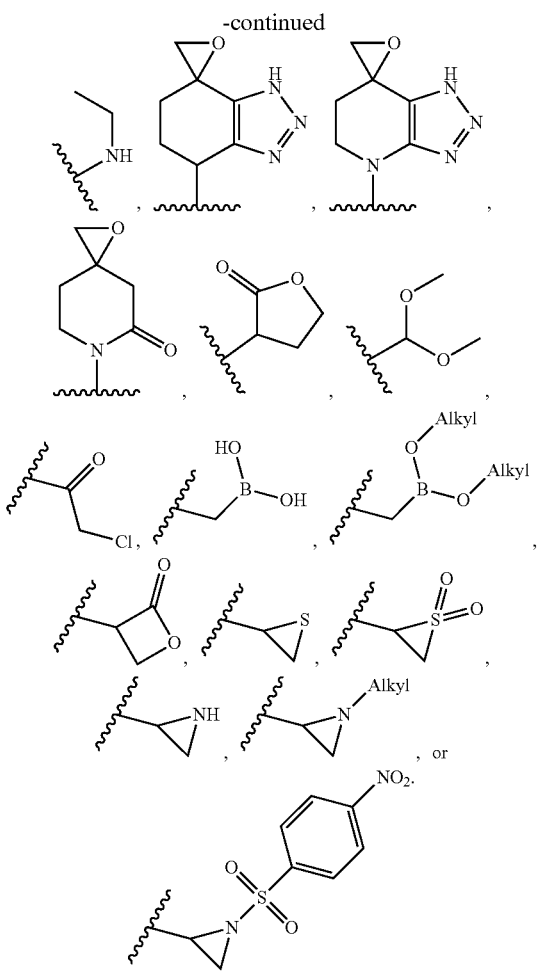

Embodiment I-62. The compound of one of embodiments I-1 to I-61, wherein -L³-L⁴-R⁵ is not

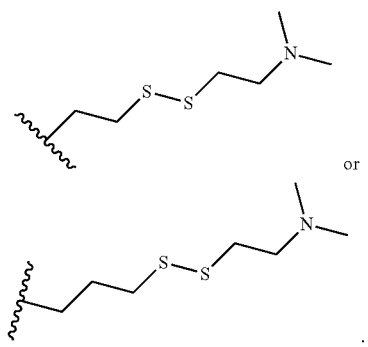

Embodiment I-63. A pharmaceutical composition comprising the compound of any one of embodiments I-1 to I-62 and a pharmaceutically acceptable excipient.

Embodiment I-64. A method of reducing the level of activity of a K-Ras protein, said method comprising contacting the K-Ras protein with a compound of one of embodiments 1 to 62.

Embodiment I-65. The method of embodiment I-64, wherein the compound contacts the K-Ras amino acid corresponding to H95 of human K-Ras.

Embodiment I-66. The method of embodiment I-64, wherein the compound covalently binds the K-Ras amino acid corresponding to H95 of human K-Ras.

Embodiment I-67. The method of one of embodiments I-64 to I-66, wherein the K-Ras protein is human K-Ras 4A.

Embodiment I-68. The method of one of embodiments I-64 to I-66, wherein the K-Ras protein is human K-Ras 4B.

Embodiment I-69. The method of one of embodiments I-64 to I-66, comprising reducing the level of activity of both human K-Ras 4A and human K-Ras 4B.

Embodiment I-70. The method of one of embodiments I-64 to I-69, wherein the activity of the K-Ras protein is increasing cell proliferation.

Embodiment I-71. The method of one of embodiments I-64 to I-70, wherein the activity of the K-Ras protein is not GTPase activity.

Embodiment I-72. A method for treating cancer, said method comprising administering to a subject in need thereof a therapeutically effective amount of a compound of one of embodiments I-1 to I-62.

Embodiment I-73. The method of embodiment I-72, wherein said cancer is pancreatic cancer, lung cancer, or colorectal cancer.

Embodiment I-74. The method of embodiment I-72, wherein said cancer is associated with K-Ras activity.

Embodiment I-75. Use of a compound of one of Embodiments I-1 to I-62 in the manufacture of a medicament for reducing the level of activity of a K-Ras protein in a subject in need thereof.

Embodiment I-76. The use of Embodiment I-75, wherein the compound contacts the K-Ras amino acid corresponding to H95 of human K-Ras.

Embodiment I-77. The use of Embodiment I-75, wherein the compound covalently binds the K-Ras amino acid corresponding to H95 of human K-Ras.

Embodiment I-78. The use of one of Embodiments I-75 to I-77, wherein the K-Ras protein is human K-Ras 4A.

Embodiment I-79. The use of one of Embodiments I-75 to I-77, wherein the K-Ras protein is human K-Ras 4B.

Embodiment I-80. The use of one of Embodiments I-75 to I-77, comprising reducing the level of activity of both human K-Ras 4A and human K-Ras 4B.

Embodiment I-81. The use of one of Embodiments I-75 to I-80, wherein the activity of the K-Ras protein is increasing cell proliferation.

Embodiment I-82. The use of one of Embodiments I-75 to I-81, wherein the activity of the K-Ras protein is not GTPase activity.

Embodiment I-83. Use of a compound of one of Embodiments I-1 to I-62 in the manufacture of a medicament for treating cancer in a subject in need thereof.

Embodiment I-84. The use of Embodiment I-83, wherein said cancer is pancreatic cancer, lung cancer, or colorectal cancer.

Embodiment I-85. The use of Embodiment I-83, wherein said cancer is associated with K-Ras activity.

Embodiment I-86. A compound of one of Embodiments I-1 to I-62 for use a method for reducing the level of activity of a K-Ras protein in a subject in need thereof.

Embodiment I-87. The compound for use of Embodiment I-86, wherein the compound contacts the K-Ras amino acid corresponding to H95 of human K-Ras.

Embodiment I-88. The compound for use of Embodiment I-86, wherein the compound covalently binds the K-Ras amino acid corresponding to H95 of human K-Ras.

Embodiment I-89. The compound for use of one of Embodiments I-86 to I-88, wherein the K-Ras protein is human K-Ras 4A.

Embodiment I-90. The compound for use of one of Embodiments I-86 to I-88, wherein the K-Ras protein is human K-Ras 4B.

Embodiment I-91. The compound for use of one of Embodiments I-86 to I-88, comprising reducing the level of activity of both human K-Ras 4A and human K-Ras 4B.

Embodiment I-92. The compound for use of one of Embodiments I-86 to I-91, wherein the activity of the K-Ras protein is increasing cell proliferation.

Embodiment I-93. The compound for use of one of Embodiments I-86 to I-92, wherein the activity of the K-Ras protein is not GTPase activity.

Embodiment I-94. A compound of one of Embodiments I-1 to I-62 for use in a method for treating cancer in a subject in need thereof.

Embodiment I-95. The compound for use of Embodiment I-94, wherein said cancer is pancreatic cancer, lung cancer, or colorectal cancer.

Embodiment I-96. The compound for use of Embodiment I-94, wherein said cancer is associated with K-Ras activity.

Embodiment II-1. A compound having the formula:

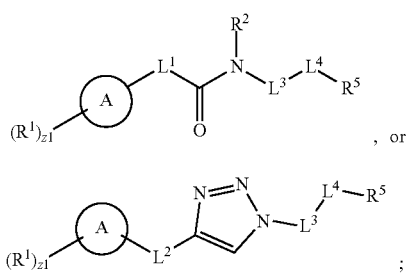

or a pharmaceutically acceptable salt thereof, wherein:

Ring A is an aryl or heteroaryl;

$R^1$ is independently halogen, —$CX^1_3$, —$CHX^1_2$, —$CH_2X^1$, —CN, —$SO_{n1}R^{1D}$, —$SO_{v1}NR^{1A}R^{1B}$, —$NHNR^{1A}R^{1B}$, —$ONR^{1A}R^{1B}$, —NHC=(O)NHNR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;

$R^2$ is independently hydrogen, —$CX^2_3$, —$CHX^2_2$, —$CH_2X^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ is a bond, substituted or unsubstituted alkylene, substituted or unsubstituted cycloalkylene, or

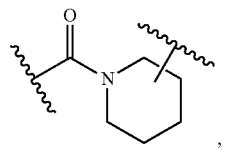

$L^3$ is a bond, —S(O)$_2$—, —N(R$^3$)—, —O—, —S—, —C(O)—, —C(O)N(R$^3$)—, —N(R$^3$)C(O)—, —N(R$^3$)C(O)NH—, —NHC(O)N(R$^3$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently hydrogen, —$CX^3_3$, —$CHX^3_2$, —$CH_2X^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^4$ is a bond, —S(O)$_2$—, —N(R$^4$)—, —O—, —S—, —C(O)—, —C(O)N(R$^4$)—, —N(R$^4$)C(O)—, —N(R$^4$)C(O)NH—, —NHC(O)N(R$^4$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^4$ is independently hydrogen, —$CX^4_3$, —$CHX^4_2$, —$CH_2X^4$, —C(O)R$^{4A}$, —C(O)OR$^4$A —C(O)NR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or E;

E is a histidine binding moiety;

each $R^{1A}$, $R^{1B}$, $R^{1C}$, $R^{1D}$, $R^{2A}$, $R^{2B}$, $R^{3A}$, $R^{3B}$, $R^{4A}$, and $R^{4B}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ and $R^{1B}$ substituents bonded to the same nitrogen atom may optionally be joined to form a substituted or unsubstituted heterocycloalkyl or substituted or unsubstituted heteroaryl;

$R^{2A}$ and $R^{2B}$ substituents bonded to the same nitrogen atom may optionally be joined to form a substituted or unsubstituted heterocycloalkyl or substituted or unsubstituted heteroaryl;

$R^{3A}$ and $R^{3B}$ substituents bonded to the same nitrogen atom may optionally be joined to form a substituted or unsubstituted heterocycloalkyl or substituted or unsubstituted heteroaryl;

$R^{4A}$ and $R^{4B}$ substituents bonded to the same nitrogen atom may optionally be joined to form a substituted or unsubstituted heterocycloalkyl or substituted or unsubstituted heteroaryl;

each X, X$^1$, X$^2$, X$^3$, and X$^4$ is independently —F, —Cl, —Br, or —I;

n1 is independently an integer from 0 to 4; and m1 and v1 are independently 1 or 2.

Embodiment II-2. The compound of embodiment II-1, wherein the compound is of Formula (I):

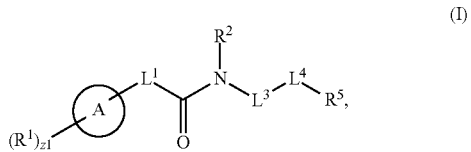

(I)

or a pharmaceutically acceptable salt thereof, wherein:

Ring A is an aryl or heteroaryl;

R$^1$ is independently halogen, —CX$^1_3$, —CHX$^1_2$, —CH$_2$X$^1$, —CN, —SO$_{n1}$R$^{1D}$, —SO$_{v1}$NR$^{1A}$R$^{1B}$, —NHNR$^{1A}$R$^{1B}$, —ONR$^{1A}$R$^{1B}$, —NHC=(O)NHNR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

two adjacent R$^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;

R$^2$ is independently hydrogen, —CX$^2_3$, —CHX$^2_2$, —CH$_2$X$^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

L$^1$ is a bond, substituted or unsubstituted alkylene, substituted or unsubstituted cycloalkylene, or

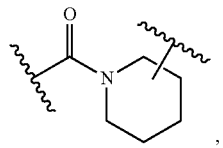

,

L$^3$ is a bond, —S(O)$_2$—, —N(R$^3$)—, —O—, —S—, —C(O)—, —C(O)N(R$^3$)—, —N(R$^3$)C(O)—, —N(R$^3$)C(O) NH—, —NHC(O)N(R$^3$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^3$ is independently hydrogen, —CX$^3_3$, —CHX$^3_2$, —CH$_2$X$^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^4$ is a bond, —S(O)$_2$—, —N(R$^4$)—, —O—, —S—, —C(O)—, —C(O)N(R$^4$)—, —N(R$^4$)C(O)—, —N(R$^4$)C(O) NH—, —NHC(O)N(R$^4$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^4$ is independently hydrogen, —CX$^4_3$, —CHX$^4_2$, —CH$_2$X$^4$, —C(O)R$^{4A}$, —C(O)OR$^{4A}$, —C(O)NR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or E;

E is a histidine binding moiety;

each R$^{1A}$, R$^{1B}$, R$^{1C}$, R$^{1D}$, R$^{2A}$, R$^{2B}$, R$^{3A}$, R$^{3B}$, R$^{4A}$, and R$^{4B}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$ and R$^{1B}$ substituents bonded to the same nitrogen atom may optionally be joined to form a substituted or unsubstituted heterocycloalkyl or substituted or unsubstituted heteroaryl;

R$^{2A}$ and R$^{2B}$ substituents bonded to the same nitrogen atom may optionally be joined to form a substituted or unsubstituted heterocycloalkyl or substituted or unsubstituted heteroaryl;

R$^{3A}$ and R$^{3B}$ substituents bonded to the same nitrogen atom may optionally be joined to form a substituted or unsubstituted heterocycloalkyl or substituted or unsubstituted heteroaryl;

R$^{4A}$ and R$^{4B}$ substituents bonded to the same nitrogen atom may optionally be joined to form a substituted or unsubstituted heterocycloalkyl or substituted or unsubstituted heteroaryl;

each X, X$^1$, X$^2$, X$^3$, and X$^4$ is independently —F, —Cl, —Br, or —I;

n1 is independently an integer from 0 to 4; and m1 and v1 are independently 1 or 2.

Embodiment II-3. The compound of embodiment II-1 or II-2, or a pharmaceutically acceptable salt thereof, wherein:

Ring A is heteroaryl;

R$^1$ is independently halogen, —CX$^1_3$, —CHX$^1_2$, —CH$_2$X$^1$, —CN, —SO$_{n1}$R$^{1D}$, —SO$_{v1}$NR$^{1A}$R$^{1B}$, —NHNR$^{1A}$R$^{1B}$, —ONR$^{1A}$R$^{1B}$, —NHC=(O)NHNR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

two adjacent R$^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;

R$^2$ is independently hydrogen, —CX$^2_3$, —CHX$^2_2$, —CH$_2$X$^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$L^1$ is a bond, substituted or unsubstituted alkylene, substituted or unsubstituted cycloalkylene, or

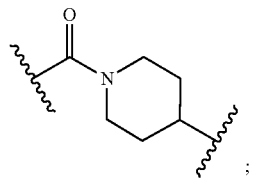 [SMILES: *C(=O)N1CCC(*)CC1]

$L^3$ is a bond, $-S(O)_2-$, $-N(R^3)-$, $-O-$, $-S-$, $-C(O)-$, $-C(O)N(R^3)-$, $-N(R^3)C(O)-$, $-N(R^3)C(O)NH-$, $-NHC(O)N(R^3)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently hydrogen, $-CX^3_3$, $-CHX^3_2$, $-CH_2X^3$, $-C(O)R^{3A}$, $-C(O)OR^{3A}$, $-C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^4$ is a bond, $-S(O)_2-$, $-N(R^4)-$, $-O-$, $-S-$, $-C(O)-$, $-C(O)N(R^4)-$, $-N(R^4)C(O)-$, $-N(R^4)C(O)NH-$, $-NHC(O)N(R^4)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^4$ is independently hydrogen, $-CX^4_3$, $-CHX^4_2$, $-CH_2X^4$, $-C(O)R^{4A}$, $-C(O)OR^{4A}$, $-C(O)NR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or E;

E is a histidine binding moiety;

each $R^{1A}$, $R^{1B}$, $R^{1C}$, $R^{1D}$, $R^{2A}$, $R^{2B}$, $R^{3A}$, $R^{3B}$, $R^{4A}$, and $R^{4B}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ and $R^{1B}$ substituents bonded to the same nitrogen atom may optionally be joined to form a substituted or unsubstituted heterocycloalkyl or substituted or unsubstituted heteroaryl;

$R^{2A}$ and $R^{2B}$ substituents bonded to the same nitrogen atom may optionally be joined to form a substituted or unsubstituted heterocycloalkyl or substituted or unsubstituted heteroaryl;

$R^{3A}$ and $R^{3B}$ substituents bonded to the same nitrogen atom may optionally be joined to form a substituted or unsubstituted heterocycloalkyl or substituted or unsubstituted heteroaryl;

$R^{4A}$ and $R^{4B}$ substituents bonded to the same nitrogen atom may optionally be joined to form a substituted or unsubstituted heterocycloalkyl or substituted or unsubstituted heteroaryl;

each X, $X^1$, $X^2$, $X^3$, and $X^4$ is independently $-F$, $-Cl$, $-Br$, or $-I$;

n1 is independently an integer from 0 to 4; and m1 and v1 are independently 1 or 2.

Embodiment II-4. The compound of any one of embodiments II-1 to II-3, or a pharmaceutically acceptable salt thereof, wherein:

Ring A is heteroaryl;

$R^1$ is independently halogen, $-CX^1_3$, $-CHX^1_2$, $-CH_2X^1$, $-CN$, $-SO_{n1}R^{1D}$, $-SO_{v1}NR^{1A}R^{1B}$, $-ONR^{1A}R^{1B}$, $-N(O)_{m1}$, $-NR^{1A}R^{1B}$, $-OR^{1D}$, $-OCX^1_3$, $-OCHX^1_2$, $-OCH_2X^1$, substituted or unsubstituted alkyl, substituted or unsubstituted cycloalkyl, substituted or unsubstituted heterocycloalkyl, substituted or unsubstituted aryl, or substituted or unsubstituted heteroaryl;

z1 is an integer from 0 to 4;

$R^2$ is independently hydrogen, $-CX^2_3$, $-CHX^2_2$, $-CH_2X^2$, or substituted or unsubstituted alkyl;

$L^1$ is a bond, substituted or unsubstituted alkylene, or

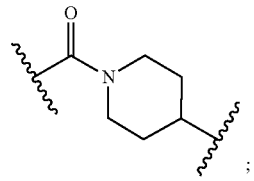 [SMILES: *C(=O)N1CCC(*)CC1]

$L^3$ is a bond or substituted or unsubstituted alkylene;

$L^4$ is a bond, $-O-$, $-N(R^4)-$, or $-C(O)-$;

$R^4$ is hydrogen or substituted or unsubstituted alkyl;

$R^5$ is substituted or unsubstituted alkyl, substituted or unsubstituted cycloalkyl, substituted or unsubstituted heterocycloalkyl, substituted or unsubstituted aryl, or substituted or unsubstituted heteroaryl;

each $R^{1A}$, $R^{1B}$, $R^{1C}$, and $R^{1D}$ is independently hydrogen, $-CX_3$, $-CHX_2$, $-CH_2X$, substituted or unsubstituted alkyl, substituted or unsubstituted cycloalkyl, substituted or unsubstituted heterocycloalkyl, substituted or unsubstituted aryl, or substituted or unsubstituted heteroaryl;

each X, $X^1$, and $X^2$ are independently $-F$, $-Cl$, $-Br$, or $-I$; n1 is independently an integer from 0 to 4; and m1 and v1 are independently 1 or 2.

Embodiment II-5. The compound of Embodiment II-1 or II-2, or a pharmaceutically acceptable salt thereof, wherein when Ring A is aryl, $L^1$ is a bond, substituted or unsubstituted alkylene, or substituted or unsubstituted cycloalkylene.

Embodiment II-6. The compound of embodiment II-1 or II-2, wherein the compound is of Formula (I), or a pharmaceutically acceptable salt thereof, wherein:

Ring A is aryl;

$R^1$ is independently halogen, $-CX^1_3$, $-CHX^1_2$, $-CH_2X^1$, $-CN$, $-SO_{n1}R^{1D}$, $-SO_{v1}NR^{1A}R^{1B}$, $-NHNR^{1A}R^{1B}$, $-ONR^{1A}R^{1B}$, $-NHC=(O)NHNR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;

$R^2$ is independently hydrogen, —$CX^2_3$, —$CHX^2_2$, —$CH_2X^2$, —$C(O)R^{2A}$, —$C(O)OR^{2A}$, —$C(O)NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$L^1$ is a bond, substituted or unsubstituted alkylene, or substituted or unsubstituted cycloalkylene;

$L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —$NHC(O)N(R^3)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently hydrogen, —$CX^3_3$, —$CHX^3_2$, —$CH_2X^3$, —$C(O)R^{3A}$, —$C(O)OR^{3A}$, —$C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —$NHC(O)N(R^4)$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^4$ is independently hydrogen, —$CX^4_3$, —$CHX^4_2$, —$CH_2X^4$, —$C(O)R^{4A}$, —$C(O)OR^{4A}$, —$C(O)NR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or E;

E is a histidine binding moiety;

each $R^{1A}$, $R^{1B}$, $R^{1C}$, $R^{1D}$, $R^{2A}$, $R^{2B}$, $R^{3A}$, $R^{3B}$, $R^{4A}$, and $R^{4B}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ and $R^{1B}$ substituents bonded to the same nitrogen atom may optionally be joined to form a substituted or unsubstituted heterocycloalkyl or substituted or unsubstituted heteroaryl;

$R^{2A}$ and $R^{2B}$ substituents bonded to the same nitrogen atom may optionally be joined to form a substituted or unsubstituted heterocycloalkyl or substituted or unsubstituted heteroaryl;

$R^{3A}$ and $R^{3B}$ substituents bonded to the same nitrogen atom may optionally be joined to form a substituted or unsubstituted heterocycloalkyl or substituted or unsubstituted heteroaryl;

$R^{4A}$ and $R^{4B}$ substituents bonded to the same nitrogen atom may optionally be joined to form a substituted or unsubstituted heterocycloalkyl or substituted or unsubstituted heteroaryl;

each X, $X^1$, $X^2$, $X^3$, and $X^4$ is independently —F, —Cl, —Br, or —I;

n1 is independently an integer from 0 to 4; and m1 and v1 are independently 1 or 2.

Embodiment II-7. The compound of any one of embodiments II-1, II-2, or II-5, or a pharmaceutically acceptable salt thereof, wherein:

Ring A is aryl;

$R^1$ is independently halogen, —$CX^1_3$, —$CHX^1_2$, —$CH_2X^1$, —CN, —$SO_{n1}R^{1D}$, —$SO_{v1}NR^{1A}R^{1B}$, —$ONR^{1A}R^{1B}$, —$N(O)_{m1}$, —$NR^{1A}R^{1B}$, —$OR^{1D}$, —$OCX^1_3$, —$OCHX^1_2$, —$OCH_2X^1$, substituted or unsubstituted alkyl, substituted or unsubstituted cycloalkyl, substituted or unsubstituted heterocycloalkyl, substituted or unsubstituted aryl, or substituted or unsubstituted heteroaryl;

z1 is an integer from 0 to 4;

$R^2$ is independently hydrogen, —$CX^2_3$, —$CHX^2_2$, —$CH_2X^2$, or substituted or unsubstituted alkyl;

$L^1$ is a bond, or substituted or unsubstituted alkylene;

$L^3$ is a bond or substituted or unsubstituted alkylene;

$L^4$ is a bond, —O—, —$N(R^4)$—, or —C(O)—;

$R^4$ is hydrogen or substituted or unsubstituted alkyl;

$R^5$ is substituted or unsubstituted alkyl, substituted or unsubstituted cycloalkyl, substituted or unsubstituted heterocycloalkyl, substituted or unsubstituted aryl, or substituted or unsubstituted heteroaryl;

each $R^{1A}$, $R^{1B}$, $R^{1C}$, and $R^{1D}$ is independently hydrogen, —$CX_3$, —$CHX_2$, —$CH_2X$, substituted or unsubstituted alkyl, substituted or unsubstituted cycloalkyl, substituted or unsubstituted heterocycloalkyl, substituted or unsubstituted aryl, or substituted or unsubstituted heteroaryl;

each X, $X^1$, and $X^2$ are independently —F, —Cl, —Br, or —I;

n1 is independently an integer from 0 to 4; and m1 and v1 are independently 1 or 2.

Embodiment II-8. The compound of any one of embodiments II-1 to II-7, or a pharmaceutically acceptable salt thereof, wherein $L^1$ is unsubstituted alkylene.

Embodiment II-9. The compound of any one of embodiments 1 to 7, or a pharmaceutically acceptable salt thereof, wherein $L^1$ is alkylene substituted with cycloalkyl.

Embodiment II-10. The compound of any one of embodiments II-1 to II-7, or a pharmaceutically acceptable salt thereof, wherein $L^1$ is a bond.

Embodiment II-11. The compound of embodiment II-1, wherein the compound is of Formula (II):

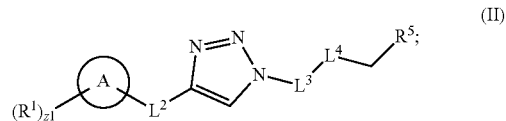

or a pharmaceutically acceptable salt thereof, wherein:

Ring A is an aryl or heteroaryl;

$R^1$ is independently halogen, —$CX^1_3$, —$CHX^1_2$, —$CH_2X^1$, —CN, —$SO_{n1}R^{1D}$, —$SO_{v1}NR^{1A}R^{1B}$, —NHNR$^{1A}$R$^{1B}$, —ONR$^{1A}$R$^{1B}$, —NHC=(O)NHNR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent R$^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;

R$^2$ is independently hydrogen, —CX$^2_3$, —CHX$^2_2$, —CH$_2$X$^2$, —C(O)R$^{2A}$, —C(O)OR$^{2A}$, —C(O)NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

L$^3$ is a bond, —S(O)$_2$—, —N(R$^3$)—, —O—, —S—, —C(O)—, —C(O)N(R$^3$)—, —N(R$^3$)C(O)—, —N(R$^3$)C(O)NH—, —NHC(O)N(R$^3$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^3$ is independently hydrogen, —CX$^3_3$, —CHX$^3_2$, —CH$_2$X$^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^4$ is a bond, —S(O)$_2$—, —N(R$^4$)—, —O—, —S—, —C(O)—, —C(O)N(R$^4$)—, —N(R$^4$)C(O)—, —N(R$^4$)C(O)NH—, —NHC(O)N(R$^4$)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^4$ is independently hydrogen, —CX$^4_3$, —CHX$^4_2$, —CH$_2$X$^4$, —C(O)R$^{4A}$, —C(O)OR$^{4A}$, —C(O)NR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or E;

E is a histidine binding moiety;

each R$^{1A}$, R$^{1B}$, R$^{1C}$, R$^{1D}$, R$^{2A}$, R$^{2B}$, R$^{3A}$, R$^{3B}$, R$^{4A}$, and R$^{4B}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$ and R$^{1B}$ substituents bonded to the same nitrogen atom may optionally be joined to form a substituted or unsubstituted heterocycloalkyl or substituted or unsubstituted heteroaryl;

R$^{2A}$ and R$^{2B}$ substituents bonded to the same nitrogen atom may optionally be joined to form a substituted or unsubstituted heterocycloalkyl or substituted or unsubstituted heteroaryl;

R$^{3A}$ and R$^{3B}$ substituents bonded to the same nitrogen atom may optionally be joined to form a substituted or unsubstituted heterocycloalkyl or substituted or unsubstituted heteroaryl;

R$^{4A}$ and R$^{4B}$ substituents bonded to the same nitrogen atom may optionally be joined to form a substituted or unsubstituted heterocycloalkyl or substituted or unsubstituted heteroaryl;

each X, X$^1$, X$^2$, X$^3$, and X$^4$ is independently —F, —Cl, —Br, or —I; n1 is independently an integer from 0 to 4; and m1 and v1 are independently 1 or 2.

Embodiment II-12. The compound of embodiment II-11, or a pharmaceutically acceptable salt thereof, wherein:

Ring A is an aryl or heteroaryl;

R$^1$ is independently halogen, —CX$^1_3$, —CHX$^1_2$, —CH$_2$X$^1$, —CN, —SO$_{n1}$R$^{1D}$, —SO$_{v1}$NR$^{1A}$R$^{1B}$, —ONR$^{1A}$R$^{1B}$, —N(O)$_{m1}$, —NR$^{1A}$R$^{1B}$, —OR$^{1D}$, —OCX$^1_3$, —OCHX$^1_2$, —OCH$_2$X$^1$, substituted or unsubstituted alkyl, substituted or unsubstituted cycloalkyl, substituted or unsubstituted heterocycloalkyl, substituted or unsubstituted aryl, or substituted or unsubstituted heteroaryl;

z1 is an integer from 0 to 4;

L$^2$ is —S—, —SO—, —S(O)$_2$—, —NHC(O)—, —C(O)NH—, —C(O)NHCH$_2$—, —CH$_2$NHC(O)—, substituted or unsubstituted alkylene, or substituted or unsubstituted heteroalkylene;

L$^3$ is a bond or substituted or unsubstituted alkylene;

L$^4$ is a bond, —O—, —N(R$^4$)—, or —C(O)—;

R$^4$ is independently hydrogen, —CX$^4_3$, —CHX$^4_2$, —CH$_2$X$^4$, —C(O)R$^{4A}$, —C(O)OR$^{4A}$, —C(O)NR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is substituted or unsubstituted alkyl, substituted or unsubstituted cycloalkyl, substituted or unsubstituted heterocycloalkyl, substituted or unsubstituted aryl, or substituted or unsubstituted heteroaryl; each R$^{1A}$, R$^{1B}$, R$^{1C}$, R$^{1D}$, R$^{4A}$, and R$^{4B}$ is independently hydrogen, —X$_3$, —CHX$_2$, —CH$_2$X, substituted or unsubstituted alkyl, substituted or unsubstituted cycloalkyl, substituted or unsubstituted heterocycloalkyl, substituted or unsubstituted aryl, or substituted or unsubstituted heteroaryl; each X, X$^1$, X$^4$ is independently —F, —Cl, —Br, or —I; n1 is independently an integer from 0 to 4; and m1 and v1 are independently 1 or 2.

Embodiment II-13. The compound of any one of embodiments II-1, II-11, or II-12, or a pharmaceutically acceptable salt thereof, wherein L$^2$ is —S(O)$_2$—, —C(O)NH—, —C(O)NHCH$_2$—, substituted or unsubstituted alkylene, or substituted or unsubstituted heteroalkylene.

Embodiment II-14. The compound of any one of embodiments II-1, II-11, or II-12, or a pharmaceutically acceptable salt thereof, wherein L$^2$ is substituted heteroalkylene.

Embodiment II-15. The compound of any one of embodiments II-1, II-11, or II-12, or a pharmaceutically acceptable salt thereof, wherein L$^2$ is —S(O)$_2$— or —C(O)NHCH$_2$—.

Embodiment II-16. The compound of any one of embodiments II-1 to II-15, or a pharmaceutically acceptable salt thereof, wherein each R$^1$ is independently halogen, —OR$^{1D}$, —NR$^{1A}$R$^{1B}$, —CN, or substituted or unsubstituted alkyl, wherein each R$^{1A}$, R$^{1B}$, and R$^{1D}$ is independently hydrogen, substituted or unsubstituted alkyl, substituted or unsubstituted cycloalkyl, substituted or unsubstituted aryl, or substituted or unsubstituted heteroaryl.

Embodiment II-17. The compound of any one of embodiments II-1 to II-16, or a pharmaceutically acceptable salt thereof, wherein each $R^1$ is independently halogen, —CN, —$CX^1_3$, —$CHX^1_2$, —$CH_2X^1$, —$OCX^1_3$, —$OCHX^1_2$, —$OCH_2X^1$, —$OR^{1D}$, or —$NR^{1A}R^{1B}$, wherein each $R^{1A}$, $R^{1B}$, and $R^{1D}$ is independently hydrogen, substituted or unsubstituted alkyl, or substituted or unsubstituted aryl.

Embodiment II-18. The compound of any one of embodiments II-1 to II-17, or a pharmaceutically acceptable salt thereof, wherein $R^5$ is substituted $C_1$-$C_6$ alkyl, substituted or unsubstituted 3- to 6-membered heterocycloalkyl, substituted or unsubstituted phenyl, or substituted or unsubstituted 5 to 6 membered heteroaryl.

Embodiment II-19. The compound of embodiment II-18, or a pharmaceutically acceptable salt thereof, wherein $R^5$ is $R^{13}$-substituted $C_1$-$C_6$ alkyl, wherein $R^{13}$ is independently selected from the group consisting of —$OR^{14}$, oxo, and —$S(O)_2R^{14}$, wherein each $R^{14}$ is independently hydrogen, halogen, or substituted or unsubstituted aryl.

Embodiment II-20. The compound of any one of embodiments II-1 to II-18, or a pharmaceutically acceptable salt thereof, wherein $R^5$ is substituted or unsubstituted 3- to 6-membered heterocycloalkyl.

Embodiment II-21. The compound of any one of embodiments II-1 to II-20, or a pharmaceutically acceptable salt thereof, wherein $R^5$ is:

A.

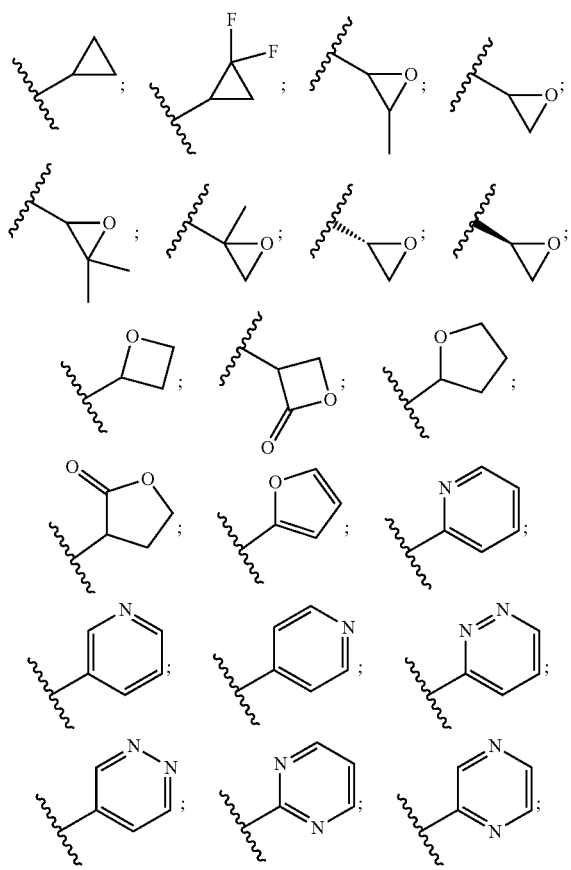

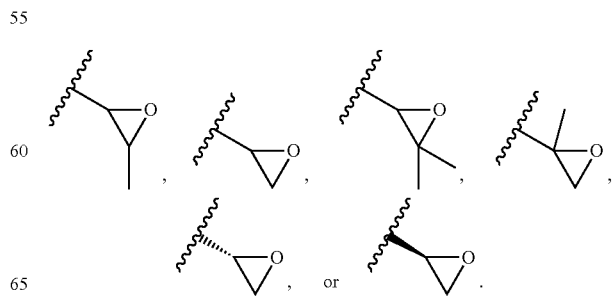

Embodiment II-22. The compound of any one of embodiments II-1 to II-18, or a pharmaceutically acceptable salt thereof, wherein $R^5$ is:

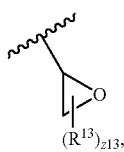

wherein $R^{13}$ is hydrogen, halogen, substituted or unsubstituted alkyl; and z13 is an integer from 0 to 3.

Embodiment II-23. The compound of any one of embodiments II-1 to II-18, II-21, or II-22, or a pharmaceutically acceptable salt thereof, wherein $R^5$ is:

Embodiment II-24. The compound of any one of embodiments II-1, or II-11 to II-23, or a pharmaceutically acceptable salt thereof, wherein Ring A is aryl.

Embodiment II-25. The compound of any one of embodiments II-1, II-2, or II-6 to II-24, or a pharmaceutically acceptable salt thereof, wherein Ring A is phenyl.

Embodiment II-26. The compound of any one of embodiments II-1 to II-4, or II-11 to II-23, or a pharmaceutically acceptable salt thereof, wherein Ring A is a 5- to 10-membered heteroaryl.

Embodiment II-27. The compound of embodiment II-26, or a pharmaceutically acceptable salt thereof, wherein Ring A is indolinyl, indazolyl, benzimidazolyl, benzoxazolyl, azaindolyl, purinyl, indolyl, pyrazinyl, pyrrolyl, imidazolyl, pyrazolyl, triazolyl, tetrazolyl, benzofuranyl, indolyl, or benzothienyl.

Embodiment II-28. The compound of embodiment II-27, or a pharmaceutically acceptable salt thereof, wherein Ring A is indolyl.

Embodiment II-29. The compound of any one of embodiments II-1 to II-28, or a pharmaceutically acceptable salt thereof, wherein $L^3$ is substituted or unsubstituted $C_1$-$C_8$ alkylene.

Embodiment II-30. The compound of any one of embodiments II-1 to II-29, or a pharmaceutically acceptable salt thereof, wherein $L^3$ is unsubstituted methylene.

Embodiment II-31. The compound of any one of embodiments II-1 to II-30, or a pharmaceutically acceptable salt thereof, wherein $L^3$ is

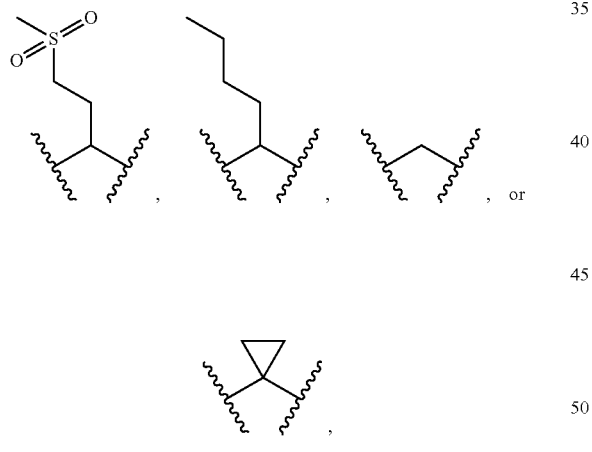

, or

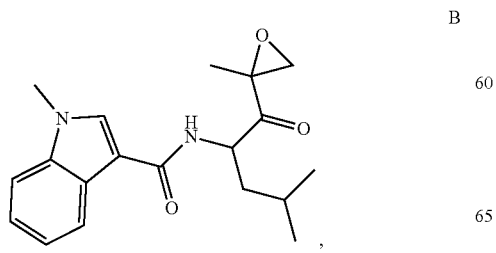

Embodiment II-32. The compound of embodiment II-1 or II-2, wherein the compound is:

B

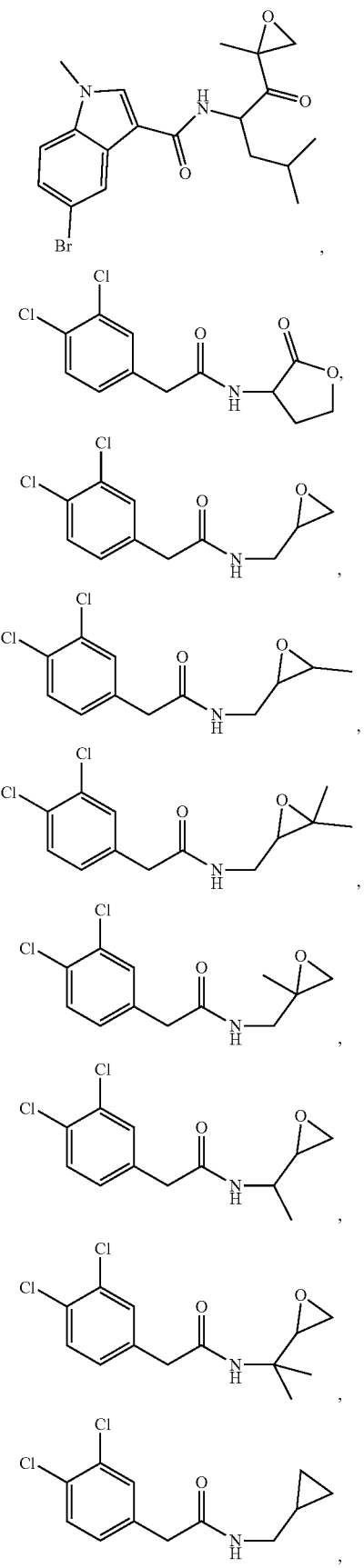

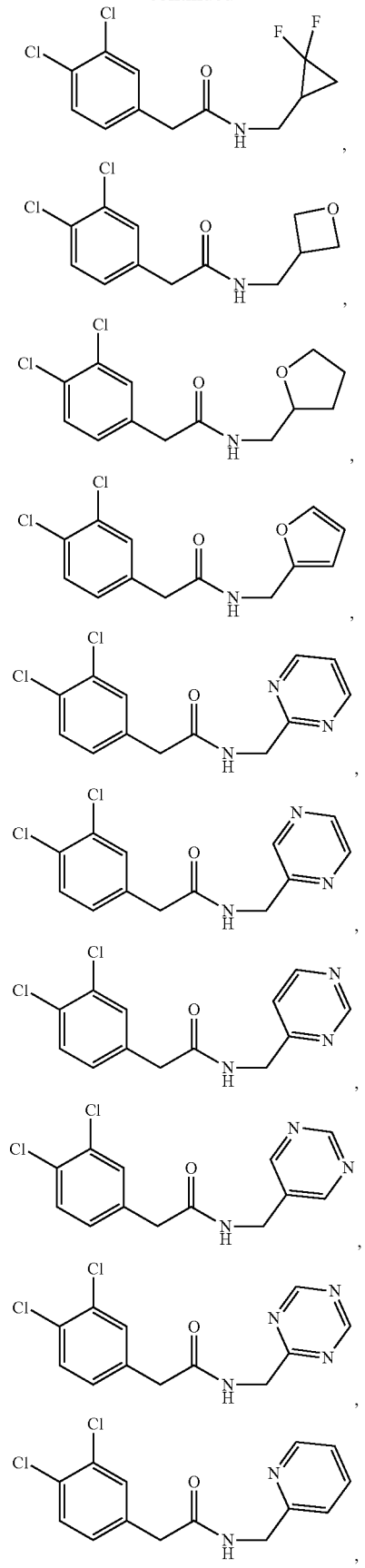
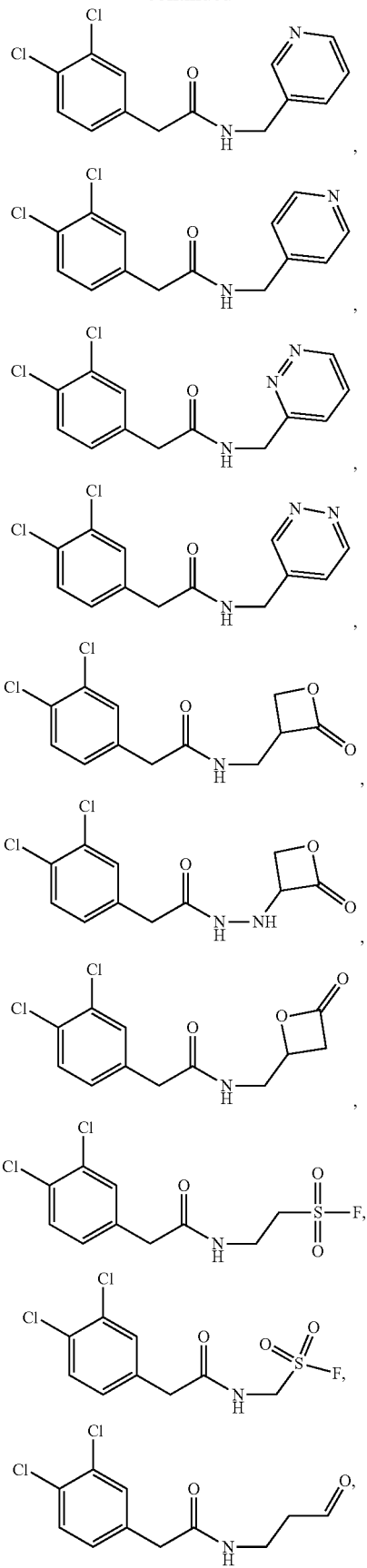

273
-continued
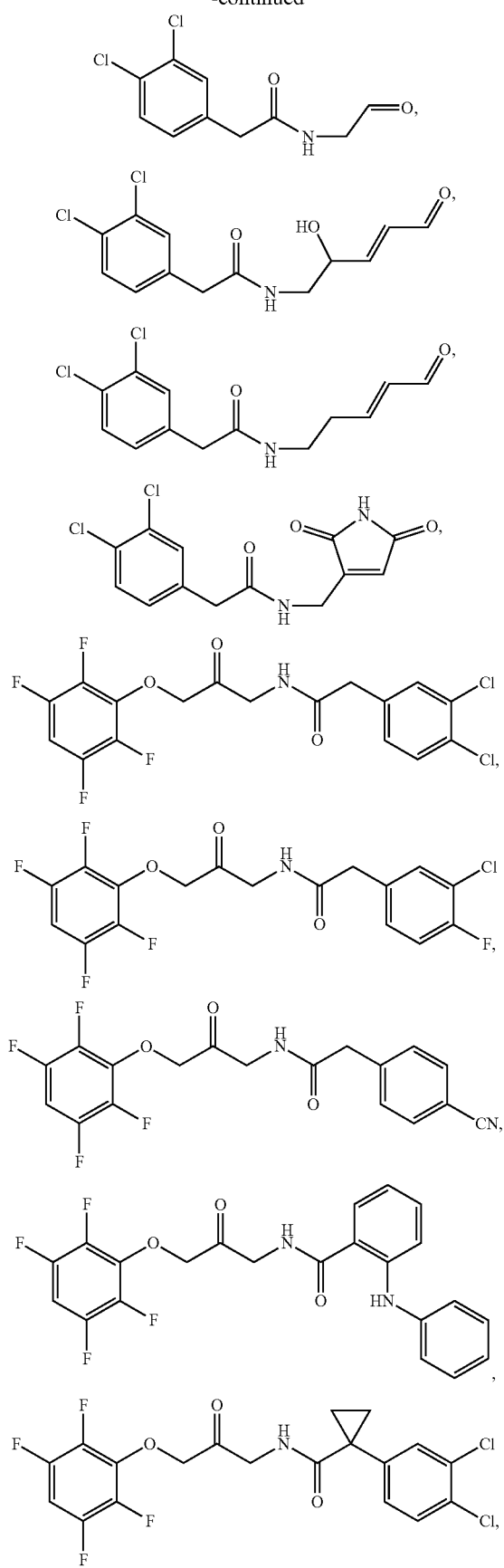
274
-continued
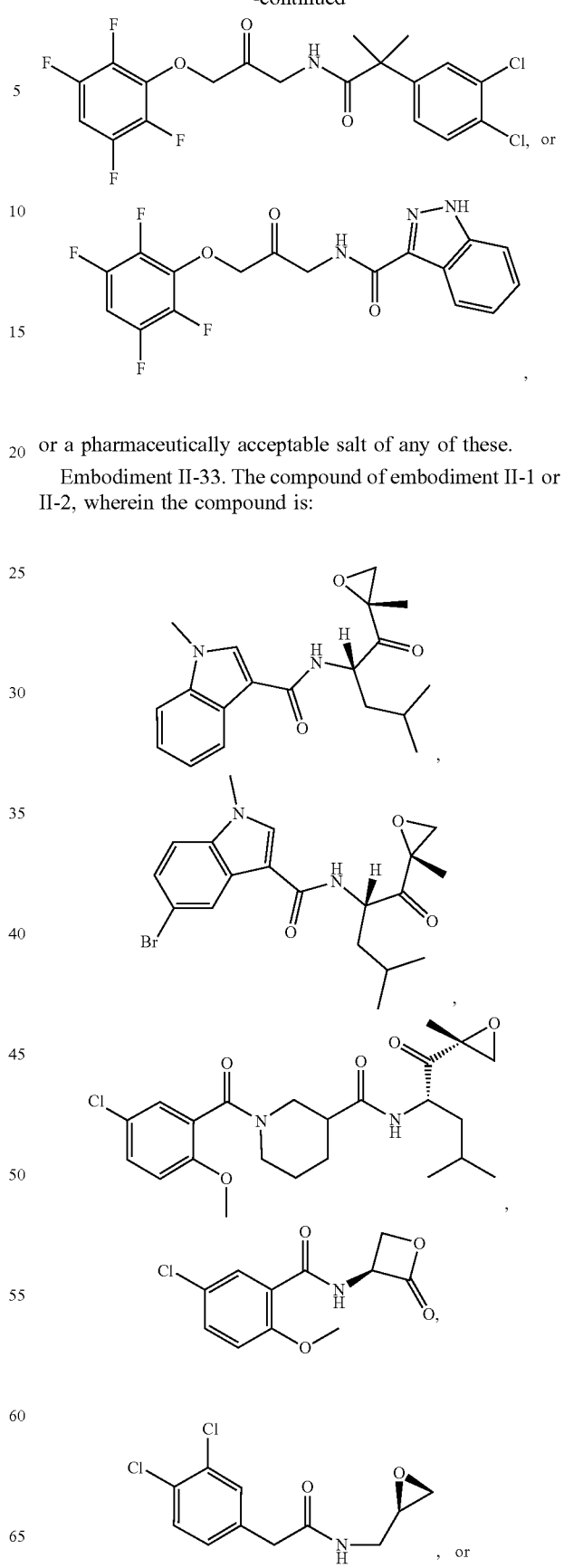
or a pharmaceutically acceptable salt of any of these.
Embodiment II-33. The compound of embodiment II-1 or II-2, wherein the compound is:

275
-continued
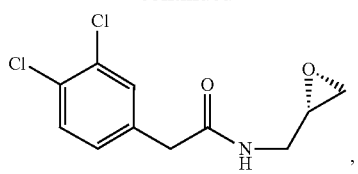
or a pharmaceutically acceptable salt of any of these.
Embodiment II-34. The compound of embodiment II-1 or II-11, wherein the compound is:
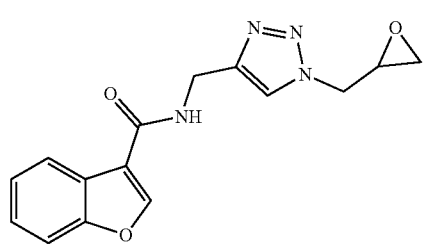
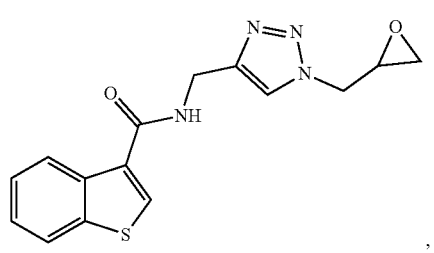
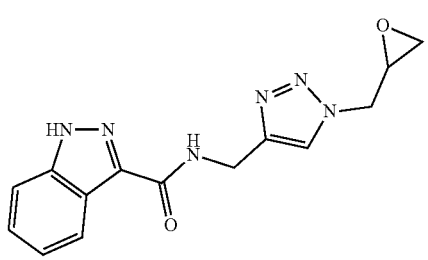
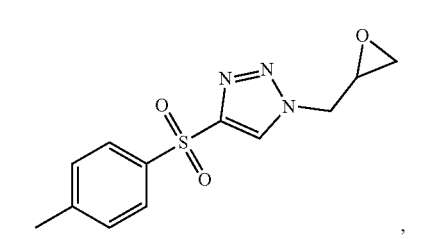
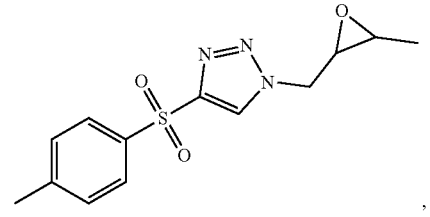
276
-continued
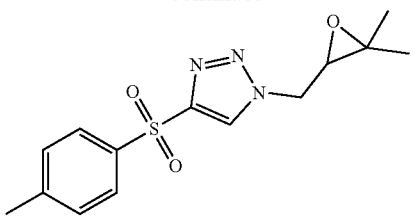
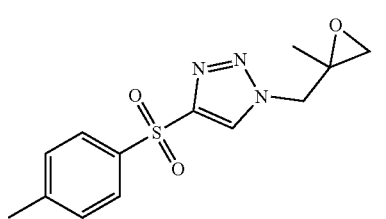
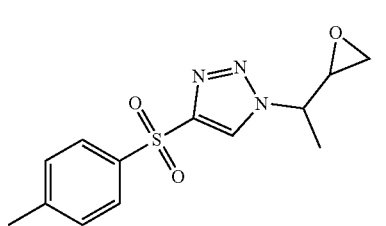
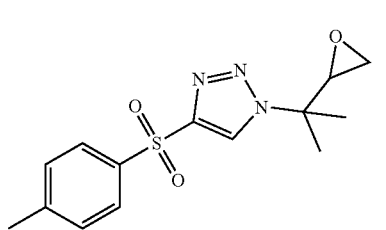
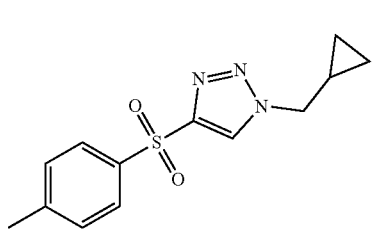
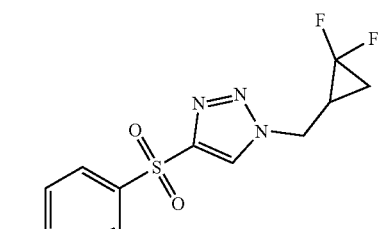
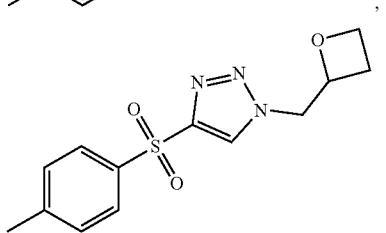

277
-continued
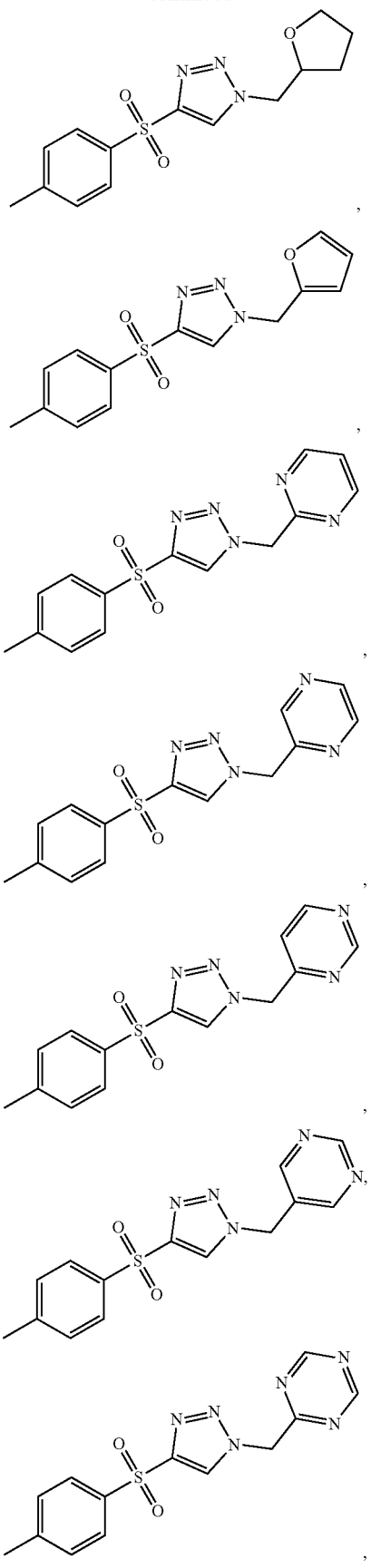
278
-continued
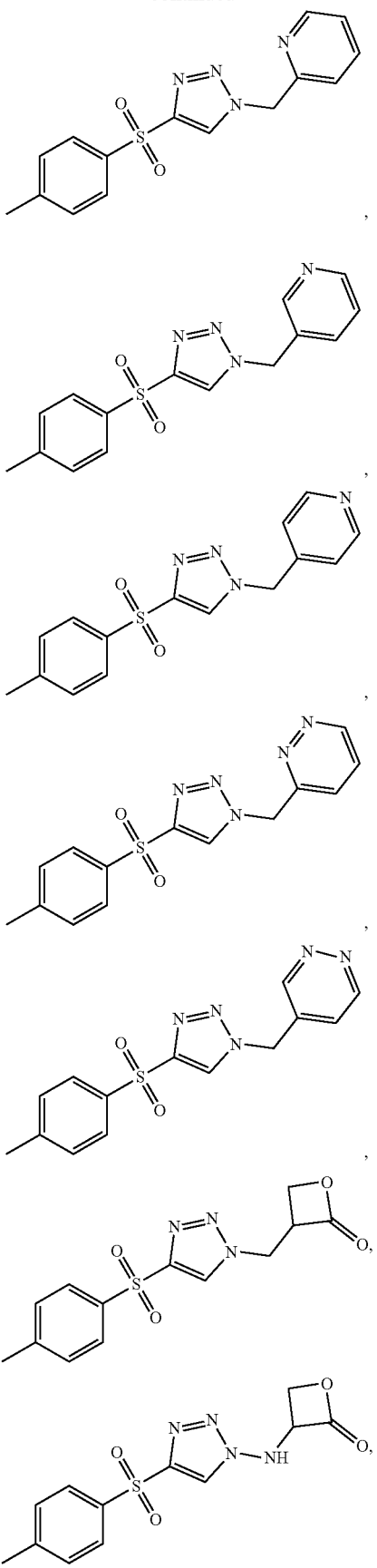

279
-continued
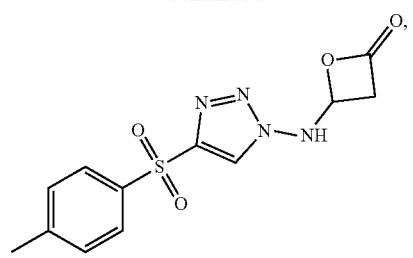
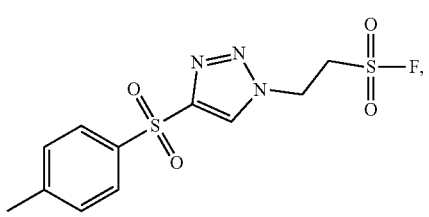
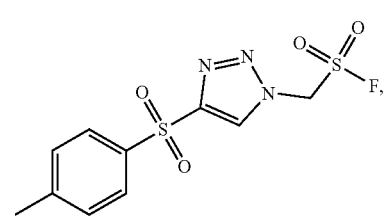
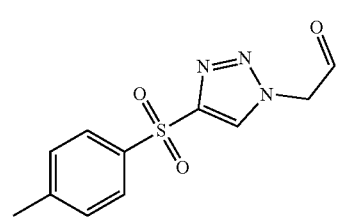
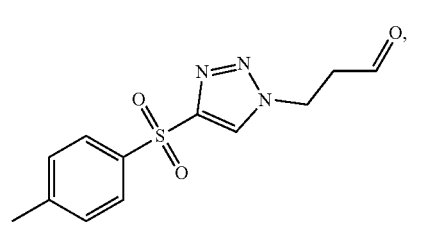
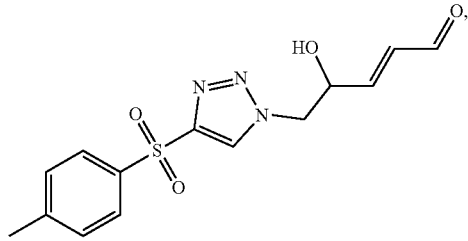
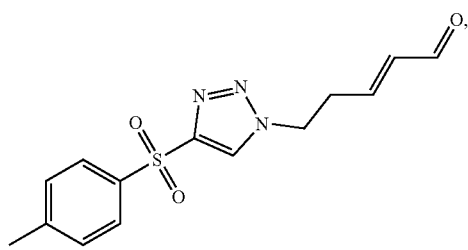
280
-continued
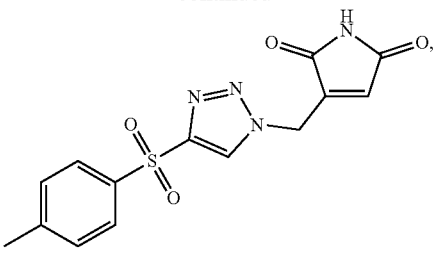
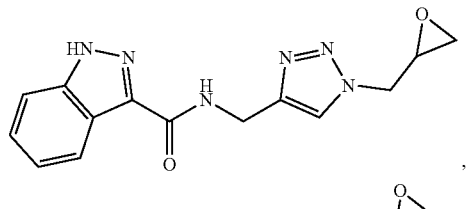
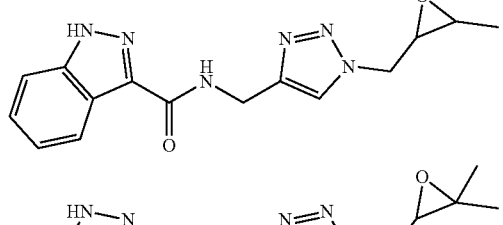
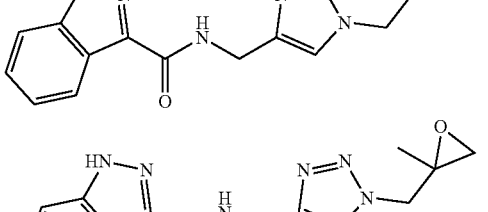
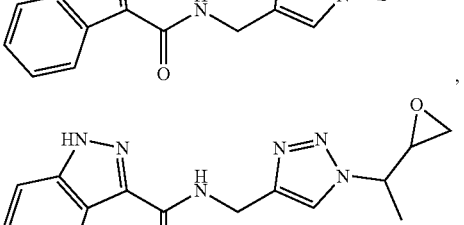
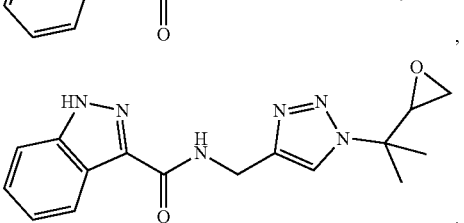
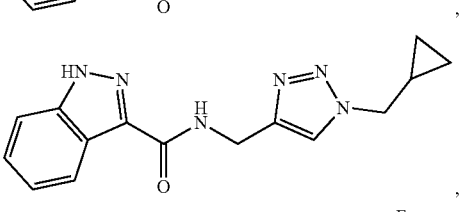
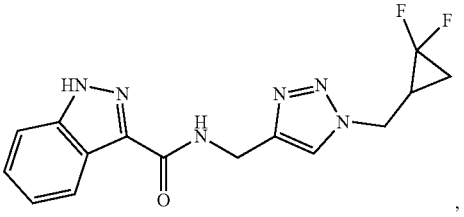

281
-continued
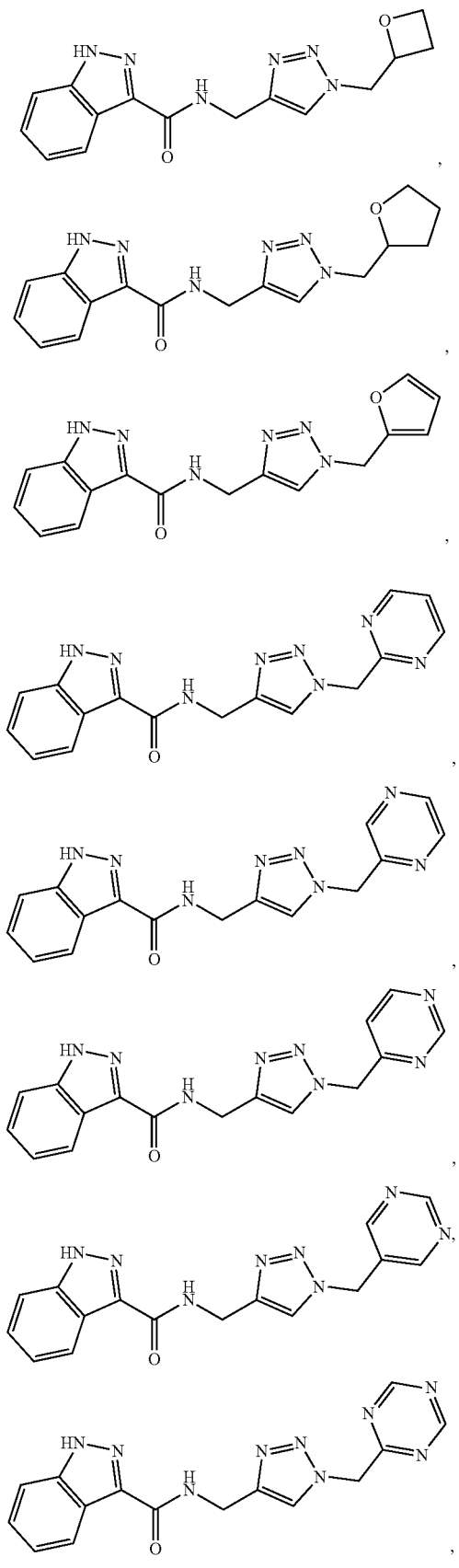
282
-continued
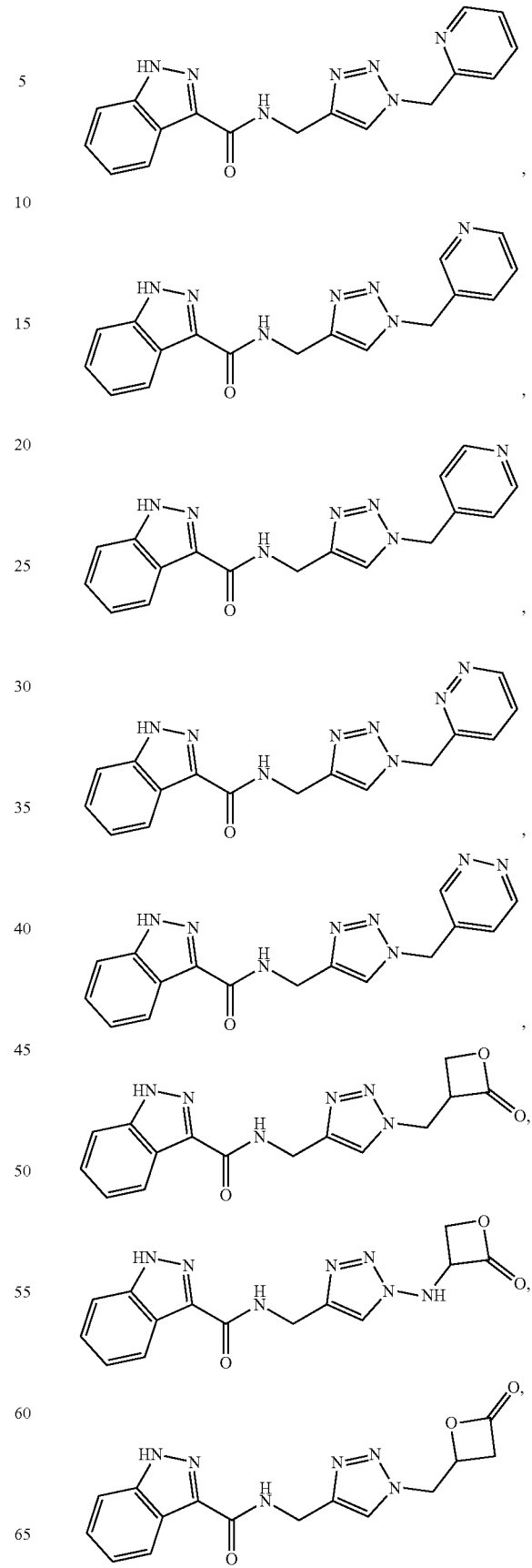

283
-continued
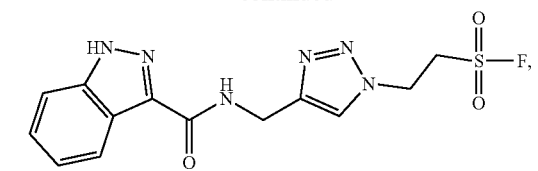
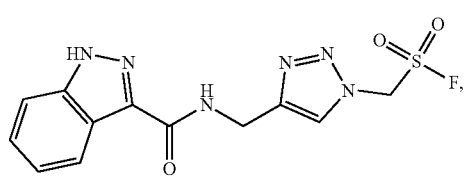
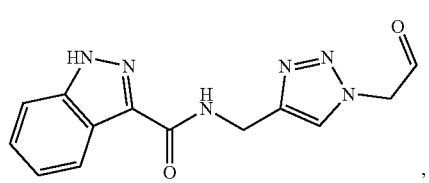
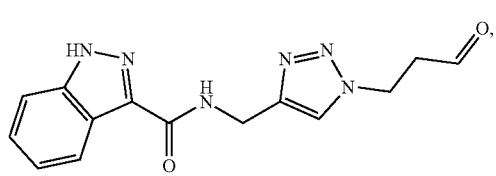
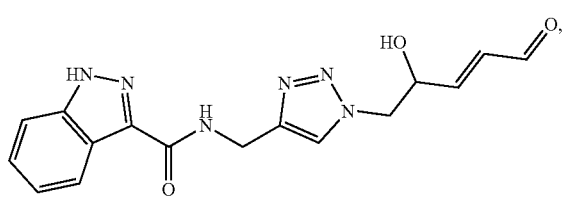
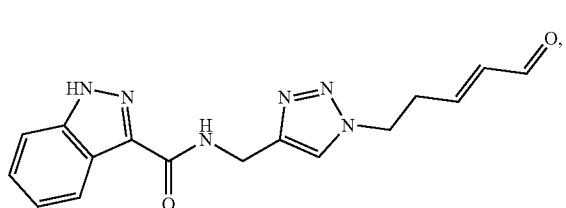
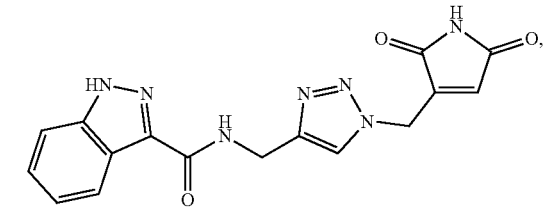
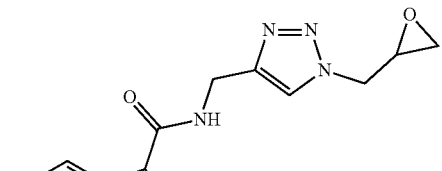
284
-continued
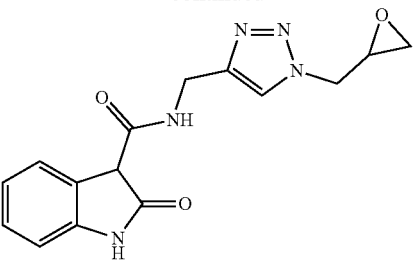
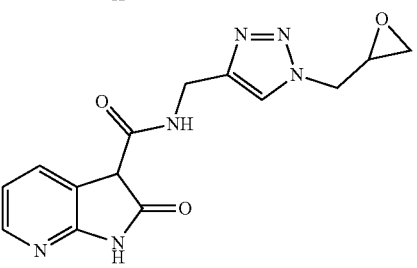
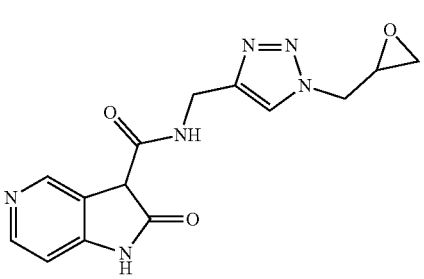
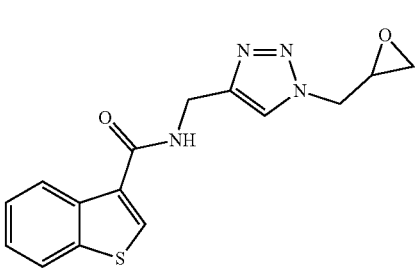
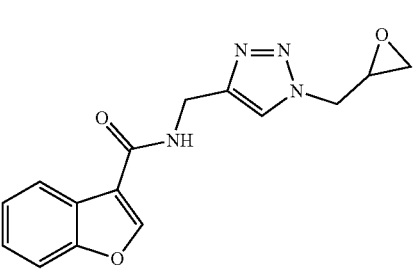
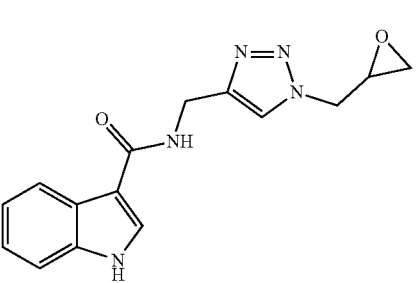

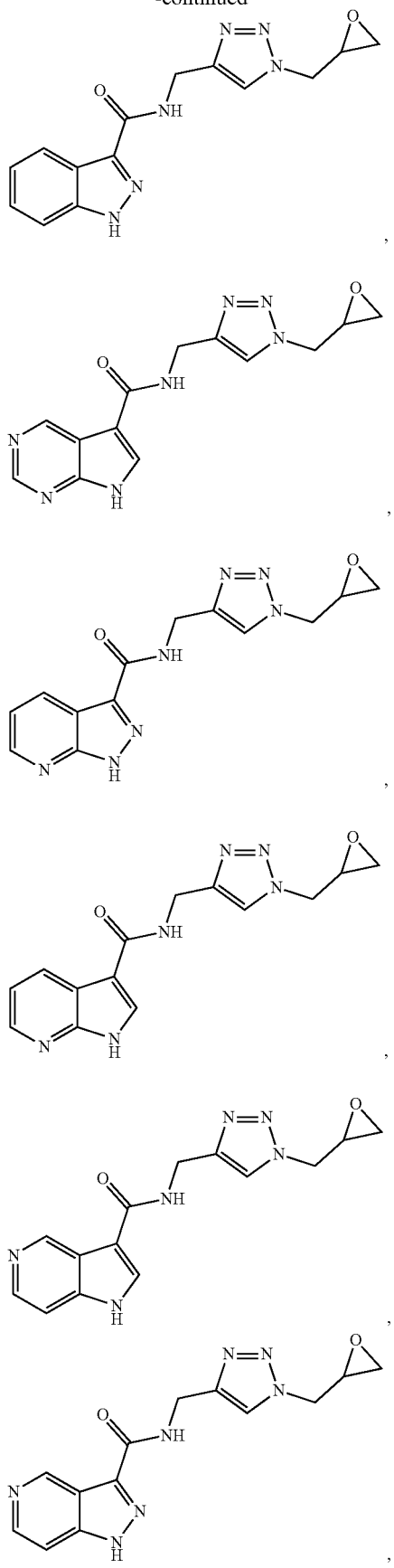
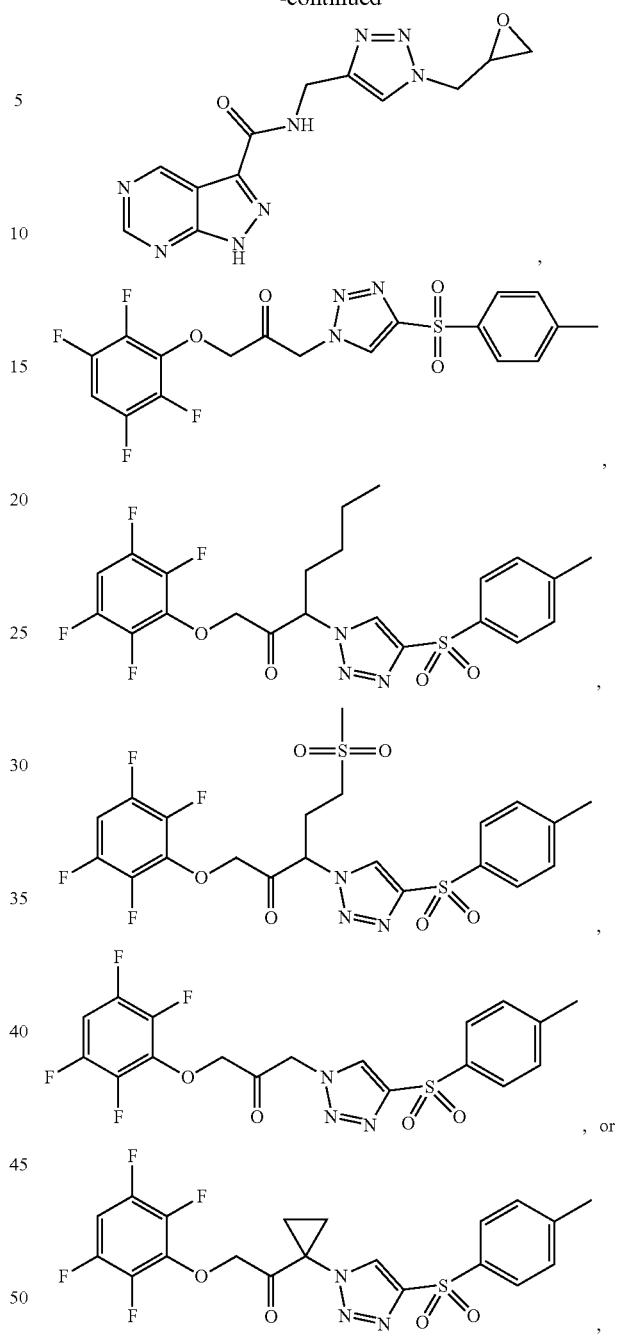
or a pharmaceutically acceptable salt of any of these.
Embodiment II-35. The compound of embodiment II-1 or II-11, wherein the compound is:
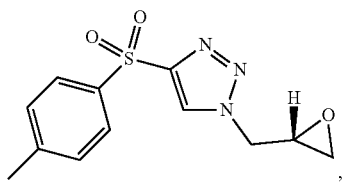
D

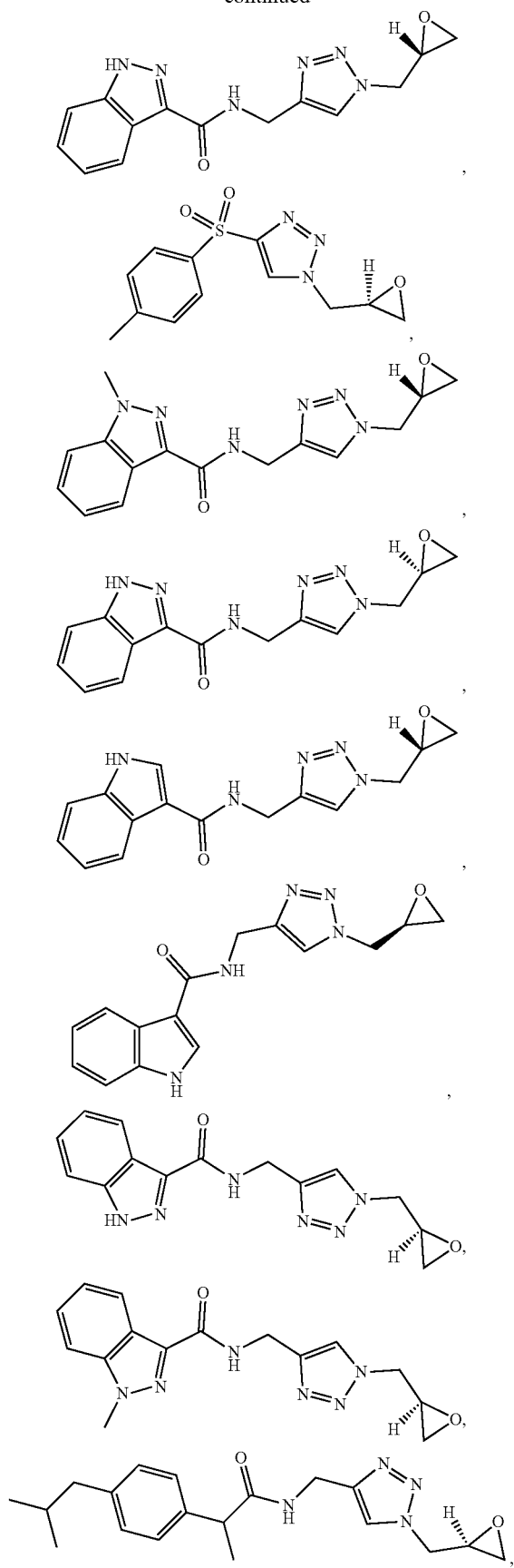
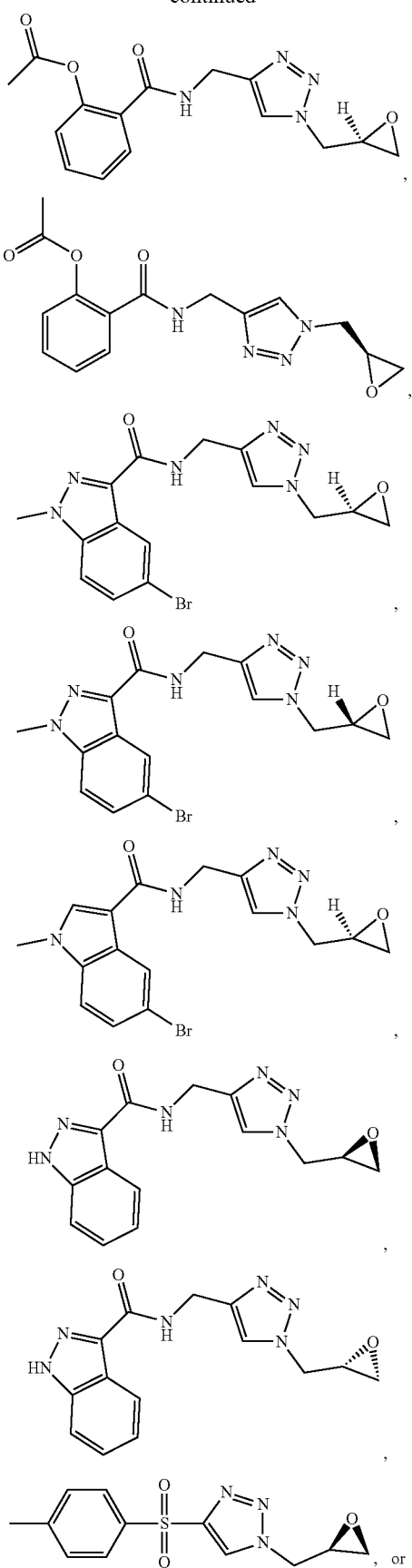

-continued

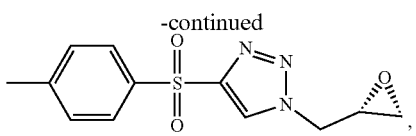

or a pharmaceutically acceptable salt of any of these.

Embodiment II-36A pharmaceutical composition comprising the compound of any one of embodiments II-1 to II-35, or a pharmaceutically acceptable salt thereof, and a pharmaceutically acceptable excipient.

Embodiment II-37A method of reducing the level of a K-Ras protein in a subject in need thereof, comprising administering to the subject a compound of one of embodiments II-1 to II-35, or a pharmaceutically acceptable salt thereof.

Embodiment II-38. A method of reducing the activity level of a K-Ras protein in a subject in need thereof, comprising administering to the subject a compound of one of embodiments II-1 to II-35, or a pharmaceutically acceptable salt thereof.

Embodiment II-39. The method of embodiment II-37 or II-38, wherein the compound or pharmaceutically acceptable salt thereof contacts the amino acid corresponding to H95 of human K-Ras.

Embodiment II-40. The method of embodiment II-37 or II-38, wherein the compound or pharmaceutically acceptable salt thereof covalently binds the amino acid corresponding to H95 of human K-Ras.

Embodiment II-41. The method of any one of embodiments II-37 to II-40, wherein the K-Ras protein is human K-Ras 4A.

Embodiment II-42. The method of any one of embodiments II-37 to II-40, wherein the K-Ras protein is human K-Ras 4B.

Embodiment II-43. The method of any one of embodiments II-37 or II-39 to II-42, comprising reducing the level of both human K-Ras 4A and human K-Ras 4B.

Embodiment II-44. The method of any one of embodiments II-38 to II-42, comprising reducing the activity level of both human K-Ras 4A and human K-Ras 4B.

Embodiment II-45. A method for treating a disorder in a subject in need thereof, comprising administering to the subject a therapeutically effective amount of a compound of any one of embodiments II-1 to II-35, or a pharmaceutically acceptable salt thereof.

Embodiment II-46. The method of embodiment II-45, wherein the disorder is cancer.

Embodiment II-47. The method of embodiment II-46, wherein the cancer is pancreatic cancer, lung cancer, colorectal cancer, optic pathway glioma, rhabdomyosarcoma, neuroblastoma, juvenile myelomonocytic leukemia, malignant peripheral nerve sheath tumors, gastrointestinal stromal tumors, somatostatinomas, pheochromocytomas, or breast cancer.

Embodiment II-48. The method of embodiment II-45, wherein the disorder is neurofibromatosis type 1, Noonan syndrome, cardio-facio-cutaneous syndrome, or Legius syndrome.

Embodiment II-49. The method of any one of embodiments II-45 to II-48, wherein the disorder is associated with a mutation of K-Ras.

Embodiment II-50. Use of a compound of any one of embodiments II-1 to II-35, or a pharmaceutically acceptable salt thereof, in the manufacture of a medicament for reducing the level of a K-Ras protein in a subject in need thereof.

Embodiment II-51. Use of a compound of any one of embodiments II-1 to II-35, or a pharmaceutically acceptable salt thereof, in the manufacture of a medicament for reducing the activity level of a K-Ras protein in a subject in need thereof.

Embodiment II-52. The use of embodiment II-50 or II-51, wherein the K-Ras protein is human K-Ras 4B.

Embodiment II-53. Use of a compound of any one of embodiments II-1 to II-35, or a pharmaceutically acceptable salt thereof, in the manufacture of a medicament for treating a disorder in a subject in need thereof.

Embodiment II-54. The use of embodiment II-53, wherein the disorder is cancer.

Embodiment II-55. The use of embodiment II-54, wherein the cancer is pancreatic cancer, lung cancer, colorectal cancer, optic pathway glioma, rhabdomyosarcoma, neuroblastoma, juvenile myelomonocytic leukemia, malignant peripheral nerve sheath tumors, gastrointestinal stromal tumors, somatostatinomas, pheochromocytomas, or breast cancer.

Embodiment II-56. The use of embodiment II-53, wherein the disorder is neurofibromatosis type 1, Noonan syndrome, cardio-facio-cutaneous syndrome, or Legius syndrome.

Embodiment II-57. The use of any one of embodiments II-53 to II-56, wherein the disorder is associated with a mutation of K-Ras.

Embodiment II-58. A compound according to any one of embodiments II-1 to II-35, or a pharmaceutically acceptable salt thereof, for use in a method of reducing the level of a K-Ras protein in a subject in need thereof.

Embodiment II-59. A compound according to any one of embodiments II-1 to II-35, or a pharmaceutically acceptable salt thereof, for use in a method of reducing the activity level of a K-Ras protein in a subject in need thereof.

Embodiment II-60. The compound for use of embodiment II-58 or II-59, wherein the K-Ras protein is human K-Ras 4B.

Embodiment II-61. A compound according to any one of embodiments II-1 to II-35, or a pharmaceutically acceptable salt thereof, for use in a method of treating a disorder in a subject in need thereof.

Embodiment II-62. The compound for use in embodiment II-61, wherein the disorder is cancer.

Embodiment II-63. The compound for use of embodiment II-62, wherein the cancer is pancreatic cancer, lung cancer, colorectal cancer, optic pathway glioma, rhabdomyosarcoma, neuroblastoma, juvenile myelomonocytic leukemia, malignant peripheral nerve sheath tumors, gastrointestinal stromal tumors, somatostatinomas, pheochromocytomas, or breast cancer.

Embodiment II-64. The compound for use of embodiment II-61, wherein the disorder is neurofibromatosis type 1, Noonan syndrome, cardio-facio-cutaneous syndrome, or Legius syndrome.

Embodiment II-65. The compound for use of any one of embodiments II-61 to II-64, wherein the disorder is associated with a mutation of K-Ras.

What is claimed is:

1. A compound having formula (II):

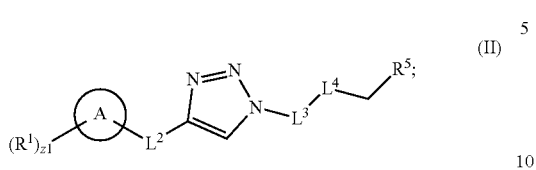

or a pharmaceutically acceptable salt thereof, wherein:

Ring A is phenyl, indolinyl, indazolyl, benzimidazolyl, benzoxazolyl, azaindolyl, purinyl, indolyl, pyrazinyl, pyrrolyl, imidazolyl, pyrazolyl, triazolyl, tetrazolyl, benzofuranyl, benzothienyl,

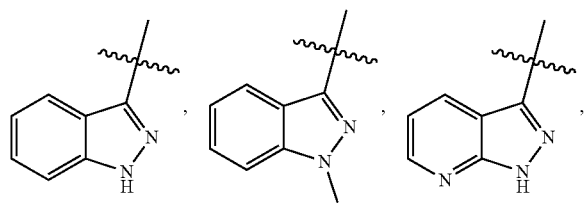

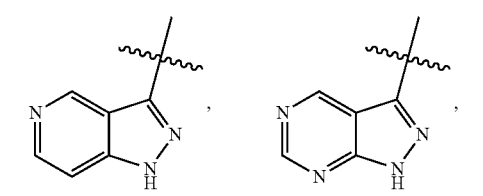

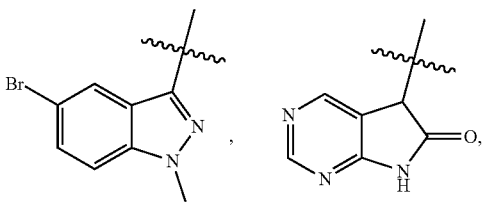

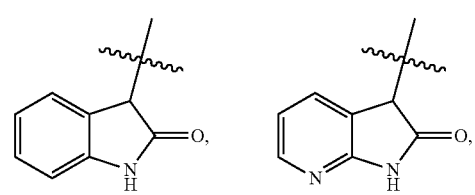

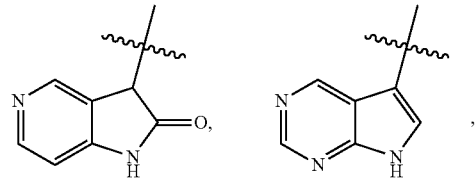

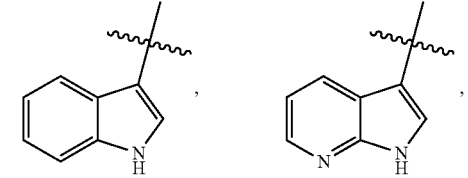

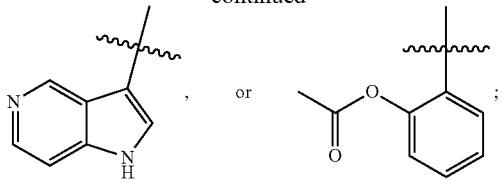, or $R^1$ is independently halogen, $-CX^1_3$, $-CHX^1_2$, $-CH_2X^1$, $-CN$, $-SO_{n1}R^{1D}$, $-SO_{v1}NR^{1A}R^{1B}$, $-NHNR^{1A}R^{1B}$, $-ONR^{1A}R^{1B}$, $-NHC=(O)NHNR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-OCX^1_3$, $-OCHX^1_2$, $-OCH_2X^1$, substituted or unsubstituted alkyl, substituted or unsubstituted heteroalkyl, substituted or unsubstituted cycloalkyl, or substituted or unsubstituted heterocycloalkyl; or two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;

$L^2$ is $-S(O)_2-$, $-C(O)NH-$, or $-C(O)NHCH_2-$;

$L^3$ is a bond, $-S(O)_2-$, $-N(R^3)-$, $-O-$, $-S-$, $-C(O)-$, $-C(O)N(R^3)-$, $-N(R^3)C(O)-$, $-N(R^3)C(O)NH-$, $-NHC(O)N(R^3)-$, $-C(O)O-$, $-OC(O)-$, unsubstituted alkylene, unsubstituted heteroalkylene, substituted or unsubstituted cycloalkylene, substituted or unsubstituted arylene, or unsubstituted heteroarylene;

$R^3$ is independently hydrogen, $-CX^3_3$, $-CHX^3_2$, $-CH_2X^3$, $-C(O)R^{3A}$, $-C(O)OR^{3A}$, $-C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^4$ is a bond, $-S(O)_2-$, $-N(R^4)-$, $-O-$, $-S-$, $-C(O)-$, $-C(O)N(R^4)-$, $-N(R^4)C(O)-$, $-N(R^4)C(O)NH-$, $-NHC(O)N(R^4)-$, $-C(O)O-$, $-OC(O)-$, substituted or unsubstituted alkylene, unsubstituted heteroalkylene, substituted or unsubstituted cycloalkylene, or substituted or unsubstituted heterocycloalkylene;

$R^4$ is independently hydrogen, $-CX^4_3$, $-CHX^4_2$, $-CH_2X^4$, $-C(O)R^{4A}$, $-C(O)OR^{4A}$, $-C(O)NR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently:

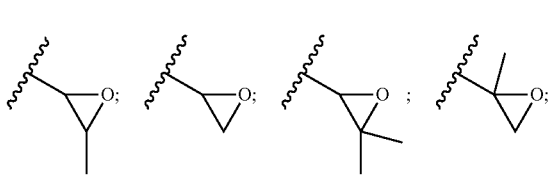

-continued

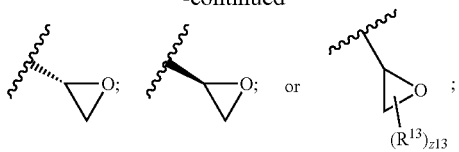

wherein $R^{13}$ is hydrogen, halogen, substituted or unsubstituted alkyl; and z13 is an integer from 0 to 3;

each $R^{1A}$, $R^{1B}$, $R^{1C}$, $R^{1D}$, $R^{3A}$, $R^{3B}$, $R^{4A}$, and $R^{4B}$ is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ and $R^{1B}$ substituents bonded to the same nitrogen atom may optionally be joined to form a substituted or unsubstituted heterocycloalkyl or substituted or unsubstituted heteroaryl;

$R^{3A}$ and $R^{3B}$ substituents bonded to the same nitrogen atom may optionally be joined to form a substituted or unsubstituted heterocycloalkyl or substituted or unsubstituted heteroaryl;

$R^{4A}$ and $R^{4B}$ substituents bonded to the same nitrogen atom may optionally be joined to form a substituted or unsubstituted heterocycloalkyl or substituted or unsubstituted heteroaryl;

each X, $X^1$, $X^3$, and $X^4$ is independently —F, —Cl, —Br, or —I;

n1 is independently an integer from 0 to 4; and m1 and v1 are independently 1 or 2.

2. The compound of claim 1, or a pharmaceutically acceptable salt thereof, wherein:

Ring A is indolinyl, indazolyl, benzimidazolyl, benzoxazolyl, azaindolyl, purinyl, indolyl, pyrazinyl, pyrrolyl, imidazolyl, pyrazolyl, triazolyl, tetrazolyl, benzofuranyl, benzothienyl,

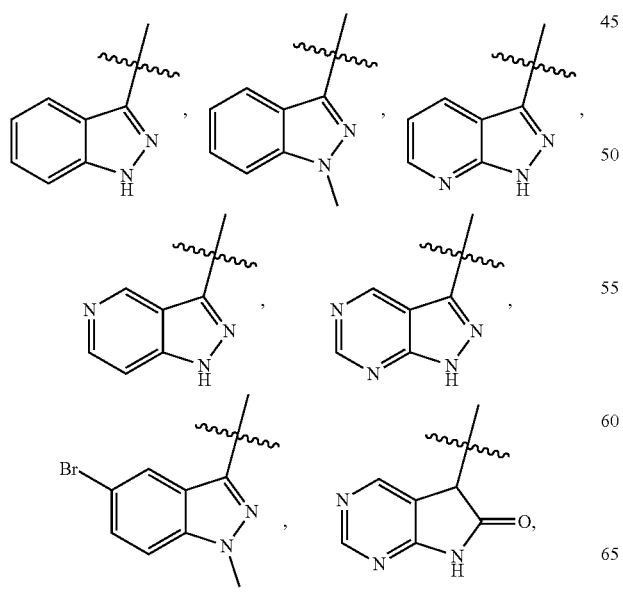

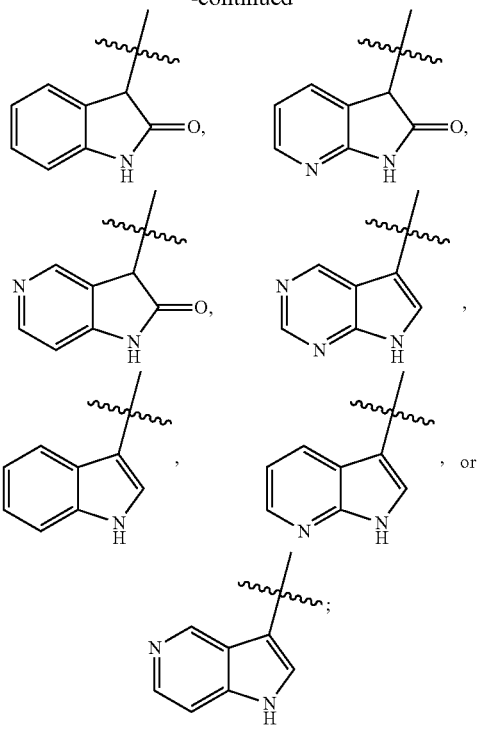

$R^1$ is independently halogen, —$CX^1_3$, —$CHX^1_2$, —$CH_2X^1$, —CN, —$SO_{n1}R^{1D}$, —$SO_{v1}NR^{1A}R^{1B}$, —$NHNR^{1A}R^{1B}$, —$ONR^{1A}R^{1B}$, —NHC=(O)$NHNR^{1A}R^{1B}$, —$NHC(O)NR^{1A}R^{1B}$, $N(O)_{m1}$, —$NR^{1A}R^{1B}$, —$C(O)R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$OCX^1_3$, —$OCHX^1_2$, —$OCH_2X^1$, substituted or unsubstituted alkyl, substituted or unsubstituted heteroalkyl, substituted or unsubstituted cycloalkyl, or substituted or unsubstituted heterocycloalkyl; or two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;

$L^3$ is a bond, —$S(O)_2$—, —$N(R^3)$—, —O—, —S—, —C(O)—, —$C(O)N(R^3)$—, —$N(R^3)C(O)$—, —$N(R^3)C(O)NH$—, —$NHC(O)N(R^3)$—, —C(O)O—, —OC(O)—, unsubstituted alkylene, unsubstituted heteroalkylene, substituted or unsubstituted cycloalkylene, substituted or unsubstituted arylene, or unsubstituted heteroarylene;

$R^3$ is independently hydrogen, —$CX^3_3$, —$CHX^3_2$, —$CH_2X^3$, —$C(O)R^{3A}$, —$C(O)OR^{3A}$, —C(O)$NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^4$ is a bond, —$S(O)_2$—, —$N(R^4)$—, —O—, —S—, —C(O)—, —$C(O)N(R^4)$—, —$N(R^4)C(O)$—, —$N(R^4)C(O)NH$—, —$NHC(O)N(R^4)$—, —C(O)O—, —OC(O)—, substituted or unsubstituted alkylene, unsubstituted heteroalkylene, substituted or unsubstituted cycloalkylene, or substituted or unsubstituted heterocycloalkylene;

R$^4$ is independently hydrogen, —CX$^4_3$, —CHX$^4_2$, —CH$_2$X$^4$, —C(O)R$^{4A}$, —C(O)OR$^{4A}$, —C(O)NR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each R$^{1A}$, R$^{1B}$, R$^{1C}$, R$^{1D}$, R$^{3A}$, R$^{3B}$, R$^{4A}$, and R$^{4B}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$ and R$^{1B}$ substituents bonded to the same nitrogen atom may optionally be joined to form a substituted or unsubstituted heterocycloalkyl or substituted or unsubstituted heteroaryl;

R$^{3A}$ and R$^{3B}$ substituents bonded to the same nitrogen atom may optionally be joined to form a substituted or unsubstituted heterocycloalkyl or substituted or unsubstituted heteroaryl;

R$^{4A}$ and R$^{4B}$ substituents bonded to the same nitrogen atom may optionally be joined to form a substituted or unsubstituted heterocycloalkyl or substituted or unsubstituted heteroaryl;

each X, X$^1$, X$^3$, and X$^4$ is independently —F, —Cl, —Br, or —I;

n1 is independently an integer from 0 to 4; and m1 and v1 are independently 1 or 2.

3. The compound of claim 1, or a pharmaceutically acceptable salt thereof, wherein:

ring A is indolinyl, indazolyl, benzimidazolyl, benzoxazolyl, azaindolyl, purinyl, indolyl, pyrazinyl, pyrrolyl, imidazolyl, pyrazolyl, triazolyl, tetrazolyl, benzofuranyl, benzothienyl,

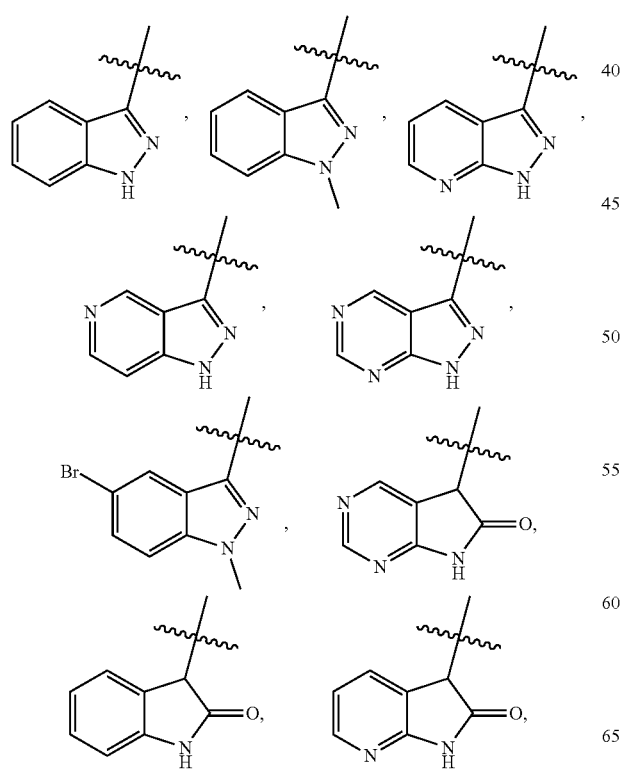

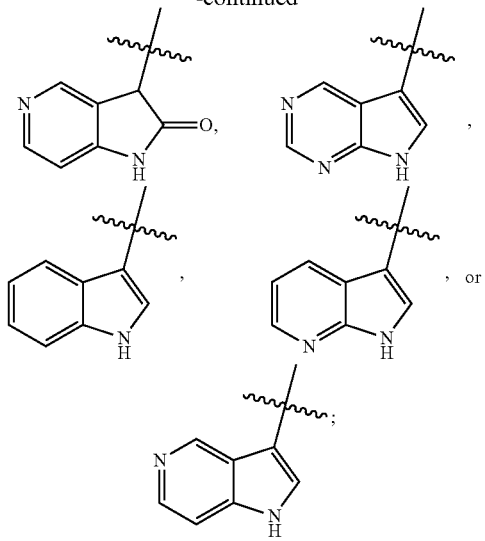

R$^1$ is independently halogen, —CX$^1_3$, —CHX$^1_2$, —CH$_2$X$^1$, —CN, —SO$_{n1}$R$^{1D}$, —SO$_{v1}$NR$^{1A}$R$^{1B}$, —ONR$^{1A}$R$^{1B}$, —N(O)$_{m1}$, —NR$^{1A}$R$^{1B}$, —OR$^{1D}$, —OCX$^1_3$, —OCHX$^1_2$, —OCH$_2$X$^1$, substituted or unsubstituted alkyl, substituted or unsubstituted cycloalkyl, or substituted or unsubstituted heterocycloalkyl;

z1 is an integer from 0 to 4;

L$^3$ is a bond or unsubstituted alkylene;

L$^4$ is a bond, —O—, —N(R$^4$)—, or —C(O)—;

R$^4$ is hydrogen or substituted or unsubstituted alkyl;

R$^5$ is independently:

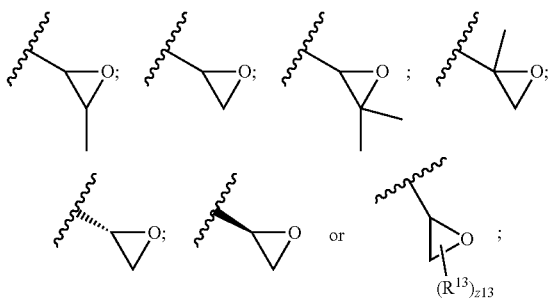

wherein R$^{13}$ is hydrogen, halogen, substituted or unsubstituted alkyl; and z13 is an integer from 0 to 3;

each R$^{1A}$, R$^{1B}$, R$^{1C}$, and R$^{1D}$ is independently hydrogen, —CX$_3$, —CHX$_2$, —CH$_2$X, substituted or unsubstituted alkyl, substituted or unsubstituted cycloalkyl, substituted or unsubstituted heterocycloalkyl, substituted or unsubstituted aryl, or substituted or unsubstituted heteroaryl;

each X and X$^1$ are independently —F, —Cl, —Br, or —I;

n1 is independently an integer from 0 to 4; and m1 and v1 are independently 1 or 2.

4. The compound of claim 1, wherein the compound is of Formula (I), or a pharmaceutically acceptable salt thereof, wherein:

Ring A is phenyl;

R$^1$ is independently halogen, —CX$^1_3$, —CHX$^1_2$, —CH$_2$X$^1$, —CN, —SO$_{n1}$R$^{1D}$, -SO$_{v1}$NR$^{1A}$R$^{1B}$, —NHNR$^{1A}$R$^{1B}$, —ONR$^{1A}$R$^{1B}$, —NHC=(O)NHNR$^{1A}$R$^{1B}$, —NHC(O)NR$^{1A}$R$^{1B}$, N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, or substituted or unsubstituted heterocycloalkyl; or two adjacent R$^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;

L$^3$ is a bond, —S(O)$_2$—, —N(R$^3$)—, —O—, —S—, —C(O)—, —C(O)N(R$^3$)—, —N(R$^3$)C(O)—, —N(R$^3$)C(O)NH—, —NHC(O)N(R$^3$)—, —C(O)O—, —OC(O)—, unsubstituted alkylene, unsubstituted heteroalkylene, substituted or unsubstituted cycloalkylene, substituted or unsubstituted arylene, or unsubstituted heteroarylene;

R$^3$ is independently hydrogen, —CX$^3_3$, —CHX$^3_2$, —CH$_2$X$^3$, —C(O)R$^{3A}$, —C(O)OR$^{3A}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^4$ is a bond, —S(O)$_2$—, —N(R$^4$)—, —O—, —S—, —C(O)—, —C(O)N(R$^4$)—, —N(R$^4$)C(O)—, —N(R$^4$)C(O)NH—, —NHC(O)N(R$^4$)—, —C(O)O—, —OC(O)—, substituted or unsubstituted alkylene, unsubstituted heteroalkylene, substituted or unsubstituted cycloalkylene, or substituted or unsubstituted heterocycloalkylene;

R$^4$ is independently hydrogen, —CX$^4_3$, —CHX$^4_2$, —CH$_2$X$^4$, —C(O)R$^{4A}$, —C(O)OR$^{4A}$, —C(O)NR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

each R$^{1A}$, R$^{1B}$, R$^{1C}$, R$^{1D}$, R$^{3A}$, R$^{3B}$, R$^{4A}$, and R$^{4B}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$ and R$^{1B}$ substituents bonded to the same nitrogen atom may optionally be joined to form a substituted or unsubstituted heterocycloalkyl or substituted or unsubstituted heteroaryl;

R$^{3A}$ and R$^{3B}$ substituents bonded to the same nitrogen atom may optionally be joined to form a substituted or unsubstituted heterocycloalkyl or substituted or unsubstituted heteroaryl;

R$^{4A}$ and R$^{4B}$ substituents bonded to the same nitrogen atom may optionally be joined to form a substituted or unsubstituted heterocycloalkyl or substituted or unsubstituted heteroaryl;

each X, X$^1$, X$^3$, and X$^4$ is independently —F, —Cl, —Br, or —I;

n1 is independently an integer from 0 to 4; and m1 and v1 are independently 1 or 2.

5. The compound of claim 1, or a pharmaceutically acceptable salt thereof, wherein:

Ring A is phenyl;

R$^1$ is independently halogen, —CX$^1_3$, —CHX$^1_2$, —CH$_2$X$^1$, —CN, —SO$_{n1}$R$^{1D}$, —SO$_{v1}$NR$^{1A}$R$^{1B}$, —ONR$^{1A}$R$^{1B}$, —N(O)$_{m1}$, —NR$^{1A}$R$^{1B}$, —OR$^{1D}$, —OCX$^1_3$, —OCHX$^1_2$, —OCH$_2$X$^1$, substituted or unsubstituted alkyl, substituted or unsubstituted cycloalkyl, substituted or unsubstituted heterocycloalkyl;

z1 is an integer from 0 to 4;

L$^3$ is a bond or unsubstituted alkylene;

L$^4$ is a bond, —O—, —N(R$^4$)—, or —C(O)—;

R$^4$ is hydrogen or substituted or unsubstituted alkyl;

R$^5$ is independently:

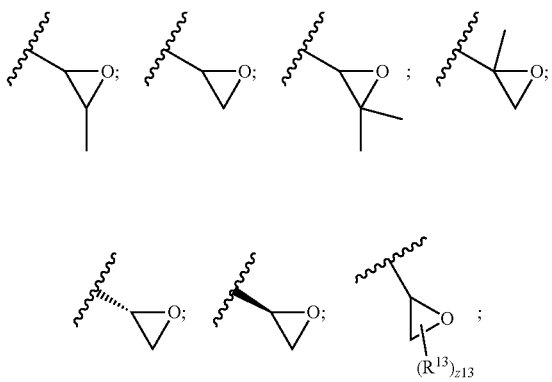

wherein R$^{13}$ is hydrogen, halogen, substituted or unsubstituted alkyl; and z13 is an integer from 0 to 3;

each R$^{1A}$, R$^{1B}$, R$^1c$ and R$^{1D}$ is independently hydrogen, —CX$_3$, —CHX$_2$, —CH$_2$X, substituted or unsubstituted alkyl, substituted or unsubstituted cycloalkyl, substituted or unsubstituted heterocycloalkyl, substituted or unsubstituted aryl, or substituted or unsubstituted heteroaryl;

each X and X$^1$ are independently —F, —Cl, —Br, or —I;

n1 is independently an integer from 0 to 4; and m1 and v1 are independently 1 or 2.

6. The compound of claim 1, or a pharmaceutically acceptable salt thereof, wherein L$^2$ is —S(O)$_2$— or —C(O)NHCH$_2$—.

7. The compound of claim 1, or a pharmaceutically acceptable salt thereof, wherein each R$^1$ is independently halogen, —OR$^{1D}$, NR$^{1A}$R$^{1B}$, —CN, or substituted or unsubstituted alkyl, wherein each R$^{1A}$, R$^{1B}$, and R$^{1D}$ is independently hydrogen, substituted or unsubstituted alkyl, substituted or unsubstituted cycloalkyl, substituted or unsubstituted aryl, or substituted or unsubstituted heteroaryl.

8. The compound of claim 1, or a pharmaceutically acceptable salt thereof, wherein each R$^1$ is independently halogen, —CN, —CX$^1_3$, —CHX$^1_2$, —CH$_2$X$^1$, —OCX$^1_3$, —OCHX$^1_2$, —OCH$_2$X$^1$, —OR$^{1D}$, or —NR$^{1A}$R$^{1B}$, wherein each R$^{1A}$, R$^{1B}$, and R$^{1D}$ is independently hydrogen, substituted or unsubstituted alkyl, or substituted or unsubstituted aryl.

9. The compound of claim 1, or a pharmaceutically acceptable salt thereof, wherein $R^5$ is:

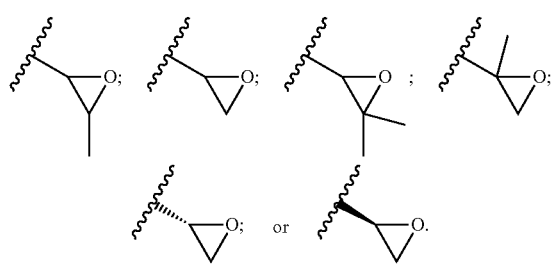

10. The compound of claim 1, or a pharmaceutically acceptable salt thereof, wherein $R^5$ is:

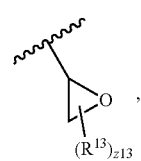

wherein $R^{13}$ is hydrogen, halogen, substituted or unsubstituted alkyl; and z13 is an integer from 0 to 3.

11. The compound of claim 1, or a pharmaceutically acceptable salt thereof, wherein ring A is phenyl.

12. The compound of claim 1, or a pharmaceutically acceptable salt thereof, wherein ring A is indolyl.

13. The compound of claim 1, or a pharmaceutically acceptable salt thereof, wherein $L^3$ is unsubstituted $C_1$-$C_8$ alkylene.

14. The compound of claim 1, or a pharmaceutically acceptable salt thereof, wherein $L^3$ is unsubstituted methylene.

15. The compound of claim 1, wherein the compound is:

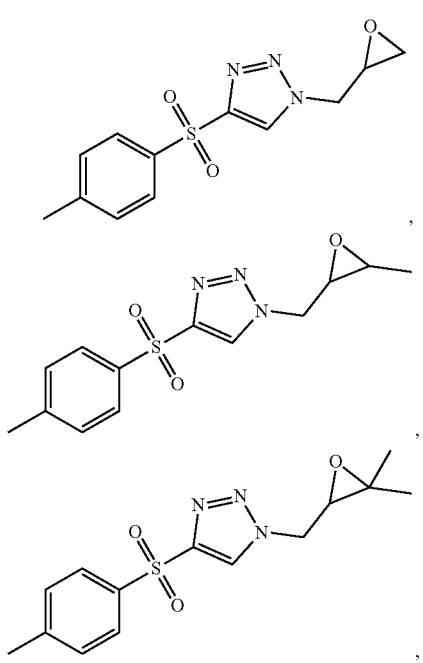

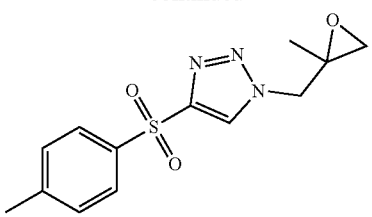

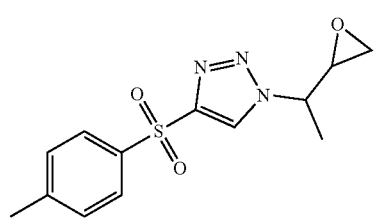

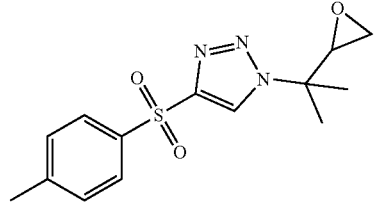

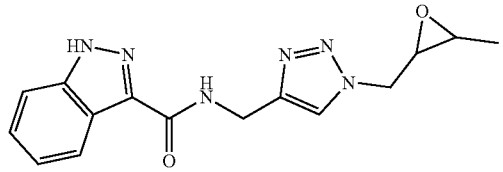

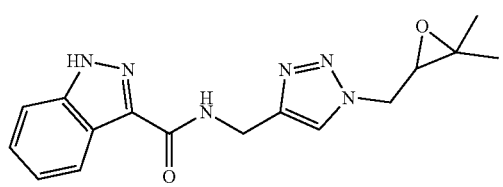

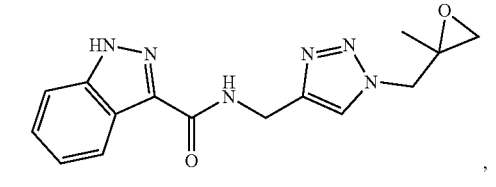

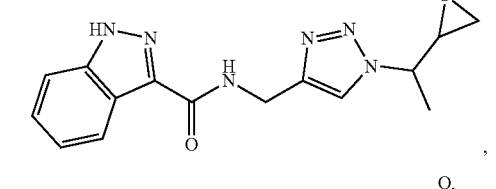

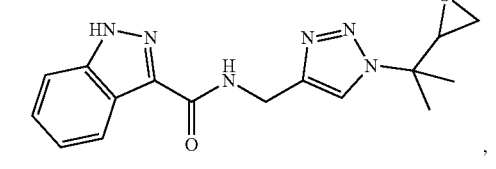

305
-continued
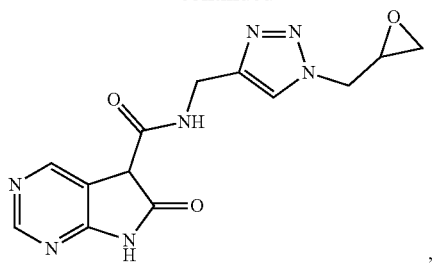
,
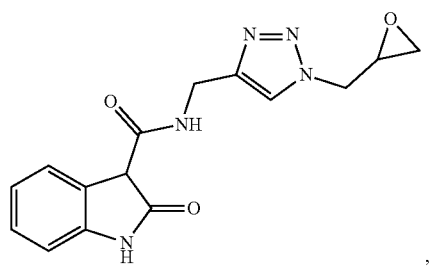
,
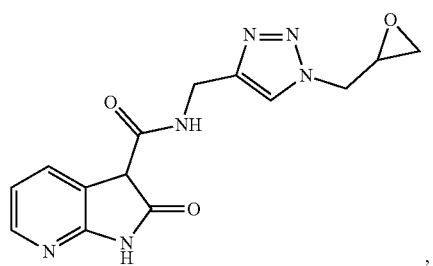
,
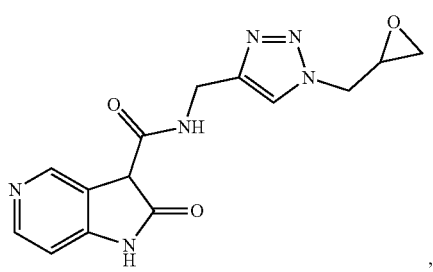
,
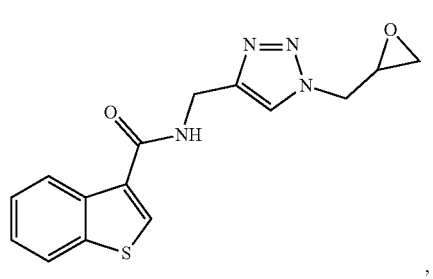
,
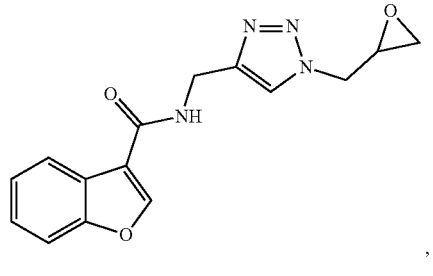
,
306
-continued
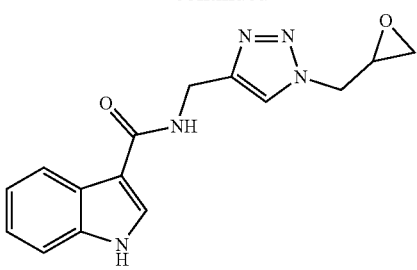
,
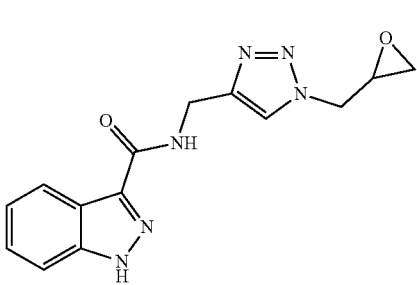
,
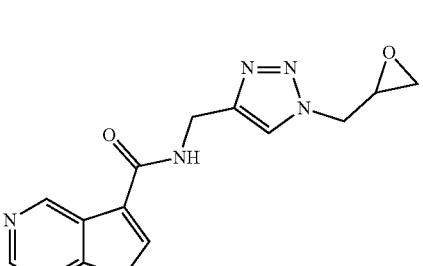
,
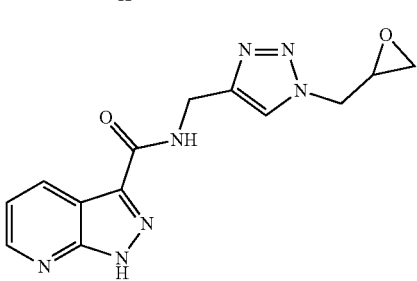
,
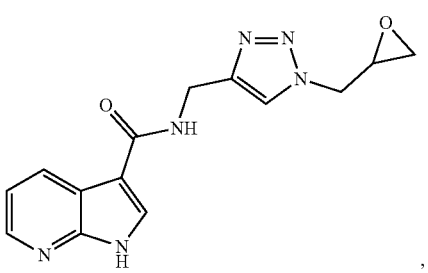
,
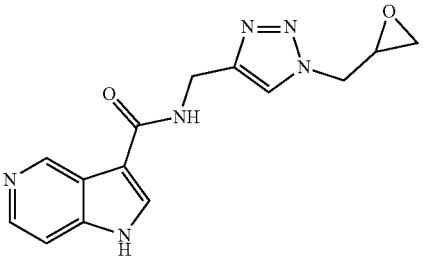
,

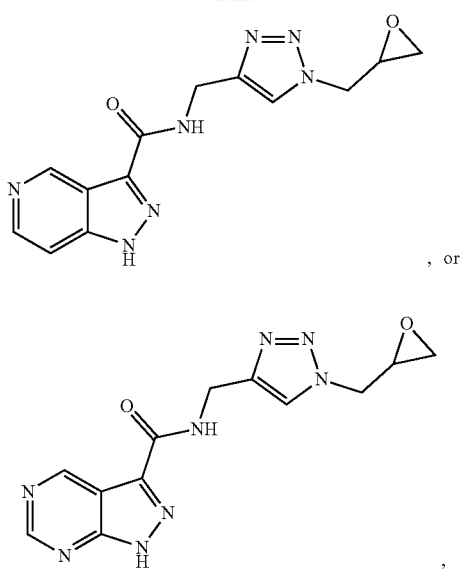
or a pharmaceutically acceptable salt thereof.
16. The compound of claim 1, wherein the compound is:
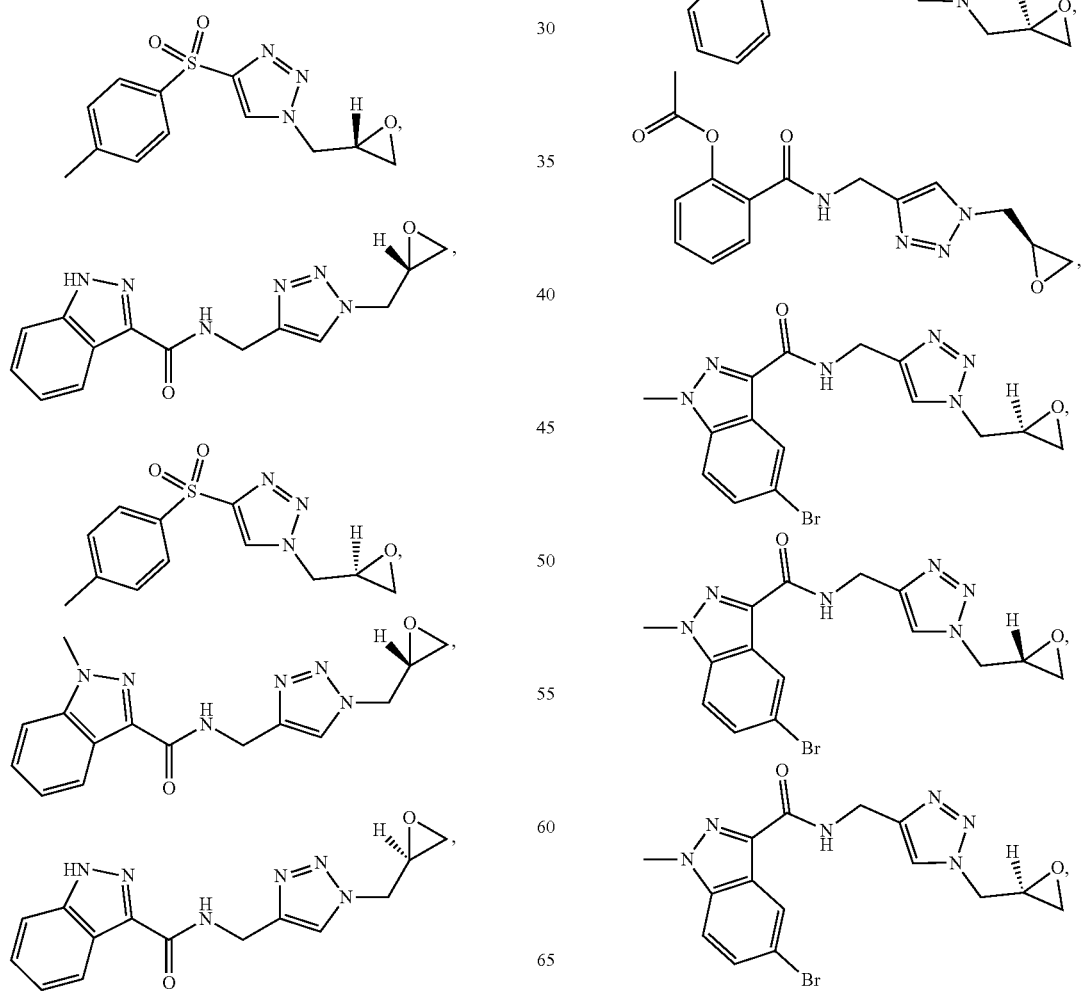

309

-continued

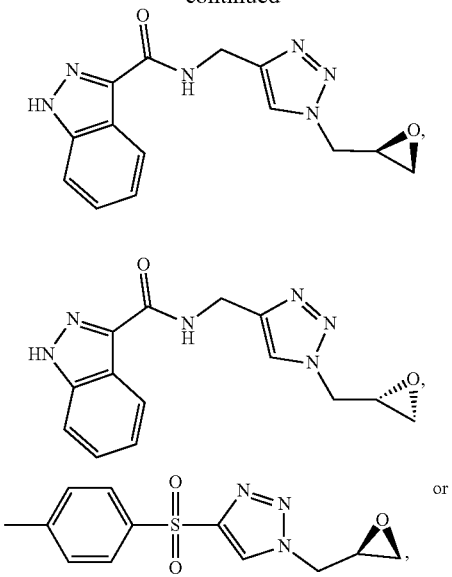

310

-continued

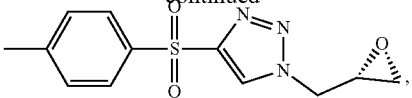

or a pharmaceutically acceptable salt thereof.

17. A pharmaceutical composition comprising the compound of claim 1, or a pharmaceutically acceptable salt thereof, and a pharmaceutically acceptable excipient.

18. A method of reducing the level of a K-Ras protein in a subject in need thereof, comprising administering to the subject an effective amount of a compound of claim 1, or a pharmaceutically acceptable salt thereof.

19. A method of reducing the activity level of a K-Ras protein in a subject in need thereof, comprising administering to the subject an effective amount of a compound of claim 1, or a pharmaceutically acceptable salt thereof.

20. A method for treating cancer in a subject suffering from said cancer, comprising administering to the subject a therapeutically effective amount of a compound of claim 1, or a pharmaceutically acceptable salt thereof, wherein said cancer is pancreatic cancer, lung cancer, or colorectal cancer.

* * * * *